(12) United States Patent
Ramurthy et al.

(10) Patent No.: US 7,932,262 B2
(45) Date of Patent: Apr. 26, 2011

(54) QUINAZOLINES FOR PDK1 INHIBITION

(75) Inventors: Savithri Ramurthy, Walnut Creek, CA (US); Xiaodong Lin, Walnut Creek, CA (US); Sharadha Subramanian, San Ramon, CA (US); Alice Rico, Castro Valley, CA (US); Xiaojong M. Wang, Livermore, CA (US); Rama Jain, Fremont, CA (US); Jeremy M. Murray, Emeryville, CA (US); Stephen E. Basham, Oakland, CA (US); Robert L. Warne, San Leandro, CA (US); Wei Shu, Danville, CA (US); Yasheen Zhou, Moraga, CA (US); Jeffrey Dove, Castro Valley, CA (US); Mina Aikawa, Alameda, CA (US); Payman Amiri, Walnut Creek, CA (US); Weibo Wang, Moraga, CA (US); Johanna M. Jansen, San Francisco, CA (US); Allan S. Wagman, Belmont, CA (US); Keith B. Pfister, San Ramon, CA (US); Simon Ng, Walnut Creek, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/295,967

(22) PCT Filed: Apr. 5, 2007

(86) PCT No.: PCT/US2007/008592
§ 371 (c)(1),
(2), (4) Date: Nov. 2, 2009

(87) PCT Pub. No.: WO2007/117607
PCT Pub. Date: Oct. 18, 2007

(65) Prior Publication Data
US 2010/0048561 A1 Feb. 25, 2010

Related U.S. Application Data

(60) Provisional application No. 60/790,304, filed on Apr. 6, 2006.

(51) Int. Cl.
*A61K 31/517* (2006.01)
(52) U.S. Cl. ..................... 514/266.4; 544/292
(58) Field of Classification Search .................... 544/292
See application file for complete search history.

(56) References Cited

U.S. PATENT DOCUMENTS

| | | | |
|---|---|---|---|
| 4,169,846 A | 10/1979 | Kidani et al. | |
| 4,323,581 A | 4/1982 | Gander | |
| 4,689,338 A | 8/1987 | Gerster | |
| 4,929,624 A | 5/1990 | Gerster et al. | |
| 5,041,424 A | 8/1991 | Saulnier et al. | |
| 5,238,944 A | 8/1993 | Wick et al. | |
| 5,266,575 A | 11/1993 | Gerster et al. | |
| 5,268,376 A | 12/1993 | Gester | |
| 5,346,905 A | 9/1994 | Gerster | |
| 5,352,784 A | 10/1994 | Nikolaides et al. | |
| 5,389,640 A | 2/1995 | Gerster et al. | |
| 5,395,937 A | 3/1995 | Nikolaides et al. | |
| 5,457,105 A | 10/1995 | Barker | |
| 5,478,932 A | 12/1995 | Rinehart et al. | |
| 5,482,936 A | 1/1996 | Lindstrom | |
| 5,494,916 A | 2/1996 | Lindstrom et al. | |
| 5,525,613 A | 6/1996 | Wynn et al. | |
| 5,616,582 A | 4/1997 | Barker | |
| 5,621,100 A | 4/1997 | Lewis et al. | |
| 5,747,498 A | 5/1998 | Schnur et al. | |
| 5,770,599 A | 6/1998 | Gibson | |
| 5,780,454 A | 7/1998 | Adams et al. | |
| 5,883,113 A | 3/1999 | Tang et al. | |
| 6,025,387 A | 2/2000 | Yoo et al. | |
| 6,083,505 A | 7/2000 | Miller et al. | |
| 6,258,812 B1 | 7/2001 | Bold et al. | |
| 6,331,555 B1 | 12/2001 | Hirth et al. | |
| 0,134,846 A1 | 7/2003 | Windsor et al. | |
| 6,605,617 B2 | 8/2003 | Renhowe et al. | |
| 0,171,303 A1 | 9/2003 | Gallop et al. | |
| 0,073,044 A1 | 4/2004 | Sharma et al. | |
| 6,727,256 B1 | 4/2004 | Carter et al. | |
| 6,774,237 B2 | 8/2004 | Renhowe et al. | |
| 6,982,260 B1 | 1/2006 | Barvian et al. | |

FOREIGN PATENT DOCUMENTS

WO    WO-88/07045    9/1988

(Continued)

OTHER PUBLICATIONS

International Preliminary Report on Patentability for PCT/US2007/008592, issued on Oct. 8, 2008, 9 pages. International Search Report for PCT/US2007/008592, mailed on Sep. 27, 2007, 4 pages.
Lee, "Diffusion-Controlled Matrix Systems" pp. 155-198 in Treatise on Controlled Drug Delivery (1992), Kydonieus, ed., Marcel Dekker, Inc., New York.
Parsons et al., Nature (2005) 436:792.
Prescott, ed., Methods in Cell Biology, vol. XIV (1976), Academic Press, New York, p. 33.
Ron and Langer, "Erodible Systems" pp. 199-224 in Treatise on Controlled Drug Delivery (1992), Kydonieus, ed., Marcel Dekker, Inc., New York.
Office Action for San Marino Patent Application No. SM-AP-200800059, mailed on Feb. 23, 2009, 2 pages [English translation included].

*Primary Examiner* — James O Wilson
*Assistant Examiner* — Brian McDowell
(74) *Attorney, Agent, or Firm* — Vinit Kathardekar

(57) ABSTRACT

The invention provides quinazoline compounds that are inhibitors of PDK1. Also provided are pharmaceutical compositions including the compounds, and methods of treating proliferative diseases, such as cancers, with the compounds or compositions.

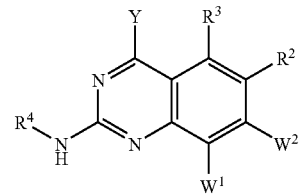

24 Claims, No Drawings

FOREIGN PATENT DOCUMENTS

| | | |
|---|---|---|
| WO | WO-89/07105 | 8/1989 |
| WO | WO-93/07153 | 4/1993 |
| WO | WO-93/08809 | 5/1993 |
| WO | WO-94/05304 | 3/1994 |
| WO | WO-94/06799 | 3/1994 |
| WO | WO-94/10202 | 5/1994 |
| WO | WO-95/12660 | 5/1995 |
| WO | WO-95/17182 | 6/1995 |
| WO | WO-96/06116 | 2/1996 |
| WO | WO-96/13506 | 5/1996 |
| WO | WO-96/30347 | 10/1996 |
| WO | WO-97/07081 | 2/1997 |
| WO | WO-97/20842 | 6/1997 |
| WO | WO-97/21701 | 6/1997 |
| WO | WO-97/29780 | 8/1997 |
| WO | WO-98/04541 | 2/1998 |
| WO | WO-98/05769 | 2/1998 |
| WO | WO-98/43095 | 10/1998 |
| WO | WO-99/02162 | 1/1999 |
| WO | WO-99/61422 | 12/1999 |
| WO | WO-00/27422 | 5/2000 |
| WO | WO-01/00245 | 1/2001 |
| WO | WO-01/04125 | 1/2001 |
| WO | WO-01/32651 | 5/2001 |
| WO | WO-01/38315 | 5/2001 |
| WO | WO-01/60814 | 8/2001 |
| WO | WO-01/79255 | 10/2001 |
| WO | WO-02/02552 | 1/2002 |
| WO | WO-02/30941 | 4/2002 |
| WO | WO-02/057423 | 7/2002 |
| WO | WO-02/062826 | 8/2002 |
| WO | WO-03/004505 | 1/2003 |
| WO | WO-03/024978 | 3/2003 |
| WO | WO-03/064397 | 8/2003 |
| WO | WO-03/082272 | 10/2003 |
| WO | WO-2004/006834 | 1/2004 |
| WO | WO-2004/009769 | 1/2004 |
| WO | WO-2004/060308 | 7/2004 |
| WO | WO-2004/064759 | 8/2004 |
| WO | WO-2004/065378 | 8/2004 |
| WO | WO-2004/087153 | 10/2004 |
| WO | WO-2005/030776 | 4/2005 |
| WO | WO-2006/031878 | 3/2006 |
| WO | WO-2006/118256 | 11/2006 |
| WO | WO 2006/137421 | 12/2006 |
| WO | WO-2007/084786 | 7/2007 |

QUINAZOLINES FOR PDK1 INHIBITION

RELATED APPLICATION

This application is the national phase under 35 U.S.C. §371 of PCT International Application No. PCT/US2007/008592, filed Apr. 5, 2007 which designates the United States of America, and which claims the benefit of priority of U.S. Provisional Application No. 60/790,304, filed Apr. 6, 2006, both of which are hereby incorporated herein by reference in their entirety.

FIELD OF THE INVENTION

The present invention generally relates to small molecule inhibitors of 3-phosphoinositide-dependent kinase (PDK1). In some embodiments, the compounds can be used as therapeutics in the treatment of cellular proliferative diseases.

BACKGROUND OF THE INVENTION

PDK1 (3-Phosphoinositide-dependent kinase 1) is a serine/threonine kinase belonging to the AGC kinase super family. PDK1 was first identified as the upstream kinase responsible for activating protein kinase B/AKT in the presence of phosphoinositide lipids ($PIP_3$). PDK1 activates AKT by phosphorylating a specific residue (threonine 308) located in the activation loop of this kinase. Subsequent research has shown that PDK1 is responsible for phosphorylating the activation-loop of many AGC kinases including p90 ribosomal S6 kinase (RSK), protein kinase C family members (PKC), p70 ribosomal S6 kinase (70S6K), and the serum and glucocorticoid-induced protein kinase (SGK). Thus, PDK1 is a central activator of multiple signaling pathways that are involved in cell proliferation, survival and control of apoptosis importantly, alterations in these signaling pathways are frequently observed in a variety of human cancers. For example, AKT is highly activated in a large percentage of common tumor types including melanoma, breast, lung, prostate and ovarian cancers. RSK levels are elevated in prostate cancers, and an RSK-specific inhibitor (SL0101) has recently been shown to inhibit the proliferation of multiple prostate cancer cell lines. Similarly, PKCε has been shown to play an important role in regulating apoptosis and promoting survival of glioma cells.

The human PDK1 gene encodes a 556 amino acid protein with an amino-terminal catalytic domain and a non-catalytic carboxy terminal containing a pleckstrin homology domain (PH). Recent studies suggest that PDK1 is a constitutively active kinase, and that PDK1 regulation occurs through the localization or conformational state of PDK1 target proteins. For example, the PH domain of PDK1 is required for the binding of $PIP_3$ lipids produced by PI3kinase (PI3K). PDK1 binding of $PIP_3$ lipids results in membrane co-localization with AKT, another PH domain containing protein. Once co-localized, PDK1 activates AKT by phosphorylating threonine-308. Alternatively, PDK1 can activate other AGC kinases independent of $PIP_3$ lipids by binding directly to a conserved motif found on these targets. Because PDK1 regulates two distinct classes of downstream signaling substrates (PI3K-dependent and independent targets), inhibitors of this enzyme could have important therapeutic value in a variety of human cancers. For instance, PDK1 inhibitors could be efficacious in tumors in which the PI3K signaling pathway is upregulated due to activating mutations, amplification of PI3K itself or its upstream receptor tyrosine kinases, or deletion of PTEN, the phosphatase the counteracts PI3K activity. The finding that mice expressing half the normal amount of PTEN are protected from developing a wide range of tumors by reducing PDK1 expression levels supports this idea. Alternatively, PDK1 inhibitors could be useful in treating cancers driven by $PIP_3$-independent PDK1 signaling pathways (e.g. K-ras or H-ras driven cancers).

Finally, the recent identification of PDK1 mutations ($PDK1^{T354M}$, $PDK1^{D527E}$) in human colorectal cancers suggests that inhibitors of this kinase may have therapeutic value by directly inhibiting either wild-type or mutant forms of this protein. See, Parsons et al., Nature 436, 792 (11 Aug. 2005) "Colorectal cancer: Mutations in a signaling pathway."

In summary, PDK1 is a central activator of several signaling pathways that are frequently altered in human cancers making it an attractive target for therapeutic intervention.

U.S. Pat. No. 6,982,260 discloses quinazoline compounds for inhibition of cyclin-dependent kinases, and International Application PCT/IB2004/000091 discloses 2-aminopyridine substituted heterocycles as inhibitors for cellular proliferation.

This invention is directed to the discovery of novel compounds for PDK1 inhibition and use of these compounds to treat a variety of diseases or disorders involving cellular proliferation.

BRIEF SUMMARY OF THE INVENTION

In one aspect, the present invention provides PDK1, Cdk1, and/or Cdk2 inhibitors that are useful as therapeutic agents, for the treatment of diseases and disorders characterized by abnormal cellular proliferation, for example cancers of the prostate, lung, colon, breast, among others.

In some embodiments, the instant invention provides compounds that have the Formula I:

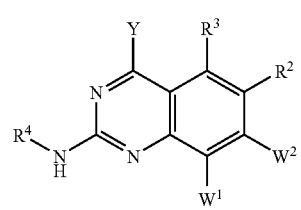

wherein,
one of $W^1$ or $W^2$ is $R^1$ and the other is —L—$A^1$;
L is a covalent bond, carbonyl, carbonylamino, aminocarbonyl, —O—, —S—, —SO—, —$SO_2$—, —NH—, $C_{1-3}$ alkyl, substituted $C_{1-3}$ alkyl, or an alkyl interrupted with —O—, —S—, —SO—, —$SO_2$—, —NH—, carbonyl, carbonylamino, or aminocarbonyl;
$A^1$ is aryl, substituted aryl, heteroaryl, substituted heteroaryl, heterocyclyl, or substituted heterocyclyl;
Y is H, $C_{1-3}$ alkyl, halo, cyano, nitro, or amino;
$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, substituted heteroaryl, cycloalkyl, substituted cycloalkyl, heterocyclyl, or substituted heterocyclyl;

provided when $R^4$ is heteroaryl or substituted heteroaryl, $W^2$ is not aryl or heteroaryl; or a stereoisomer, tautomer, or pharmaceutically acceptable salt thereof.

In some further embodiments, the compounds of the invention have the Formula I:

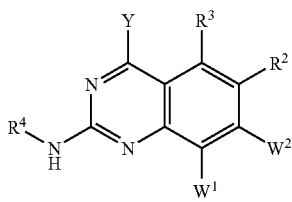

I wherein:

one of $W^1$ or $W^2$ is $R^1$ and the other is —L—$A^1$;

L is a covalent bond, carbonyl, carbonylamino, aminocarbonyl, —O—, —S—, —SO—, —$SO_2$—, —NH—, $C_{1-3}$ alkyl, substituted $C_{1-3}$ alkyl, or an alkyl interrupted with —O—, —S—, —SO—, —$SO_2$—, —NH—, carbonyl, carbonylamino, or aminocarbonyl;

$A^1$ is hydroxyl, amino, alkyl, substituted alkyl, aryl, substituted aryl, heteroaryl, substituted heteroaryl, cyclyl, or substituted cyclyl, heterocyclyl, or substituted heterocyclyl, provided when $W^2$ is hydroxyl or methoxy, $A^1$ is not isopropyl or cyclopentyl;

Y is H, $C_{1-3}$ alkyl, halo, cyano, nitro, or amino;

$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, or substituted heteroaryl; or a stereoisomer, tautomer, or pharmaceutically acceptable salt thereof.

In some further embodiments, compounds of the invention have the Formula II:

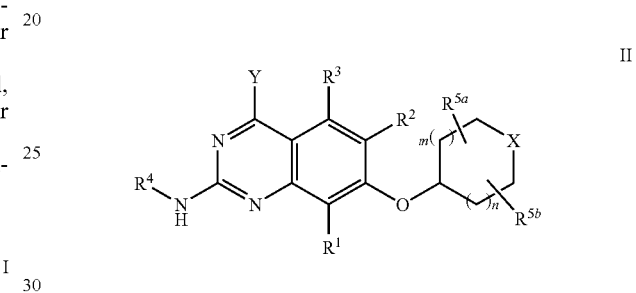

II wherein:

X is O or $NR^6$;

Y is H, $C_{1-3}$ alkyl, halo, cyano, nitro, or amino;

$R^{5a}$ and $R^{5b}$ are each independently H, halo, hydroxy, alkyl, substituted alkyl, alkoxy, substituted alkoxy, amino, or substituted amino;

$R^6$ is H, acyl, substituted carbonyl, sulfonyl, alkyl, or substituted alkyl;

or $R^{5a}$ and $R^6$ are taken together to form a bridging alkylene moiety;

or $R^{5a}$ and $R^{5b}$ are taken together to form a bridging alkylene moiety;

m and n are independently 0, 1 or 2;

$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and R$^4$ is aryl, substituted aryl, heteroaryl, substituted heteroaryl, cycloalkyl, substituted cycloalkyl, heterocyclyl, or substituted heterocyclyl; or a stereoisomer, tautomer, or pharmaceutically acceptable salt thereof.

In some further embodiments, the compounds of the invention have the Formula III:

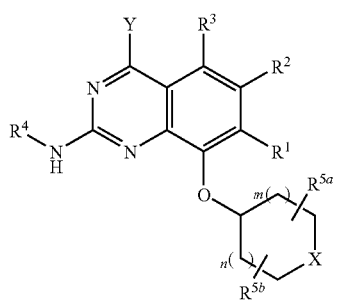

III wherein,

X is O or NR$^6$;

Y is H, C$_{1-3}$ alkyl, halo, cyano, nitro, or amino;

R$^{5a}$ and R$^{5b}$ are each independently H, halo, hydroxy, alkyl, substituted alkyl, alkoxy, substituted alkoxy, amino, or substituted amino;

R$^6$ is H, acyl, substituted carbonyl, sulfonyl, alkyl, or substituted alkyl;

or R$^{5a}$ and R$^6$ are taken together to form a bridging alkylene moiety;

or R$^{5a}$ and R$^{5b}$ are taken together to form a bridging alkylene moiety;

m and n are independently 0, 1 or 2;

R$^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

R$^2$ and R$^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and R$^4$ is aryl, substituted aryl, heteroaryl, substituted heteroaryl, cycloalkyl, substituted cycloalkyl, heterocyclyl, or substituted heterocyclyl; or a stereoisomer, tautomer, or pharmaceutically acceptable salt thereof.

In some further embodiments, the invention provides compositions, preferably pharmaceutical compositions, that contain one or more compounds of the invention. In further embodiments, the invention provides methods of treating diseases or disorders that are characterized by, inter alia, abnormal cellular proliferation, for example cancer and/or precancerous lesions, that employ compounds of the invention. The invention further provides methods of inhibiting tumor cell growth in a subject, that employ compounds of the invention. The invention further provides methods of manufacturing compounds and compositions described herein, and method for the use of the quinazolines of the invention in methods for manufacturing medicaments for use in the methods of the invention. In each of the embodiments of the invention, compounds, such as those of Formula I, can be used in the manufacture of a medicament for inhibiting PDK1.

In further embodiments, the invention provides the use of the compounds of the invention, in the manufacture of medicament for PDK1 inhibition, and/or for treatment of one or more of the aforementioned diseases or disorders.

Further embodiments of the invention include those described in the detailed description.

DETAILED DESCRIPTION

In accordance with the present invention, Applicants have discovered novel quinazoline PDK1 inhibitors that will provide effective treatments for disorders such as those described herein and those apparent to one skilled in the art.

In some embodiments, the present invention provides compounds that have the Formula I:

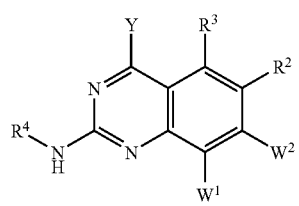

I wherein, one of W$^1$ or W$^2$ is R$^1$ and the other is —L—A$^1$;

L is a covalent bond, carbonyl, carbonylamino, aminocarbonyl, —O—, —S—, —SO—, —SO$_2$—, —NH—, C$_{1-3}$ alkyl, substituted C$_{1-3}$ alkyl, or an alkyl interrupted with —O—, —S—, —SO—, —SO$_2$—, —NH—, carbonyl, carbonylamino, or aminocarbonyl;

A$^1$ is aryl, substituted aryl, heteroaryl, substituted heteroaryl, heterocyclyl, or substituted heterocyclyl;

Y is H, C$_{1-3}$ alkyl, halo, cyano, nitro, or amino;

R$^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, substituted heteroaryl, cycloalkyl, substituted cycloalkyl, heterocyclyl, or substituted heterocyclyl; or a stereoisomer, tautomer, or pharmaceutically acceptable salt thereof.

The quinazoline compounds of this invention inhibit of PDK1 activity or inhibit cell proliferation. In some embodiments, the quinazoline compounds have low $IC_{50}$ values with regard to inhibition of PDK1 activity (i.e., the concention of a compound that is required for 50% inhibition of PDK1 activity) or low $EC_{50}$ with regard to inhibition of cell proliferation (i.e., the concentration of a compound which is required to induce inhibitory response against cell proliferation halfway between the baseline and maximum). For example, some quinazoline compounds exhibit $IC_{50}$ or $EC_{50}$ values of about 25 µM or less, about 10 µM or less, about 1 µM or less, or about 0.1 µM or even less according to the PDK1 kinase alpha screen assay and cell proliferation described herein.

In more particular embodiments, —L—$A^1$ is a heterocyclyloxy group having the structure:

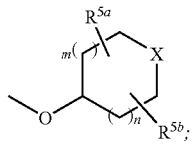

wherein,

X is O or $NR^6$;

$R^{5a}$ and $R^{5b}$ are each independently H, halo, hydroxy, alkyl, substituted alkyl, alkoxy, substituted alkoxy, amino, or substituted amino;

$R^6$ is H, acyl, substituted carbonyl, sulfonyl, alkyl, or substituted alkyl;

or $R^{5a}$ and $R^6$ are taken together to form a bridging alkylene moiety;

or $R^{5a}$ and $R^{5b}$ are taken together to form a bridging alkylene moiety;

m and n are independently 0, 1 or 2.

In a more particular embodiment $W^1$ is —L—$A^1$.

In another more particular embodiment $W^2$ is —L—$A^1$.

In some embodiments, $R^4$ is substituted phenyl.

In some embodiments, $R^4$ is phenyl substituted with a group of formula —$X^1$—$N(R_{501})(R_{502})$; wherein $X^1$ is $SO_2$ or $C(=O)$; and $R_{501}$ and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino. In some such embodiments, $X^1$ is $SO_2$. In some such embodiments, —$N(R_{501})(R_{502})$ forms —$NH_2$, —NH-alkyl, —NH-alkyl substituted with alkoxy, —NH-cycloalkyl, morpholino, —NH-(alkyl)-pyrrolidinyl or piperizinyl optionally substituted with alkyl. In some further such embodiments, —$N(R_{501})(R_{502})$ forms —$NH_2$, —NH—$CH(CH_3)_2$, —NH—$(CH_2)_2$—O—$CH_3$, —NH-cyclopropyl, morpholin-4-yl, 4-methyl-piperizine-1-yl, or —NH—$(CH_2)_2$-pyrrolidin-1-yl.

In some embodiments, $R^4$ is substituted phenyl and $X^1$ is $C(=O)$. In some such embodiments, —$N(R_{501})(R_{502})$ forms —$NH_2$, —NH-alkyl, —NH-alkyl substituted with alkoxy, or —NH-cycloalkyl.

In some embodiments, $R^2$ is H or halogen.

In some embodiments, $R^3$ is H.

In some further embodiments, $W^2$ is H, halogen, cyano, heteroaryl, substituted heteroaryl, phenyl, substituted phenyl, or a group of formula:

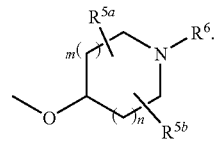

In some further embodiments, $W^2$ is H, halogen, cyano; or phenyl optionally substituted with —$C(=O)$—$N(R^{501})(R^{502})$; or a 5- or 6-membered heteroaryl group having 1 or 2 heteroatoms independently selected from O, S and N, that is optionally substituted with up to three substituents selected from alkyl, alkoxy and —$N(R^{501})(R^{502})$; or a group of formula:

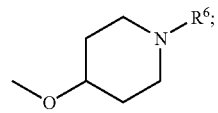

wherein each $R_{501}$ and each $R_{502}$ is independently selected from H, alkyl, substituted alkyl, alkoxyalkyl, cycloalkyl and heterocyclylalkyl.

In some embodiments, $W^2$ is H, halogen or cyano. In some further embodiments, $W^2$ is phenyl optionally substituted with —$C(=O)$—$N(R^{501})(R^{502})$; wherein $R_{501}$ and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino. In some such embodiments, $R^{501}$ and $R^{502}$ are each independently selected from H and alkyl.

In some embodiments, $W^2$ is a 5- or 6-membered heteroaryl group having 1 or 2 heteroatoms independently selected from O, S and N, that is optionally substituted with up to three substituents selected from alkyl, alkoxy and —N($R^{501}$)($R^{502}$); wherein $R_{501}$ and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino.

In some further embodiments, $W^2$ is a heteroaryl group selected from pyridinyl, pyrimidinyl, pyrazolyl, oxazolyl and thiazolyl, the heteroaryl group being optionally substituted with up to three substituents selected from alkyl, alkoxy and —N($R^{501}$)($R^{502}$); wherein $R_{501}$ and $R_{502}$ are independently selected from H, alkyl, substituted alkyl, alkoxyalkyl, cycloalkyl and heterocyclylalkyl, or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino. In some such embodiments, $R^{501}$ and $R^{502}$ are each independently selected from H and alkyl.

In some embodiments, $W^2$ is a group of formula:

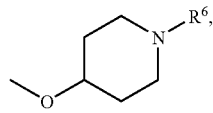

wherein $R^6$ is H or alkyl.

In some embodiments, $W^1$ is H, heteroaryl, substituted heteroaryl, or a group of formula:

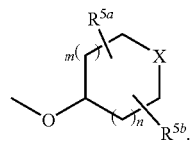

In some such embodiments, $W^1$ is a group of formula:

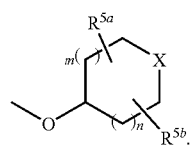

In some such embodiments, X is $NR^6$. In further such embodiments, X is $NR^6$, $R^{5b}$ is H, and $R^6$ and $R^{5b}$ together form an alkylene bridge, for example —($CH_2$)$_2$—.

In some embodiments, X is $NR^6$, and $R^{5a}$ and $R^{5b}$ together form an alkylene bridge, for example —($CH_2$)$_2$—. In some embodiments, X is $NR^6$, and $R^6$ is H or alkyl. In some embodiments, X is $NR^6$, m and n are each 1, and $R^{5a}$ and $R^{5b}$ are each H. In some such embodiments, $R^6$ is H or alkyl.

In some embodiments, X is $NR^6$, m is 1 and n is 0, and $R^{5a}$ and $R^{5b}$ are each H. In some such embodiments, $R^6$ is H or alkyl.

In some embodiments, X is $NR^6$, m is 2 and n is 0, and $R^{5a}$ and $R^{5b}$ are each H. In some such embodiments, $R^6$ is H or alkyl.

In some embodiments, X is $NR^6$, m and n are each 0, and $R^{5a}$ and $R^{5b}$ are each H. In some such embodiments, $R^6$ is H or alkyl.

In some embodiments, Y is H or $C_{1-3}$ alkyl. In other embodiments Y is H or —$CH_3$. In more particular embodiments, Y is H.

In some embodiments, $W^1$ is heteroaryl or substituted heteroaryl. In some further embodiments, $W^1$ is heteroaryl selected from pyridinyl, pyrimidinyl, pyrazolyl, oxazolyl and thiazolyl, the heteroaryl group being optionally substituted with up to three substituents selected from alkyl, alkoxy, —N($R^{501}$)($R^{502}$) and heterocyclyl; wherein $R_{50}$, and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino.

In some embodiments, $W^1$ is pyridinyl optionally substituted with up to three substituents selected from alkyl, alkoxy, —N($R^{501}$)($R^{502}$) and heterocyclyl; wherein $R_{501}$ and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino.

In some embodiments, $W^1$ is pyridinyl optionally substituted with heterocyclyl, for example a group of formula:

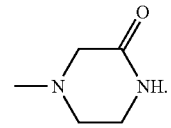

In some embodiments, $W^2$ is H, halogen, cyano, phenyl optionally substituted with —C(=O)—N($R^{501}$)($R^{502}$); or heteroaryl selected from pyridinyl, pyrimidinyl, pyrazolyl, oxazolyl and thiazolyl, the heteroaryl group being optionally substituted with up to three substituents selected from alkyl, alkoxy and —N($R^{501}$)($R^{502}$); or a group of formula:

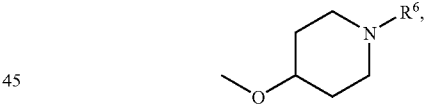

wherein $R^6$ is H or alkyl; and $R_{501}$ and $R_{502}$ are independently selected from H, alkyl, substituted alkyl, alkoxyalkyl, cycloalkyl and heterocyclylalkyl; or $R_{501}$ and $R_{502}$, taken together, form a heterocyclyl group that is optionally substituted with up to three groups independently selected from $C_{1-3}$ alkyl, hydroxyl, halo, alkoxy, amino, and substituted amino.

In some embodiments, $W^1$ is pyridinyl optionally substituted with up to three substituents selected from alkyl, alkoxy, —N($R^{501}$)($R^{502}$) and heterocyclyl; or $W^1$ is a group of formula:

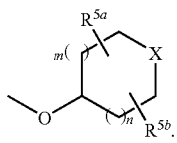

In some further embodiments, $R^4$ is substituted phenyl; $W^2$ is H, halogen, cyano, heteroaryl, substituted heteroaryl, phenyl, substituted phenyl, or a group of formula:

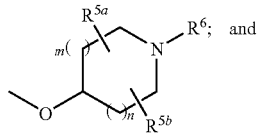

$W^1$ is H, heteroaryl, substituted heteroaryl, or a group of formula:

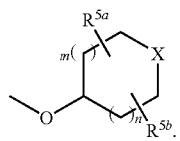

In some still further embodiments, $R_4$ is phenyl substituted with a group of formula $-X_1-N(R^{501})(R^{502})$; wherein $X_1$ is $SO_2$ or C(=O); and $R^{501}$ and $R^{502}$ are independently selected from H, alkyl, substituted alkyl, alkoxyalkyl, cycloalkyl and a group of formula -alkyl-heterocyclyl; or $R^{501}$ and $R^{502}$, taken together, form a heterocyclyl group that is optionally substituted with up to three groups independently selected from $C_{1-3}$ alkyl; $W^2$ is H, halogen, cyano; or phenyl optionally substituted with $-C(=O)-N(R^{501})(R^{502})$; or a 5- or 6-membered heteroaryl group having 1 or 2 heteroatoms independently selected from O, S and N, that is optionally substituted with up to three substituents selected from alkyl, alkoxy and $-N(R^{501})(R^{502})$; or a group of formula:

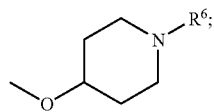

$W^1$ is a group of formula:

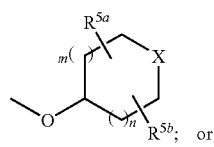

heteroaryl selected from pyridinyl, pyrimidinyl, pyrazolyl, oxazolyl and thiazolyl, the heteroaryl group being optionally substituted with up to three substituents selected from alkyl, alkoxy, $-N(R^{501})(R^{502})$ and heterocyclyl; wherein each $R^{501}$ and each $R^{502}$ is independently selected from H, alkyl, substituted alkyl, alkoxyalkyl, cycloalkyl and heterocyclylalkyl.

In some embodiments of each of the foregoing, $R^2$ is H or halogen, and $R^3$ is H.

In some embodiments, compounds of the invention have the Formula II:

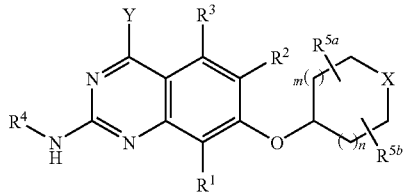

wherein:

X is O or $NR^6$;

Y is H, $C_{1-3}$ alkyl, halo, cyano, nitro, or amino;

$R^{5a}$ and $R^{5b}$ are each independently H, halo, hydroxy, alkyl, substituted alkyl, alkoxy, substituted alkoxy, amino, or substituted amino;

$R^6$ is H, acyl, substituted carbonyl, sulfonyl, alkyl, or substituted alkyl;

or $R^{5a}$ and $R^6$ are taken together to form a bridging alkylene moiety;

or $R^{5a}$ and $R^{5b}$ are taken together to form a bridging alkylene moiety;

m and n are independently 0, 1 or 2;

$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, substituted heteroaryl, cycloalkyl, substituted cycloalkyl, heterocyclyl, or substituted heterocyclyl; or a stereoisomer, tautomer, or pharmaceutically-acceptable salt thereof.

In some embodiments, $R^4$ is substituted phenyl. In some such embodiments, $R^4$ is phenyl substituted with a group of formula $-X_1-N(R^{501})(R^{502})$; wherein $X_1$ is $SO_2$ or C(=O); and $R^{501}$ and $R^{502}$ are independently selected from H, alkyl, substituted alkyl, alkoxyalkyl, cycloalkyl and heterocyclylalkyl; or $R^{501}$ and $R^{502}$, taken together, form a heterocyclyl group that is optionally substituted with up to three groups independently selected from $C_{1-3}$ alkyl In some such embodiments, $X^1$ is $SO_2$. In some further such embodiments, —N($R^{501}$)($R^{502}$) forms —NH$_2$, —NH-alkyl, —NH-alkyl substituted with alkoxy, —NH-cycloalkyl, morpholino, —NH-(alkyl)-pyrrolidinyl or piperizinyl optionally substituted with alkyl. In some further embodiments, —N($R^{501}$)($R^{502}$) forms —NH$_2$, —NH—CH(CH$_3$)$_2$, —NH—(CH$_2$)$_2$—O—CH$_3$, —NH-cyclopropyl, morpholin-4-yl, 4-methylpiperizine-1-yl, or —NH—(CH$_2$)$_2$-pyrrolidin-1-yl.

In some of the foregoing embodiments, $X^1$ is C(=O). In some such embodiments, —N($R^{501}$)($R^{502}$) forms —NH$_2$, —NH-alkyl, —NH-alkyl substituted with alkoxy, or —NH-cycloalkyl.

In some embodiments, Y is H or $C_{1-3}$ alkyl. In other embodiments Y is H or —CH$_3$. In more particular embodiments, Y is H.

In some embodiments, $R^2$ is H or halogen. In some further embodiments, $R^3$ is H.

In some embodiments, $R^1$ is selected from H, alkyl, and substituted alkyl.

In some embodiments, compounds of the invention have the Formula III:

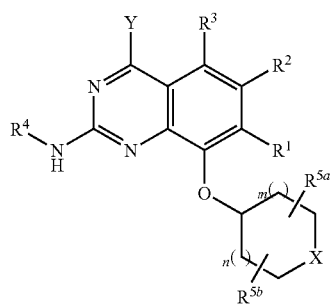

wherein,

X is O or NR$^6$;

Y is H, $C_{1-3}$ alkyl, halo, cyano, nitro, or amino;

$R^{5a}$ and $R^{5b}$ are each independently H, halo, hydroxy, alkyl, substituted alkyl, alkoxy, substituted alkoxy, amino, or substituted amino;

$R^6$ is H, acyl, substituted carbonyl, sulfonyl, alkyl, or substituted alkyl;

or $R^{5a}$ and $R^6$ are taken together to form a bridging alkylene moiety;

or $R^{5a}$ and $R^{5b}$ are taken together to form a bridging alkylene moiety;

m and n are independently 0, 1 or 2;

$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, SO$_3$H, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, substituted heteroaryl, cycloalkyl, substituted cycloalkyl, heterocyclyl, or substituted heterocyclyl; or a stereoisomer, tautomer, or pharmaceutically acceptable salt thereof.

In some such embodiments, $R^4$ is substituted phenyl. In some such embodiments, $R^4$ is phenyl substituted with a group of formula —X$_1$—N($R^{501}$)($R^{502}$); wherein $X_1$ is SO$_2$ or C(=O); and $R^{501}$ and $R^{502}$ are independently selected from H, alkyl, substituted alkyl, alkoxyalkyl, cycloalkyl and heterocyclylalkyl; or $R^{501}$ and $R^{502}$, taken together, form a heterocyclyl group that is optionally substituted with up to three groups independently selected from $C_{1-3}$ alkyl. In some such embodiments, $X^1$ is SO$_2$. In some such embodiments, —N($R^{501}$)($R^{502}$) forms —NH$_2$, —NH-alkyl, —NH-alkyl substituted with alkoxy, —NH-cycloalkyl, morpholino, —NH-(alkyl)-pyrrolidinyl or piperizinyl optionally substituted with alkyl. In some further embodiments, —N($R^{501}$)($R^{502}$) forms —NH$_2$, —NH—CH(CH$_3$)$_2$, —NH—(CH$_2$)$_2$—O—CH$_3$, —NH-cyclopropyl, morpholin-4-yl, 4-methylpiperizine-1-yl, or —NH—(CH$_2$)$_2$-pyrrolidin-1-yl.

In of the foregoing some embodiments, $X^1$ is C(=O). In some such embodiments, —N($R^{501}$)($R^{502}$) forms —NH$_2$, —NH-alkyl, —NH-alkyl substituted with alkoxy, or —NH-cycloalkyl.

In some embodiments, $R^2$ is H or halogen. In some further embodiments, $R^3$ is H.

In some embodiments, X is NR$^6$.

In some embodiments, X is NR$^6$, $R^{5b}$ is H, and $R^6$ and $R^{5b}$ together form an alkylene bridge, for example —(CH$_2$)$_2$—.

In some embodiments, X is NR$^6$, and $R^{5a}$ and $R^{5b}$ together form an alkylene bridge, for example —(CH$_2$)$_2$—.

In some embodiments, X is NR$^6$, wherein $R^6$ is H or alkyl.

In some embodiments, X is NR$^6$, m and n are each 1, and $R^{5a}$ and $R^{5b}$ are each H.

In some such embodiments, $R^6$ is H or alkyl.

In some embodiments, X is NR$^6$, m is 1 and n is 0, and $R^{5a}$ and $R^{5b}$ are each H. In some such embodiments, $R^6$ is H or alkyl.

In some embodiments, X is NR$^6$, m is 2 and n is 0, and $R^{5a}$ and $R^{5b}$ are each H. In some such embodiments, $R^6$ is H or alkyl.

In some embodiments, X is NR$^6$, m and n are each 0, and $R^{5a}$ and $R^{5b}$ are each H. In some such embodiments, $R^6$ is H or alkyl.

In some embodiments, Y is H or $C_{1-3}$ alkyl. In other embodiments Y is H or —CH$_3$. In more particular embodiments, Y is H.

In some embodiments of the compounds of Formula III, $R^1$ is selected from H, halogen, cyano, heteroaryl, substituted heteroaryl, phenyl, and substituted phenyl. In some further embodiments, $R^1$ is H, halogen, cyano; or phenyl optionally substituted with —C(=O)—N($R^{501}$)($R^{502}$); or a 5- or 6-membered heteroaryl group having 1 or 2 heteroatoms independently selected from O, S and N, that is optionally substituted with up to three substituents selected from alkyl, alkoxy and —N($R^{501}$)($R^{502}$); wherein each $R_{501}$ and each $R_{502}$ is independently selected from H, alkyl, substituted alkyl, alkoxyalkyl, cycloalkyl and heterocyclylalkyl. In some such embodiments, $R^1$ is phenyl optionally substituted with —C(=O)—N($R^{501}$)($R^{502}$). In some such embodiments, $R^{501}$ and $R^{502}$ are each independently selected from H and alkyl.

In some further embodiments, $R^1$ is H, halogen or cyano.

In some of the foregoing embodiments, $R^1$ is a 5- or 6-membered heteroaryl group having 1 or 2 heteroatoms independently selected from O, S and N, that is optionally substituted with up to three substituents selected from alkyl, alkoxy and —N($R^{501}$)($R^{502}$).

In some of the foregoing embodiments, $R^1$ is a heteroaryl group selected from pyridinyl, pyrimidinyl, pyrazolyl, oxazolyl and thiazolyl, the heteroaryl group being optionally substituted with up to three substituents selected from alkyl, alkoxy and —N($R^{501}$)($R^{502}$). In some such embodiments, $R^{501}$ and $R^{502}$ are each independently selected from H and alkyl.

In some of each of the foregoing embodiments, $R^4$ is other than pyridinyl. In some of each of the foregoing embodiments, $R^4$ is other than pyridin-2-yl.

Some compounds of the invention are shown in Tables 1-5 below. Physical data is provided in the column marked "MS (M+1) . . . " for each of the compounds, as is retention time data.

The columns labeled "PDK1 $IC_{50}$" "CPEC50 A2780," "CPEC50 PC3," and "CPEC50 PC3MM" indicates the compound's activity in the PDK1 Kinase Alpha Screen Assay and the Cell Proliferation Assay described below. The symbol "+" indicates $IC_{50}$ values or $EC_{50}$ values of 25 µM or greater (or compounds not evaluated), the symbol "++" indicates $IC_{50}$ values or $EC_{50}$ values between less than 25 µM and greater than 10 µM, the symbol "+++" indicates $IC_{50}$ values or $EC_{50}$ values of 10 µM or less and greater than 5 µM, and the symbol "+++" indicates $IC_{50}$ values or $EC_{50}$ values less than 5 µM.

TABLE 1

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 1 | | 4-[6-Bromo-8-(piperidin-4-yloxy)-quinazolin-2-ylamino]-benzenesulfonamide | 578/580, 2.03 | ++++ | ++++ | ++++ | | +++ |
| 2 | | 4-[8-(1-Aza-bicyclo[2.2.2]oct-3-yloxy)-6-bromo-quinazolin-2-yl-amino]-benzenesulfonamide | 504/506, 2.07 | ++++ | ++++ | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 3 | | [4-(Morpholine-4-sulfonyl)-phenyl]-[8-(piperidin-4-yloxy)-quinazolin-2-yl]-amine | 470.0, 2.14 | ++++ | ++++ | ++++ | | ++++ |
| 4 | | [8-(1-Isopropyl-piperidin-4-yloxy)-quinazolin-2-yl]-[4-(morpholine-4-sulfonyl)-phenyl]-amine | 512.1, 2.26 | ++++ | ++++ | ++++ | | ++++ |

TABLE 1-continued
| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 5 | 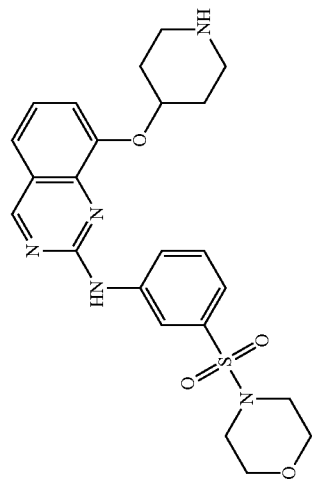 | [3-(Morpholine-4-sulfonyl)-phenyl]-[8-(piperidin-4-yloxy)-quinazolin-2-yl]-amine | 470.1, 2.11 | ++++ | ++++ | | | +++ |
| 6 | 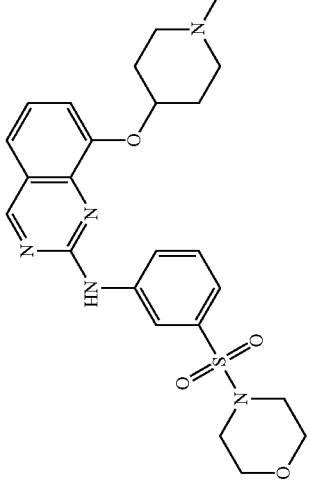 | [8-(1-Isopropyl-piperidin-4-yloxy)-quinazolin-2-yl]-[3-(morpholine-4-sulfonyl)-phenyl]-amine | 512.1, 2.24 | ++++ | ++++ | | | |
| 7 |  | [3-(4-Methyl-piperazine-1-sulfonyl)-phenyl]-[8-(piperidin-4-yloxy)-quinazolin-2-yl]-amine | 483.1, 1.80 | ++++ | ++++ | | | |

TABLE 1-continued

| Compound | | Name | LC/MS (M + 1(m/z), Rt(min)) | PDK1 IC$_{50}$ | CPEC$_{50}$ A2780 | CPEC$_{50}$ PC3 | CPED$_{50}$ PC3MM | PAKT308 PC3 IC$_{50}$ |
|---|---|---|---|---|---|---|---|---|
| 8 | Structure | N-Isopropyl-3-[8-(piperidin-4-yloxy)-quinazolin-2-yl-amino]-benzenesulfonamide | 442.1, 2.17 | ++++ | ++++ | | | |
| 9 | Structure | N-(2-Methoxy-ethyl)-3-[8-(piperidin-4-yloxy)-quinazolin-2-ylamino]-benzenesulfonamide | 458.1, 2.02 | ++++ | ++++ | | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 10 | | [4-(4-Methyl-piperazine-1-sulfonyl)-phenyl]-[8-(piperidin-4-yloxy)-quinazolin-2-yl]-amine | 483.1, 1.84 | ++++ | ++++ | | | |
| 11 | | N-Isopropyl-4-[8-(piperidin-4-yloxy)-quinazolin-2-ylamino]-benzenesulfonamide | 442.1, 2.16 | ++++ | ++++ | ++++ | ++++ | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 12 | | N-(2-Methoxy-ethyl)-4-[8-(piperidin-4-yloxy)-quinazolin-2-ylamino]-benzenesulfonamide | 458.1, 2.03 | ++++ | ++++ | ++++ | | ++++ |
| 13 | | N-Cyclopropyl-4-[8-(piperidin-4-yloxy)-quinazolin-2-ylamino]-benzenesulfonamide | 440.1, 2.12 | ++++ | ++++ | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 14 | | 4-[8-(Piperidin-4-yl-oxy)-quinazolin-2-ylamino]-N-(2-pyrrolidin-1-yl-ethyl)-benzenesulfonamide | 497.1, 1.85 | ++++ | ++++ | ++++ | | +++ |
| 15 | | 3-[8-(Piperidin-4-yl-oxy)-quinazolin-2-ylamino]-N-(2-pyrrolidin-1-yl-ethyl)-benzenesulfonamide | 497.1, 1.80 | ++++ | +++ | | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 16 | | N-Cyclopropyl-3-[8-(piperidin-4-yloxy)-quinazolin-2-ylamino]-benzenesulfonamide | 440.1, 2.10 | ++++ | ++++ | | | |
| 17 | | 4-[7-Bromo-8-(piperidin-4-yloxy)-quinazolin-2-ylamino]-benzenesulfonamide | 478.0, 2.07 | ++++ | ++++ | | | |
| 18 | | 4-[8-(Piperidin-4-yloxy)-7-pyridin-3-yl-quinazolin-2-ylamino]-benzenesulfonamide | 477.1, 1.70 | ++++ | ++++ | | | +++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 19 | | 4-[8-(Piperidin-4-yl-oxy)-2-(4-sulfamoyl-phenylamino)-quinazolin-7-yl]-benzamide | 519.1, 1.98 | ++++ | +++ | | | |
| 20 | | 4-[8-(Piperidin-4-yl-oxy)-7-pyridin-4-yl-quinazolin-2-ylamino]-benzenesulfonamide | 477.1, 1.69 | ++++ | ++++ | | | |
| 21 | | 4-[7-(6-Amino-pyridin-3-yl)-8-(piperidin-4-yloxy)-quinazolin-2-ylamino]-benzenesulfonamide | 492.1, 1.75 | ++++ | ++++ | | | +++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 22 | | 4-[7-(2-Amino-pyrimidin-5-yl)-8-(piperidin-4-yloxy)-quinazolin-2-ylamino]-benzenesulfonamide | 493.1, 1.80 | ++++ | +++ | | | |
| 23 | | 4-[7-(5-Methoxy-pyridin-3-yl)-8-(piperidin-4-yloxy)-quinazolin-2-ylamino]-benzenesulfonamide | 507.1, 1.83 | ++++ | ++++ | | | +++ |
| 24 | | 4-[8-(Piperidin-4-yloxy)-7-(1H-pyrazol-4-yl)-quinazolin-2-ylamino]-benzenesulfonamide | 466.1, 1.88 | ++++ | ++++ | | | +++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 25 | | 4-[7-(1-Methyl-1H-pyrazol-4-yl)-8-(piperidin-4-yloxy)-quinazolin-2-ylamino]-benzenesulfonamide | 480.1, 1.97 | ++++ | ++++ | | | +++ |
| 26 | | 4-[7-Oxazol-2-yl-8-(piperidin-4-yloxy)-quinazolin-2-ylamino]-benzenesulfonamide | 467.1, 1.94 | ++++ | ++++ | | | +++ |
| 27 | | 4-[8-(Piperidin-4-yloxy)-7-thiazol-2-yl-quinazolin-2-ylamino]-benzenesulfonamide | 483.1, 2.08 | ++++ | ++++ | | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 28 | | 4-[8-(Piperidin-4-yloxy)-7-pyridin-2-yl-quinazolin-2-ylamino]-benzenesulfonamide | 477.1, 1.73 | ++++ | ++++ | | | +++ |
| 29 | | 4-[7-Cyano-8-(piperidin-4-yloxy)-quinazolin-2-ylamino]-benzenesulfonamide | 425.1, 1.95 | ++++ | ++++ | | | |
| 30 | | 4-[8-(Piperidin-4-yloxy)-quinazolin-2-ylamino]-benzamide | 364.1, 1.81 | ++++ | ++++ | | | |

TABLE 1-continued

| Compound | Structure | Name | LC/MS (M + 1(m/z), Rt(min)) | PDK1 IC$_{50}$ | CPEC$_{50}$ A2780 | CPEC$_{50}$ PC3 | CPED$_{50}$ PC3MM | PAKT308 PC3 IC$_{50}$ |
|---|---|---|---|---|---|---|---|---|
| 31 | | 4-[8-(Piperidin-4-yloxy)-quinazolin-2-ylamino]-benzenesulfonamide | 400.1, 1.91 | ++++ | ++++ | ++++ | ++++ | ++++ |
| 32 | Chiral | 4-[8-((S)-Pyrrolidin-3-yloxy)-quinazolin-2-ylamino]-benzenesulfonamide | 386.1, 1.88 | ++++ | ++++ | | | |
| 33 | | 4-[8-(1-Aza-bicyclo[2.2.2]oct-3-yloxy)-quinazolin-2-ylamino]-benzenesulfonamide | 426.1, 2.11 | ++++ | ++++ | | | |

TABLE 1-continued

| Compound | Structure | Name | LC/MS (M + 1(m/z), Rt(min)) | PDK1 IC$_{50}$ | CPEC$_{50}$ A2780 | CPEC$_{50}$ PC3 | CPED$_{50}$ PC3MM | PAKT308 PC3 IC$_{50}$ |
|---|---|---|---|---|---|---|---|---|
| 34 | Chiral | 4-[8-((S)-1-Methyl-pyrrolidin-3-yloxy)-quinazolin-2-ylamino]-benzenesulfonamide | 400.1, 1.89 | ++++ | ++++ | | | |
| 35 | | 4-[8-(1-Methyl-piperidin-4-yloxy)-quinazolin-2-ylamino]-benzenesulfonamide | 414.2, 1.95 | ++++ | ++++ | | | ++++ |
| 36 | | 4-[8-(1-Isopropyl-piperidin-4-yloxy)-quinazolin-2-ylamino]-benzenesulfonamide | 442.1, 2.11 | ++++ | ++++ | ++++ | ++++ | ++++ |

TABLE 1-continued

| Compound Structure | | Name | LC/MS (M + 1(m/z), Rt(min)) | PDK1 IC$_{50}$ | CPEC$_{50}$ A2780 | CPEC$_{50}$ PC3 | CPED$_{50}$ PC3MM | PAKT308 PC3 IC$_{50}$ |
|---|---|---|---|---|---|---|---|---|
| 37 | Chiral | 4-[8-((R)-Pyrrolidin-3-yloxy)-quinazolin-2-ylamino]-benzenesulfonamide | 386.1, 1.85 | ++++ | ++++ | | | +++ |
| 38 | Chiral | 4-[8-((R)-1-Methyl-pyrrolidin-3-yloxy)-quinazolin-2-ylamino]-benzenesulfonamide | 400.1, 1.86 | ++++ | ++++ | | | |
| 39 | | 4-[8-(1-Methyl-piperidin-3-yloxy)-quinazolin-2-ylamino]-benzenesulfonamide | 414.1, 1.97 | ++++ | ++++ | | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 40 | Chiral; 4-[8-((S)-3-quinuclidinyloxy)-quinazolin-2-ylamino]-benzenesulfonamide structure | 4-[8-((S)-3-quinuclidinyloxy)-quinazolin-2-ylamino]-benzenesulfonamide | 426.1, 1.72 | ++++ | ++++ | ++++ | ++++ | ++++ |
| 41 | 4-[8-(8-Methyl-8-azabicyclo[3.2.1]oct-3-yloxy)-quinazolin-2-ylamino]-benzenesulfonamide structure | 4-[8-(8-Methyl-8-azabicyclo[3.2.1]oct-3-yloxy)-quinazolin-2-ylamino]-benzenesulfonamide | 440.1, 2.05 | ++++ | ++++ | ++++ | | ++++ |
| 42 | 4-[7-(1-Isopropyl-piperidin-4-yloxy)-quinazolin-2-ylamino]-benzenesulfonamide structure | 4-[7-(1-Isopropyl-piperidin-4-yloxy)-quinazolin-2-ylamino]-benzenesulfonamide | 442.0, 2.02 | ++++ | ++++ | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 43 | | 4-[8-(1-Isopropyl-piperidin-4-yloxy)-quinazolin-2-ylamino]-N-methyl-benzamide | 420.1, 2.13 | ++++ | ++++ | | | ++++ |
| 44 | | N-Isopropyl-4-[8-(1-isopropyl-piperidin-4-yloxy)-quinazolin-2-ylamino]-benzamide | 448.1, 2.42 | ++++ | ++++ | ++++ | | ++++ |
| 45 | | 4-[8-(1-Isobutyl-piperidin-4-yloxy)-quinazolin-2-ylamino]-benzenesulfonamide | 456.2, 2.25 | ++++ | ++++ | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 46 | | 4-[8-(1-Ethyl-piperidin-4-yloxy)-quinazolin-2-ylamino]-benzenesulfonamide | 428.1, 2.05 | ++++ | ++++ | | | +++ |
| 47 | | 4-[8-(1-Isopropyl-azetidin-3-yloxy)-quinazolin-2-ylamino]-benzenesulfonamide | 414.1, 1.93 | ++++ | ++++ | | | |
| 48 | | 4-[8-(Azetidin-3-yloxy)-quinazolin-2-ylamino]-benzenesulfonamide | 372.1, 1.76 | ++++ | +++ | | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPEC$_{50}$ PC3MM | PAKT308 PC3 IC$_{50}$ |
|---|---|---|---|---|---|---|---|---|
| 49 | | 4-[8-(1-Isobutyl-azetidin-3-yloxy)-quinazolin-2-ylamino]-benzenesulfonamide | 428.1, 2.14 | ++++ | ++++ | | | |
| 50 | | 4-[8-(1-Ethyl-azetidin-3-yloxy)-quinazolin-2-ylamino]-benzenesulfonamide | 400.1, 1.91 | ++++ | ++++ | | | |
| 51 | | 4-[7-(Piperidin-4-yloxy)-quinazolin-2-ylamino]-benzenesulfonamide | 400.1, 1.813 | ++++ | ++++ | ++++ | ++++ | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 52 | | 4-[7-(1-Methyl-piperidin 4-yloxy)-quinazolin-2-ylamino]-benzenesulfonamide | 414.1, 1.803 | ++++ | ++++ | ++++ | ++++ | ++++ |
| 53 | | [7-(1-Methyl-piperidin-4-yloxy)-quinazolin-2-yl]-[4-(morpholine-4-sulfonyl)-phenyl]-amine | 484.1, 2.07 | ++++ | ++++ | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 54 | | [7-(1-Isopropyl-piperidin-4-yloxy)-quinazolin-2-yl]-[4-(morpholine-4-sulfonyl)-phenyl]-amine | 512.1, 2.18 | ++++ | ++++ | ++++ | | |
| 55 | | (3,5-Dimethoxy-phenyl)-[7-(piperidin-4-yloxy)-quinazolin-2-yl]-amine | 381.1, 2.19 | ++++ | | ++++ | | ++++ |
| 56 | | (3,5-Dimethoxy-phenyl)-[7-(1-ethyl-piperidin-4-yloxy)-quinazolin-2-yl]-amine | 409.4, 2.39 | ++++ | | ++++ | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 57 | | (4-Chloro-phenyl)-[7-(1-isopropyl-piperidin-4-yloxy)-quinazolin-2-yl]-amine | 397.1, 2.53 | ++++ | | ++++ | | |
| 58 | | N-Isopropyl-4-[7-(1-isopropyl-piperidin-4-yloxy)-quinazolin-2-ylamino]-benzenesulfonamide | 484.2, 2.19 | ++++ | | ++++ | | ++++ |
| 59 | | (4-Fluoro-phenyl)-[7-(piperidin-4-yloxy)-quinazolin-2-yl]-amine | 339.0, 1.92 | ++++ | | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 60 | | (4-Fluoro-phenyl)-[7-(1-isopropyl-piperidin-4-yloxy)-quinazolin-2-yl]-amine | 381.1, 2.07 | ++++ | | +++ | | |
| 61 | | C-{4-[7-(1-Isopropyl-piperidin-4-yloxy)-quinazolin-2-ylamino]-phenyl}-N-methyl-methanesulfonamide | 470.1, 1.84 | ++++ | | ++++ | +++ | ++++ |
| 62 | | 2-Chloro-N*4*-[7-(1-isopropyl-piperidin-4-yloxy)-quinazolin-2-yl]-benzene-1,4-diamine | 412.1, 1.86 | ++++ | | +++ | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 63 | | N-{2-Methyl-4-[7-(piperidin-4-yloxy)-quinazolin-2-ylamino]-phenyl}-acetamide | 392.2, 1.70 | ++++ | | ++++ | | ++++ |
| 64 | | 4-[7-(1-Oxo-1,2,3,4-tetrahydro-isoquinolin-6-yl)-8-(piperidin-4-yloxy)-quinazolin-2-ylamino]-benzenesulfonamide | 545.1, 2.07 | ++++ | +++ | | | |
| 65 | | 4-[7-(1-Isobutyl-1H-pyrazol-4-yl)-8-piperidin-4-yloxy)-quinazolin-2-ylamino]-benzenesulfonamide | 522.1, 2.27 | ++++ | ++++ | | | +++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 66 | | 4-[8-(Piperidin-4-yloxy)-7-pyrazin-2-yl-quinazolin-2-ylamino]-benzenesulfonamide | 478.0, 1.91 | ++++ | ++++ | | | +++ |
| 67 | | 4-[7-Phenyl-8-(piperidin-4-yloxy)-quinazolin-2-ylamino]-benzenesulfonamide | 476.1, 2.28 | ++++ | ++++ | ++++ | | ++++ |
| 68 | | 4-[7-(6-Amino-5-trifluoromethyl-pyridin-3-yl)-8-(piperidin-4-yloxy)-quinazolin-2-ylamino]-benzenesulfonamide | 560.1, 2.11 | ++++ | | ++++ | | +++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 69 | | 4-[7-(6-Amino-4-trifluoromethyl-pyridin-3-yl)-8-(piperidin-4-yloxy)-quinazolin-2-ylamino]-benzenesulfonamide | 560.1, 1.99 | ++++ | | +++ | | |
| 70 | | 2-{4-[8-(1-Isopropyl-piperidin-4-yloxy)-quinazolin-2-ylamino]-phenyl}-N-methyl-acetamide | 434.1, 1.85 | ++++ | | ++++ | | + |

TABLE 1-continued
| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 71 | 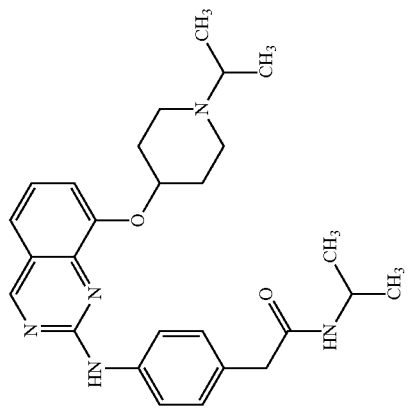 | N-Isopropyl-2-{4-[8-(1-isopropyl-piperidin-4-yloxy)-quinazolin-2-ylamino]-phenyl}-acetamide | 462.2, 2.09 | ++++ | ++++ | ++++ | | +++ |
| 72 | 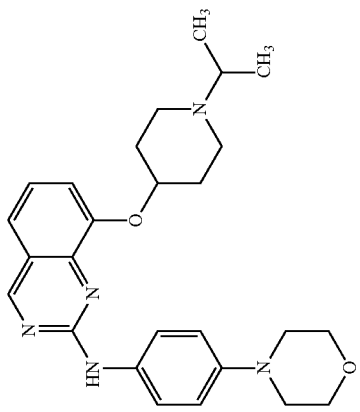 | [8-(1-Isopropyl-piperidin-4-yloxy)-quinazolin-2-yl]-(4-morpholin-4-yl-phenyl)-amine | 448.2, 1.92 | ++++ | ++++ | ++++ | | ++++ |

TABLE 1-continued
| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 73 | 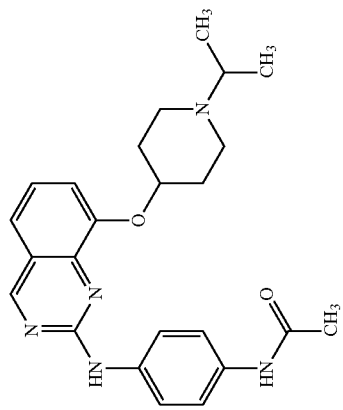 | N-{4-[8-(1-Isopropyl-piperidin-4-yloxy)-quinazolin-2-ylamino]-phenyl}-acetamide | 420.1, 1.90 | ++++ | | ++++ | | +++ |
| 74 | 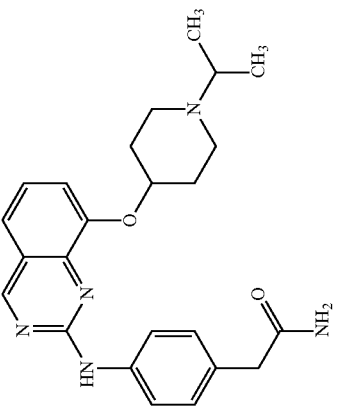 | 2-{4-[8-(1-Isopropyl-piperidin-4-yloxy)-quinazolin-2-ylamino]-phenyl}-acetamide | 420.1, 1.79 | ++++ | | ++++ | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 75 | | Pyrrolidine-1-carboxylic acid {4-[8-(1-isopropyl-piperidin-4-yloxy)-quinazolin-2-ylamino]-phenyl}-amide | 475.2, 2.15 | ++++ | | ++++ | | |
| 76 | | 2-{3-[8-(1-Isopropyl-piperidin-4-yloxy)-quinazolin-2-ylamino]-phenyl}-acetamide | 420.1, 1.83 | ++++ | | ++++ | | |
| 77 | | 2-{3-[8-(1-Isopropyl-piperidin-4-yloxy)-quinazolin-2-ylamino]-phenyl}-N-methyl-acetamide | 434.2, 1.87 | ++++ | | ++++ | | ++++ |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 78 | | 2-{3-[8-(1-Isopropyl-piperidin-4-yloxy)-quinazolin-2-ylamino]-phenyl}-N-(3-methylcarbamoylmethyl-phenyl)-acetamide | 567.2, 2.05 | ++++ | | ++++ | | |
| 79 | | N-Isopropyl-2-{3-[8-(1-isopropyl-piperidin-4-yloxy)-quinazolin-2-ylamino]-phenyl}-acetamide | 462.2, 2.05 | ++++ | | ++++ | | |
| 80 | | [8-(1-Isopropyl-piperidin-4-yloxy)-quinazolin-2-yl]-(3-morpholin-4-yl-phenyl)-amine | 448.2, 2.01 | ++++ | | +++ | | |
| 81 | | N-{3-[8-(1-Isopropyl-piperidin-4-yloxy)-quinazolin-2-ylamino]-phenyl}-acetamide | 420.2, 1.90 | ++++ | | ++++ | | ++++ |

TABLE 1-continued

| Compound Structure | | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 82 | [structure] | C-{4-[8-(1-Isopropyl-piperidin-4-yloxy)-quinazolin-2-ylamino]-phenyl}-N-methyl-methanesulfonamide | 470.1, 2.00 | ++++ | | ++++ | | |
| 83 | [structure] | (4-Fluoro-phenyl)-[8-(1-isopropyl-piperidin-4-yloxy)-quinazolin-2-yl]-amine | 381.1, 2.17 | ++++ | | +++ | | |
| 84 | [structure] | (4-Chloro-phenyl)-[8-(1-isopropyl-piperidin-4-yloxy)-quinazolin-2-yl]-amine | 397.1, 2.37 | ++++ | | ++++ | | |

TABLE 1-continued

| Compound | Structure | Name | LC/MS (M + 1(m/z), Rt(min)) | PDK1 IC$_{50}$ | CPEC$_{50}$ A2780 | CPED$_{50}$ PC3 | CPED$_{50}$ PC3MM | PAKT308 PC3 IC$_{50}$ |
|---|---|---|---|---|---|---|---|---|
| 85 | | [8-(1-Isopropyl-piperidin-4-yloxy)-quinazolin-2-yl]-(4-trifluoromethyl-phenyl)-amine | 431.1, 3.09 | ++++ | | ++++ | | |
| 86 | | 4-[6-Ethynyl-8-(1-isopropyl-piperidin-4-yloxy)-quinazolin-2-ylamino]-benzenesulfonamide | 466, 2.87 | ++++ | | ++++ | | ++++ |

TABLE 2
| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 87 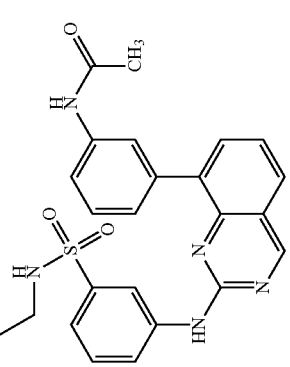 | N-{3-[2-(3-Butylsulfamoyl-phenylamino)-quinazolin-8-yl]-phenyl}-acetamide | 489.6 (FW) | +++ | | | | |
| 88 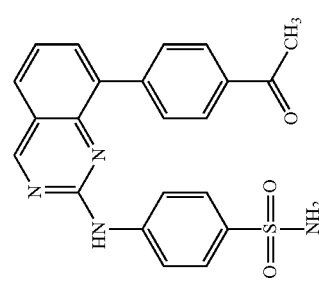 | 4-[8-(4-Acetyl-phenyl)-quinazolin-2-ylamino]-benzenesulfonamide | 419.0, 2.69 | ++++ | +++ | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 89 | | 4-[8-[4-(2H-Pyrazol-3-yl)-phenyl]-quinazolin-2-ylamino]-benzenesulfonamide | 443.2, 2.33 | ++++ | ++++ | | | |
| 90 | | 3-[2-(4-Sulfamoyl-phenylamino)-quinazolin-8-yl]-benzamide | 420.0, 2.25 | ++++ | ++++ | | | |
| 91 | | 4-[8-(3-Methanesulfonyl-phenyl)-quinazolin-2-ylamino]-benzenesulfonamide | 455.0, 2.45 | ++++ | ++++ | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 92 | 4-[8-(3-Methanesulfonylaminophenyl)-quinazolin-2-ylamino]-benzenesulfonamide | 470.0, 2.47 | ++++ | ++++ | | | |
| 93 | N-{3-[2-(4-Sulfamoyl-phenylamino)-quinazolin-8-yl]-phenyl}-acetamide | 434.0, 2.39 | ++++ | ++++ | | | |
| 94 | N-{3-[2-(4-Sulfamoyl-phenylamino)-quinazolin-8-yl]-phenyl]-sulfonamide | 456.0, 2.30 | ++++ | ++++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 95 | | 4-(8-Benzo[1,3]dioxol-5-yl-quinazolin-2-ylamino)-benzenesulfonamide | 421.0, 2.78 | ++++ | ++++ | | | |
| 96 | | 4-[2-(4-Sulfamoyl-phenylamino)-quinazolin-8-yl]-benzamide | 420.1, 2.28 | ++++ | ++++ | | | |
| 97 | | 4-[8-(2-Fluoro-pyridin-4-yl)-quinazolin-2-ylamino]-benzenesulfonamide | 396.0, 2.55 | ++++ | ++++ | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 98 | | 4-(8-Pyridin-3-yl-quinazolin-2-ylamino)-benzenesulfonamide | 378.0, 1.84 | ++++ | +++ | | | |
| 99 | | 4-(8-Pyridin-4-yl-quinazolin-2-ylamino)-benzenesulfonamide | 378.0, 1.83 | ++++ | +++ | | | |
| 100 | | 4-{8-[2-(2-Methoxy-ethylamino)-pyridin-4-yl]-quinazolin-2-ylamino}-benzenesulfonamide | 451.0, 2.01 | ++++ | ++++ | | | |

TABLE 2-continued

| Compound | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 101 | N-(2-{4-[2-(4-Sulfamoyl-phenylamino)-quinazolin-8-yl]-pyridin-2-ylamino}-ethyl)-acetamide | 478.0, 1.89 | ++++ | ++++ | | | |
| 102 | 4-{8-[2-(2-Pyrrolidin-1-yl-ethylamino)-pyridin-4-yl]-quinazolin-2-ylamino}-benzenesulfonamide | 490.1, 1.79 | ++++ | ++++ | | | |
| 103 | 4-(8-Isoxazol-4-yl-quinazolin-2-ylamino)-benzenesulfonamide | 368.0, 2.40 | ++++ | ++++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 104 | | 4-[8-(1H-Pyrazol-4-yl)-quinazolin-2-ylamino]-benzenesulfonamide | 367.1, 2.13 | ++++ | ++++ | | | |
| 105 | | 4-[8-(2-Morpholin-4-yl-pyridin-4-yl)-quinazolin-2-ylamino]-benzenesulfonamide | 463.0, 1.98 | ++++ | +++ | | | |
| 106 | | 4-{8-[2-(4-Methyl-piperazin-1-yl)-pyridin-4-yl]-quinazolin-2-ylamino}-benzenesulfonamide | 476.1, 1.79 | ++++ | ++++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 107 | | 4-{8-[2-(1,1-Dioxo-1 lambda*6*-thiomorpholin-4-yl)-pyridin-4-yl]-quinazolin-2-ylamino}-benzenesulfonamide | 511.0, 1.99 | ++++ | ++++ | | | |
| 108 | | 4-{8-[2-(3-Oxo-piperazin-1-yl)-pyridin-4-yl]-quinazolin-2-ylamino}-benzenesulfonamide | 476.0, 1.84 | ++++ | ++++ | | | |
| 109 | | 4-[8-(2-Amino-pyridin-4-yl)-quinazolin-2-ylamino]-benzenesulfonamide | 393.1, 1.89 | ++++ | +++ | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 110 | | 4-(8-Phenyl-quinazolin-2-ylamino)-benzenesulfonamide | 377.0, 2.84 | ++++ | ++++ | | | |
| 111 | | 4-(7-Pyridin-4-yl-quinazolin-2-ylamino)-benzenesulfonamide | 378.1, 1.65 | | | | | |
| 112 | | 2-Fluoro-4-[2-(4-sulfamoyl-phenylamino)-quinazolin-7-yl]-benzamide | 438.0, 2.19 | ++++ | +++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 113 | | 4-[8-(Pyrrolidine-1-carbonyl)-quinazolin-2-ylamino]-benzenesulfonamide | 398.0, 2.06 | ++++ | +++ | | | |
| 114 | | 2-(4-Sulfamoyl-phenylamino)-quinazoline-8-carboxylic acid (2-methoxy-ethyl)-amide | 402.0, 2.09 | +++ | ++++ | | | |
| 115 | | 2-(4-Sulfamoyl-phenylamino)-quinazoline-8-carboxylic acid (2-pyrrolidin-1-yl-ethyl)-amide | 441.0, 1.84 | +++ | ++++ | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 116 | 4-{7-[4-(2-Methoxy-ethyl)-piperazine-1-carbonyl]-quinazolin-2-ylamino}-benzenesulfonamide | 471.0, 1.67 | ++ | +++ | | | |
| 117 | 4-[8-(5-Chloro-2-methoxy-pyridin-4-yl)-quinazolin-2-ylamino]-benzenesulfonamide | 442.0, 3.70 | ++++ | ++++ | | | |
| 118 | 4-[7-(4-Isopropyl-piperazine-1-carbonyl)-quinazolin-2-ylamino]-benzenesulfonamide | 455.1, 1.71 | ++ | +++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 119 | | 2-(4-Sulfamoyl-phenylamino)-quinazoline-7-carboxylic acid (1-methyl-piperidin-4-yl)-amide | 441.1, 1.74 | ++++ | +++ | | | |
| 120 | | 4-[8-(Morpholine-4-carbonyl)-quinazolin-2-ylamino]-benzenesulfonamide | 414.0, 1.92 | +++ | +++ | | | |
| 121 | | 4-[8-(4-Methyl-piperazine-1-carbonyl)-quinazolin-2-ylamino]-benzenesulfonamide | 427.1, 1.59 | ++++ | +++ | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 122 | | 4-[8-(1,1-Dioxo-1lambda*6*-thiomorpholine-4-carbonyl)-quinazolin-2-ylamino]-benzenesulfonamide | 462.0, 1.83 | ++ | +++ | | | |
| 123 | | 3-[2-(4-Sulfamoyl-phenylamino)-quinazolin-7-yl]-benzamide | 419.9, 2.569 | ++++ | +++ | | | |
| 124 | | 4-[2-(4-Sulfamoyl-phenylamino)-quinazolin-7-yl]-benzamide | 420.1, 3.24 | ++++ | +++ | | | |

TABLE 2-continued

| Compound | Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 125 | | 2-[2-(4-Sulfamoyl-phenylamino)-quinazolin-7-yl]-benzamide | 420.0, 2.404 | ++++ | | | | |
| 126 | | N-{3-[2-(4-Sulfamoyl-phenylamino)-quinazolin-7-yl]-phenyl}-acetamide | 434.0, 2.882 | +++ | | | | |
| 127 | | N-{3-[2-(4-Sulfamoyl-phenylamino)-quinazolin-7-yl]-phenyl}-sulfonamide | 456.0, 2.766 | ++++ | +++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 128 | | 4-[7-(3-Methanesulfonyl-phenyl)-quinazolin-2-ylamino]-benzenesulfonamide | 454.9, 3.039 | ++++ | | | | |
| 129 | | 4-[7-(3-Methanesulfonylamino-phenyl)-quinazolin-2-ylamino]-benzenesulfonamide | 469.9, 3.91 | ++ | | | | |
| 130 | | 4-[7-(6-Amino-pyridin-3-yl)-quinazolin-2-ylamino]-benzenesulfonamide | 393.0, 1.948 | ++++ | ++++ | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 131 | | 5-[2-(4-Sulfamoyl-phenylamino)-quinazolin-7-yl]-pyridine-2-carboxylic acid amide | 421.0, 2.10 | ++++ | +++ | | | |
| 132 | | 4-[7-(1H-Pyrazol-4-yl)-quinazolin-2-ylamino]-benzenesulfonamide | 367.0, 1.92 | ++++ | ++++ | | | |
| 133 | | 4-(7-Pyridin-3-yl-quinazolin-2-ylamino)-benzenesulfonamide | 378.0, 1.73 | ++++ | ++++ | | | ++++ |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 134 | 4-[7-Hydroxy-8-(1-isopropyl-piperidin-4-yl)-quinazolin-2-ylamino]-benzenesulfonamide | 442.0, 1.94 | ++++ | ++++ | ++++ | | ++++ |
| 135 | 4-[7-(4-Methyl-piperazine-1-carbonyl)-quinazolin-2-ylamino]-benzenesulfonamide | 427.1, 1.52 | ++ | +++ | | | |
| 136 | 4-[7-(1-Methyl-1H-pyrazol-4-yl)-quinazolin-2-ylamino]-benzenesulfonamide | 381.0, 2.49 | ++++ | ++++ | ++++ | | ++++ |

TABLE 2-continued

| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 137 | 4-[7-(2-Fluoro-pyridin-3-yl)-quinazolin-2-ylamino]-benzenesulfonamide | 396.0, 3.07 | ++++ | ++++ | ++++ | | ++++ |
| 138 | 4-[7-(5-Methoxy-pyridin-3-yl)-quinazolin-2-ylamino]-benzenesulfonamide | 408.0, 2.12 | ++++ | ++++ | | | +++ |
| 139 | 4-{7-[4-(Morpholine-4-carbonyl)-phenyl]-quinazolin-2-ylamino}-benzenesulfonamide | 490.0, 2.84 | ++++ | +++ | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 140 | 2-(4-Sulfamoyl-phenylamino)-quinazoline-8-carboxylic acid piperidin-3-ylamide | 427.1, 1.83 | ++++ | +++ | | | |
| 141 | 4-[8-((R)-3-Dimethylamino-pyrrolidine-1-carbonyl)-quinazolin-2-ylamino]-benzenesulfonamide | 441.0, 1.59 | ++++ | +++ | | | |
| 142 | 2-(4-Sulfamoyl-phenylamino)-quinazoline-8-carboxylic acid piperidin-4-ylamide | 427.1, 1.78 | ++++ | +++ | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 143 | 4-[8-((S)-3-Dimethylamino-pyrrolidine-1-carbonyl)-quinazolin-2-ylamino]-benzenesulfonamide | 441.1, 1.59 | ++++ | +++ | | | |
| 144 | 2-(4-Sulfamoyl-phenylamino)-quinazoline-8-carboxylic acid (R)-3-quinuclidinylamide | 453.1, 1.80 | +++ | +++ | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 145 | 4-[8-(3-Oxo-piperazine-1-carbonyl)-quinazolin-2-ylamino]-benzenesulfonamide | 427.0, 1.66 | | | | | |
| 146 | 2-(4-Sulfamoyl-phenylamino)-quinazoline-8-carboxylic acid (S)-3-quinuclidinylamide | 453.1, 1.80 | | | | | |
| 147 | 4-[7-(1H-Indazol-6-yl)-quinazolin-2-ylamino]-benzenesulfonamide | 417.0, 2.38 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 148 | | 4-[7-(2-Methoxy-pyrimidin-5-yl)-quinazolin-2-ylamino]-benzenesulfonamide | 409.0, 2.29 | | | | | |
| 149 | | 4-[7-(1H-Indazol-6-ylamino)-quinazolin-2-ylamino]-benzenesulfonamide | 432.0, 2.088 | | | | | |
| 150 | | 4-[7-(Pyrrolidine-1-carbonyl)-quinazolin-2-ylamino]-benzenesulfonamide | 398.1, 2.44 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 151 | 4-{8-(6-Amino-pyridin-3-yl)-quinazolin-2-ylamino]-benzenesulfonamide | 393.0, 1.93 | | | | | |
| 152 | 4-{8-[3-(4-Methyl-piperazine-1-carbonyl)-phenyl]-quinazolin-2-ylamino}-benzenesulfonamide | 503.0, 2.07 | | | | | |
| 153 | 4-{8-(2-Amino-pyrimidin-5-yl)-quinazolin-2-ylamino]-benzenesulfonamide | 394.0, 1.90 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 154 | 4-{8-[4-(4-Methyl-piperazine-1-carbonyl)-phenyl]-quinazolin-2-ylamino}-benzenesulfonamide | 503.1, 2.08 | | | | | |
| 155 | 4-{8-[6-(2-Methoxy-ethylamino)-pyridin-3-yl]-quinazolin-2-ylamino}-benzenesulfonamide | 451.0, 2.03 | | | | | |
| 156 | 4-{8-(6-Morpholin-4-yl-pyridin-3-yl)-quinazolin-2-ylamino]-benzenesulfonamide | 463.1, 1.99 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 157 | | 4-{8-[6-(4-Methyl-piperazin-1-yl)-pyridin-3-yl]-quinazolin-2-ylamino}-benzenesulfonamide | 476.1, 1.86 | | | | | |
| 158 | | 4-{8-[6-[3-Oxo-piperazin-1-yl]-pyridin-3-yl]-quinazolin-2-ylamino}-benzenesulfonamide | 476.1, 1.89 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 159 | | N-(2-{5-[2-(4-Sulfamoyl-phenylamino)-quinazolin-8-yl]-pyridin-2-ylamino}-ethyl)-acetamide | 478.1, 1.93 | | | | | |
| 160 | | 4-{8-[6-(2-Pyrrolidin-1-yl-ethylamino)-pyridin-3-yl]-quinazolin-2-ylamino}-benzenesulfonamide | 490.1, 1.82 | | | | | |
| 161 | | 4-[8-(6-Isopropylamino-pyridin-3-yl)-quinazolin-2-ylamino]-benzenesulfonamide | 435.1, 2.10 | | | | | |

TABLE 2-continued
| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 162 | 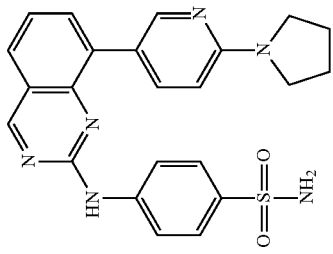 | 4-[8-(6-Pyrrolidin-1-yl-pyridin-3-yl)-quinazolin-2-ylamino]-benzenesulfonamide | 447.1, 2.14 | | | | | |
| 163 | 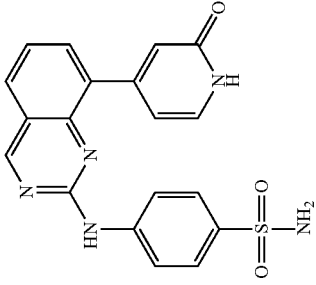 | 4-[8-(2-Oxo-1,2-dihydro-pyridin-4-yl)-quinazolin-2-ylamino]-benzenesulfonamide | 394.0, 2.02 | | | | | |

TABLE 2-continued

| Compound | Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 164 | | 4-{8-[6-(1,1-Dioxo-1lambda*6*-thiomorpholin-4-yl)-pyridin-3-yl]-quinazolin-2-ylamino}-benzenesulfonamide | 511.0, 2.11 | | | | | |
| 165 | | 4-[7-(2,6-Difluoro-pyridin-3-yl)-quinazolin-2-ylamino]-benzenesulfonamide | 414.0, 2.68 | | | | | |
| 166 | | 4-[7-(6-Fluoro-pyridin-3-yl)-quinazolin-2-ylamino]-benzenesulfonamide | 396.0, 2.47 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 167 | | 2-(4-Sulfamoyl-phenylamino)-quinazoline-7-carboxylic acid (5-chloro-2-methyl-phenyl)-amide | 468.0, 2.73 | | | | | |
| 168 | | 2-(4-Sulfamoyl-phenylamino)-quinazoline-7-carboxylic acid (3-carbamoyl-4-methyl-thiophen-2-yl)-amide | 483.0, 2.47 | | | | | |
| 169 | | 4-[7-(1-Oxo-1,2,3,4-tetrahydro-isoquinolin-6-yl)-quinazolin-2-ylamino]-benzenesulfonamide | 446.0, 2.734 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 170 | | 2-(4-Sulfamoyl-phenylamino)-quinazoline-7-carboxylic acid (2-carbamoyl-5-methyl-phenyl)-amide | 477.0, 2.49 | | | | | |
| 171 | | 4-[7-(1-Methyl-piperidin-4-ylamino)-quinazolin-2-ylamino]-benzenesulfonamide | 413.1, 1.59 | | | | | |
| 172 | | 4-[7-(2-Oxo-1,2-dihydro-pyrimidin-5-yl)-quinazolin-2-ylamino]-benzenesulfonamide | 395.0, 1.71 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 173 | 4-[7-(1,3,5-Trimethyl-1H-pyrazol-4-yl)-quinazolin-2-ylamino]-benzenesulfonamide | 409.1, 2.48 | | | | | |
| 174 | 4-[7-(1-Isobutyl-1H-pyrazol-4-yl)-quinazolin-2-ylamino]-benzenesulfonamide | 423.1, 3.30 | | | | | |
| 175 | 4-{7-[2-(2-Pyrrolidin-1-yl-ethylamino)-pyridin-4-yl]-quinazolin-2-ylamino}-benzenesulfonamide | 490.1, 1.79 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 176 | 4-[7-(2-Pyrrolidin-1-yl-pyridin-4-yl)-quinazolin-2-ylamino]-benzenesulfonamide | 447.1, 2.29 | | | | | |
| 177 | 4-[7-(2-Morpholin-4-yl-pyridin-4-yl)-quinazolin-2-ylamino]-benzenesulfonamide | 463.1, 2.101 | | | | | |
| 178 | 4-[7-(3,5-Dimethyl-1H-pyrazol-4-yl)-quinazolin-2-ylamino]-benzenesulfonamide | 395.0, 1.94 | | | | | |

TABLE 2-continued

| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 179 | 4-(7-Isoxazol-4-yl-quinazolin-2-ylamino)-benzenesulfonamide | 368.0, 2.10 | | | | | |
| 180 | 4-[7-(3,5-Dimethyl-isoxazol-4-yl)-quinazolin-2-ylamino]-benzenesulfonamide | 396.0, 2.40 | | | | | |
| 181 | [4-(Morpholine-4-sulfonyl)-phenyl]-[7-(1H-pyrazol-4-yl)-quinazolin-2-yl]-amine | 437.1, 2.34 | | | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 182 | | 4-[7-Hydroxy-8-(1-methyl-piperidin-4-yl)-quinazolin-2-ylamino]-benzenesulfonamide | 414.1, 2.01 | | | | | |
| 183 | | 4-[8-(4-Methyl-piperazin-1-ylmethyl)-quinazolin-2-ylamino]-benzenesulfonamide | 413.1, 1.60 | | | | | |
| 184 | | 4-(8-Morpholin-4-ylmethyl-quinazolin-2-ylamino)-benzenesulfonamide | 400.1, 1.71 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 185 | 4-[8-(4-Fluoro-phenylamino)-quinazolin-2-ylamino]-benzenesulfonamide | 410.1, 2.93 | | | | | |
| 186 | 4-{7-[6-(2-Pyrrolidin-1-yl-ethylamino)-pyridin-3-yl]-quinazolin-2-ylamino}-benzenesulfonamide | 490.1, 1.78 | | | | | |
| 187 | 4-{7-[6-(4-Methyl-piperazin-1-yl)-pyridin-3-yl]-quinazolin-2-ylamino}-benzenesulfonamide | 476.1, 1.86 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 188 | | 4-[7-(6-Pyrrolidin-1-yl-pyridin-3-yl)-quinazolin-2-ylamino]-benzenesulfonamide | 447.1, 2.22 | | | | | |
| 189 | | 4-[7-(6-Morpholin-4-yl-pyridin-3-yl)-quinazolin-2-ylamino]-benzenesulfonamide | 463.1, 2.11 | | | | | |
| 190 | | 4-{7-[2-(4-Methyl-piperazin-1-yl)-pyridin-4-yl]-quinazolin-2-ylamino}-benzenesulfonamide | 476.1, 1.85 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 191 | 4-{7-[1-(3-Methyl-butyl)-1H-pyrazol-4-yl]-quinazolin-2-ylamino}-benzenesulfonamide | 437.1, 3.61 | | | | | |
| 192 | 4-[6-Fluoro-8-(1-oxo-1,2,3,4-tetrahydro-isoquinolin-6-yl)-quinazolin-2-ylamino]-benzenesulfonamide | 464.0, 3.047 | | | | | |
| 193 | 4-[8-(6-Amino-pyridin-3-yl)-6-fluoro-quinazolin-2-ylamino]-benzenesulfonamide | 411.0, 2.173 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 194 | | 4-[6-Fluoro-2-(4-sulfamoyl-phenylamino)-quinazolin-8-yl]-benzamide | 438.0, 2.961 | | | | | |
| 195 | | 4-[8-(1-Oxo-1,2,3,4-tetrahydro-isoquinolin-6-yl)-quinazolin-2-ylamino]-benzenesulfonamide | 446.0, 2.935 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 196 | | 4-{6-Fluoro-8-[6-(4-methyl-piperazin-1-yl)-pyridin-3-yl]-quinazolin-2-ylamino}-benzenesulfonamide | 494.0, 2.107 | | | | | |
| 197 | | 4-{6-Fluoro-8-[6-(3-oxo-piperazin-1-yl)-pyridin-3-yl]-quinazolin-2-ylamino}-benzenesulfonamide | 494.0, 2.131 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 198 | | 4-[6-Fluoro-8-(6-pyrrolidin-1-yl-pyridin-3-yl)-quinazolin-2-ylamino]-benzenesulfonamide | 465.0, 2.434 | | | | | |
| 199 | | N-(2-{5-[6-Fluoro-2-(4-sulfamoyl-phenylamino)-quinazolin-8-yl]-pyridin-2-ylamino}-ethyl)-acetamide | 496.0, 2.434 | | | | | |
| 200 | | 4-[6-Fluoro-8-[6-(2-pyrrolidin-1-yl-ethylamino)-pyridin-3-yl]-quinazolin-2-ylamino]-benzenesulfonamide | 508.1, 1.959 | | | | | |

TABLE 2-continued

| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 201 | 4-[6-Fluoro-8-[6-(2-methoxy-ethylamino)-pyridin-3-yl]-quinazolin-2-ylamino]-benzenesulfonamide | 469.0, 2.319 | | | | | |
| 202 | 4-[6-Fluoro-8-(6-morpholin-4-yl-pyridin-3-yl)-quinazolin-2-ylamino]-benzenesulfonamide | 481.0, 2.328 | | | | | |
| 203 | 4-[8-(Pyridin-3-ylamino)-quinazolin-2-ylamino]-benzenesulfonamide | 393.0, 1.83 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 204 | | 4-[8-(3-Oxo-piperazin-1-ylmethyl)-quinazolin-2-ylamino]-benzenesulfonamide | 413.0, 1.65 | | | | | |
| 205 | | 4-[8-(Isopropylamino-methyl)-quinazolin-2-ylamino]-benzenesulfonamide | 372.0, 1.82 | | | | | |
| 206 | | 4-[7,8-Bis-(1-methyl-1H-pyrazol-4-yl)-quinazolin-2-ylamino]-benzenesulfonamide | 461.0, 2.13 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 207 | 4-(7,8-Di-pyridin-3-yl-quinazolin-2-ylamino)-benzenesulfonamide | 455.0, 1.63 | | | | | |
| 208 | 4-[7,8-Bis-(6-amino-pyridin-3-yl)-quinazolin-2-ylamino]-benzenesulfonamide | 485.0, 1.69 | | | | | |
| 209 | 4-[8-(Benzylamino-methyl)-quinazolin-2-ylamino]-benzenesulfonamide | 420.1, 2.06 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 210 | 4-{8-[(Benzyl-methyl-amino)-methyl]-quinazolin-2-ylamino}-benzenesulfonamide | 434.0, 2.07 | | | | | |
| 211 | 4-(8-Pyrrolidin-1-ylmethyl-quinazolin-2-ylamino)-benzenesulfonamide | 384.1, 1.85 | | | | | |
| 212 | 4-[7-(1-Methyl-1H-pyrazol-4-yl)-8-phenyl-quinazolin-2-ylamino]-benzenesulfonamide | 457.0, 2.52 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 213 | | 4-[8-(6-Amino-pyridin-3-yl)-7-(1-methyl-1H-pyrazol-4-yl)-quinazolin-2-ylamino]-benzenesulfonamide | 473.1, 1.94 | | | | | |
| 214 | | 4-[8-[4-(4-Methyl-piperazine-1-carbonyl)-phenyl]-7-(1-methyl-1H-pyrazol-4-yl)-quinazolin-2-ylamino]-benzenesulfonamide | 583.1, 2.06 | | | | | |
| 215 | | 4-[8-(6-Fluoro-pyridin-3-yl)-7-(1-methyl-1H-pyrazol-4-yl)-quinazolin-2-ylamino]-benzenesulfonamide | 476.0, 2.33 | | | | | |

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 216 | | 4-[8-[6-(2-Methoxy-ethylamino)-pyridin-3-yl]-7-(1-methyl-1H-pyrazol-4-yl)-quinazolin-2-ylamino]-benzenesulfonamide | 531.1, 2.02 | | | | | |
| 217 | | 4-[7-(1-Methyl-1H-pyrazol-4-yl)-8-(6-morpholin-4-yl-pyridin-3-yl)-quinazolin-2-ylamino]-benzenesulfonamide | 543.0, 2.00 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 218 | | 4-[8-[6-(4-Methyl-piperazin-1-yl)-pyridin-3-yl]-7-(1-methyl-1H-pyrazol-4-yl)-quinazolin-2-ylamino]-benzenesulfonamide | 556.1, 1.92 | | | | | |
| 219 | | 4-[7,8-Bis-(6-fluoro-pyridin-3-yl)-quinazolin-2-ylamino]-benzenesulfonamide | 491.0, 2.60 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 220 | | 4-{8-[6-(1,1-Dioxo-1lambda*6**-thiomorpholin-4-yl)-pyridin-3-yl]-6-fluoro-quinazolin-2-ylamino}-benzenesulfonamide | 528.9, 2.730 | | | | | |
| 221 | | 4-[6-Fluoro-8-(6-isopropylamino-pyridin-3-yl)-quinazolin-2-ylamino]-benzenesulfonamide | 453.0, 2.468 | | | | | |

TABLE 2-continued

| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 222 | 4-{6-Fluoro-8-[4-(4-methyl-piperazine-1-carbonyl)-phenyl]-quinazolin-2-ylamino}-benzenesulfonamide | 521.0, 2.43 | | | | | |
| 223 | 4-(8-Diethylaminomethyl-quinazolin-2-ylamino)-benzenesulfonamide | 386.0, 1.82 | | | | | |
| 224 | 4-(8-{[(Pyridin-3-ylmethyl)-amino]-methyl}-quinazolin-2-ylamino)-benzenesulfonamide | 421.0, 1.61 | | | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 225 | | 4-(8-{[2-(3H-Imidazol-4-yl)-ethylamino]-methyl}-quinazolin-2-ylamino)-benzenesulfonamide | 424.0, 1.60 | | | | | |
| 226 | | 1-[2-(4-Sulfamoyl-phenylamino)-quinazolin-8-ylmethyl]-piperidine-4-carboxylic acid amide | 441.0, 1.68 | | | | | |
| 227 | | 4-{8-[((Tetrahydro-pyran-4-ylamino)-methyl]-quinazolin-2-ylamino}-benzenesulfonamide | 414.1, 1.75 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 228 | | 4-(8-Cyclohexylaminomethyl-quinazolin-2-ylamino)-benzenesulfonamide | 412.1, 2.01 | | | | | |
| 229 | | 4-(8-{[(Tetrahydro-furan-2-ylmethyl)-amino]-methyl}-quinazolin-2-ylamino)-benzenesulfonamide | 414.2, 1.92 | | | | | |
| 230 | | 4-[8-(3,4-Dihydro-1H-isoquinolin-2-ylmethyl)-quinazolin-2-ylamino]-benzenesulfonamide | 446.2, 2.13 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 231 | 4-[8-(4-Acetyl-piperazin-1-ylmethyl)-quinazolin-2-ylamino]-benzenesulfonamide | 441.2, 1.60 | | | | | |
| 232 | 4-[8-(4-Isopropyl-piperazin-1-ylmethyl)-quinazolin-2-ylamino]-benzenesulfonamide | 441.2, 1.53 | | | | | |
| 233 | 4-[6-Chloro-8-(1-methyl-1H-pyrazol-4-yl)-quinazolin-2-ylamino]-benzenesulfonamide | 414.9, 3.386 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 234 | 4-{6-[6-(2-pyrrolidin-1-yl-ethylamino)-pyridin-3-yl]-quinazolin-2-ylamino}-benzenesulfonamide | 524.1, 2.174 | | | | | |
| 235 | 4-{6-[6-(3-oxo-piperazin-1-yl)-pyridin-3-yl]-quinazolin-2-ylamino}-benzenesulfonamide | 510.0, 2.343 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 236 | | 4-[8-(6-Amino-5-trifluoromethyl-pyridin-3-yl)-quinazolin-2-ylamino]-benzenesulfonamide | 461.1, 2.24 | | | | | |
| 237 | | 4-[8-(6-Amino-4-trifluoromethyl-pyridin-3-yl)-quinazolin-2-ylamino]-benzenesulfonamide | 461.1, 2.15 | | | | | |
| 238 | | 4-[8-(1-Methyl-1H-pyrazol-4-yl)-quinazolin-2-ylamino]-benzenesulfonamide | 381.0, 2.28 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 239 | | 4-[8-(1-Isobutyl-1H-pyrazol-4-yl)-quinazolin-2-ylamino]-benzenesulfonamide | 423.1, 2.71 | | | | | |
| 240 | | 4-{8-[(2-Pyrrolidin-1-yl-ethylamino)-methyl]-quinazolin-2-ylamino}-benzenesulfonamide | 427.1, 1.65 | | | | | |
| 241 | Chiral | 4-{8-((S)-3-Dimethylamino-pyrrolidin-1-ylmethyl)-quinazolin-2-ylamino]-benzenesulfonamide | 427.1, 1.64 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 242 | | 4-{8-[(1-Methyl-piperidin-4-ylamino)-methyl]-quinazolin-2-ylamino}-benzenesulfonamide | 427.1, 1.60 | | | | | |
| 243 | Chiral | 4-{8-((R)-3-Dimethylamino-pyrrolidin-1-ylmethyl)-quinazolin-2-ylamino]-benzenesulfonamide | 427.1, 1.64 | | | | | |
| 244 | | 4-[7-(2-Fluoro-6-methyl-pyridin-3-yl)-quinazolin-2-ylamino]-benzenesulfonamide | 410.0, 2.56 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 245 | | 2-(4-Fluoro-phenylamino)-8-(1-isopropyl-piperidin-4-yl)-quinazolin-7-ol | 381.1, 2.42 | | | | | |
| 246 | | 4-[8-(5-Pyrrolidin-1-ylmethyl-pyridin-3-yl)-quinazolin-2-ylamino]-benzenesulfonamide | 461.1, 1.79 | | | | | |
| 247 | | 4-[8-(5-Morpholin-4-ylmethyl-pyridin-3-yl)-quinazolin-2-ylamino]-benzenesulfonamide | 477.1, 1.79 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 248 | 4-{8-[5-(4-Methyl-piperazin-1-ylmethyl)-pyridin-3-yl]-quinazolin-2-ylamino}-benzenesulfonamide | 490.1, 1.70 | | | | | |
| 249 | 4-{8-[5-(3-Oxo-piperazin-1-ylmethyl)-pyridin-3-yl]-quinazolin-2-ylamino}-benzenesulfonamide | 490.1, 1.76 | | | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 250 | | 4-{7-(1-Methyl-1H-pyrazol-4-yl)-8-[6-(2-pyrrolidin-1-yl-ethylamino)-pyridin-3-yl]-quinazolin-2-ylamino}-benzenesulfonamide | 570.2, 1.88 | | | | | |
| 251 | | 4-{8-[5-(Isopropylamino-methyl)-pyridin-3-yl]-quinazolin-2-ylamino}-benzenesulfonamide | 449.1, 1.78 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 252 | | 1-{5-[2-(4-Sulfamoyl-phenylamino)-quinazolin-8-yl]-pyridin-3-ylmethyl}-piperidine-4-carboxylic acid amide | 518.1, 1.74 | | | | | |
| 253 | | 4-(8-{5-[(Tetrahydro-pyran-4-ylamino)-methyl]-pyridin-3-yl}-quinazolin-2-ylamino)-benzenesulfonamide | 491.1, 1.76 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 254 | 4-{8-[5-(4-Acetyl-piperazin-1-ylmethyl)-pyridin-3-yl]-quinazolin-2-ylamino}-benzenesulfonamide | 518.1, 1.77 | | | | | |
| 255 | 4-{8-(5-{[Methyl-(tetrahydro-pyran-4-yl)-amino]-methyl}-pyridin-3-yl)-quinazolin-2-ylamino]-benzenesulfonamide | 505.1, 1.82 | | | | | |

TABLE 2-continued

| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 256 | Chiral | 4-{8-[6-((R)-3-Dimethylamino-pyrrolidin-1-yl)-pyridin-3-yl]-quinazolin-2-ylamino}-benzenesulfonamide | 490.1, 1.77 | | | | | |
| 257 | Chiral | 4-{8-[6-((S)-3-Dimethylamino-pyrrolidin-1-yl)-pyridin-3-yl]-quinazolin-2-ylamino}-benzenesulfonamide | 490.1, 1.77 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 258 | 4-{8-[6-(2-Morpholin-4-yl-ethylamino)-pyridin-3-yl]-quinazolin-2-ylamino}-benzenesulfonamide | 506.1, 1.82 | | | | | |
| 259 | 4-{8-[6-(2-Diethylamino-ethylamino)-pyridin-3-yl]-quinazolin-2-ylamino}-benzenesulfonamide | 492.1, 1.87 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 260 | | 4-{8-[6-(1-Methyl-piperidin-4-ylamino)-pyridin-3-yl]-quinazolin-2-ylamino}-benzenesulfonamide | 490.1, 1.82 | | | | | |
| 261 | | 4-{8-[6-(4-Isopropyl-piperazin-1-yl)-pyridin-3-yl]-quinazolin-2-ylamino}-benzenesulfonamide | 504.1, 1.92 | | | | | |

TABLE 2-continued

| Compound | Structure | Name | LC/MS (M + 1 (m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 262 | | 2-(4-Chloro-phenylamino)-8-(1-isopropyl-piperidin-4-yl)-quinazolin-7-ol | 397.1, 2.53 | | | | | |
| 263 | | 5-[2-(4-Sulfamoyl-phenylamino)-quinazolin-8-yl]-nicotinic acid | 422.1, 1.94 | | | | | |

TABLE 2-continued
| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 264 |  | 4-{8-[6-(2-Pyrrolidin-1-yl-ethylamino)-pyridin-3-yl)-6-trifluoromethyl-quinazolin-2-ylamino}-benzenesulfonamide | 558.0, 2.11 | | | | | |
| 265 | 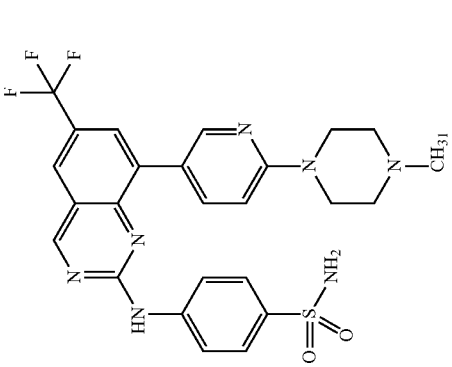 | 4-{8-[6-(4-Methyl-piperazin-1-yl)-pyridin-3-yl]-6-trifluoromethyl-quinazolin-2-ylamino}-benzenesulfonamide | 544.1, 2.20 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 266 | | 4-{8-[6-(3-Oxo-piperazin-1-yl)-pyridin-3-yl]-6-trifluoromethyl-quinazolin-2-ylamino}-benzenesulfonamide | 544.1, 2.14 | | | | | |
| 267 | | 4-{8-[6-(3-Isopropylamino-propylamino)-pyridin-3-yl]-quinazolin-2-ylamino}-benzenesulfonamide | 492.1, 1.87 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 268 | 4-{8-[6-(3-Pyrrolidin-1-yl-propylamino)-pyridin-3-yl]-quinazolin-2-ylamino}-benzenesulfonamide | 504.1, 1.87 | | | | | |
| 269 | 4-(8-{6-[((S)-1-Ethyl-pyrrolidin-2-ylmethyl)-amino]-pyridin-3-yl}-quinazolin-2-ylamino)-benzenesulfonamide | 504.1, 1.88 | | | | | |
| 270 | 4-(8-{6-[((R)-1-Ethyl-pyrrolidin-2-ylmethyl)-amino]-pyridin-3-yl}-quinazolin-2-ylamino)-benzenesulfonamide | 504.1, 2.00 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 271 | | 4-(8-{6-[(1-Methyl-piperidin-4-ylmethyl)-amino]-pyridin-3-yl}-quinazolin-2-ylamino)-benzenesulfonamide | 504.1, 1.85 | | | | | |
| 272 | Chiral | 4-{8-[5-((R)-3-Dimethylamino-pyrrolidine-1-carbonyl)-pyridin-3-yl]-quinazolin-2-ylamino}-benzenesulfonamide | 518.2, 1.78 | | | | | |
| 273 | | 4-{8-[5-(4-Methyl-piperazine-1-carbonyl)-pyridin-3-yl]-quinazolin-2-ylamino}-benzenesulfonamide | 504.1, 1.79 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 274 | 4-{8-[5-((S)-3-Dimethylamino-pyrrolidine-1-carbonyl)-pyridin-3-yl]-quinazolin-2-ylamino}-benzenesulfonamide | 518.2, 1.77 | | | | | |
| 275 | N-(2-Pyrrolidin-1-yl-ethyl)-5-[2-(4-sulfamoyl-phenylamino)-quinazolin-8-yl]-nicotinamide | 518.2, 1.85 | | | | | |
| 276 | 4-{8-[5-(4-Dimethylamino-piperidine-1-carbonyl)-pyridin-3-yl]-quinazolin-2-ylamino}-benzenesulfonamide | 532.1, 1.79 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 277 | N-(1-Methyl-piperidin-4-yl)-5-[2-(4-sulfamoyl-phenylamino)-quinazolin-8-yl]-nicotinamide | 518.1, 1.79 | | | | | |
| 278 | N-(1-Methyl-piperidin-4-ylmethyl)-5-[2-(4-sulfamoyl-phenylamino)-quinazolin-8-yl]-nicotinamide | 532.1, 1.80 | | | | | |
| 279 | 4-{8-[5-(3-Oxo-piperazine-1-carbonyl)-pyridin-3-yl]-quinazolin-2-ylamino}-benzenesulfonamide | 504.0, 1.83 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 280 | | 4-{8-[5-(Morpholine-4-carbonyl)-pyridin-3-yl]-quinazolin-2-ylamino}-benzenesulfonamide | 491.1, 2.00 | | | | | |
| 281 | | 4-{8-[4-(4-Methyl-piperazin-1-yl)-phenyl]-quinazolin-2-ylamino}-benzenesulfonamide | 475.1, 2.22 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 282 | | 4-[8-(4-Morpholin-4-ylmethyl-phenyl)-quinazolin-2-ylamino]-benzenesulfonamide | 476.1, 2.11 | | | | | |
| 283 | | 4-[8-(1,2,3,6-Tetrahydro-pyridin-4-yl)-quinazolin-2-ylamino]-benzenesulfonamide | 382.1, 1.88 | | | | | |
| 284 | | [7-(1-Isobutyl-1H-pyrazol-4-yl)-quinazolin-2-yl]-(4-morpholin-4-yl-phenyl)-amine | 429.0, 2.898 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 285 | N-Isopropyl-4-{8-[6-(2-pyrrolidin-1-yl-ethylamino)-pyridin-3-yl]-quinazolin-2-ylamino}-benzamide | 496.3, 1.71 | | | | | |
| 286 | (4-Fluoro-phenyl)-{8-[6-(2-pyrrolidin-1-yl-ethylamino)-pyridin-3-yl]-quinazolin-2-yl}-amine | 429.1, 2.05 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 287 | (4-Chloro-phenyl)-{8-[6-(2-pyrrolidin-1-yl-ethylamino)-pyridin-3-yl]-quinazolin-2-yl}-amine | 445.1, 2.16 | | | | | |
| 288 | (4-Morpholin-4-yl-phenyl)-{8-[6-(2-pyrrolidin-1-yl-ethylamino)-pyridin-3-yl]-quinazolin-2-yl}-amine | 496.2, 1.86 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 289 | {8-[6-(2-Pyrrolidin-1-yl-ethylamino)-pyridin-3-yl]-quinazolin-2-yl}-(4-trifluoromethyl-phenyl)-amine | 479.1, 2.25 | | | | | |
| 290 | N-Methyl-C-(4-{8-[6-(2-pyrrolidin-1-yl-ethylamino)-pyridin-3-yl]-quinazolin-2-ylamino}-phenyl)-methanesulfonamide | 518.1, 1.91 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 291 | (4-Fluoro-phenyl)-{8-[6-(4-methyl-piperazin-1-yl)-pyridin-3-yl]-quinazolin-2-yl}-amine | 415.1, 2.08 | | | | | |
| 292 | 5-{8-[6-(2-Pyrrolidin-1-yl-ethylamino)-pyridin-3-yl]-quinazolin-2-ylamino}-1,3-dihydro-benzoimidazol-2-one | 467.4, 1.50 | | | | | |

TABLE 2-continued

| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 293 | N-(2-Methyl-5-{8-[6-(2-pyrrolidin-1-yl-ethylamino)-pyridin-3-yl]-quinazolin-2-ylamino}-phenyl)-methanesulfonamide | 518.2, 1.69 | | | | | |
| 294 | 7-(1-Isobutyl-1H-pyrazol-4-yl)-quinazolin-2-yl]-(3-morpholin-4-yl-phenyl)-amine | 429.1, 3.148 | | | | | |
| 295 | N-Isopropyl-4-{8-[6-(2-pyrrolidin-1-yl-ethylamino)-pyridin-3-yl]-quinazolin-2-ylamino}-benzenesulfonamide | 532.1, 2.05 | | | | | |

TABLE 2-continued
| Compound Structure | | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 296 | 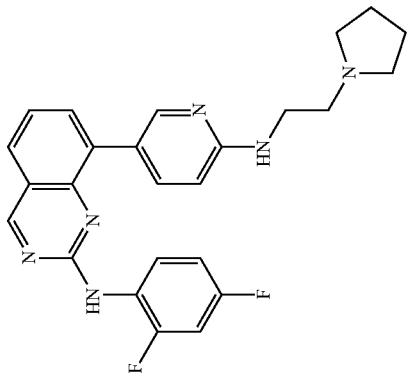 | (2,4-Difluoro-phenyl)-{8-[6-(2-pyrrolidin-1-yl-ethylamino)-pyridin-3-yl]-quinazolin-2-yl}-amine | 447.1, 2.02 | | | | | |
| 297 | 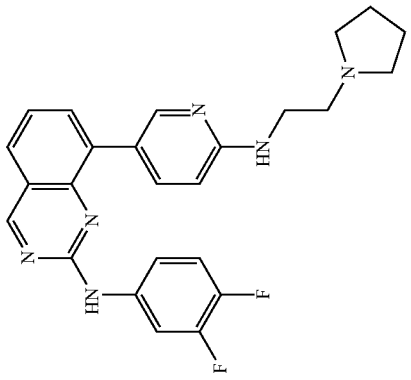 | (3,4-Difluoro-phenyl)-{8-[6-(2-pyrrolidin-1-yl-ethylamino)-pyridin-3-yl]-quinazolin-2-yl}-amine | 447.1, 2.03 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 298 | | 2-(4-{8-[6-(2-Pyrrolidin-1-yl-ethylamino)-pyridin-3-yl]-quinazolin-2-ylamino}-phenyl)-ethanol | 455.2, 1.94 | | | | | |
| 299 | | (3-Fluoro-phenyl)-{8-[6-(2-pyrrolidin-1-yl-ethylamino)-pyridin-3-yl]-quinazolin-2-yl}-amine | 429.1, 2.07 | | | | | |

TABLE 2-continued
| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 300 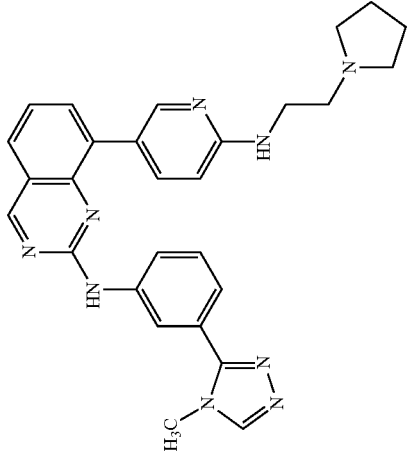 | [3-(4-Methyl-4H-[1,2,4]triazol-3-yl)-phenyl]-{8-[6-(2-pyrrolidin-1-yl-ethylamino)-pyridin-3-yl]-quinazolin-2-yl}-amine | 492.1, 1.87 | | | | | |
| 301 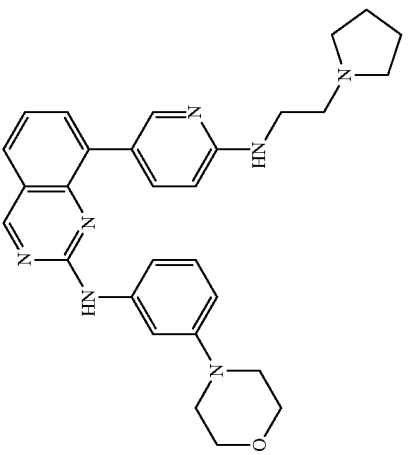 | (3-Morpholin-4-yl-phenyl)-{8-[6-(2-pyrrolidin-1-yl-ethylamino)-pyridin-3-yl]-quinazolin-2-yl}-amine | 496.2, 1.98 | | | | | |

TABLE 2-continued
| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 302 | 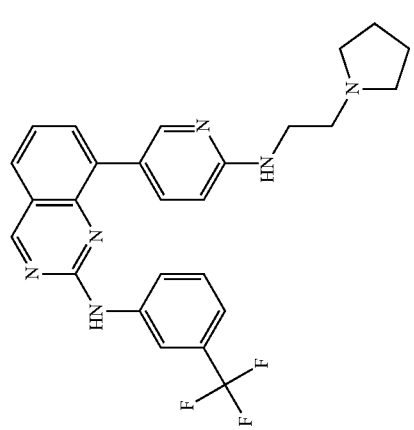 | {8-[6-(2-Pyrrolidin-1-yl-ethylamino)-pyridin-3-yl]-quinazolin-2-yl}-(3-trifluoromethyl-phenyl)-amine | 479.1, 2.29 | | | | | |
| 303 | 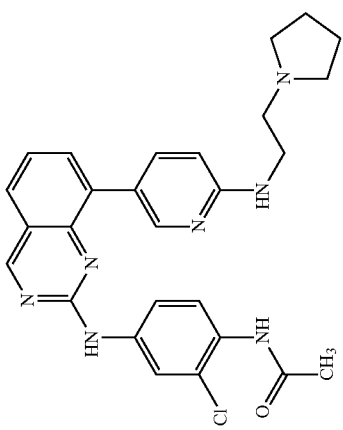 | N-(2-Chloro-4-{8-[6-(2-pyrrolidin-1-yl-ethylamino)-pyridin-3-yl]-quinazolin-2-ylamino}-phenyl)-acetamide | 502.1, 1.63 | | | | | |

TABLE 2-continued
| Compound Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 304 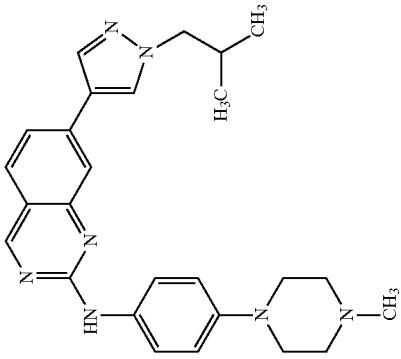 | [7-(1-Isobutyl-1H-pyrazol-4-yl)-quinazolin-2-yl]-[4-(4-methyl-piperazin-1-yl)-phenyl]-amine | 442.1, 3.526 | | | | | |
| 305 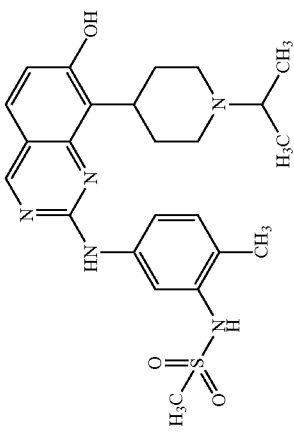 | N-{5-[7-Hydroxy-8-(1-isopropyl-piperidin-4-yl)-quinazolin-2-ylamino]-2-methyl-phenyl}-methanesulfonamide | 470.1, 2.17 | | | | | |

TABLE 2-continued

| Compound Structure | Name | LC/MS (M + 1(m/z), Rt(min) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|
| 306 | N-(2-Methyl-4-{8-[6-(2-pyrrolidin-1-yl-ethylamino)-pyridin-3-yl]-quinazolin-2-ylamino}-phenyl)-acetamide | 482.2, 1.90 | | | | | |
| 307 | (4-Methanesulfonyl-phenyl)-{8-[6-(2-pyrrolidin-1-yl-ethylamino)-pyridin-3-yl]-quinazolin-2-yl}-amine | 489.1, 1.90 | | | | | |

TABLE 2-continued

| Compound | Structure | Name | LC/MS (M + 1(m/z), Rt(min)) | PDK1 IC$_{50}$ | CP EC$_{50}$ A2780 | CP EC$_{50}$ PC3 | CP EC$_{50}$ PC3MM | PAKT308 PC3 IC$_{50}$ |
|---|---|---|---|---|---|---|---|---|
| 308 | | {8-[6-(4-Methyl-piperazin-1-yl)-pyridin-3-yl]-quinazolin-2-yl}-[4-(morpholine-4-sulfonyl)-phenyl]-amine | 546.1, 2.09 | | | | | |
| 309 | | 2-(4-Fluoro-3-methyl-phenylamino)-8-(1-isopropyl-piperidin-4-yl)-quinazolin-7-ol | 395.2, 2.55 | | | | | |

TABLE 3

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 310 | 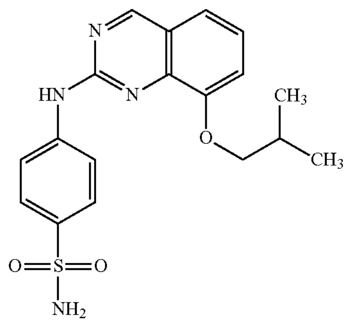 | 4-(8-isobutoxyquinazolin-2-ylamino)benzenesulfonamide | 373.1, 2.75 | Similar to example 1 | ++++ | ++++ | | |
| 311 | 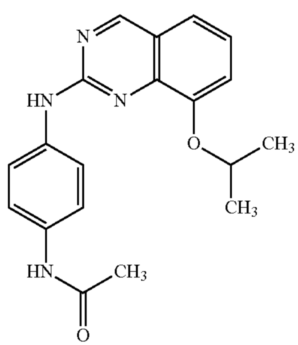 | N-(4-(8-isopropoxyquinazolin-2-ylamino)phenyl)acetamide | 337.1, 2.18 | Similar to example 1 | ++++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 312 | 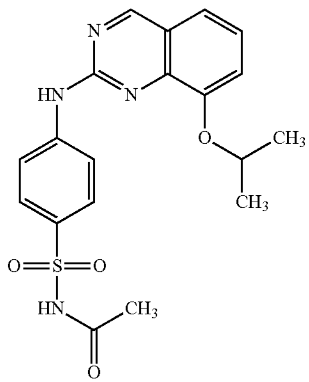 | N-(4-(8-isopropoxyquinazolin-2-ylamino)phenylsulfonyl)acetamide | 401.0, 2.60 | Similar to example 1 | ++++ | +++ | | |
| 313 | 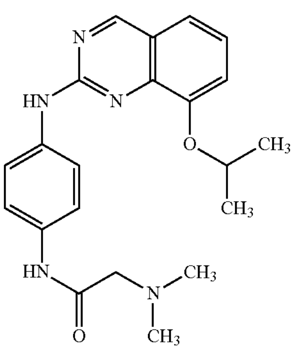 | 2-(dimethylamino)-N-(4-(8-isopropoxyquinazolin-2-ylamino)phenyl)acetamide | 380.1, 1.95 | Similar to example 1 | +++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 314 | 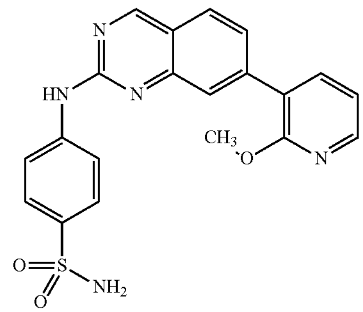 | 4-(2-methoxypyridin-3-yl)quinazolin-2-yl)amino)benzenesulfonamide | 408.1, 3.10 | Similar to example 39 | + | +++ | | |
| 315 | 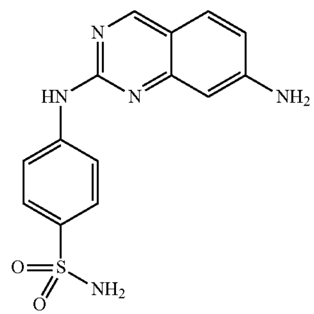 | 4-(7-aminoquinazolin-2-ylamino)benzenesulfonamide | 316.1, 1.61 | Similar to example 43 | ++++ | ++++ | | |
| 316 | 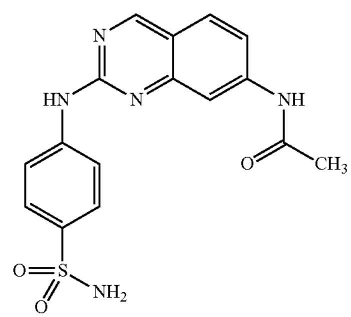 | N-(2-(4-sulfamoylphenylamino)quinazolin-7-yl)acetamide | 358.0, 1.81 | Similar to example 44 | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 317 | 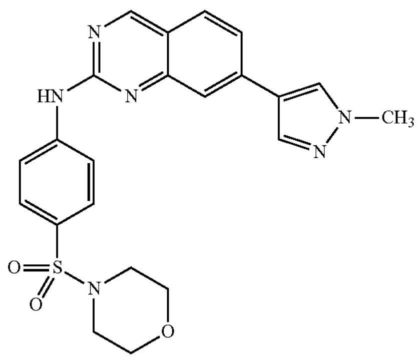 | 7-(1-methyl-1H-pyrazol-4-yl)-N-(4-(morpholinosulfonyl)phenyl)quinazolin-2-amine | 451.1, 2.53 | Similar to example 39 | + | ++++ | | |
| 318 | 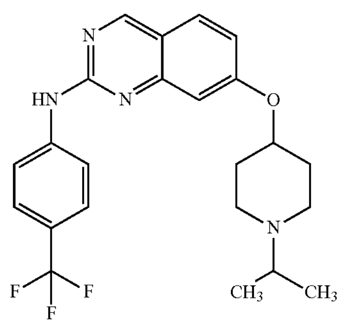 | 7-(1-isopropylpiperidin-4-yloxy)-N-(4-(trifluoromethyl)phenyl)quinazolin-2-amine | 431.1, 2.49 | Similar to example 41 | ++++ | | ++++ | |
| 319 | 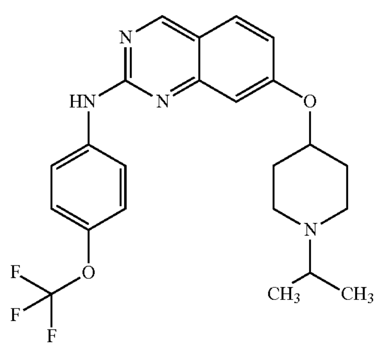 | 7-(1-isopropylpiperidin-4-yloxy)-N-(4-(trifluoromethoxy)phenyl)quinazolin-2-amine | 447.2, 2.51 | Similar to example 41 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 320 | 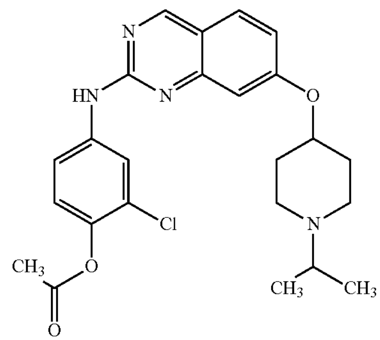 | N-(2-chloro-4-(7-(1-isopropylpiperidin-4-yloxy)quinazolin-2-ylamino)phenyl)acetamide | 454.1, 1.99 | Similar to example 41 | ++++ | | ++++ | |
| 321 | 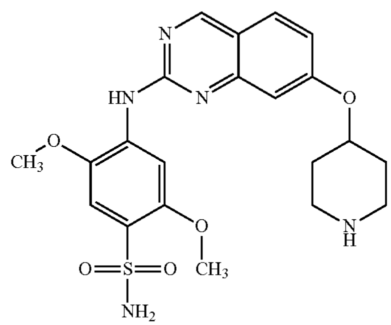 | 2,5-dimethoxy-4-(7-(piperidin-4-yloxy)quinazolin-2-ylamino)benzenesulfonamide | 460.1, 1.92 | Similar to example 42 | ++++ | | +++ | |
| 322 | 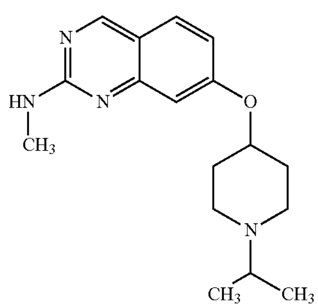 | 7-(1-isopropylpiperidin-4-yloxy)-N-methylquinazolin-2-amine | 301.1, 1.81 | Similar to example 41 | + | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 323 | 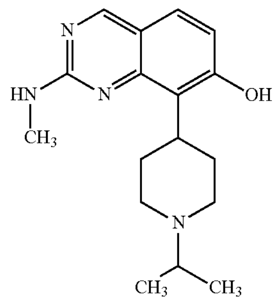 | 8-(1-isopropylpiperidin-4-yl)-2-(methylamino)quinazolin-7-ol | 301.1, 1.40 | Similar to example 41 | + | | +++ | |
| 324 | 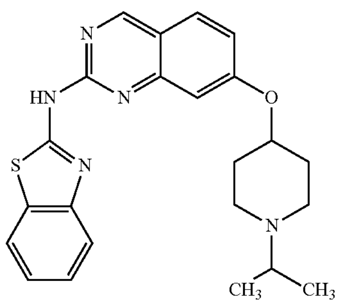 | N-(7-(1-isopropylpiperidin-4-yloxy)quinazolin-2-yl)benzo[d]thiazol-2-amine | 420.1, 2.16 | Similar to example 41 | + | | ++++ | |
| 325 | 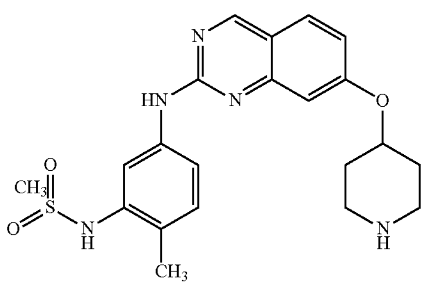 | N-(2-methyl-5-(7-piperidin-4-yloxy)quinazolin-2-ylamino)phenyl)methanesulfonamide | 428.1, 1.81 | Similar to example 37 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 326 | 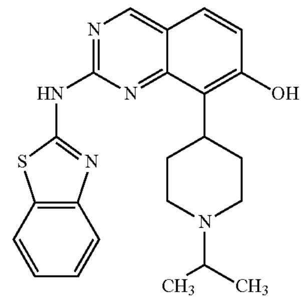 | 2-(benzo[d]thiazol-2-ylamino)-8-(1-isopropylpiperidin-4-yl)quinazolin-7-ol | 420.1, 2.44 | Similar to example 41 | ++++ | | +++ | |
| 327 | 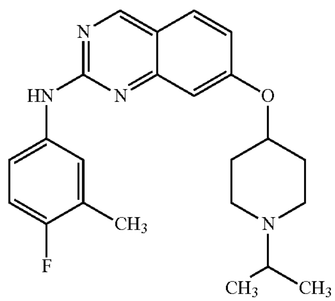 | N-(4-fluoro-3-methylphenyl)-7-(1-isopropylpiperidin-4-yloxy)quinazolin-2-amine | 395.2, 2.20 | Similar to example 41 | ++++ | | +++ | |
| 328 | 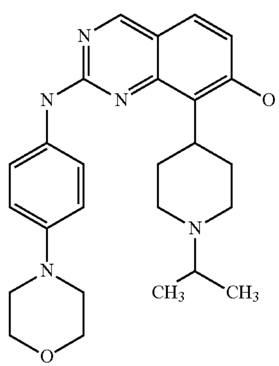 | 8-(1-isopropylpiperidin-4-yl)-2-(4-morpholinophenylamino)quinazolin-7-ol | 448.2, 2.01 | Similar to example 41 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 329 | 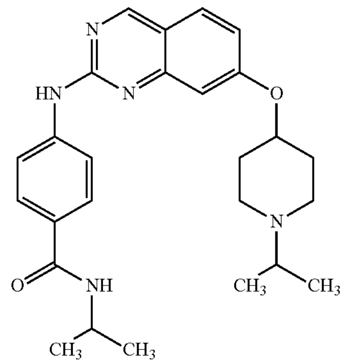 | N-isopropyl-4-(7-(1-isopropylpiperidin-4-yloxy)quinazolin-2-ylamino)benzamide | 448.1, 2.01 | Similar to example 41 | ++++ | | ++++ | |
| 330 | 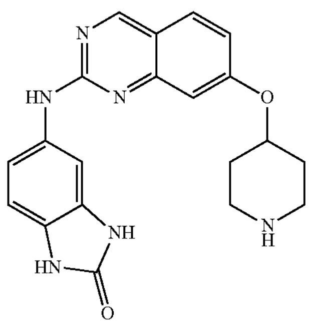 | 5-(7-(piperidin-4-yloxy)quinazolin-2-ylamino)-1H-benzo[d]imidazol-2(3H)-one | 377.1, 1.51 | Similar to example 42 | ++++ | | +++ | |
| 331 | 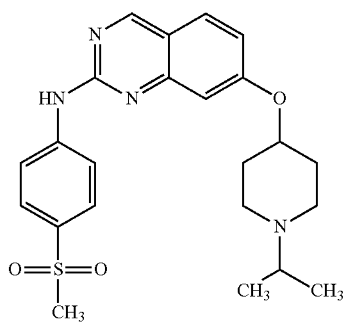 | 7-(1-isopropylpiperidin-4-yloxy)-N-(4-(methylsulfonyl)phenyl)quinazolin-2-amine | 441.1, 2.05 | Similar to example 41 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 332 | 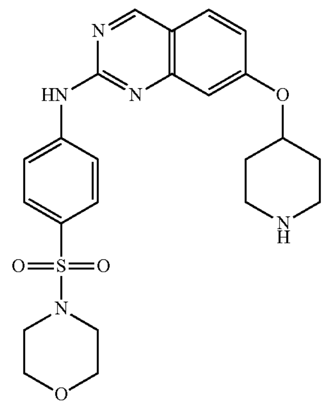 | N-(4-(morpholinosulfonyl)phenyl)-7-(piperidin-4-yloxy)quinazolin-2-amine | 470.2, 2.09 | Similar to example 37 | ++++ | | ++++ | |
| 333 | 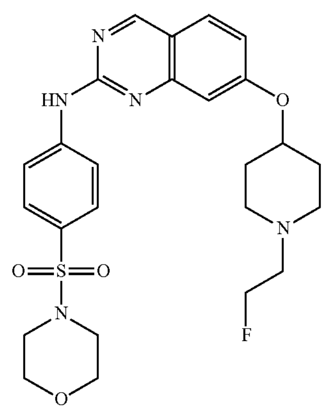 | 7-(1-(2-fluoroethyl)piperidin-4-yloxy)-N-(4-(morpholinosulfonyl)phenyl)quinazolin-2-amine | 516.1, 2.16 | Similar to example 38 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 334 | 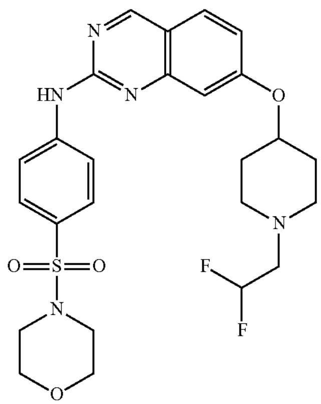 | 7-(1-(2,2-difluoroethyl)piperidin-4-yloxy)-N-(4-(morpholinosulfonyl)phenyl)quinazolin-2-amine | 534.1, 2.14 | Similar to example 38 | ++++ | | +++ | |
| 335 | 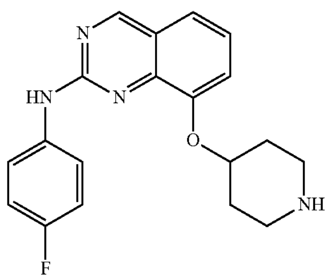 | N-(4-fluorophenyl)-8-(piperidin-4-yloxy)quinazolin-2-amine | 339.1, 2.01 | Similar to example 1 | ++++ | | ++++ | |
| 336 | 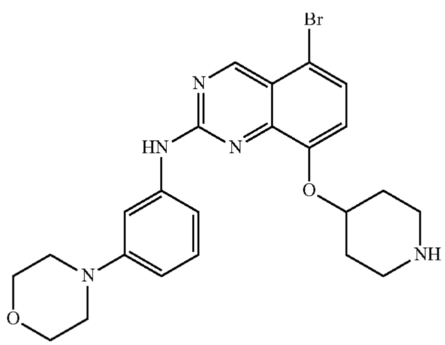 | 5-bromo-N-(3-morpholinophenyl)-8-(piperidin-4-yloxy)quinazolin-2-amine | 484.1/486.1, 2.18 | Similar to example 45 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 337 | 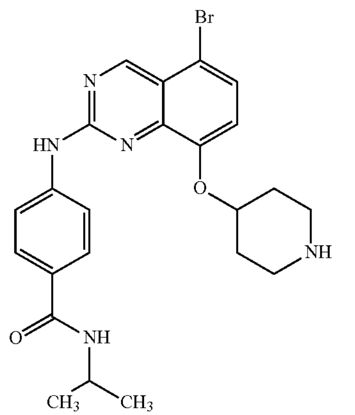 | 4-(5-bromo-8-(piperidin-4-yloxy)quinazolin-2-ylamino)-N-isopropylbenzamide | 484.1/486.1, 2.29 | Similar to example 45 | ++++ | | ++++ | |
| 338 | 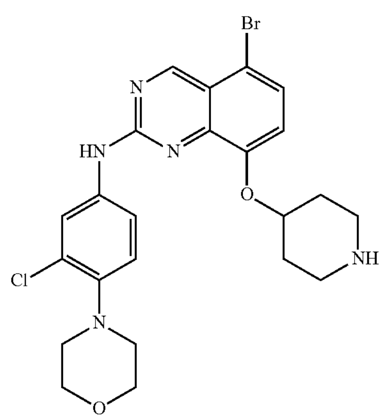 | 5-bromo-N-(3-chloro-4-morpholinophenyl)-8-(piperidin-4-yloxy)quinazolin-2-amine | 518.0/520.0, 2.49 | Similar to example 45 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 339 | 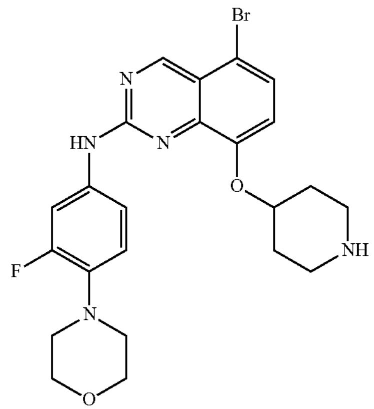 | 5-bromo-N-(3-fluoro-4-morpholinophenyl)-8-(piperidin-4-yloxy)quinazolin-2-amine | 502.1/504.1, 2.34 | Similar to example 45 | ++++ | | ++++ | |
| 340 | 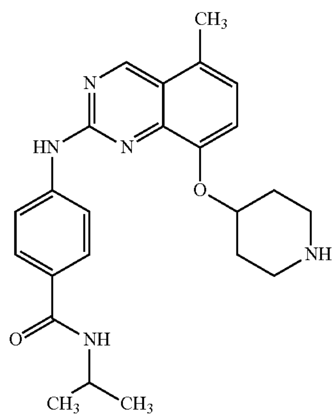 | N-isopropyl-4-(5-methyl-8-(piperidin-4-yloxy)quinazolin-2-ylamino)benzamide | 420.2, 2.14 | Similar to example 46 | ++++ | | +++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 341 | 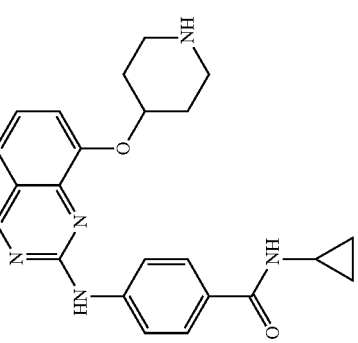 | 4-(5-bromo-8-(piperidin-4-yloxy)quinazolin-2-ylamino)-N-cyclopropylbenzamide | 482.1/484.1, 2.27 | Similar to example 45 | ++++ | | +++ | |
| 342 | 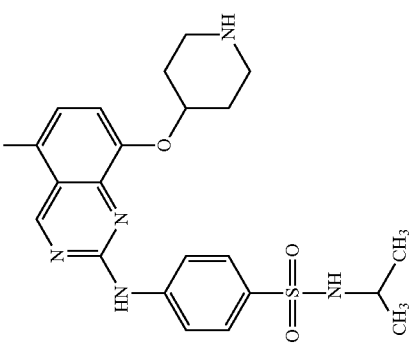 | 4-(5-bromo-8-(piperidin-4-yloxy)quinazolin-2-ylamino)-N-isopropylbenzenesulfonamide | 520.0/522.0, 2.42 | Similar to example 45 | ++++ | | ++++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 343 | 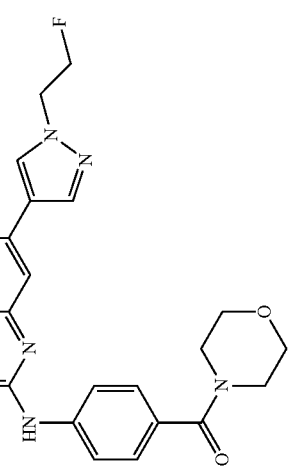 | (4-(7-(1-(2-fluoroethyl)-1H-pyrazol-4-yl)quinazolin-2-ylamino)phenyl)(morpholino)methanone | 447.2, 2.16 | Similar to example 39 | ++++ | | ++++ | |
| 344 | 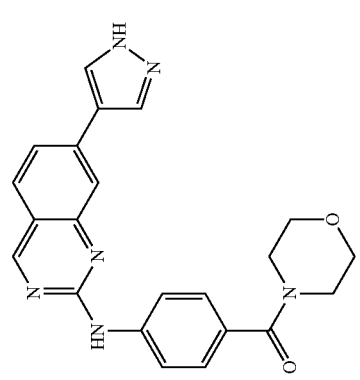 | (4-(7-(1H-pyrazol-4-yl)quinazolin-2-ylamino)phenyl)(morpholino)methanone | 401.1, 1.90 | Similar to example 39 | ++++ | | ++++ | |

TABLE 3-continued
| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 345 | 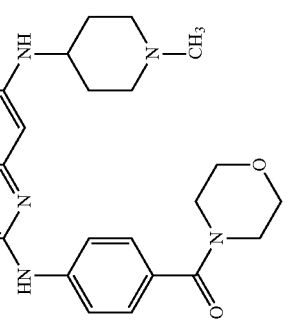 | (4-(7-(1-methylpiperidin-4-ylamino)quinazolin-2-ylamino)phenyl)(morpholino)methanone | 447.1, 1.68 | Similar to example 40 | ++++ | | ++++ | |
| 346 | 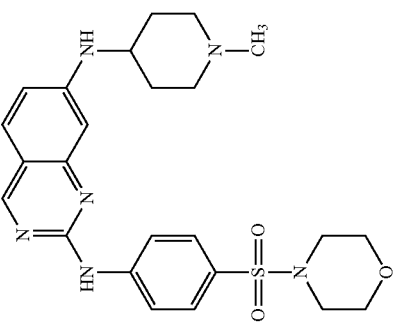 | N7-(1-methylpiperidin-4-yl)-N2-(4-(morpholinosulfonyl)phenyl)quinazoline-2,7-diamine | 483.2, 1.88 | Similar to example 40 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 347 | 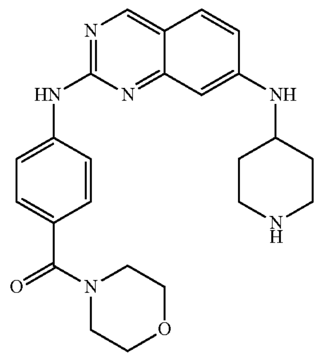 | morpholino(4-(7-(piperidin-4-ylamino)quinazolin-2-ylamino)phenyl)methanone | 433.1, 1.62 | Similar to example 40 | ++++ | | ++++ | |
| 348 | 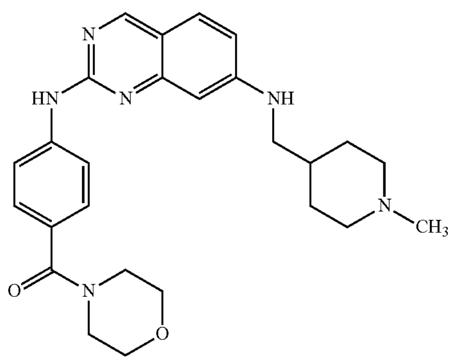 | (4-(7-((1-methylpiperadin-4-yl)methylamino)quinazolin-2-ylamino)phenyl)(morpholino)methanone | 461.2, 1.66 | Similar to example 40 | ++++ | | +++ | |

TABLE 3-continued

| Cmpd | Name | Structure | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 349 | (4-(7-(1-(2-methoxyethyl)-1H-pyrazol-4-yl)quinazolin-2-ylamino)phenyl)(morpholino)methanone | 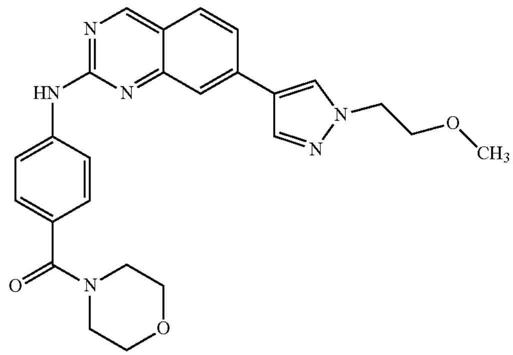 | 459.1, 2.14 | Similar to example 39 | ++++ | | ++++ | |
| 350 | N-isopropyl-4-(7-(1-methylpiperidin-4-ylamino)quinazolin-2-ylamino)benzenesulfonamide | 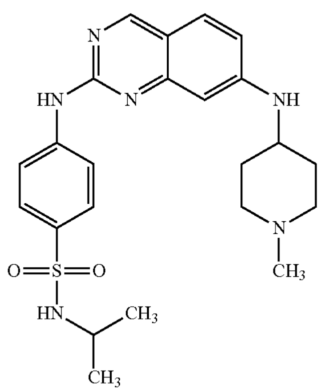 | 455.1, 1.90 | Similar to example 40 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 351 | 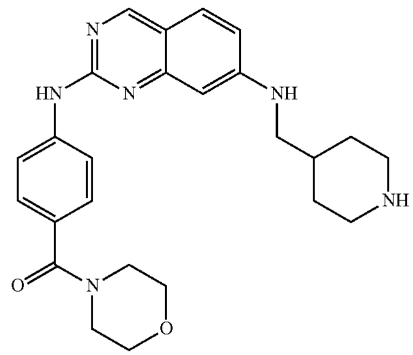 | morpholino(4-(7-(piperidin-4-ylmethylamino)quinazolin-2-ylamino)phenyl)methanone | 447.2, 1.64 | Similar to example 40 | ++++ | | +++ | |
| 352 | 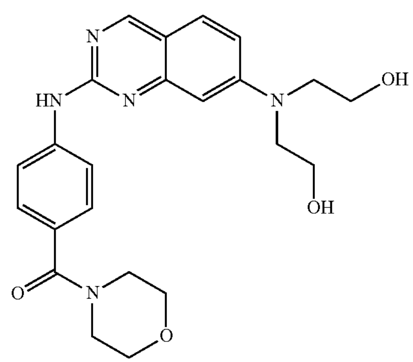 | (4-(7-(bis(2-hydroxyethyl)amino)quinazolin-2-ylamino)phenyl)(morpholino)methanone | 438.1, 1.66 | Similar to example 40 | ++++ | | +++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 353 | 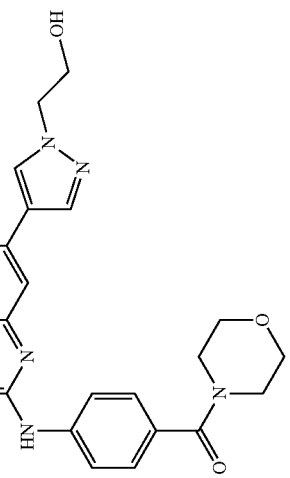 | (4-(7-(1-(2-hydroxyethyl)-1H-pyrazol-4-yl)quinazolin-2-ylamino)phenyl)(morpholino)methanone | 445.1, 1.90 | Similar to example 39 | ++++ | | +++ | |
| 354 | 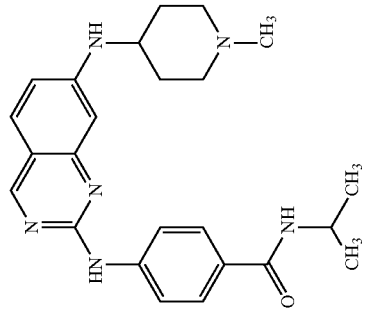 | N-isopropyl-4-(7-(1-methylpiperidin-4-ylamino)quinazolin-2-ylamino)benzamide | 419.2, 1.81 | Similar to example 40 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 355 | 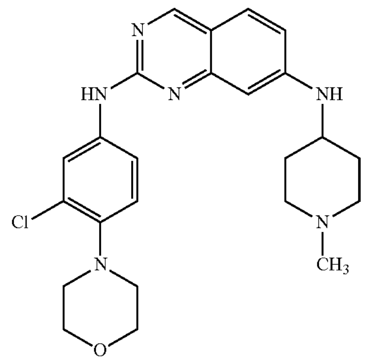 | N2-(3-chloro-4-morpholinophenyl)-N7-(1-methylpiperidin-4-yl)quinazoline-2,7-diamine | 453.2, 2.01 | Similar to example 40 | ++++ | | ++++ | |
| 356 | 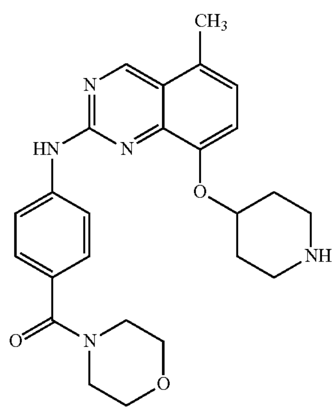 | (4-(5-methyl-8-(piperidin-4-yloxy)quinazolin-2-ylamino)phenyl)(morpholino)methanone | 448.2, 1.97 | Similar to example 46 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 357 | 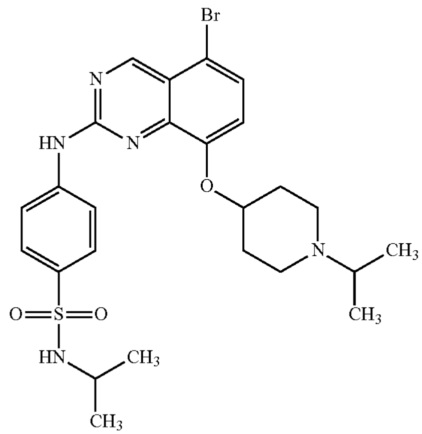 | 4-(5-bromo-8-(1-isopropylpiperidin-4-yloxy)quinazolin-2-ylamino)-N-isopropylbenzenesulfonamide | 562.1/564.1, 2.44 | Similar to example 45 | ++++ | | ++++ | |
| 358 | 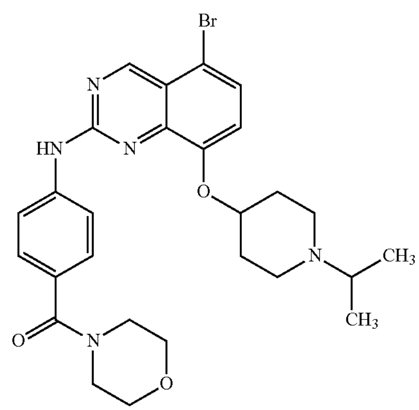 | (4-(5-bromo-8-(1-isopropylpiperidin-4-yloxy)quinazolin-2-ylamino)phenyl)(morpholino)methanone | 554.2/556.1, 2.31 | Similar to example 45 | ++++ | | +++ | |

TABLE 3-continued

| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 359 | 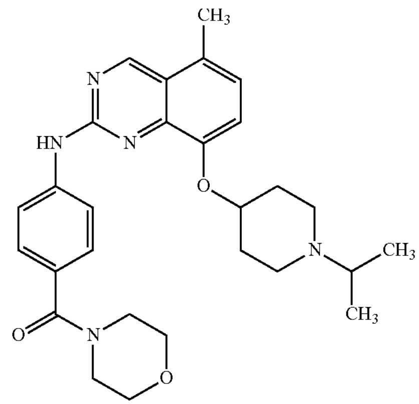 | (4-(8-(1-isopropylpiperidin-4-yloxy)-5-methylquinazolin-2-ylamino)phenyl)(morpholino)methanone | 490.2, 2.03 | Similar to example 46 | ++++ | | +++ | |
| 360 | 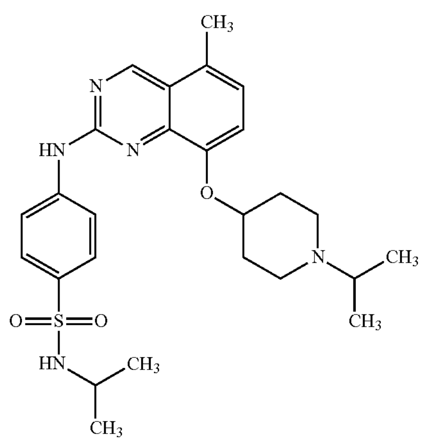 | N-isopropyl-4-(8-(1-isopropylpiperidin-4-yloxy)-5-methylquinazolin-2-ylamino)benzenesulfonamide | 498.2, 2.44 | Similar to example 46 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 361 | 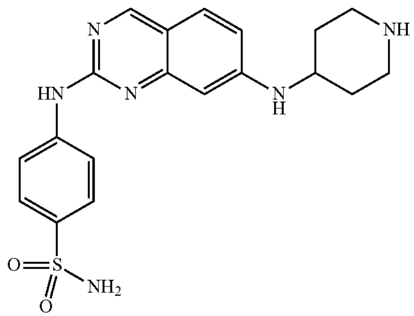 | 4-(7-(piperidin-4-ylamino)quinazolin-2-ylamino)benzenesulfonamide | 399.1, 1.51 | Similar to example 40 | ++++ | | +++ | |
| 362 | 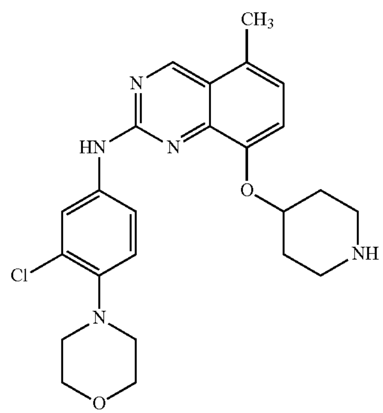 | N-(3-chloro-4-morpholinophenyl)-5-methyl-8-(piperidin-4-yloxy)quinazolin-2-amine | 454.2, 2.29 | Example 46 | ++++ | ++++ | ++++ | |

TABLE 3-continued

| Cmpd | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 363 | N2-(3-chloro-4-morpholinophenyl)-N7-(piperidin-4-yl)quinazoline-2,7-diamine | 439.1, 1.88 | Similar to example 40 | ++++ | | ++++ | |
| 364 | N-cyclopropyl-4-(5-methyl-8-(piperidin-4-yloxy)quinazolin-2-ylamino)benzamide | 418.2, 2.07 | Similar to example 46 | ++++ | ++++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 365 | 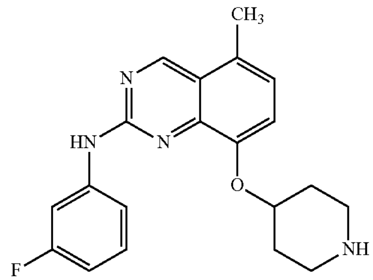 | N-(3-fluorophenyl)-5-methyl-8-(piperidin-4-yloxy)quinazolin-2-amine | 353.2, 2.25 | Similar to example 46 | ++++ | | +++ | |
| 366 | 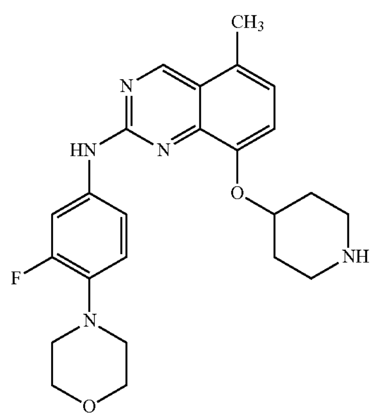 | N-(3-fluoro-4-morpholinophenyl)-5-methyl-8-(piperidin-4-yloxy)quinazolin-2-amine | 438.2, 2.14 | Similar to example 46 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 367 | 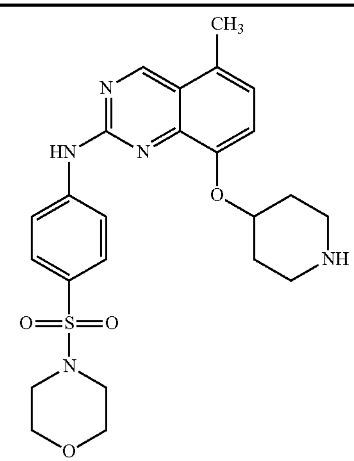 | 5-methyl-N-(4-(morpholinosulfonyl)phenyl)-8-(piperidin-4-yloxy)quinazolin-2-amine | 484.1, 2.19 | Similar to example 46 | ++++ | | +++ | |
| 368 | 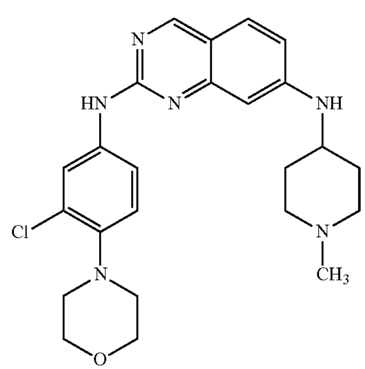 | N2-(3-fluoro-4-morpholinophenyl)-N7-(1-methylpiperidin-4-yl)quinazoline-2,7-diamine | 437.3, 1.96 | Similar to example 40 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 369 | 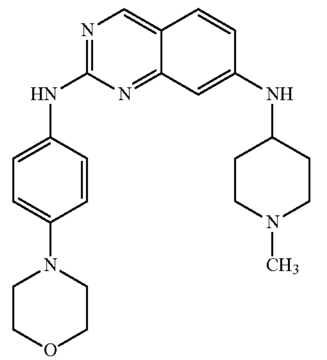 | N7-(1-methylpiperidin-4-yl)-N2-(4-morpholinophenyl)quinazoline-2,7-diamine | 419.2, 1.77 | Similar to example 40 | ++++ | | +++ | |
| 370 | 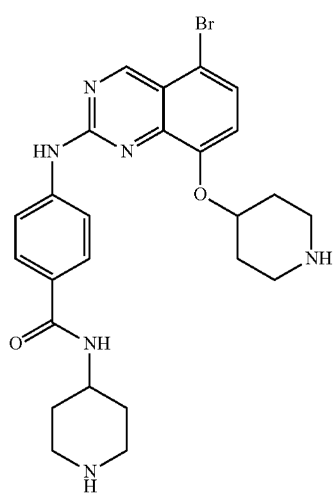 | 4-(5-bromo-8-(piperidin-4-yloxy)quinazolin-2-ylamino)-N-(piperidin-4-yl)benzamide | 525.2/527.2, 2.18 | Similar to example 45 | + | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 371 | 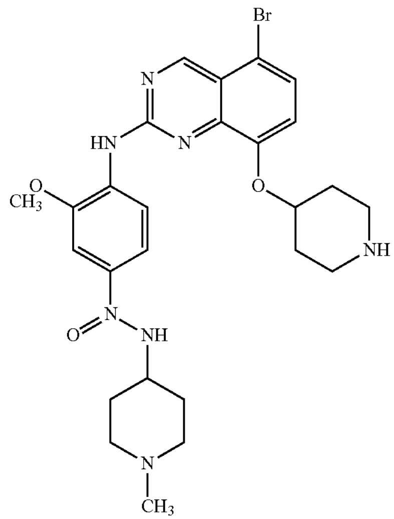 | 4-(5-bromo-8-(piperidin-4-yloxy)quinazolin-2-ylamino)-3-methoxy-N-(1-methylpiperidin-4-yl)benzamide | 569.1/571.1, 2.07 | Similar to example 47 | + | | +++ | |
| 372 | 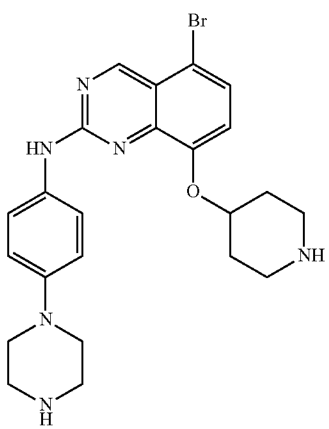 | 5-bromo-N-(4-(piperazin-1-yl)phenyl)-8-(piperidin-4-yloxy)quinazolin-2-amine | 483.1/485.1, 2.10 | Similar to example 45 | + | | ++++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 373 | 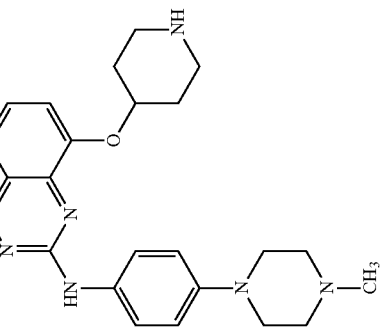 | 5-bromo-N-(4-(4-methylpiperazin-1-yl)phenyl)-8-(piperidin-4-yloxy)quinazolin-2-amine | 496.2/498.2, 2.18 | Similar to example 45 | ++ | | ++++ | |
| 374 | 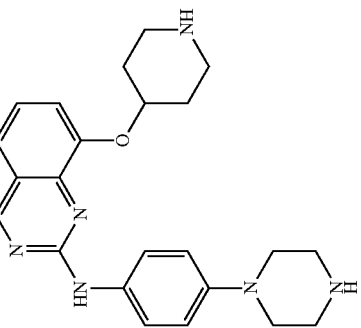 | 5-methyl-N-(4-(piperazin-1-yl)phenyl)-8-(piperidin-4-yloxy)quinazolin-2-amine | 419.2, 1.88 | Similar to example 46 | + | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 375 | 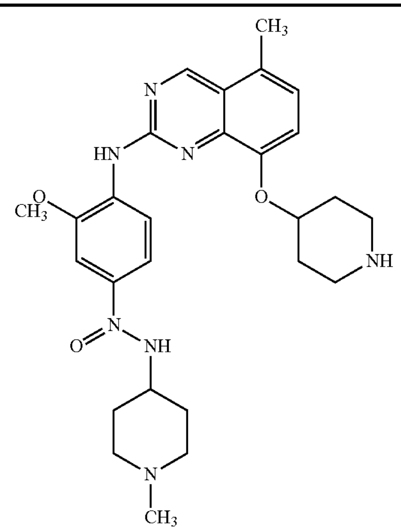 | 3-methoxy-4-(5-methyl-8-(piperidin-4-yloxy)quinazolin-2-ylamino)-N-(1-methylpiperidin-4-yl)benzamide | 505.2, 1.97 | Similar to example 46 | +++ | | +++ | |
| 376 | 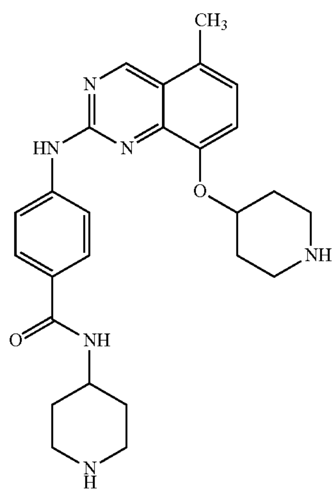 | 4-(5-methyl-8-(piperidin-4-yloxy)quinazolin-2-ylamino)-N-(piperidin-4-yl)benzamide | 461.3, 1.83 | Similar to example 46 | + | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 377 | 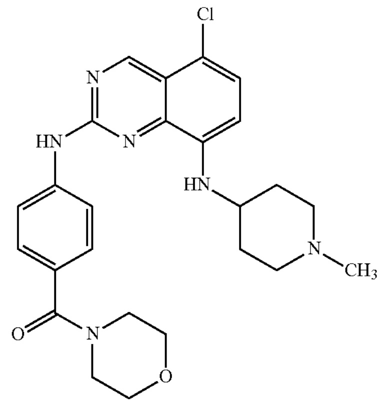 | (4-(5-chloro-8-(1-methylpiperidin-4-ylamino)quinazolin-2-ylamino)phenyl)(morpholino)methanone | 481.2, 2.27 | Similar to example 50 | ++++ | | ++++ | |
| 378 | 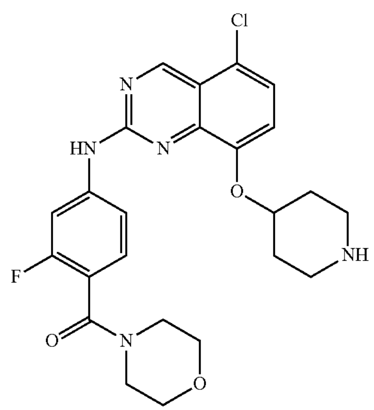 | (4-(5-chloro-8-(piperidin-4-yloxy)quinazolin-2-ylamino)-2-fluorophenyl)(morpholino)methanone | 486.1, 2.25 | Similar to example 48 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 379 | 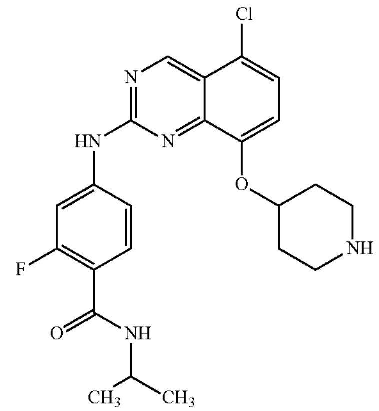 | 4-(5-chloro-8-(piperidin-4-yloxy)quinazolin-2-ylamino)-2-fluoro-N-isopropylbenzamide | 458.2, 2.40 | Similar to example 48 | ++++ | | ++++ | |
| 380 | 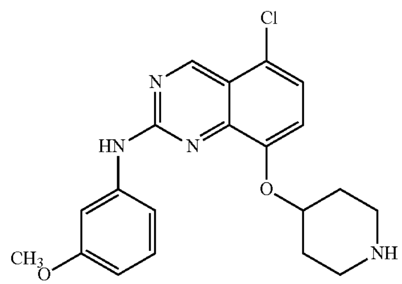 | 5-chloro-N-(3-methoxyphenyl)-8-(piperidin-4-yloxy)quinazolin-2-amine | 385.2, 2.44 | Similar to example 32 | ++++ | | ++++ | |
| 381 | 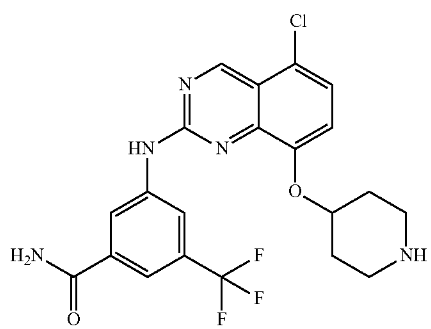 | 3-(5-chloro-8-(piperidin-4-yloxy)quinazolin-2-ylamino)-5-(trifluoromethyl)benzamide | 466.1, 2.36 | Similar to example 32 | ++++ | | ++++ | |

TABLE 3-continued

| Cmpd | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 382 | N,N'-(5-(5-chloro-8-(piperidin-4-yloxy)quinazolin-2-ylamino)-1,3-phenylene)diacetamide | 469.2, 1.99 | Similar to example 32 | ++++ | | +++ | |
| 383 | (4-(8-methoxy-5-(trifluoromethyl)quinazolin-2-ylamino)phenyl)(morpholino)methanone | 433.2, 2.59 | Similar to example 51 | ++++ | | +++ | |

Structure 382: quinazoline with 5-Cl, 8-O-(piperidin-4-yl), 2-NH linked to 3,5-bis(acetamido)phenyl.

Structure 383: quinazoline with 5-CF$_3$, 8-OCH$_3$, 2-NH linked to 4-(morpholine-4-carbonyl)phenyl.

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 384 | 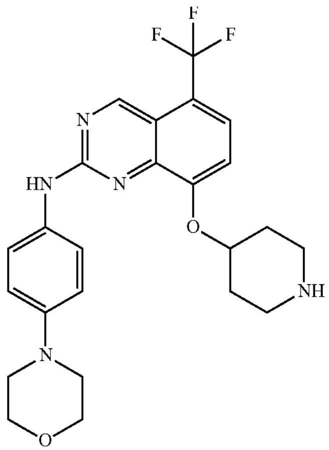 | N-(4-morpholinophenyl)-8-(piperidin-4-yloxy)-5-(trifluoromethyl)quinazolin-2-amine | 502.2, 2.29 | Similar to example 52 | ++++ | | +++ | |
| 385 | 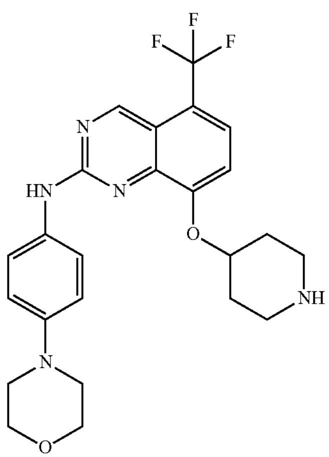 | N-(4-morpholinophenyl)-8-(piperidin-4-yloxy)-5-(trifluoromethyl)quinazolin-2-amine | 474.2, 2.16 | Similar to example 52 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 386 | 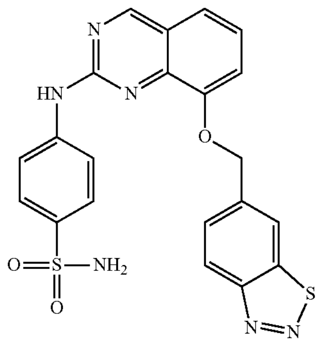 | 4-(8-(benzo[d][1,2,3]thiadiazol-6-ylmethoxy)quinazolin-2-ylamino)benzenesulfonamide | 465 | Similar to example 1 | ++++ | ++++ | | |
| 387 | 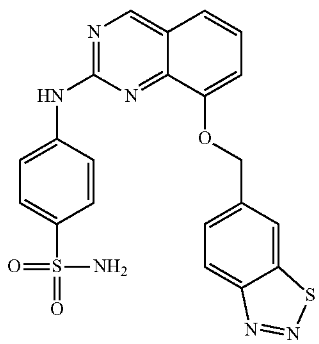 | 4-(8-(benzo[d][1,2,3]thiadiazol-6-ylmethoxy)quinazolin-2-ylamino)benzenesulfonamide | 365, 2.10 | Similar to example 1, using 1-(methylsulfonyl)piperazine for SNAR step and 2-propanol for Mitsunobu | ++++ | ++++ | | |
| 388 | 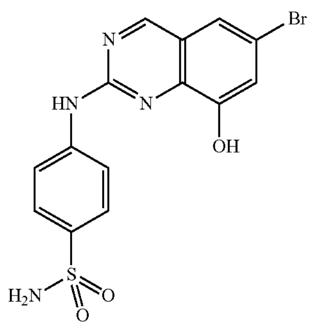 | 4-(6-bromo-8-hydroxyquinazolin-2-ylamino)benzenesulfonamide | 395/397, 2.53 | Similar to example 1, steps 1 and 2 | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 389 | 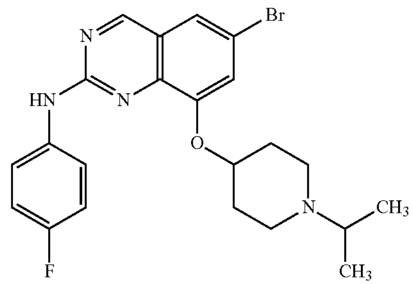 | 6-bromo-N-(4-fluorophenyl)-8-(1-isopropylpiperidin-4-yloxy)quinazolin-2-amine | 459/461 | Similar to example 1, using 4-fluoroaniline for SNAR and 4-hydroxy-1-isopropylpiperidine for Mitsunobu | ++++ | | ++++ | |
| 390 | 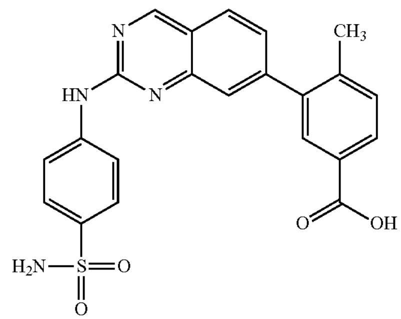 | 4-methyl-3-(2-(4-sulfamoylphenylamino)quinazolin-7-yl)benzoic acid | 435, 2.50 | Similar to example 25, using 5-carboxy-2-methylbenzeneboronic acid in step 7 | ++++ | | +++ | |
| 391 | 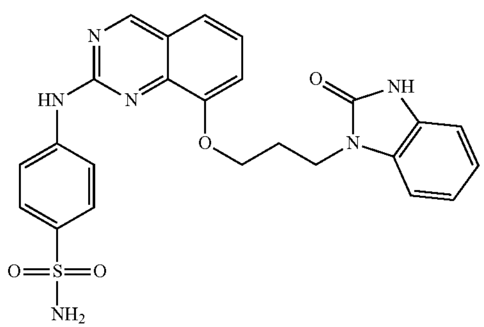 | 4-(8-(3-(2-oxo-2,3-dihydro-1H-benzo[d]imidazol-1-yl)propoxy)quinazolin-2-ylamino)benzenesulfonamide | 491.2, 2.20 | Similar to example 2 and example 32, step 3 | ++++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 392 | 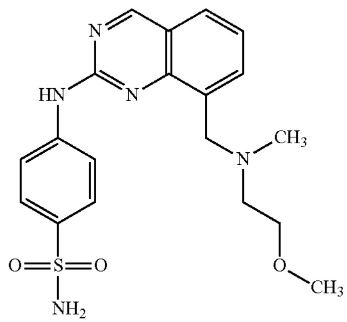 | 4-(8-(((2-methoxyethyl)(methyl)amino)methyl)quinazolin-2-ylamino)benzenesulfonamide | 402.2, 1.69 | Similar to example 43 | ++++ | ++++ | | |
| 393 | 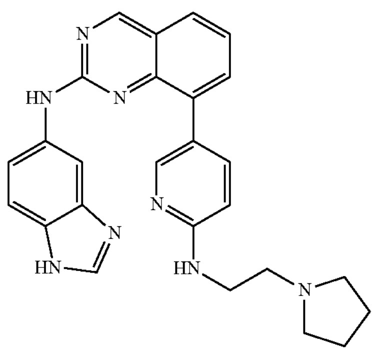 | N-(1H-benzo[d]imidazol-5-yl)-8-(6-(2-(pyrrolidin-1-yl)ethylamino)pyridin-3-yl)quinazolin-2-amine | 451.1, 1.74 | Similar to example 2 and example 55 | ++++ | | ++++ | |
| 394 | 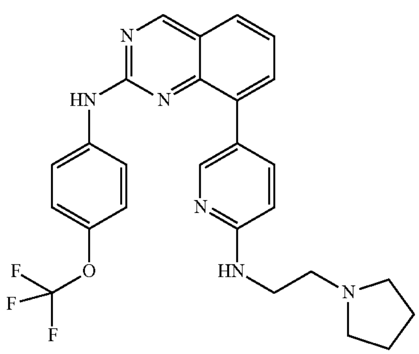 | 8-(6-(2-(pyrrolidin-1-yl)ethylamino)pyridin-3-yl)-N-(4-(trifluoromethoxy)phenyl)quinazolin-2-amine | 479.2, 2.03 | Similar to example 2 and example 55 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 395 | 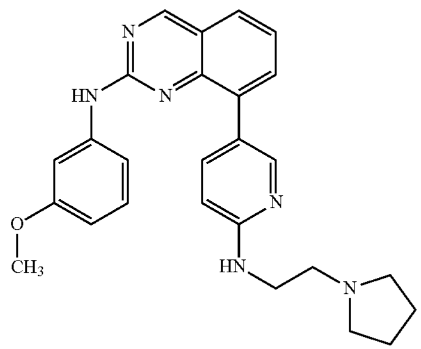 | N-(3-methoxyphenyl)-8-(6-(2-(pyrrolidin-1-yl)ethylamino)pyridin-3-yl)quinazolin-2-amine | 441.1, 2.02 | Similar to example 2 and example 55 | ++++ | | ++++ | |
| 396 | 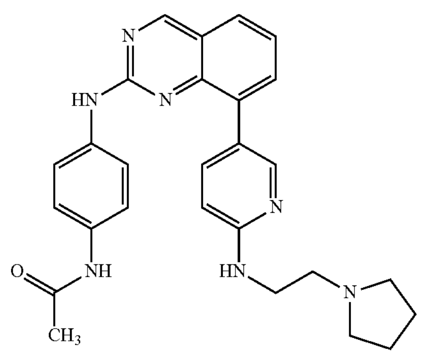 | N-(4-(8-(6-(2-(pyrrolidin-1-yl)ethylamino)pyridin-3-yl)quinazolin-2-ylamino)phenyl)acetamide | 468.1, 1.86 | Similar to example 2 and example 55 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 397 | 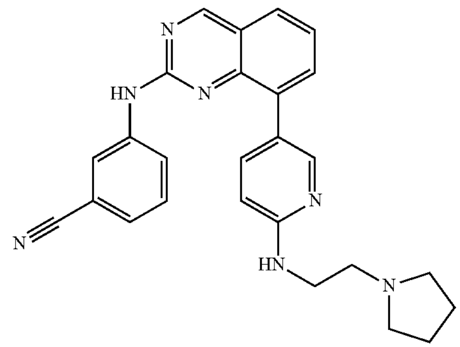 | 3-(8-(6-(2-(pyrrolidin-1-yl)ethylamino)pyridin-3-yl)quinazolin-2-ylamino)benzonitrile | 436.1, 1.98 | Similar to example 2 and example 55 | ++++ | | ++++ | |
| 398 | 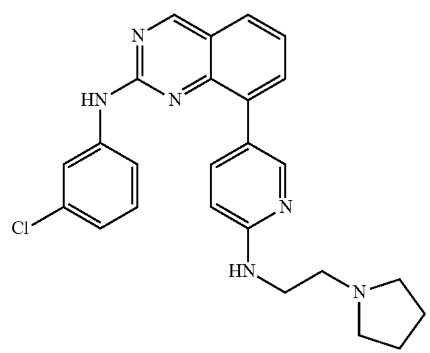 | N-(3-chlorophenyl)-8-(6-(2-(pyrrolidin-1-yl)ethylamino)pyridin-3-yl)quinazolin-2-amine | 445.1, 2.08 | Similar to example 2 and example 55 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 399 | 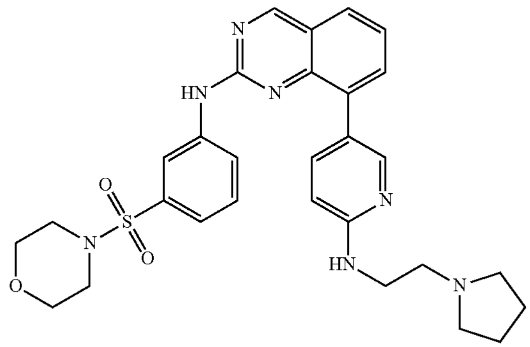 | N-(3-(morpholinosulfonyl)phenyl)-8-(6-(2-(pyrrolidin-1-yl)ethylamino)pyridin-3-yl)quinazolin-2-amine | 560.1, 1.97 | Similar to example 2 and example 55 | ++++ | | ++++ | |
| 400 | 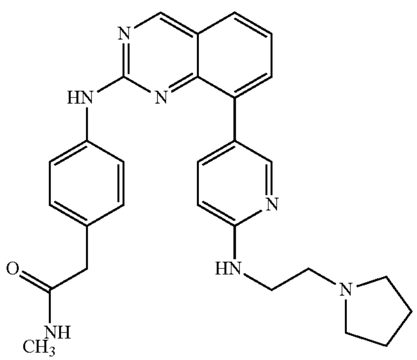 | N-methyl-2-(4-(8-(6-(2-(pyrrolidin-1-yl)ethylamino)pyridin-3-yl)quinazolin-2-ylamino)phenyl)acetamide | 482.2, 1.85 | Similar to example 2 and example 55 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 401 | 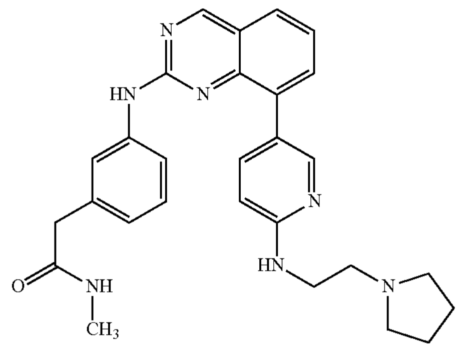 | N-methyl-2-(3-(8-(6-(2-(pyrrolidin-1-yl)ethylamino)pyridin-3-yl)quinazolin-2-ylamino)phenyl)acetamide | 482.2, 1.84 | Similar to example 2 and example 55 | ++++ | | ++++ | |
| 402 | 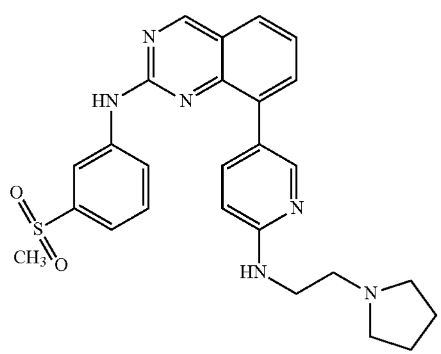 | N-(3-(methylsulfonyl)phenyl)-8-(6-(2-(pyrrolidin-1-yl)ethylamino)pyridin-3-yl)quinazolin-2-amine | 489.2, 1.63 | Similar to example 2 and example 55 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 403 | 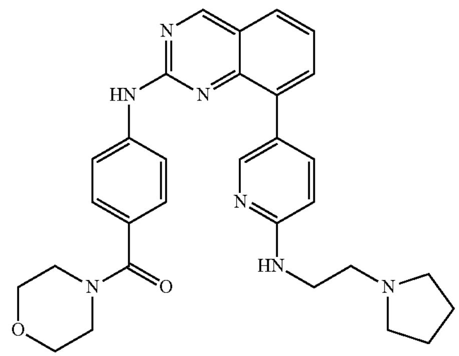 | morpholino(4-(8-(6-(2-(pyrrolidin-1-yl)ethylamino)pyridin-3-yl)quinazolin-2-ylamino)phenyl)methanone | 524.2, 1.93 | Similar to example 2 and example 55 | ++++ | | ++++ | |
| 404 | 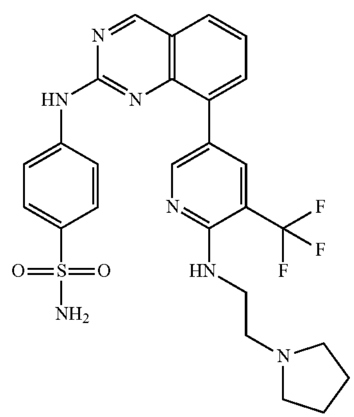 | 4-(8-(6-(2-(pyrrolidin-1-yl)ethylamino)-5-(trifluoromethyl)pyridin-3-yl)quinazolin-2-ylamino)benzenesulfonamide | 558.0, 2.36 | Similar to example 2 and example 55 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 405 | 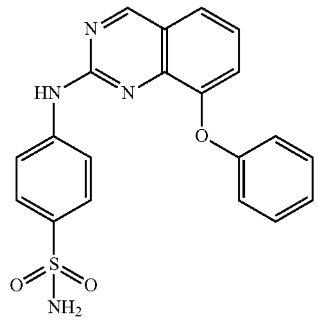 | 4-(8-phenoxyquinazolin-2-ylamino)benzenesulfonamide | 393, 2.70 | Similar to example 57 | ++++ | ++++ | ++++ | ++++ |
| 406 | 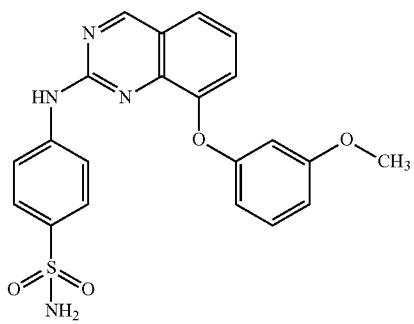 | 4-(8-(3-methoxyphenoxy)quinazolin-2-ylamino)benzenesulfonamide | 423, 2.72 | Similar to example 57 | ++++ | ++++ | | |
| 407 | 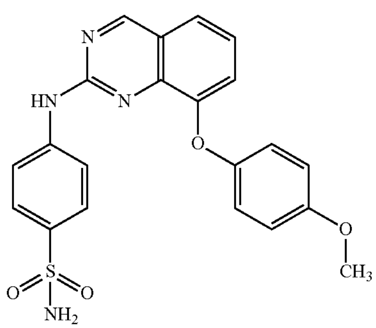 | 4-(8-(4-methoxyphenoxy)quinazolin-2-ylamino)benzenesulfonamide | 423, 2.77 | Similar to example 57 | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 408 | 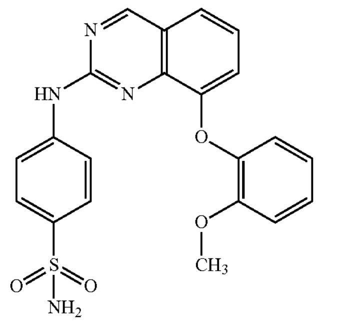 | 4-(8-(2-methoxyphenoxy)quinazolin-2-ylamino)benzenesulfonamide | 423, 2.70 | Similar to example 57 | ++++ | | | |
| 409 | 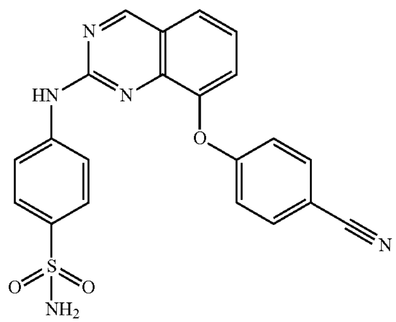 | 4-(8-(4-cyanophenoxy)quinazolin-2-ylamino)benzenesulfonamide | 418, 2.64 | Similar to example 57 | ++++ | +++ | | |
| 410 | 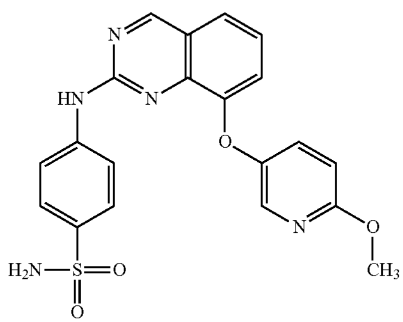 | 4-(8-(6-methoxypyridin-3-yloxy)quinazolin-2-ylamino)benzenesulfonamide | 424, 2.11 | Similar to example 57 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 411 | 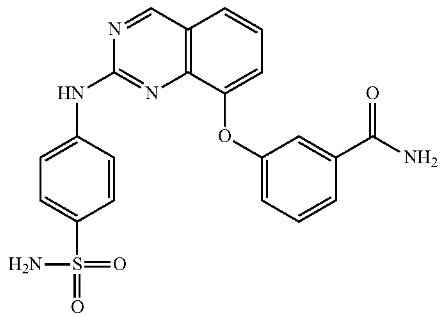 | 3-(2-(4-sulfamoylphenylamino)quinazolin-8-yloxy)benzamide | 436, 2.26 | Similar to example 57 | ++++ | | | |
| 412 | 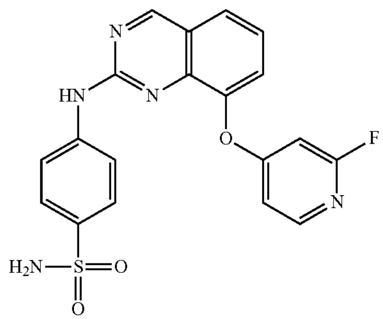 | 4-(8-(2-fluoropyridin-4-yloxy)quinazolin-2-ylamino)benzenesulfonamide | 412, 2.48 | Similar to example 57 | ++++ | | | |
| 413 | 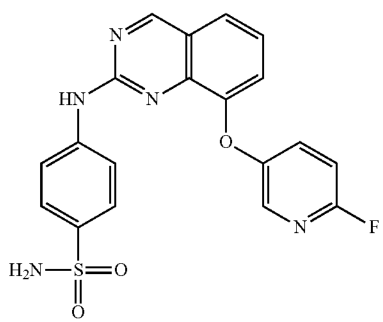 | 4-(8-(6-fluoropyridin-3-yloxy)quinazolin-2-ylamino)benzenesulfonamide | 412, 2.53 | Similar to example 57 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 414 | 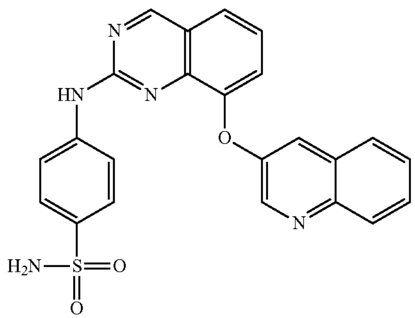 | 4-(8-(quinolin-3-yloxy)quinazolin-2-ylamino)benzenesulfonamide | 444, 2.33 | Similar to example 57 | + | | | |
| 415 | 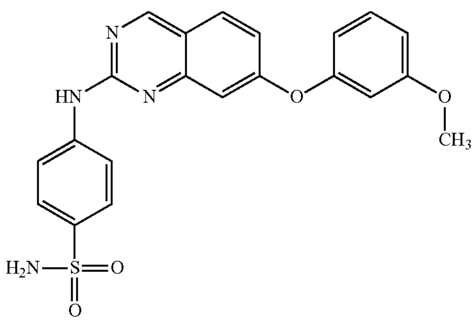 | 4-(7-(3-methoxyphenoxy)quinazolin-2-ylamino)benzenesulfonamide | 423, 2.81 | Similar to example 58 | ++++ | ++++ | | |
| 416 | 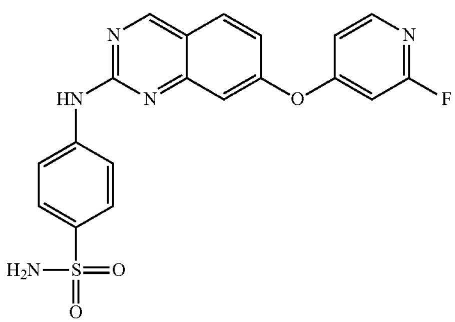 | 4-(7-(2-fluoropyridin-4-yloxy)quinazolin-2-ylamino)benzenesulfonamide | 412, 2.51 | Similar to example 58 | ++++ | | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 417 | 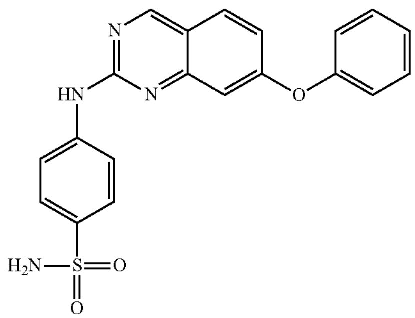 | 4-(7-phenoxyquinazolin-2-ylamino)benzenesulfonamide | | Similar to example 58 | + | | | |
| 418 | 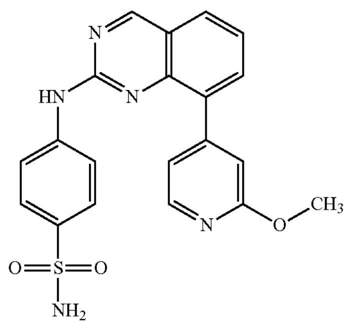 | 4-(8-(2-methoxypyridin-4-yl)quinazolin-2-ylamino)benzenesulfonamide | 408.0, 2.30 | Suzuki (see example 8 step 1) Then example 56 | + | | | |
| 419 | 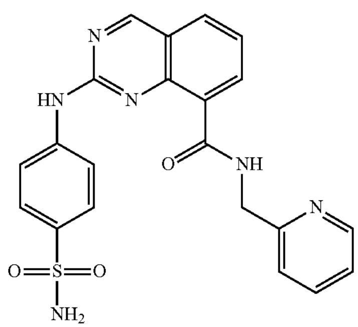 | N-(pyridin-2-ylmethyl)-2-(4-sulfamoylphenylamino)quinazoline-8-carboxamide | 435.0, 1.82 | | + | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 420 | 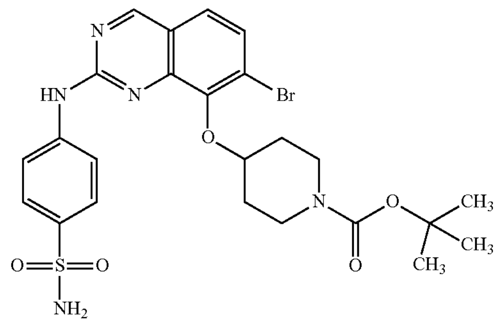 | tert-butyl 4-(7-bromo-2-(4-sulfamoylphenylamino)quinazolin-8-yloxy)piperidine-1-carboxylate | 578.0/580.0, 3.24 | Similar to example 7 | + | ++++ | | |
| 421 | 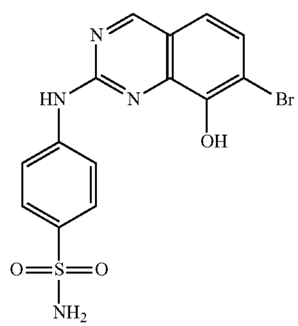 | 4-(7-bromo-8-hydroxyquinazolin-2-ylamino)benzenesulfonamide | 394.9/396.9, 2.51 | example 5 then example 9 step 3 | +++ | ++++ | | |
| 422 | 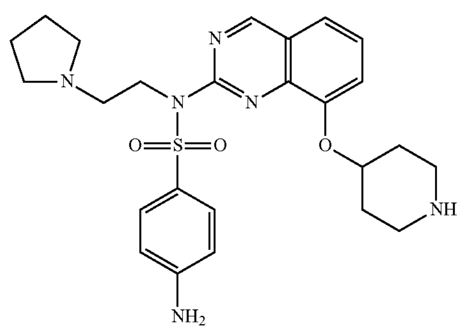 | 4-amino-N-(8-(piperidin-4-yloxy)quinazolin-2-yl)-N-(2-(pyrrolidin-1-yl)ethyl)benzenesulfonamide | 497.2, 1.73 | example 7 with 5.5 eq of KOtBu 110 c 50 hrs, then example 8 step 2 | +++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 423 | 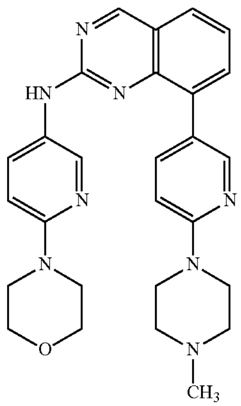 | 8-(6-(4-methylpiperazin-1-yl)pyridin-3-yl)-N-(6-morpholinopyridin-3-yl)quinazolin-2-amine | 483.1, 1.75 | Suzuki (see example 8 step 1) | ++++ | | ++++ | |
| 424 | 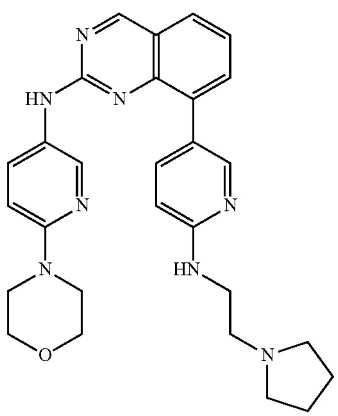 | N-(6-morpholinopyridin-3-yl)-8-(6-(2-(pyrrolidin-1-yl)ethylamino)pyridin-3-yl)quinazolin-2-amine | 497.2, 1.75 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 425 | 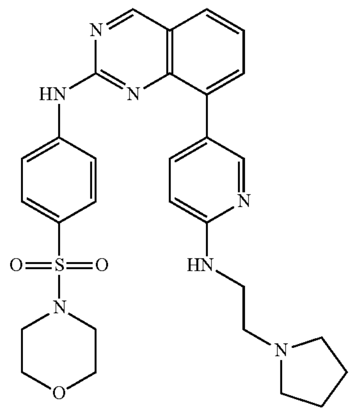 | N-(4-(morpholinosulfonyl)phenyl)-8-(6-(2-(pyrrolidin-1-yl)ethylamino)pyridine-3-yl)quinazolin-2-amine | 560.2, 2.04 | Suzuki (see example 8 step 1) | ++++ | | ++++ | |
| 426 | 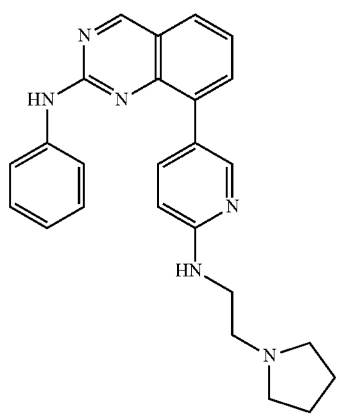 | N-phenyl-8-(6-(2-(pyrrolidin-1-yl)ethylaminopyridin-3-yl)quinazolin-2-amine | 411.2, 2.02 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 427 | 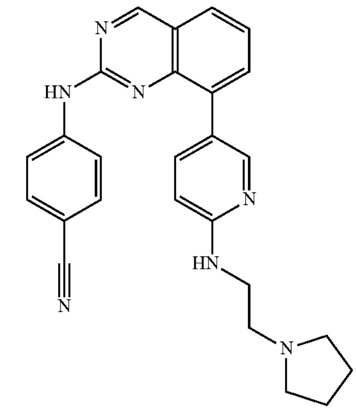 | 4-(8-(6-(2-(pyrrolidin-1-yl)ethylamino)pyridin-3-yl)quinazolin-2-ylamino)benzonitrile | 436.1, 2.03 | Suzuki (see example 8 step 1) | ++++ | | ++++ | |
| 428 | 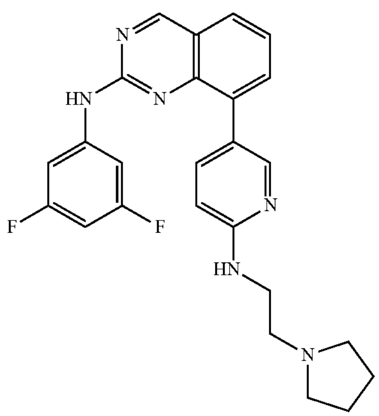 | N-(3,5-difluorophenyl)-8-(6-(2-(pyrrolidin-1-yl)ethylamino)pyridin-3-yl)quinazolin-2-amine | 447.1, 2.11 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 429 | 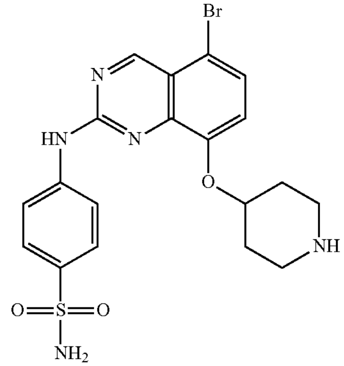 | 4-(5-bromo-8-(piperidin-4-yloxy)quinazolin-2-ylamino)benzenesulfonamide | 478.0/480.0, 2.16 | example 9 step 3 then example 8 step 2 | ++++ | | +++ | |
| 430 | 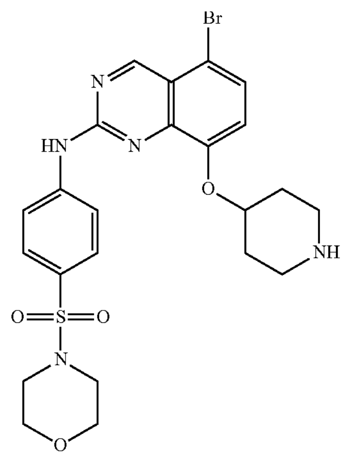 | 5-bromo-N-(4-(morpholinosulfonyl)phenyl)-8-(piperidin-4-yloxy)quinazolin-2-amine | 548.0/550.0, 2.39 | example 9 step 3 then example 8 step 2 | ++++ | | ++++ | |

TABLE 3-continued

| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 431 | 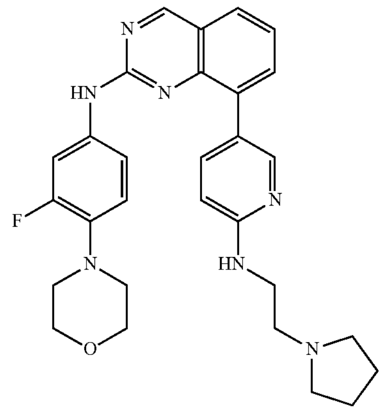 | N-(3-fluoro-4-morpholinophenyl)-8-(6-(2-(pyrrolidin-1-yl)ethylamino)pyridine-3-yl)quinazolin-2-amine | 514.2, 2.02 | Suzuki (see example 8 step 1 | ++++ | | ++++ | |
| 432 | 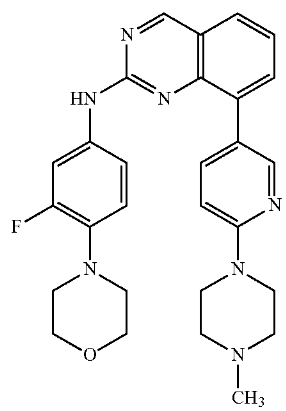 | N-(3-fluoro-4-morpholinophenyl)-8-(6-(4-methylpiperazin-1-yl)pyridin-3-yl)quinazolin-2-amine | 500.2, 2.03 | Suzuki (see example 8 step 1 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 433 | 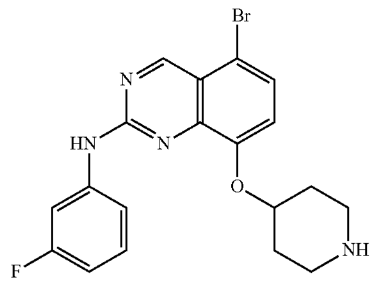 | 5-bromo-N-(3-fluorophenyl)-8-(piperidin-4-yloxy)quinazolin-2-amine | 417.0/419.0, 2.50 | example 9 step 3 then example 8 step 2 | ++++ | | ++++ | |
| 434 | 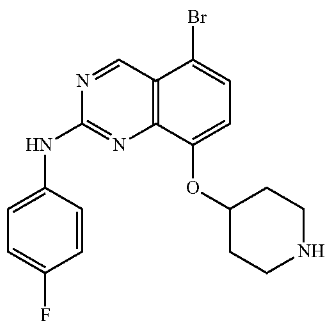 | 5-bromo-N-(4-fluorophenyl)-8-(piperidin-4-yloxy)quinazolin-2-amine | 417.0/419.0, 2.46 | example 9 step 3 then example 8 step 2 | ++++ | | ++++ | |
| 435 | 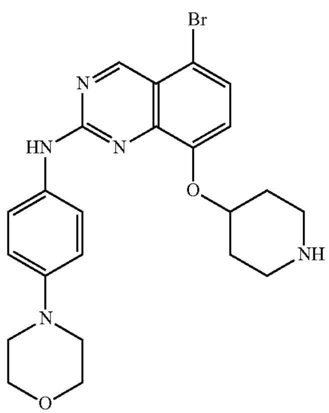 | 5-bromo-N-(4-morpholinophenyl)-8-(piperidin-4-yloxy)quinazolin-2-amine | 484.0/486.0, 2.05 | example 9 step 3 then example 8 step 2 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 436 | 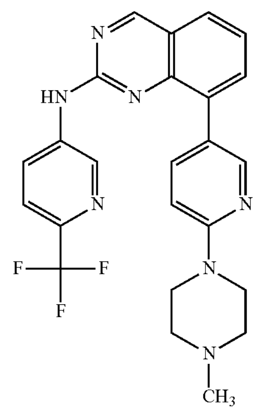 | 8-(6-(4-methylpiperazin-1-yl)pyridin-3-yl)-N-(6-(trifluoromethyl)pyridine-3-yl)quinazolin-2-amine | 466.1, 2.10 | Suzuki (see example 8 step 1) | ++++ | | ++++ | |
| 437 | 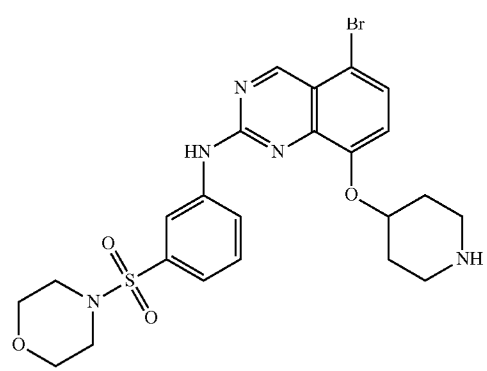 | 5-bromo-N-(3-(morpholinosulfonyl)phenyl)-8-(piperidin-4-yloxy)quinazolin-2-amine | 548.0/550.0, 2.40 | example 9 step 3 then example 8 step 2 | +++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 438 | 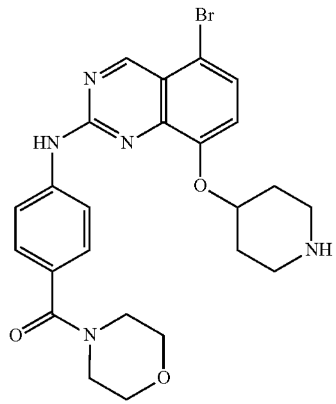 | (4-(5-bromo-8-(piperidin-4-yloxy)quinazolin-2-ylamino)phenyl)(morpholino)methanone | 512.1/514.1, 2.23 | example 9 step 3 then example 8 step 2 | ++++ | | ++++ | |
| 439 | 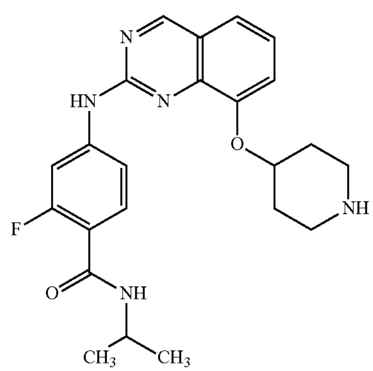 | 2-fluoro-N-isopropyl-4-(8-(piperidin-4-yloxy)quinazolin-2-ylamino)benzamide | 424.2, 2.18 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 440 | 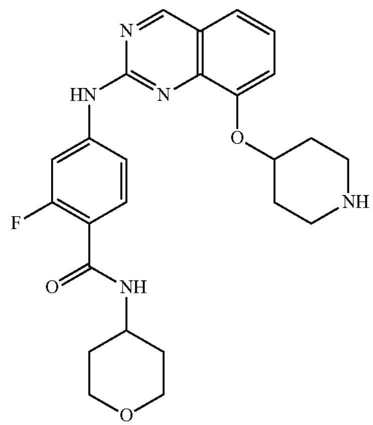 | 2-fluoro-4-(8-(piperidin-4-yloxy)quinazolin-2-ylamino)-N-(tetrahydro-2H-pyran-4-yl)benzamide | 466.2, 2.05 | | ++++ | | ++++ | |
| 441 | 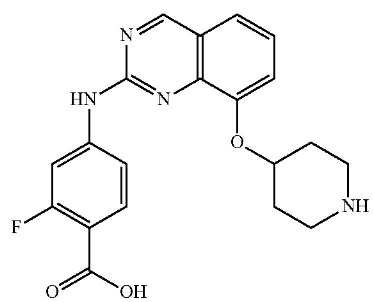 | 2-fluoro-4-(8-(piperidin-4-yloxy)quinazolin-2-ylamino)benzoic acid | 383.0, 2.02 | example 9 step 3 then example 8 step 2 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 442 | 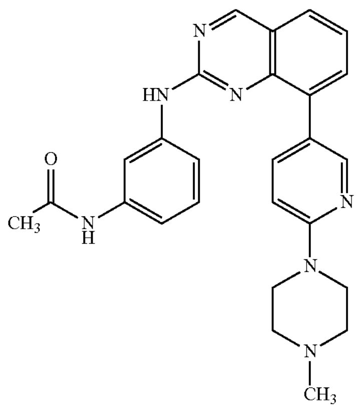 | N-(3-(8-(6-(4-methylpiperazin-1-yl)pyridin-3-yl)quinazolin-2-ylamino)phenyl)acetamide | 454.1, 1.88 | Suzuki (see example 8 step 1) | ++++ | | ++++ | |
| 443 | 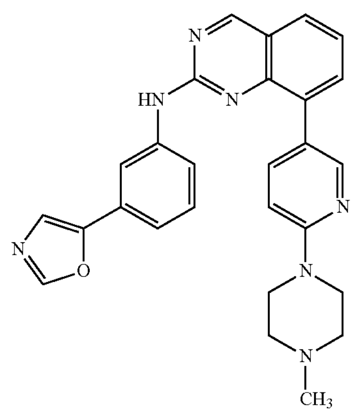 | 8-(6-(4-methylpiperazin-1-yl)pyridin-3-yl)-N-(3-(oxazol-5-yl)phenyl)quinazolin-2-amine | 464.1, 2.08 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 444 | 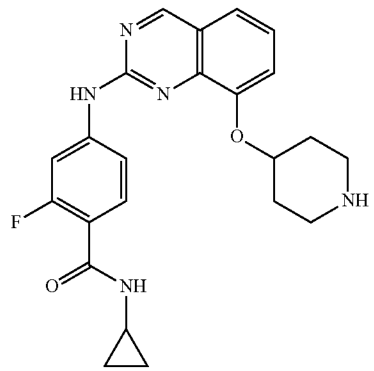 | N-cyclopropyl-2-fluoro-4-(8-(piperidin-4-yloxy)quinazolin-2-ylamino)benzamide | 422.1, 2.08 | | ++++ | | ++++ | |
| 445 | 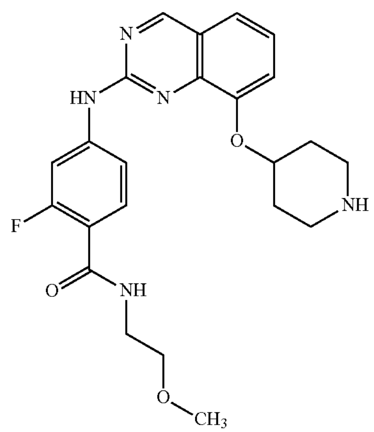 | 2-fluoro-N-(2-methoxyethyl)-4-(8-(piperidin-4-yloxy)quinazolin-2-ylamino)benzamide | 440.1, 2.02 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 446 | 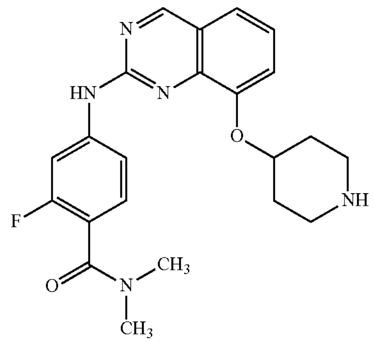 | 2-fluoro-N,N-dimethyl-4-(8-(piperidin-4-yloxy)quinazolin-2-ylamino)benzamide | 410.1, 2.03 | | ++++ | | ++++ | |
| 447 | 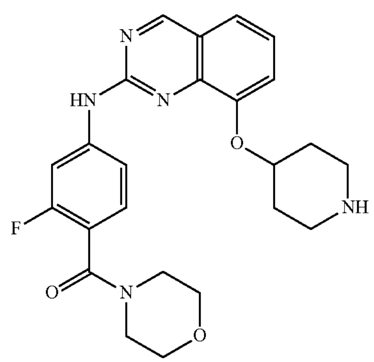 | (2-fluoro-4-(8-(piperidin-4-yloxy)quinazolin-2-ylamino)phenyl)(morpholino)methanone | 452.1, 2.01 | | ++++ | | ++++ | |

TABLE 3-continued

| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 448 | 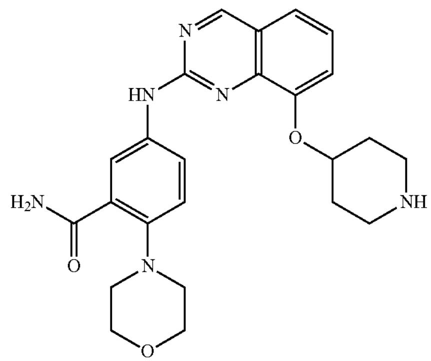 | 2-morpholino-5-(8-(piperidin-4-yloxy)quinazolin-2-ylamino)benzamide | 449.1, 1.77 | example 9 step 3 then example 8 step 2 | ++++ | | +++ | |
| 449 | 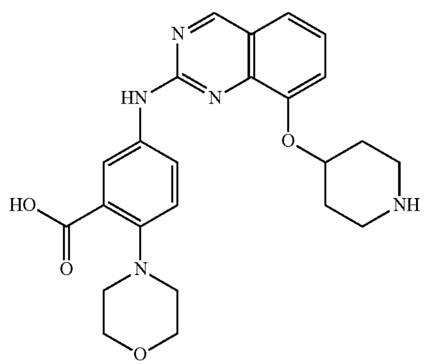 | 2-morpholino-5-(8-(piperidin-4-yloxy)quinazolin-2-ylamino)benzoic acid | 450.2, 1.82 | example 9 step 3 then example 8 step 2 | ++++ | | +++ | |
| 450 | 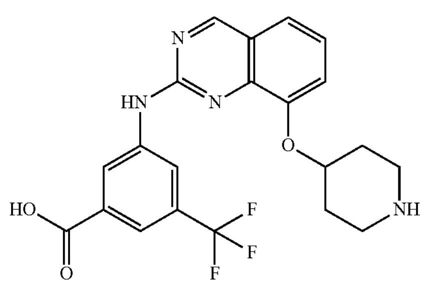 | 3-(8-piperidin-4-yloxy)quinazolin-2-ylamino)-5-(trifluoromethyl)benzoic acid | 433.1, 2.28 | example 9 step 3 then example 8 step 2 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 451 | 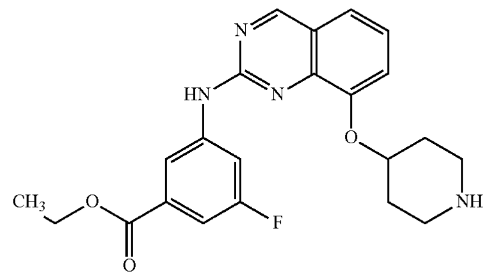 | ethyl 3-fluoro-5-(8-(piperidin-4-yloxy)quinazolin-2-ylamino)benzoate | 411.1, 2.43 | example 9 step 3 then example 8 step 2 | ++++ | | ++++ | |
| 452 | 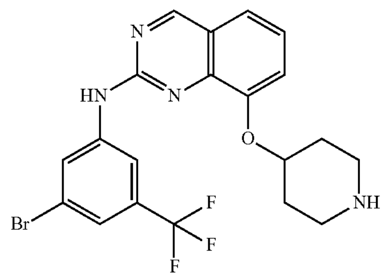 | N-(3-bromo-5-(trifluoromethyl)phenyl)-8-(piperidin-4-yloxy)quinazolin-2-amine | 467.0/469, 2.62 | example 9 step 3 then example 8 step 2 | ++++ | | ++++ | |
| 453 | 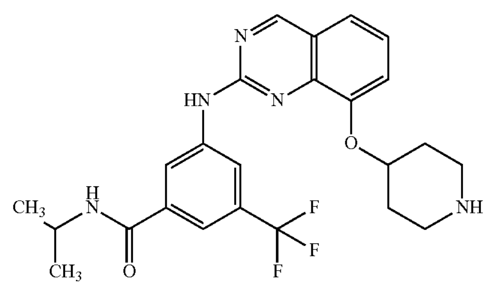 | N-isopropyl-3-(8-(piperidin-4-yloxy)quinazolin-2-ylamino)-5-(trifluoromethyl)benzamide | 474.2, 2.39 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 454 | 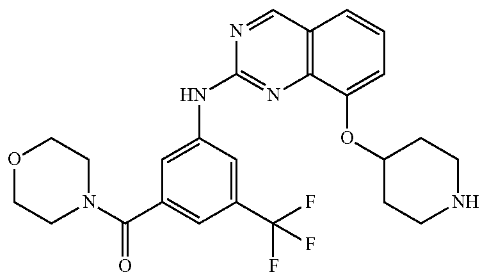 | morpholino(3-(8-(piperidin-4-yloxy)quinazolin-2-ylamino)-5-(trifluoromethyl)phenyl)methanone | 502.2, 2.24 | | ++++ | | +++ | |
| 455 | 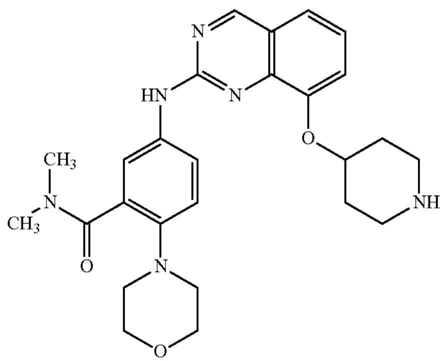 | N,N-dimethyl-2-morpholino-5-(8-(piperidin-4-yloxy)quinazolin-2-ylamino)benzamide | 477.2, 1.98 | | ++++ | | +++ | |
| 456 | 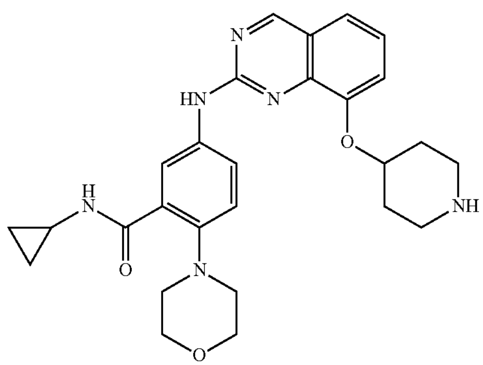 | N-cyclopropyl-2-morpholino-5-(8-(piperidin-4-yloxy)quinazolin-2-ylamino)benzamide | 489.2, 2.00 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 457 | 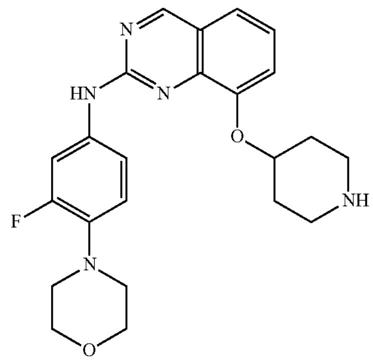 | N-(3-fluoro-4-morpholinophenyl)-8-(piperidin-4-yloxy)quinazolin-2-amine | 424.2, 2.05 | example 9 step 3 then example 8 step 2 | ++++ | | ++++ | |
| 458 | 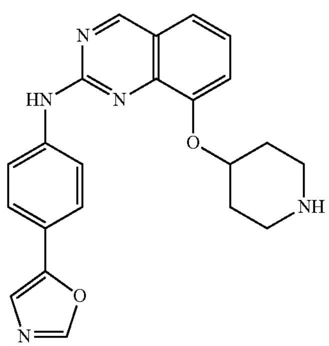 | N-(4-(oxazol-5-yl)phenyl)-8-(piperidin-4-yloxy)quinazolin-2-amine | 388.1, 2.08 | example 9 step 3 then example 8 step 2 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 459 | 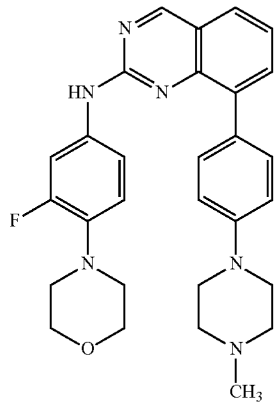 | N-(3-fluoro-4-morpholinophenyl)-8-(4-(4-methylpiperazin-1-yl)phenyl)quinazolin-2-amine | 499.2, 2.39 | Suzuki (see example 8 step 1) | ++++ | | ++++ | |
| 460 | 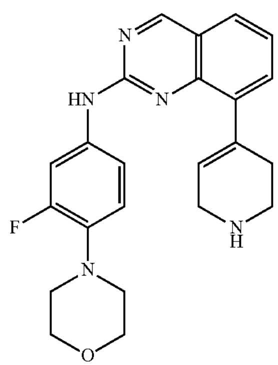 | N-(3-fluoro-4-morpholinophenyl)-8-(1,2,3,6-tetrahydropyridin-4-yl)quinazolin-2-amine | 406.1, 2.09 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 461 | 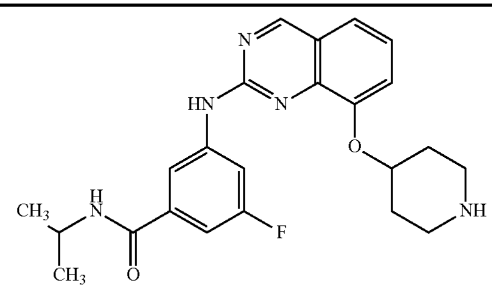 | 3-fluoro-N-isopropyl-5-(8-(piperidin-4-yloxy)quinazolin-2-ylamino)benzamide | 424.2, 2.16 | | ++++ | | ++++ | |
| 462 | 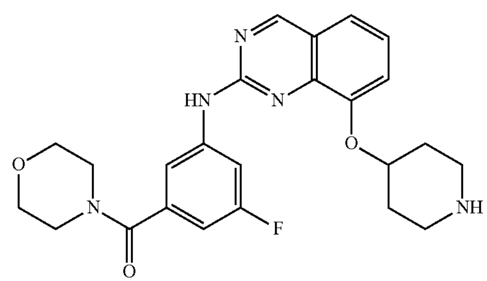 | (3-fluoro-5-(8-piperidin-4-yloxy)quinazolin-2-ylamino)phenyl)(morpholino)methanone | 452.1, 2.04 | | ++++ | | ++++ | |
| 463 | 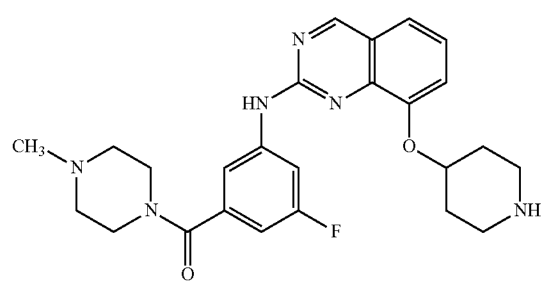 | (3-fluoro-5-(8-(piperidin-4-yloxy)quinazolin-2-ylamino)phenyl)(4-methylpiperazin-1-yl)methanone | 465.2, 1.78 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 464 | 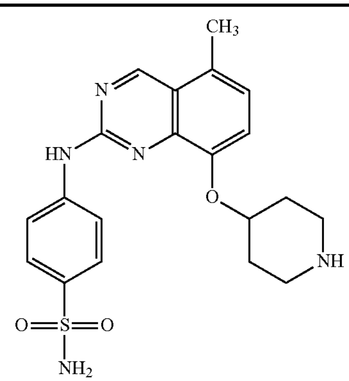 | 4-(5-methyl-8-(piperidin-4-yloxy)quinazolin-2-ylamino)benzenesulfonamide | 414.1, 1.97 | example 105 | ++++ | | +++ | |
| 465 | 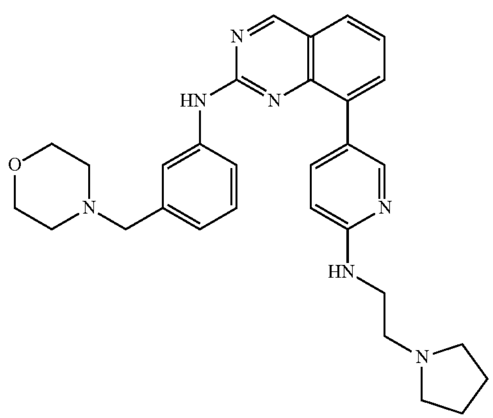 | N-(3-(morpholinomethyl)phenyl)-8-(6-(2-(pyrrolidin-1-yl)ethylamino)pyridin-3-yl)quinazolin-2-amine | 510.2, 1.78 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 466 | 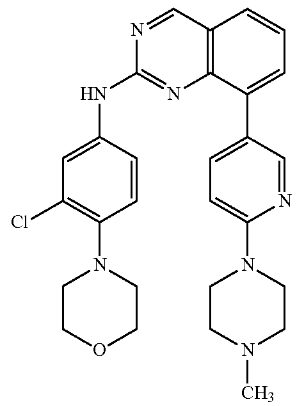 | N-(3-chloro-4-morpholinophenyl)-8-(6-(4-methylpiperazin-1-yl)pyridin-3-yl)quinazolin-2-amine | 516.1, 2.13 | Suzuki (see example 8 step 1) | ++++ | | ++++ | |
| 467 | 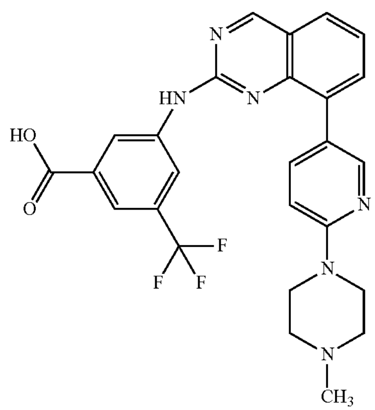 | 3-(8-(6-(4-methylpiperazin-1-yl)pyridin-3-yl)quinazolin-2-ylamino)-5-(trifluoromethyl)benzoic acid | 509.1, 2.14 | Suzuki (see example 8 step 1) | ++++ | | ++++ | |

TABLE 3-continued

| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 468 | 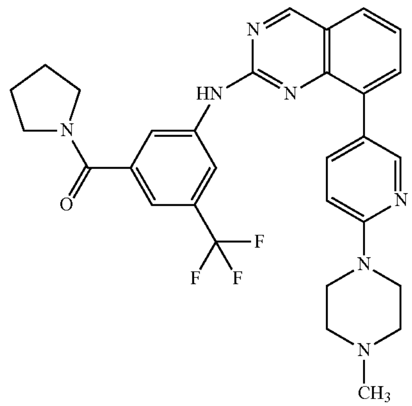 | (3-(8-(6-(4-methylpiperazin-1-yl)pyridin-3-yl)quinazolin-2-ylamino)-5-(trifluoromethyl)phenyl)(pyrrolidin-1-yl)methanone | 562.2, 2.23 | | +++ | | ++++ | |
| 469 | 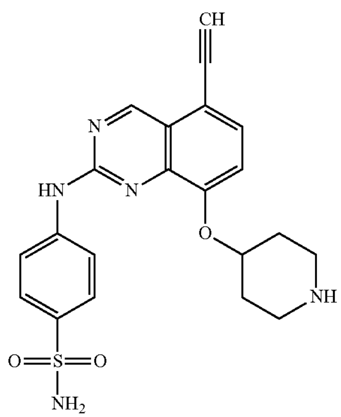 | 4-(5-ethynyl-8-(piperidin-4-yloxy)quinazolin-2-ylamino)benzenesulfonamide | 424.1, 2.06 | | ++++ | +++ | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 470 | 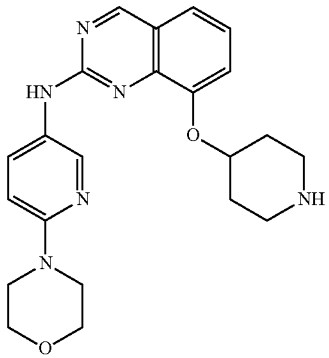 | N-(6-morpholinopyridin-3-yl)-8-(piperidin-4-yloxy)quinazolin-2-amine | 407.1, 1.69 | example 9 step 3 then example 8 step 2 | ++++ | | ++++ | |
| 471 | 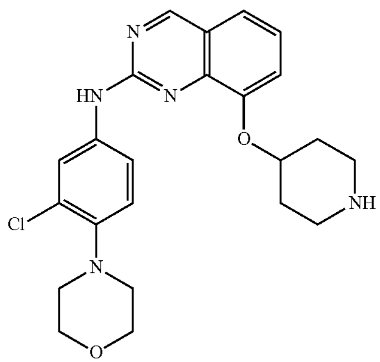 | N-(3-chloro-4-morpholinophenyl)-8-(piperidin-4-yloxy)quinazolin-2-amine | 440.1, 2.18 | example 9 step 3 then example 8 step 2 | ++++ | | ++++ | |
| 472 | 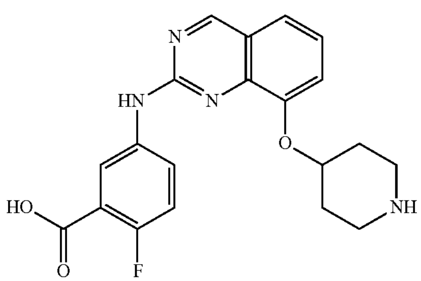 | 2-fluoro-5-(8-(piperidin-4-yloxy)quinazolin-2-ylamino)benzoic acid | 383.1, 1.92 | example 9 step 3 then example 8 step 2 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 473 | 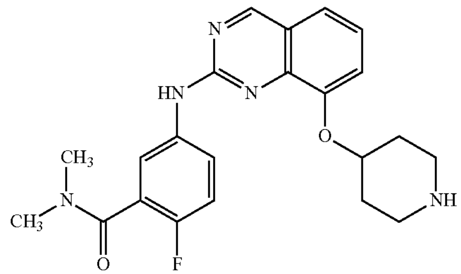 | 2-fluoro-N,N-dimethyl-5-(8-(piperidin-4-yloxy)quinazolin-2-ylamino)benzamide | 410.1, 1.96 | | ++++ | | ++++ | |
| 474 | 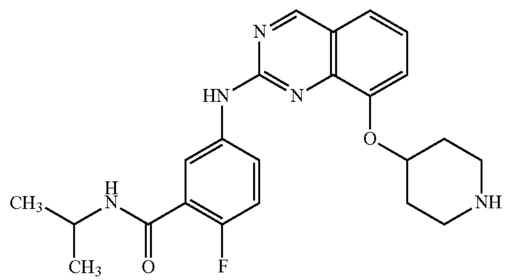 | 2-fluoro-N-isopropyl-5-(8-(piperidin-4-yloxy)quinazolin-2-ylamino)benzamide | 424.2, 2.08 | | ++++ | | ++++ | |
| 475 | 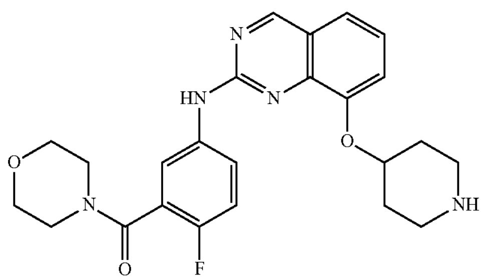 | (2-fluoro-5-(8-(piperidin-4-yloxy)quinazolin-2-ylamino)phenyl)(morpholino)methanone | 452.1, 1.93 | | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 476 | 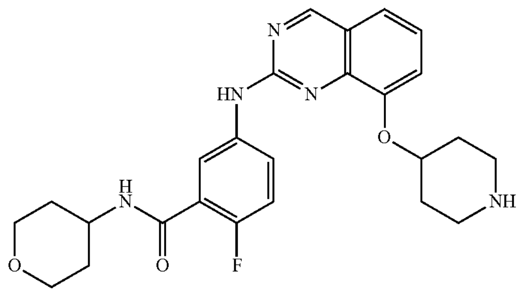 | 2-fluoro-5-(8-(piperidin-4-yloxy)quinazolin-2-ylamino)-N-(tetrahydro-2H-pyran-4-yl)benzamide | 466.1, 1.92 | | ++++ | | ++++ | |
| 477 | 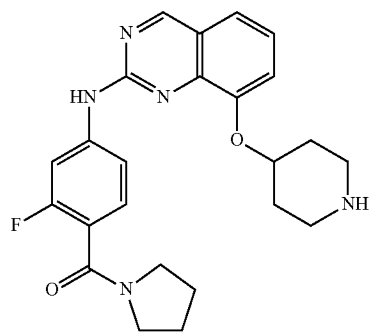 | (2-fluoro-4-(8-(piperidin-4-yloxy)quinazolin-2-ylamino)phenyl)(pyrrolidin-1-yl)methanone | 436.1, 2.12 | | ++++ | | ++++ | |
| 478 | 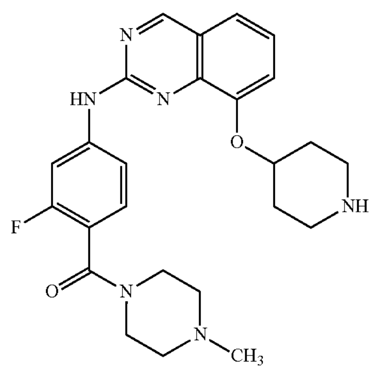 | (2-fluoro-4-(8-(piperidin-4-yloxy)quinazolin-2-ylamino)phenyl)(4-methylpiperazin-1-yl)methanone | 465.2, 1.71 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 479 | 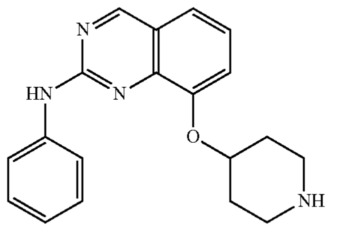 | N-phenyl-8-(piperidin-4-yloxy)quinazolin-2-amine | 321.1, 1.98 | example 9 step 3 then example 8 step 2 | ++++ | | ++++ | |
| 480 | 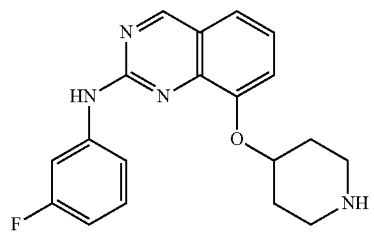 | N-(3-fluorophenyl)-8-(piperidin-4-yloxy)quinazolin-2-amine | 339.1, 2.13 | example 9 step 3 then example 8 step 2 | ++++ | | ++++ | |
| 481 | 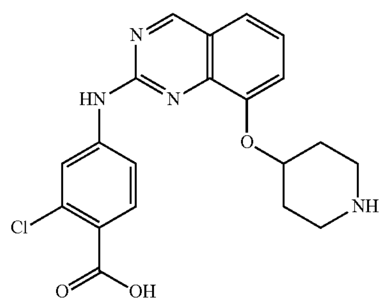 | 2-chloro-4-(8-(piperidin-4-yloxy)quinazolin-2-ylamino)benzoic acid | 399.1, 2.06 | example 9 step 3 then example 8 step 2 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 482 | 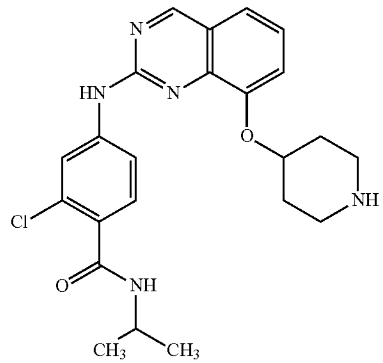 | 2-chloro-N-isopropyl-4-(8-(piperidin-4-yloxy)quinazolin-2-ylamino)benzamide | 440.1, 2.13 | | ++++ | | ++++ | |
| 483 | 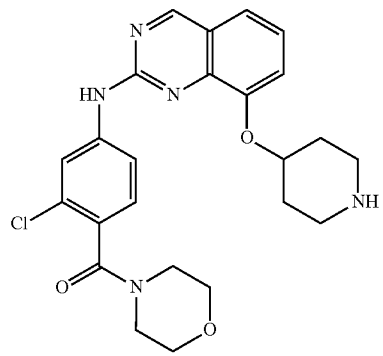 | (2-chloro-4-(8-(piperidin-4-yloxy)quinazolin-2-ylamino)phenyl)(morpholino)methanone | 468.1, 2.02 | | ++++ | | ++++ | |
| 484 | 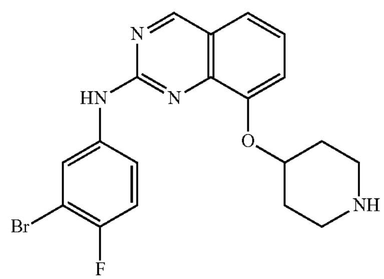 | N-(3-bromo-4-fluorophenyl)-8-(piperidin-4-yloxy)quinazolin-2-amine | 417.0/419.0, 2.32 | example 9 step 3 then example 8 step 2 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 485 | 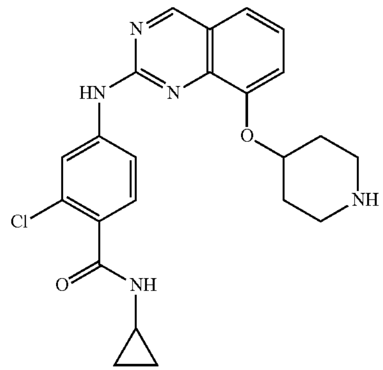 | 2-chloro-N-cyclopropyl-4-(8-(piperidin-4-yloxy)quinazolin-2-ylamino)benzamide | 438.1, 2.05 | | ++++ | | ++++ | |
| 486 | 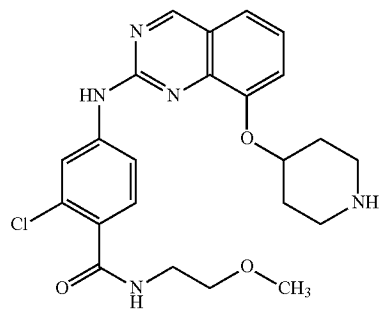 | 2-chloro-N-(2-methoxyethyl)-4-(8-(piperidin-4-yloxy)quinazolin-2-ylamino)benzamide | 456.1, 1.99 | | ++++ | | ++++ | |
| 487 | 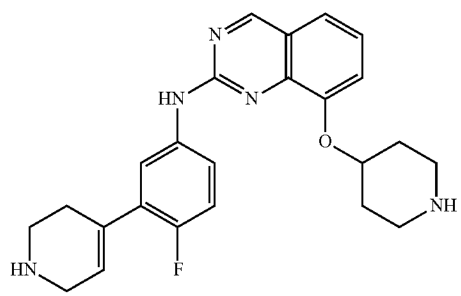 | N-(4-fluoro-3-(1,2,3,6-tetrahydropyridin-4-yl)phenyl)-8-(piperidin-4-yloxy)quinazolin-2-amine | 420.2, 1.78 | Suzuki (see example 8 step 1 and 2) | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 488 | 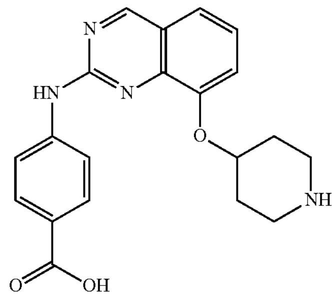 | 4-(8-(piperidin-4-yloxy)quinazolin-2-ylamino)benzoic acid | 365.1, 1.95 | example 9 step 3 then example 8 step 2 | ++++ | | ++++ | |
| 489 | 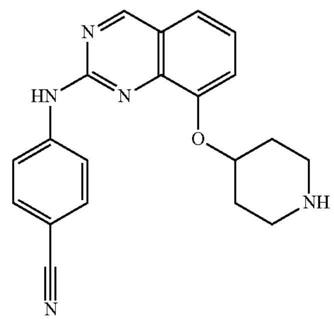 | 4-(8-(piperidin-4-yloxy)quinazolin-2-ylamino)benzonitrile | 346.1, 2.13 | example 9 step 3 then example 8 step 2 | ++++ | | ++++ | |
| 490 | 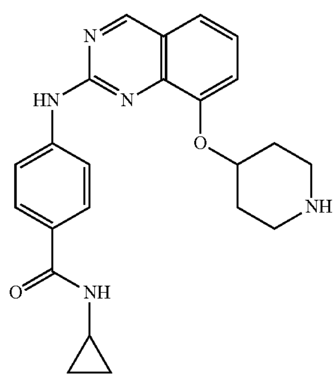 | N-cyclopropyl-4-(8-(piperidin-4-yloxy)quinazolin-2-ylamino)benzamide | 404.2, 1.95 | | ++++ | | ++++ | |

TABLE 3-continued

| Cmpd | Name | Structure | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 491 | N-isopropyl-4-(8-piperidin-4-yloxy)quinazolin-2-ylamino)benzamide | 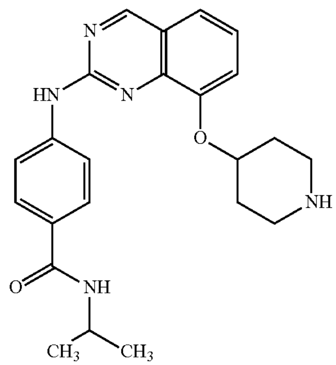 | 406.2, 2.03 | | ++++ | | ++++ | |
| 492 | N-(2-methylethyl)-4-(8-piperidin-4-yloxy)quinazolin-2-ylamino)benzamide | 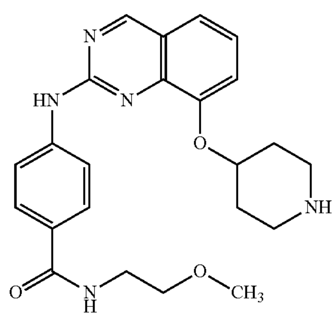 | 422.2, 1.91 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 493 | 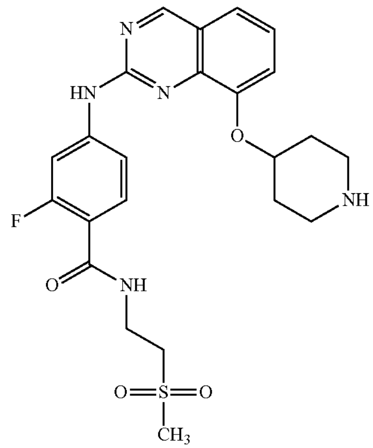 | 2-fluoro-N-(2-(methylsulfonyl)ethyl)-4-(8-(piperidin-4-yloxy)quinazolin-2-ylamino)benzamide | 488.1, 1.95 | | ++++ | | ++++ | |
| 494 | 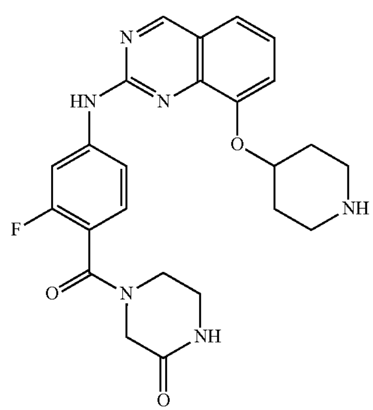 | 4-(2-fluoro-4-(8-(piperidin-4-yloxy)quinazolin-2-ylamino)benzoyl)piperazin-2-one | 465.2, 1.84 | | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 495 | 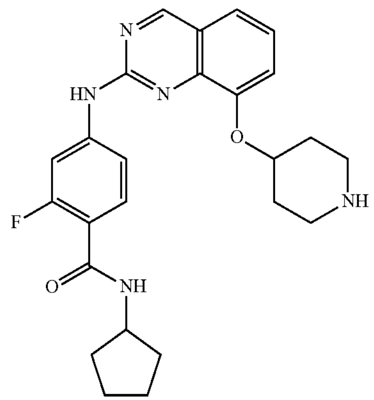 | N-cyclopentyl-2-fluoro-4-(8-(piperidin-4-yloxy)quinazolin-2-ylamino)benzamide | 450.2, 2.32 | | ++++ | | ++++ | |
| 496 | 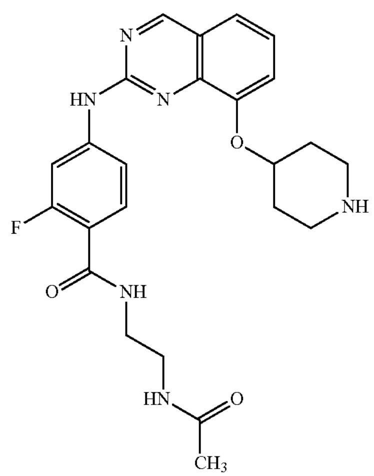 | N-(2-acetamidoethyl)-2-fluoro-4-(8-(piperidin-4-yloxy)quinazolin-2-ylamino)benzamide | 467.2, 1.89 | | ++++ | | +++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 497 | 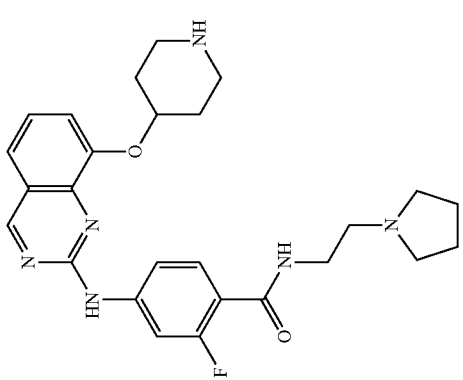 | 2-fluoro-4-(8-(piperidin-4-yloxy)quinazolin-2-ylamino)-N-(2-(pyrrolidin-1-yl)ethyl)benzamide | 479.2, 1.83 | | ++++ | | ++++ | |
| 498 | 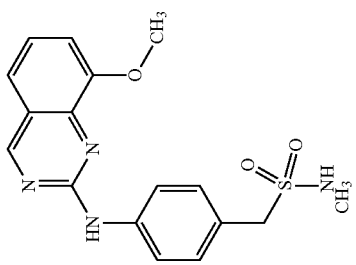 | 1-(4-(8-methoxyquinazolin-2-ylamino)phenyl)-N-methylmethanesulfonamide | 359.1 | Similar to example 2 | ++++ | +++ | | |

TABLE 3-continued

| Cmpd | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 499 | 8-isopropoxy-N-(4-(4-methylpiperazin-1-yl sulfonyl)phenyl)quinazolin-2-amine | 442.1 | Similar to example 2 | ++++ | +++ | | |
| 500 | (4-(8-methoxy-5-(trifluoromethyl)quinazolin-2-ylamino)phenyl)(morpholino)methanone | 433.2, 2.59 | Similar to example 51 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 501 | 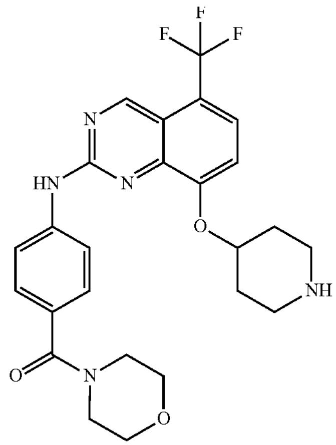 | morpholino(4-(8-(piperidin-4-yloxy)-5-(trifluoromethyl)quinazolin-2-ylamino)phenyl)methanone | 502.2, 2.29 | Similar to example 52 | ++++ | | +++ | |
| 502 | 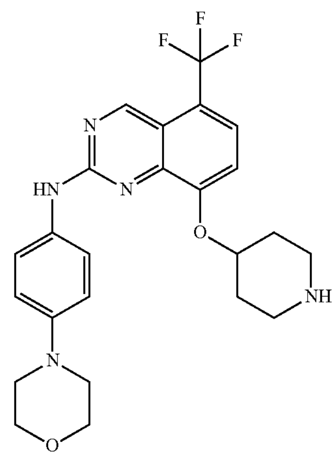 | N-(4-morpholinophenyl)-8-(piperidin-4-yloxy)-5-(trifluoromethyl)quinazolin-2-amine | 474.2, 2.16 | Similar to example 52 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 503 | 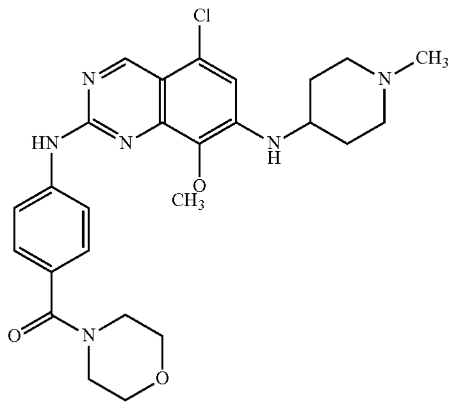 | (4-(5-chloro-8-methoxy-7-(1-methylpiperidin-4-ylamino)quinazolin-2-ylamino)phenyl)(morpholino)methanone | 48.1, 2.1 | Similar to example 34 | ++++ | | +++ | |
| 504 | 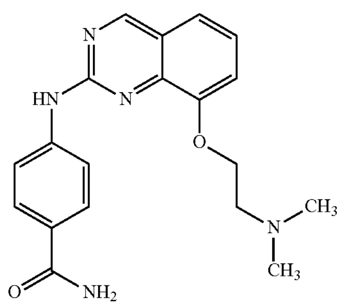 | 4-(8-(2-(dimethylamino)ethoxy)quinazolin-2-ylamino)benzamide | 352.1, 1.70 | Examples 1, using 4-aminobenzamide in place of sulfanilamide and N,N-dimethylethanolamine in place of 4-hydroxy-1-methylpiperidine | ++++ | ++++ | | |
| 505 | 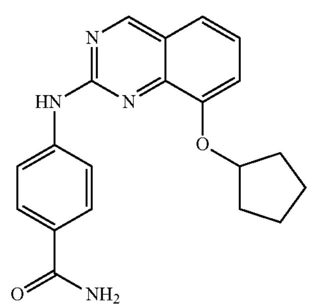 | 4-(8-(cyclopentyloxy)quinazolin-2-ylamino)benzamide | 349.1, 2.51 | Examples 1, using 4-aminobenzamide in place of sulfanilamide and cyclopentanol in place of 4-hydroxy-1-methylpiperidine | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 506 | 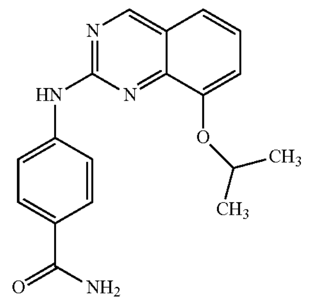 | 4-(8-isopropoxyquinazolin-2-ylamino)benzamide | 2.25, 323.2 | Examples 1, using 4-aminobenzamide in place of sulfanilamide and 2-propanol in place of 4-hydroxy-1-methylpiperidine | ++++ | ++++ | | |
| 507 | 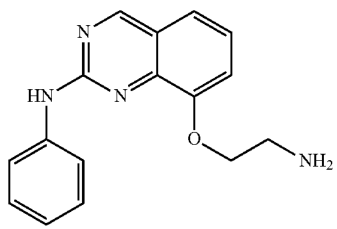 | 8-(2-aminoethoxy)-N-phenylquinazolin-2-amine | 281.1, 1.94 | Similar to Example 14 | ++++ | +++ | | |
| 508 | 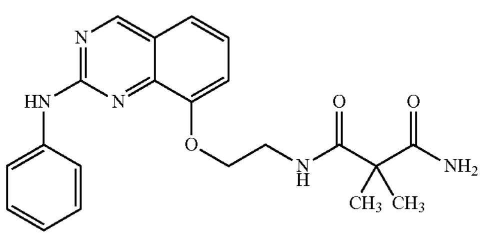 | 2,2-dimethyl-N1-(2-(2-(phenylamino)quinazolin-8-yloxy)ethyl)malonamide | 394.2, 2.07 | Similar to Example 15 | +++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 509 | 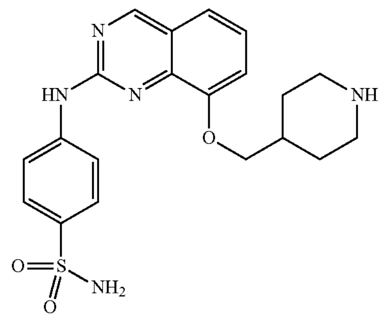 | 4-(8-(piperidin-4-ylmethoxy)quinazolin-2-ylamino)benzenesulfonamide | 414.1, 1.90 | Example 1, using 4-hydroxymethylpiperidine in place of 4-hydroxy-1-methylpiperidine | ++++ | ++++ | ++++ | ++++ |
| 510 | 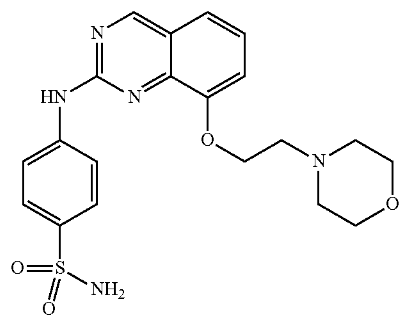 | 4-(8-(2-mropholinoethoxy)quinazolin-2-ylamino)benzenesulfonamide | 430.1, 1.77 | Example 1, using N-(2-hydroxyethyl)morpholine in place of 4-hydroxy-1-methylpiperidine | ++++ | ++++ | | |
| 511 | 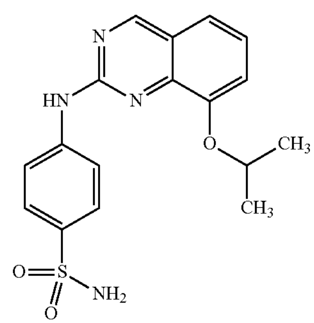 | 4-(8-isopropoxyquinazolin-2-ylamino)benzenesulfonamide | 359.1, 2.44 | Example 1, using 2-propanol in place of 4-hydroxy-1-methylpiperidine | ++++ | ++++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 512 | 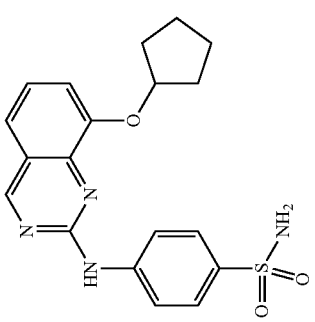 | 4-(8-(cyclopentyloxy)quinazolin-2-yl)amino)benzenesulfonamide | 385.1, 2.74 | Example 1, using cyclopropanol in place of 4-hydroxy-1-methylpiperidine | ++++ | ++++ | ++++ | |
| 513 | 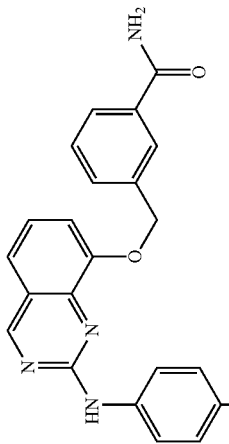 | 3-((2-(4-sulfamoylphenylamino)quinazolin-8-yloxy)methyl)benzamide | 450.0, 2.24 | Example 14 steps 1 and 2, using 3-chloromethylbenzamide in place of N-(2-bromoethyl)phthalimide and sulfanilamide in place of aniline | ++++ | ++++ | | |
| 514 | 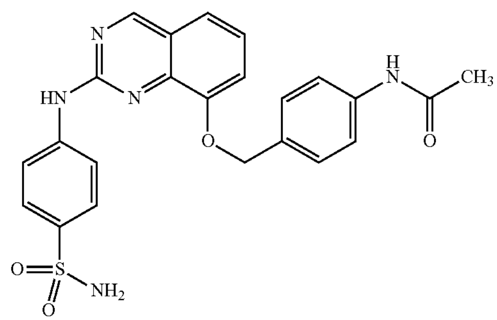 | N-(4-((2-(4-sulfamoylphenylamino)quinazolin-8-yloxy)methyl)phenyl)acetamide | 464.1, 2.32 | Example 14 steps 1 and 2, using 4-acetamidobenzyl chloride in place of N-(2-bromoethyl)phthalimide and sulfanilamide in place of aniline | ++++ | | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 515 | 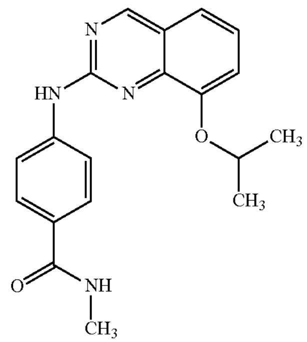 | 4-(8-isopropoxyquinazolin-2-ylamino)-N-methylbenzamide | 337.1, 2.33 | Similar to Example 16 | ++++ | ++++ | | |
| 516 | 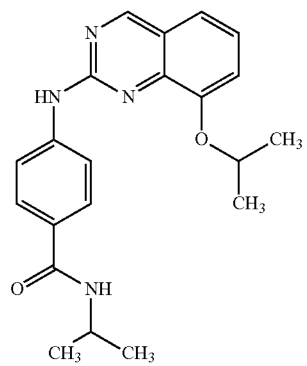 | 4-(8-isopropoxyquinazolin-2-ylamino)-N-isopropylbenzamide | 365.1, 2.67 | Example 16, using 4-amino-N-isopropylbenzamide in place of 4-amino-N-methylbenzamide | ++++ | ++++ | | |
| 517 | 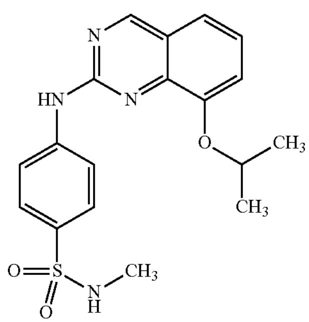 | 4-(8-isopropoxyquinazolin-2-ylamino)-N-methylbenzenesulfonamide | 373.1, 2.69 | Example 16, using 4-amino-N-methylbenzenesulfonamide in place of 4-amino-N-methylbenzamide | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 518 | 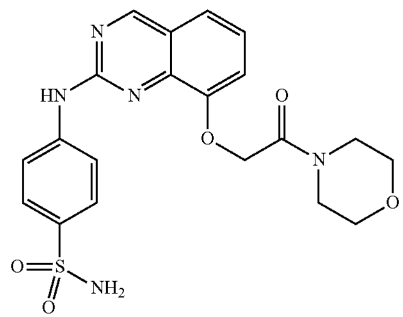 | 4-(8-(2-morpholino-2-oxoethoxy)quinazolin-2-ylamino)benzenesulfonamide | 444.0, 1.96 | Example 14 steps 1 and 2, using 2-chloro-1-morpholinoethan-1-one in place of N-(2-bromoethyl)phthalimide and sulfanilamide in place of aniline | +++ | +++ | | |
| 519 | 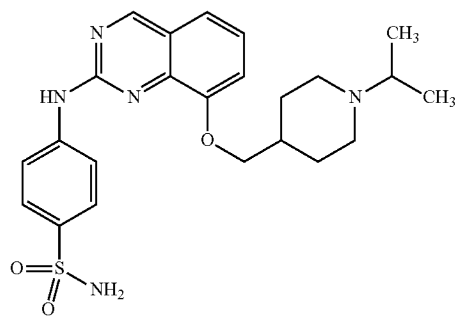 | 4-(8-((1-isopropylpiperidin-4-yl)methoxy)quinazolin-2-ylamino)benzenesulfonamide | 456.1, 2.00 | Example 1, using 4-hydroxymethyl-N-isopropylpiperidine in place of 4-hydroxy-1-methylpiperidine | ++++ | ++++ | ++++ | |
| 520 | 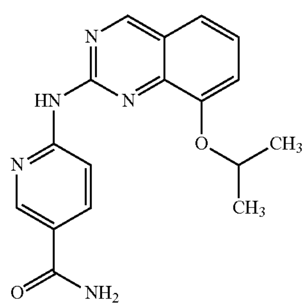 | 6-(8-isopropoxyquinazolin-2-ylamino)nicotinamide | 324.1, 1.87 | Similar to Example 16, using 2-aminonicotinamide in place of 4-amino-N-methylbenzamide | + | +++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 521 | 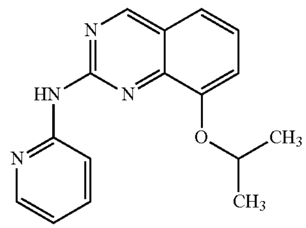 | 8-isopropoxy-N-(pyridin-2-yl)quinazolin-2-amine | 281.1, 2.09 | Similar to Example 16, using 2-aminonicotinamide in place of 4-amino-N-methylbenzamide | + | +++ | ++++ | |
| 522 | 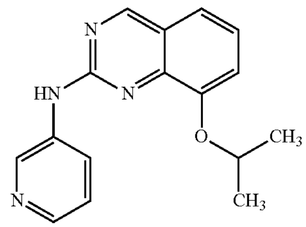 | 8-isopropoxy-N-(pyridin-3-yl)quinazolin-2-amine | 281.1, 1.98 | Similar to Example 16, using 3-aminopyridine in place of 4-amino-N-methylbenzamide | + | +++ | | |
| 523 | 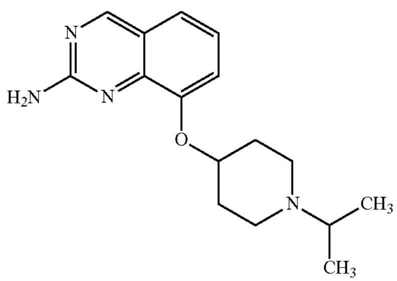 | 8-(1-isopropylpiperidin-4-yloxy)quinazolin-2-amine | 287.2, 1.22 | Similar to Example 19 | +++ | | +++ | |
| 524 | 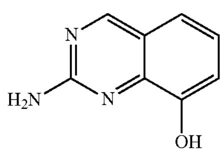 | 2-aminoquinazolin-8-ol | 162.1, 0.70 | Example 19, starting with 2-chloroquinazolin-8-ol in place of 2-chloro-8-(1-isopropylpiperidin-4-yloxy)quinazoline | ++ | | ++++ | |

TABLE 3-continued

| Cmpd | Structure Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 525 | N-(3-(8-(1-isopropylpiperidin-4-yloxy)quinazolin-2-ylamino)phenyl)pyrrolidine-1-carboxamide | 475.2, 2.02 | Example 13, using 2-chloro-8-(1-isopropylpiperidin-4-yloxy)quinazoline in place of 2-chloro-8-methoxyquinazoline and N-(3-aminophenyl)pyrrolidine-1-carboxamide in place of 3,5-dimethoxyaniline | ++++ | | ++++ | |
| 526 | N-(3,5-dimethoxyphenyl)-8-(1-isopropylpiperidin-4-yloxy)quinazolin-2-amine | 423.1, 2.29 | Example 13, using 2-chloro-8-(1-isopropylpiperidin-4-yloxy)quinazoline in place of 2-chloro-8-methoxyquinazoline | ++++ | | +++ | |
| 527 | N-(3-fluorophenyl)-8-(1-isopropylpiperidin-4-yloxy)quinazolin-2-amine | 381.1, 2.29 | Example 18 step 2, using 3-fluoroaniline in place of 2-(4-aminophenyl)-N-methylacetamide | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 528 | 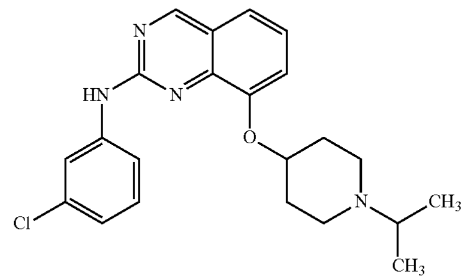 | N-(3-chlorophenyl)-8-(1-isopropylpiperidin-4-yloxy)quinazolin-2-amine | 397.1, 2.41 | Example 18 step 2, using 3-chloroaniline in place of 2-(4-aminophenyl)-N-methylacetamide | ++++ | | ++++ | |
| 529 | 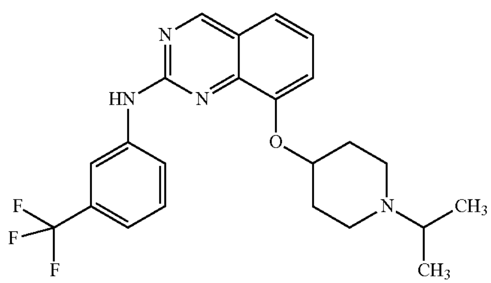 | 8-(1-isopropylpiperidin-4-yloxy)-N-(3-(trifluoromethyl)phenyl)quinazolin-2-amine | 431.1, 2.52 | Example 18 step 2, using 3-trifluoromethylaniline in place of 2-(4-aminophenyl)-N-methylacetamide | ++++ | | ++++ | |
| 530 | 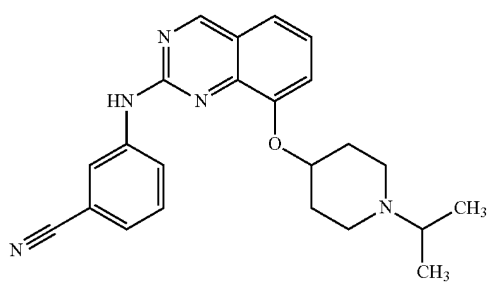 | 3-(8-(1-isopropylpiperidin-4-yloxy)quinazolin-2-ylamino)benzonitrile | 388.1, 2.25 | Example 18 step 2, using 3-aminobenzonitrile in place of 2-(4-aminophenyl)-N-methylacetamide | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 531 | 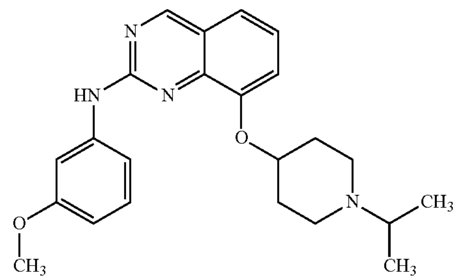 | 8-(1-isopropylpiperidin-4-yloxy)-N-(3-methoxyphenyl)quinazolin-2-amine | 393.1, 2.20 | Example 18 step 2, using 3-methoxyaniline in place of 2-(4-aminophenyl)-N-methylacetamide | ++++ | | +++ | |
| 532 | 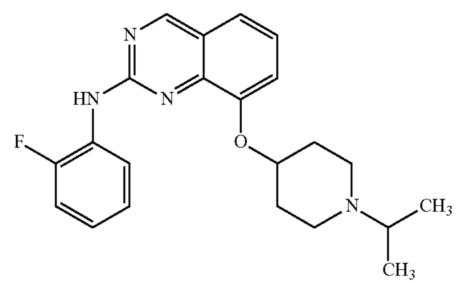 | N-(2-fluorophenyl)-8-(1-isopropylpiperidin-4-yloxy)quinazolin-2-amine | 381.1, 2.24 | Example 18 step 2, using 2-fluoroaniline in place of 2-(4-aminophenyl)-N-methylacetamide | +++ | | +++ | |
| 533 | 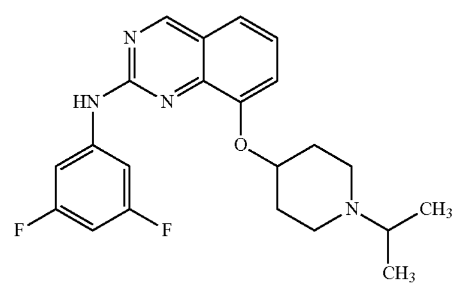 | N-(3,5-difluorophenyl)-8-(1-isopropylpiperidin-4-yloxy)quinazolin-2-amine | 399.1, 2.41 | Example 18 step 2, using 3,5-difluoroaniline in place of 2-(4-aminophenyl)-N-methylacetamide | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 534 | 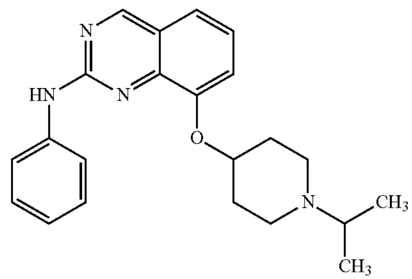 | 8-(1-isopropylpiperidin-4-yloxy)-N-phenylquinazolin-2-amine | 363.2, 2.13 | Example 18 step 2, using aniline in place of 2-(4-aminophenyl)-N-methylacetamide | ++++ | | ++++ | |
| 535 | 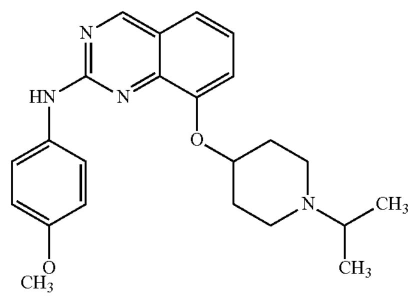 | 8-(1-isopropylpiperidin-4-yloxy)-N-(4-methoxyphenyl)quinazolin-2-amine | 393.1, 2.06 | Example 18 step 2, using 4-methoxyaniline in place of 2-(4-aminophenyl)-N-methylacetamide | ++++ | | +++ | |
| 536 | 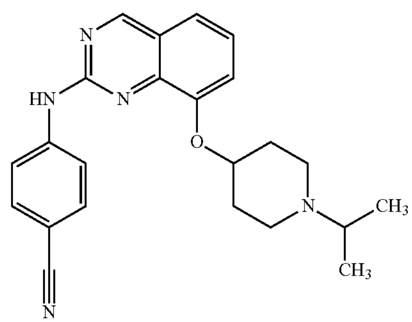 | 4-(8-(1-isopropylpiperidin-4-yloxy)quinazolin-2-ylamino)benzonitrile | 388.1, 2.22 | Example 18 step 2, using 4-aminobenzonitrile in place of 2-(4-aminophenyl)-N-methylacetamide | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 537 | 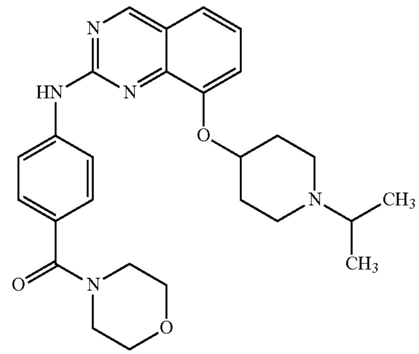 | (4-(8-(1-isopropylpiperidin-4-yloxy)quinazolin-2-ylamino)phenyl)(morpholino)methanone | 476.2, 1.99 | Example 18 step 2, using (4-aminophenyl)(morpholino)methanone in place of 2-(4-aminophenyl)-N-methylacetamide | ++++ | | +++ | |
| 538 | 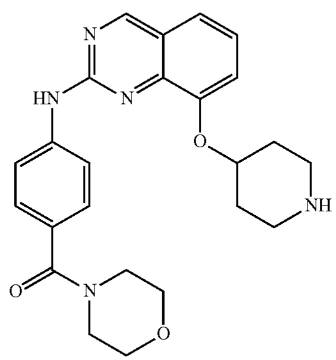 | morpholino(4-(8-(piperidin-4-yloxy)quinazolin-2-ylamino)phenyl)methanone | 434.1, 1.90 | Similar to Example 20 | ++++ | | ++++ | |
| 539 | 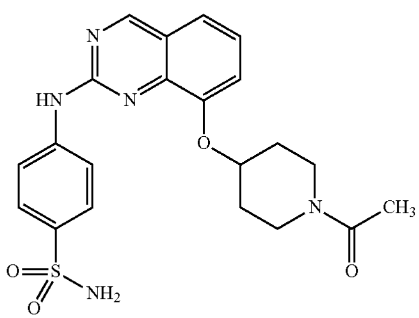 | 4-(8-(1-acetylpiperidin-4-yloxy)quinazolin-2-ylamino)benzenesulfonamide | 442.0, 2.15 | Similar to Example 21 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 540 | 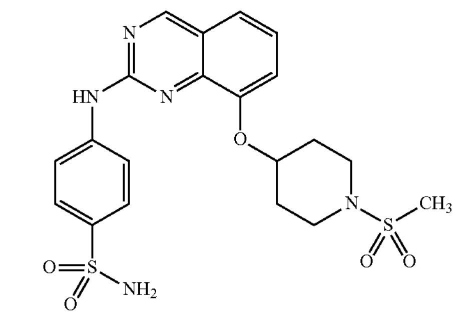 | 4-(8-(1-(methylsulfonyl)piperidin-4-yloxy)quinazolin-2-ylamino)benzenesulfonamide | 478.0, 2.33 | Similar to Example 21, using methanesulfonyl chloride in place of acetyl chloride | ++++ | | ++++ | |
| 541 | 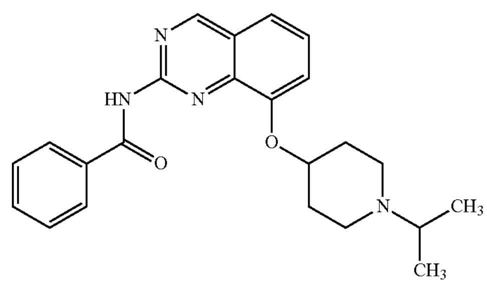 | N-(8-(1-isopropylpiperidin-4-yloxy)quinazolin-2-yl)benzamide | | | + | | +++ | |
| 542 | 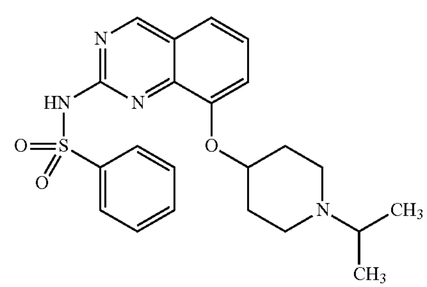 | N-(8-(1-isopropylpiperidin-4-yloxy)quinazolin-2-yl)benzenesulfonamide | | | + | | +++ | |

TABLE 3-continued

| Cmpd | Name | Structure | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 543 | 2-(1-isopropylpiperidin-4-ylamino)quinazolin-8-ol | 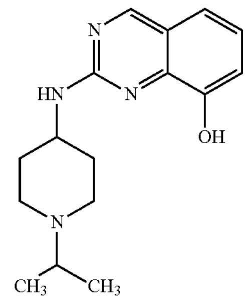 | | | + | | +++ | |
| 544 | N-(8-(1-isopropylpiperidin-4-yloxy)quinazolin-2-yl)acetamide | 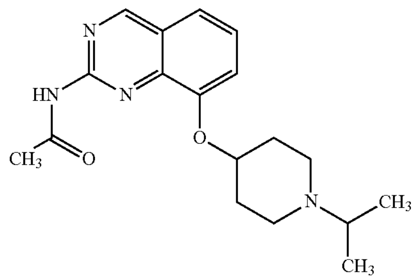 | | | + | | +++ | |
| 545 | N-(3-morpholinophenyl)-8-(piperidin-4-yloxy)quinazolin-2-amine | 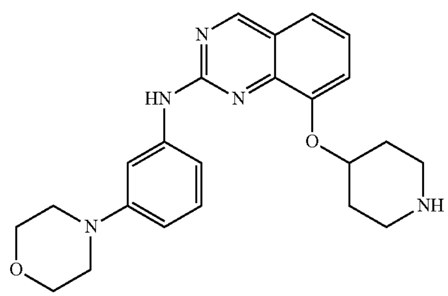 | 406.2, 1.87 | Example 20 steps 2 and 3, using 3-morpholinoaniline in place of (4-aminophenyl)(morpholino)methanone | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 546 | 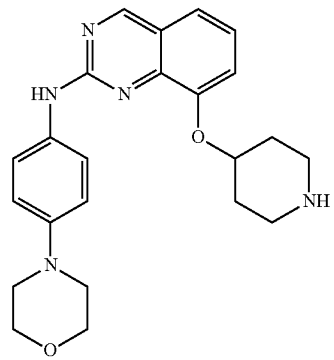 | N-(4-morpholinophenyl)-8-(piperidin-4-yloxy)quinazolin-2-amine | 406.2, 1.82 | Example 20 steps 2 and 3, using 4-morpholinoaniline in place of (4-aminophenyl)(morpholino)methanone | +++ | | ++++ | |
| 547 | 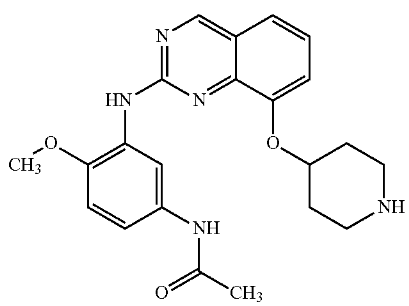 | N-(4-methoxy-3-(8-(piperidin-4-yloxy)quinazolin-2-ylamino)phenyl)acetamide | 408.1, 1.79 | Example 20 steps 2 and 3, using 3-amino-4-methoxyacetanilide in place of (4-aminophenyl)(morpholino)methanone | +++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 548 | 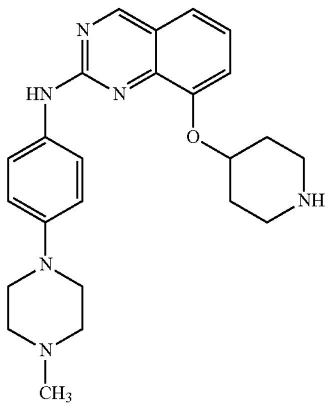 | N-(4-(4-methylpiperazin-1-yl)phenyl)-8-(piperidin-4-yloxy)quinazolin-2-amine | 419.2, 1.61 | Example 20 steps 2 and 3, using 3-amino-4-methoxyacetanilide in place of (4-aminophenyl)(morpholino)methanone | ++++ | | ++++ | |
| 549 | 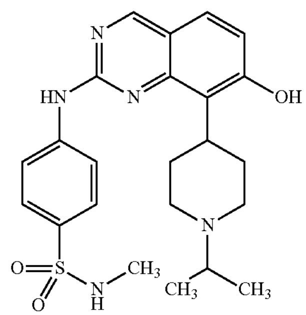 | 4-(7-(hydroxy-8-(1-isopropylpiperidin-4-yl)quinazolin-2-ylamino)-N-methylbenzenesulfonamide | 456.1, 2.10 | Example 1, using 3-(8-hydroxyquinazolin-2-ylamino)benzenesulfonamide and using methanol in place of 4-hydroxy-1-methylpipeidine | ++++ | | ++++ | |
| 550 | 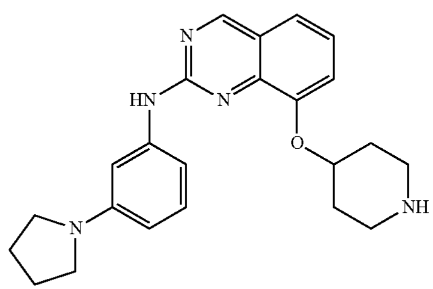 | 8-(piperidin-4-yloxy)-N-(3-(pyrrolidin-1-yl)phenyl)quinazolin-2-amine | 390.1, 1.85 | Example 20 steps 2 and 3, using 3-pyrrolidin-1-ylaniline in place of (4-aminophenyl)(morpholino)methanone | ++++ | | +++ | |

TABLE 3-continued

| Cmpd | Structure Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 551 | 8-(1-isopropylpiperidin-4-yloxy)-N-(3-(pyrrolidin-1-yl)phenyl)quinazolin-2-amine | 432.1, 2.10 | Example 18 step 2, using 3-pyrrolidin-1-ylaniline in place of 2-(4-aminophenyl)-N-methylacetamide | ++++ | | +++ | |
| 552 | 4-(4-(8-(1-isopropylpiperidin-4-yloxy)quinazolin-2-yl)piperazin-1-yl)aniline | 447.1, 1.80 | Example 18 step 2, using 4-(4-methylpiperazin-1-yl)phenylamine in place of 2-(4-aminophenyl)-N-methylacetamide | ++ | | +++ | |
| 553 | 8-(1-isopropylpiperidin-4-yloxy)-N-(4-morpholinophenyl)-6-(thiazol-2-yl)quinazolin-2-amine | 531.2, 2.12 | Example 22 step 1 using 4-morpholinoaniline in place of 3-morpholinoaniline then 214 step 2 | ++++ | | ++++ | |

TABLE 3-continued

| Cmpd | Structure | Name | LC/MS (M+1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 554 | 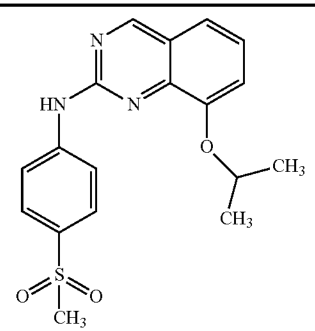 | 8-isopropoxy-N-(4-(methylsulfonyl)phenyl)quinazolin-2-amine | 358.1, 3.59 | Example 2 | ++++ | ++++ | | |
| 555 | 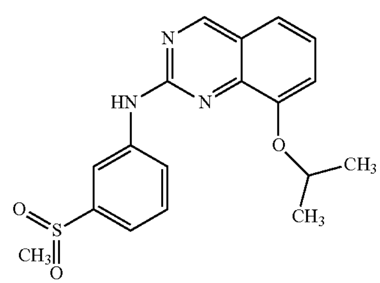 | 8-isopropoxy-N-(3-(methylsulfonyl)phenyl)quinazolin-2-amine | 358.1, 3.47 | Example 2 | ++++ | ++++ | | |
| 556 | 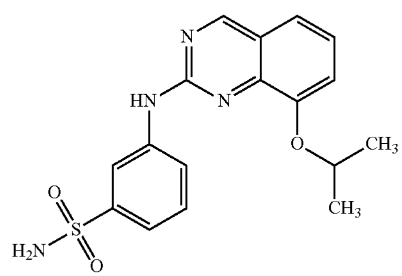 | 3-(8-isopropoxyquinazolin-2-ylamino)benzenesulfonamide | 359.1, 2.72 | Example 2 | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 557 | 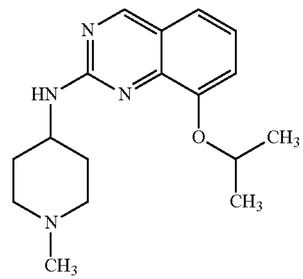 | 8-isopropoxy-N-(1-methylpiperidin-4-yl)quinazolin-2-amine | 301.1, 1.8 | Example 2 | + | +++ | | |
| 558 | 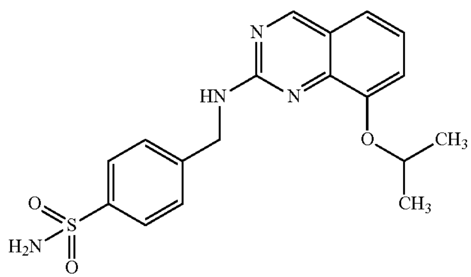 | 4-((8-isopropoxyquinazolin-2-ylamino)methyl)benzenesulfonamide | 373.1, 2.31 | Example 2 | + | +++ | | |
| 559 | 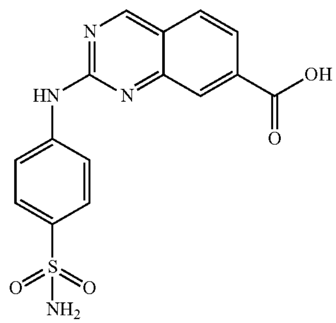 | 2-(4-sulfamoylphenylamino)quinazoline-7-carboxylic acid | 345, 2.32 | Example 29 Steps 1 to 6 | ++++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 560 | 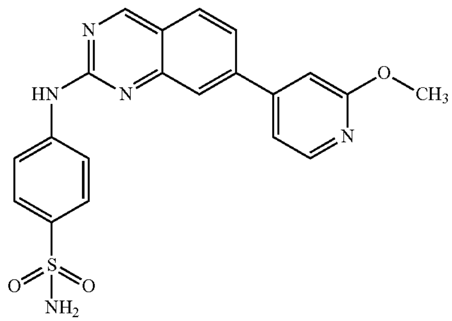 | 4-(7-(2-methoxypyridin-4-yl)quinazolin-2-ylamino)benzenesulfonamide | 408, 2.94 | Example 29 Step 1 to 2 | + | +++ | | |
| 561 | 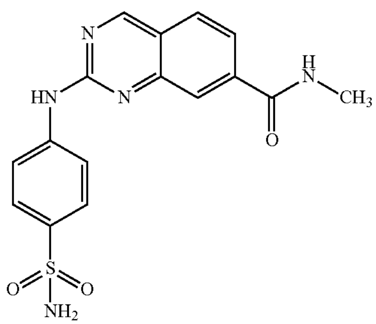 | N-methyl-2-(4-sulfamoylphenylamino)quinazoline-7-carboxamide | 358, 2.0 | Example 29 Steps 1 to 6 | ++++ | ++++ | | |
| 562 | 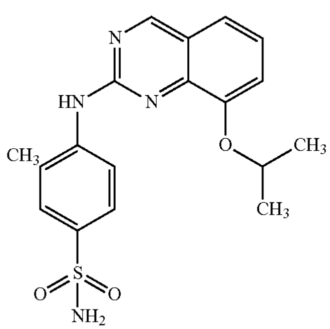 | 4-(8-isopropoxyquinazolin-2-ylamino)-3-methylbenzenesulfonamide | 373.1, 2.83 | Example 2 | ++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 563 | 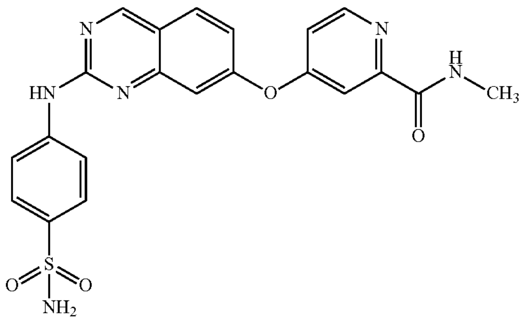 | N-methyl-4-(2-(4-sulfamoylphenylamino)quinazolin-7-yloxy)picolinamide | 451.1, 2.22 | Example 29 | + | +++ | | |
| 564 | 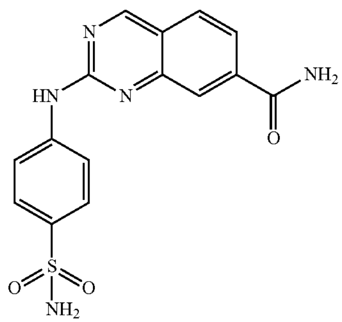 | 2-(4-sulfamoylphenylamino)quinazoline-7-carboxamide | 344, 1.85 | Example 29 Steps 1 to 6 | ++++ | ++++ | | |
| 565 | 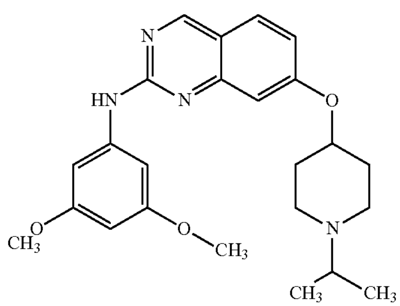 | N-(3,5-dimethoxyphenyl)-7-(1-isopropylpiperidin-4-yloxy)quinazolin-2-amine | 423.2, 2.4 | Example 42 and Example 31 | +++ | | +++ | |

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 566 | 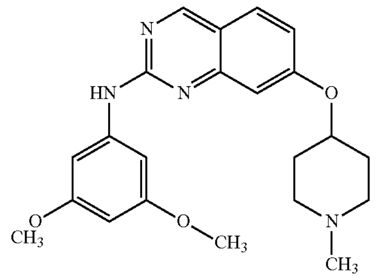 | N-(3,5-dimethoxyphenyl)-7-(1-methylpiperidin-4-yloxy)quinazolin-2-amine | 395.2, 2.34 | Example 42 and Example 32 | ++++ | | ++++ | |
| 567 | 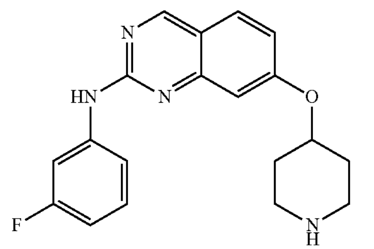 | N-(3-fluorophenyl)-7-(piperidin-4-yloxy)quinazolin-2-amine | 339.1, 2.4 | Example 42 and Example 32 | ++++ | | ++++ | |
| 568 | 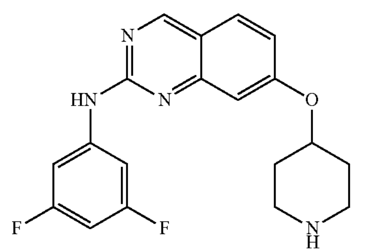 | N-(3,5-difluorophenyl)-7-(piperidin-4-yloxy)quinazolin-2-amine | 357.1, 2.4 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 569 | 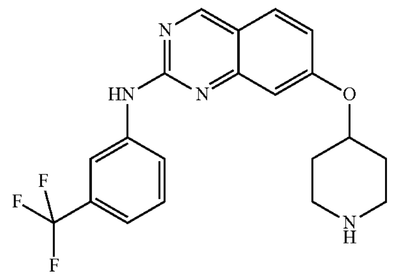 | 7-(piperidin-4-yloxy)-N-(3-(trifluoromethyl)phenyl)quinazolin-2-amine | 389.1, 2.81 | Example 42 and Example 32 | ++++ | | ++++ | |
| 570 | 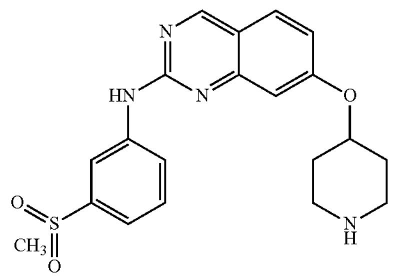 | N-(3-(methylsulfonyl)phenyl)-7-(piperidin-4-yloxy)quinazolin-2-amine | 399.1, 2.0 | Example 42 and Example 32 | ++++ | | ++++ | |
| 571 | 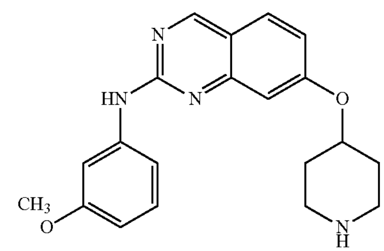 | N-(3-methoxyphenyl)-7-(piperidin-4-yloxy)quinazolin-2-amine | 351.1, 2.1 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 572 | 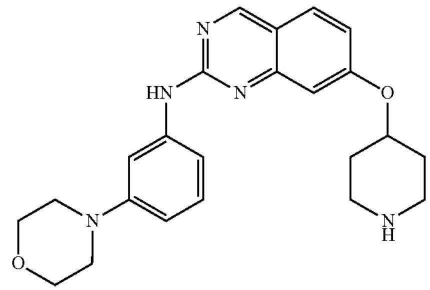 | N-(3-morpholinophenyl)-7-(piperidin-4-yloxy)quinazolin-2-amine | 406.1, 1.9 | Example 42 and Example 32 | ++++ | | ++++ | |
| 573 | 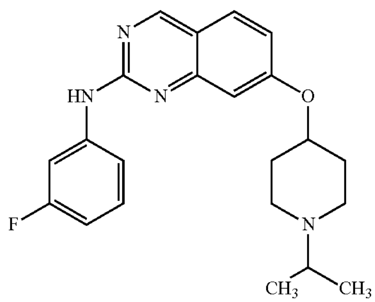 | N-(3-fluorophenyl)-7-(1-isopropylpiperidin-4-yloxy)quinazolin-2-amine | 381.1, 2.62 | Example 42 and Example 32 | ++++ | | +++ | |
| 574 | 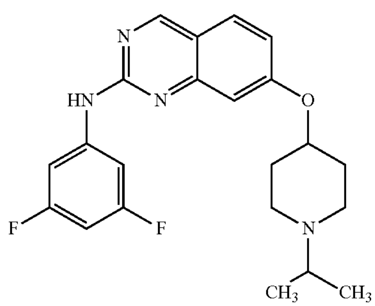 | N-(3,5-difluorophenyl)-7-(1-isopropylpiperidin-4-yloxy)quinazolin-2-amine | 399.1, 3.0 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 575 | 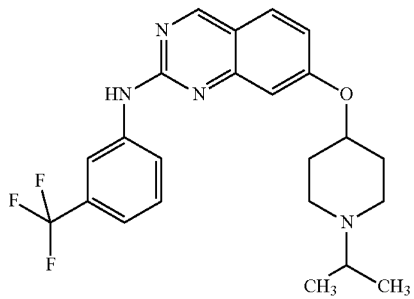 | 7-(1-isopropylpiperidin-4-yloxy)-N-(3-(trifluoromethyl)phenyl)quinazolin-2-amine | 431.1, 3.1 | Example 42 and Example 32 | ++++ | | ++++ | |
| 576 | 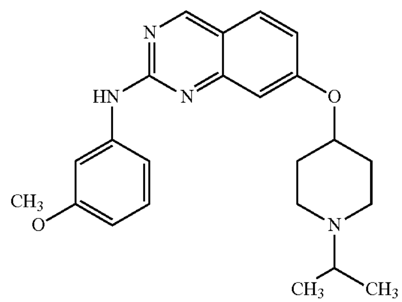 | 7-(1-isopropylpiperidin-4-yloxy)-N-(3-methoxyphenyl)quinazolin-2-amine | 393.2, 2.3 | Example 42 and Example 32 | ++++ | | +++ | |
| 577 | 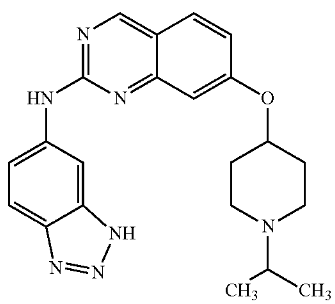 | N-(1H-benzo[d][1,2,3]triazol-6-yl)-7-(1-isopropylpiperidin-4-yloxy)quinazolin-2-amine | 404.1, 1.83 | Example 42 and Example 32 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 578 | 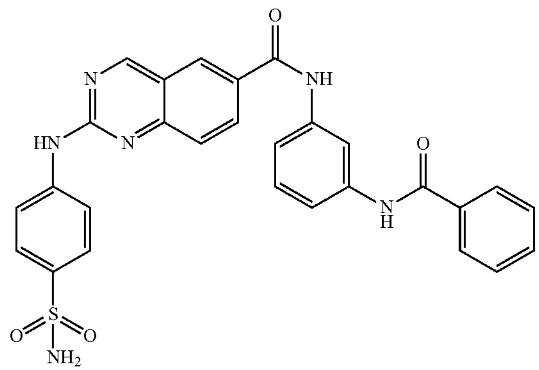 | N-(3-benzamidophenyl)-2-(4-sulfamoylphenylamino)quinazoline-6-carboxamide | 539.1, 3.42 | | + | | ++++ | |
| 579 | 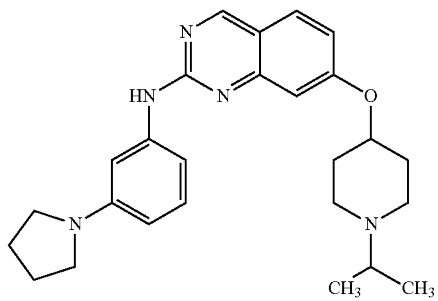 | 7-(1-isopropylpiperidin-4-yloxy)-N-(3-(pyrrolidin-1-yl)phenyl)quinazolin-2-amine | 432.2, 2.23 | Example 42 and Example 32 | ++++ | | +++ | |
| 580 | 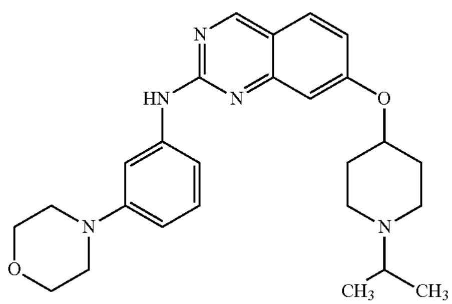 | 7-(1-isopropylpiperidin-4-yloxy)-N-(3-morpholinophenyl)quinazolin-2-amine | 448.2, 2.0 | Example 42 and Example 32 | +++ | | +++ | |

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 581 | 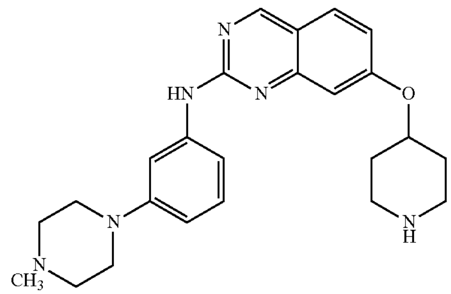 | N-(3-(4-methylpiperazin-1-yl)phenyl)-7-(piperidin-4-yloxy)quinazolin-2-amine | 419.2, 1.56 | Example 42 and Example 32 | ++++ | | ++++ | |
| 582 | 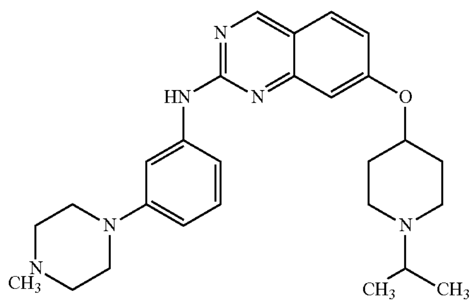 | 7-(1-isopropylpiperidin-4-yloxy)-N-(3-(4-methylpiperazin-1-yl)phenyl)quinazolin-2-amine | 461.3, 1.7 | Example 42 and Example 32 | ++++ | | +++ | |
| 583 | 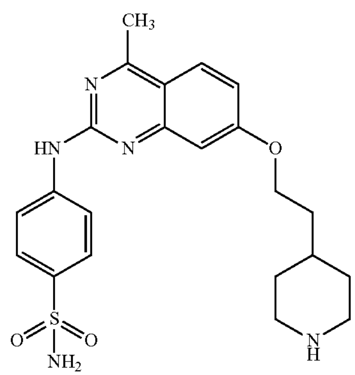 | 4-(4-methyl-7-(2-(piperidin-4-yl)ethoxy)quinazolin-2-ylamino)benzenesulfonamide | 442.2, 2.03 | Example 33 Steps 1 to 6 | ++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 584 | 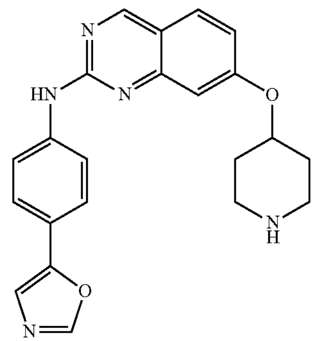 | N-(4-(oxazol-5-yl)phenyl)-7-(piperidin-4-yloxy)quinazolin-2-amine | 388.1, 2.2 | Example 42 and Example 32 | ++++ | | ++++ | |
| 585 | 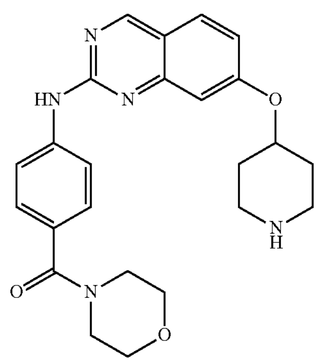 | morpholino(4-(7-(piperidin-4-yloxy)quinazolin-2-ylamino)phenyl)methanone | 434.2/1.8 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 586 | 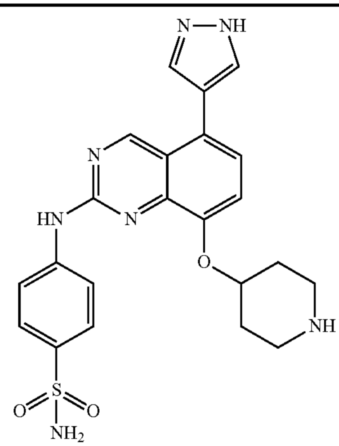 | 4-(8-(piperidin-4-yloxy)-5-(1H-pyrazol-4-yl)quinazolin-2-ylamino)benzensulfonamide | 466.1, 1.7 | Example 32 Steps 1 to 4 | +++ | | +++ | |
| 587 | 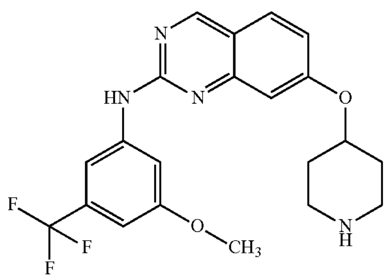 | N-(3-methoxy-5-(trifluoromethyl)phenyl)-7-(piperidin-4-yloxy)quinazolin-2-amine | 419.1, 2.91 | Example 42 and Example 32 | ++++ | | ++++ | |
| 588 | 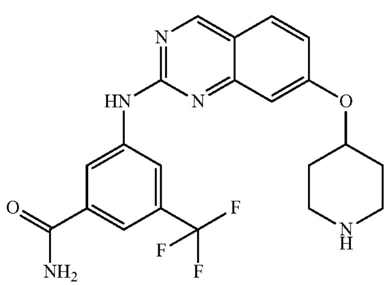 | 3-(7-(piperidin-4-yloxy)quinazolin-2-ylamino)-5-(trifluoromethyl)benzamide | 432.2, 2.3 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 589 | 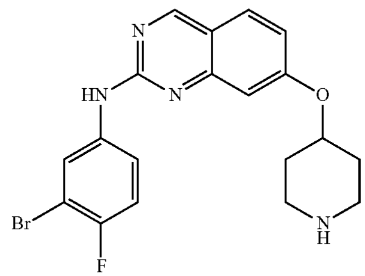 | N-(3-bromo-4-fluorophenyl)-7-(piperidin-4-yloxy)quinazolin-2-amine | 419.1, 2.61 | Example 42 and Example 32 | ++++ | | ++++ | |
| 590 | 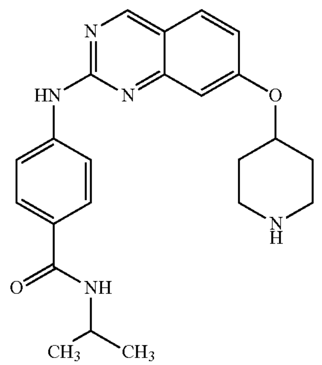 | N-isopropyl-4-(7-(piperidin-4-yloxy)quinazolin-2-ylamino)benzamide | 406.2, 2.02 | Example 42 and Example 32 | ++++ | | ++++ | |
| 591 | 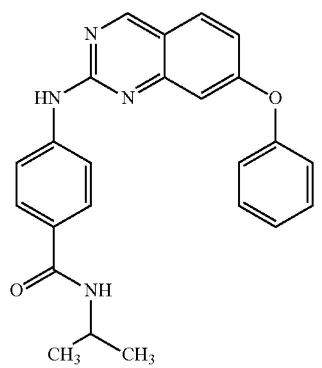 | N-isopropyl-4-(7-phenoxyquinazolin-2-ylamino)benzamide | 399.1, 3.9 | Example 58 | + | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 592 | 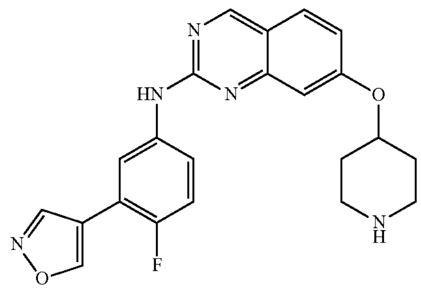 | N-(4-fluoro-3-(isoxazol-4-yl)phenyl)-7-(piperidin-4-yloxy)quinazolin-2-amine | 406.1, 2.5 | Example 42 and Example 32 | ++++ | | +++ | |
| 593 | 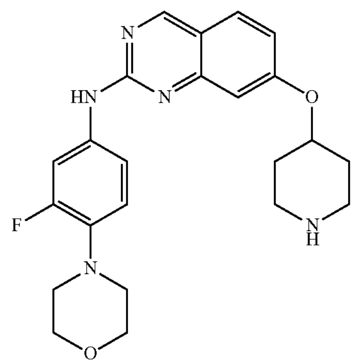 | N-(3-fluoro-4-morpholinophenyl)-7-(piperidin-4-yloxy)quinazolin-2-amine | 424.2, 2.1 | Example 42 and Example 32 | ++++ | | ++++ | |
| 594 | 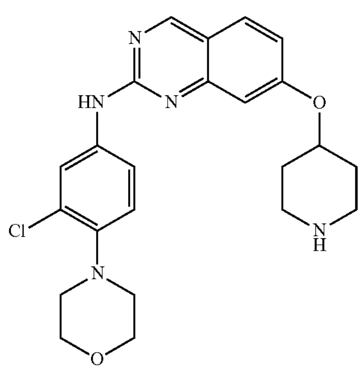 | N-(3-chloro-4-morpholinophenyl)-7-(piperidin-4-yloxy)quinazolin-2-amine | 440.1, 2.4 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 595 | 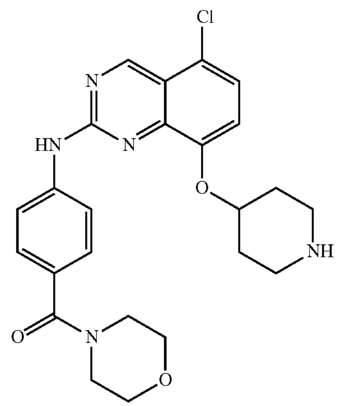 | (4-(5-chloro-8-(piperidin-4-yloxy)quinazolin-2-ylamino)phenyl)(morpholino)methanone | 468.1, 2.53 | Example 32 Steps 1 to 4 | ++++ | | +++ | |
| 596 | 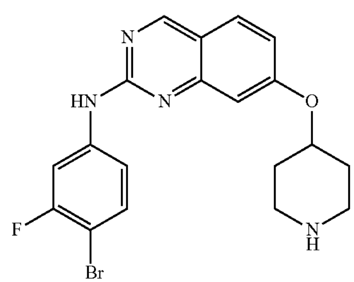 | N-(4-bromo-3-fluorophenyl)-7-(piperidin-4-yloxy)quinazolin-2-amine | 419.1, 2.9 | Example 42 and Example 32 | ++++ | | ++++ | |

TABLE 3-continued

| Cmpd | Structure | Name | LC/MS (M + 1(m/z), Rt(min) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 597 | 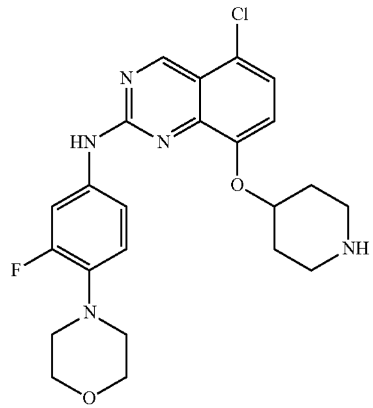 | 5-chloro-N-(3-fluoro-4-morpholinophenyl)-8-(piperidin-4-yloxy)quinazolin-2-amine | 458.1, 2.75 | Example 32 Steps 1 to 4 | ++++ | | +++ | |
| 598 | 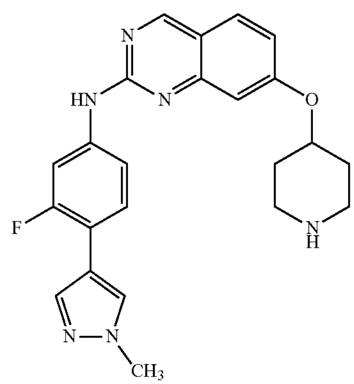 | N-(3-fluoro-4-(1-methyl-1H-pyrazol-4-yl)phenyl)-7-(piperidin-4-yloxy)quinazolin-2-amine | 417, 2.0 | Example 42 and Example 32 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 599 | 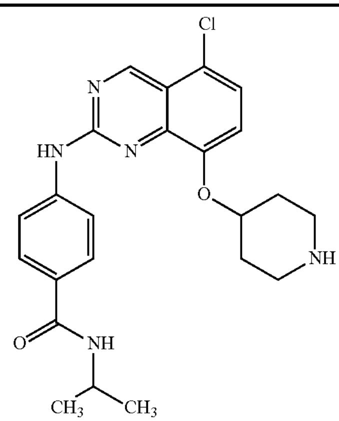 | 4-(5-chloro-8-(piperidin-4-yloxy)quinazolin-2-ylamino)-N-isopropylbenzamide | 440.2, 2.73 | Example 32 Steps 1 to 4 | ++++ | | ++++ | |
| 600 | 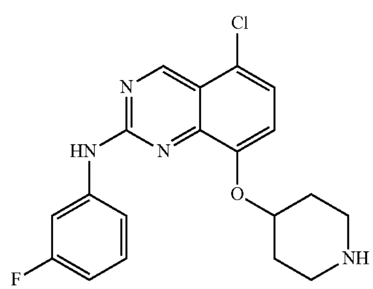 | 5-chloro-N-(3-fluorophenyl)-8-(piperidin-4-yloxy)quinazolin-2-amine | 373.1, 2.95 | Example 32 Steps 1 to 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 601 | 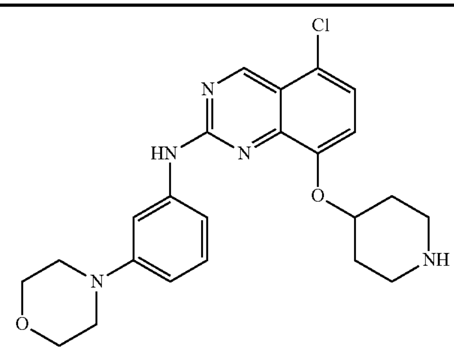 | 5-chloro-N-(3-morpholinophenyl)-8-(piperidin-4-yloxy)quinazolin-2-amine | 440.1, 2.4 | Example 32 Steps 1 to 4 | ++++ | | +++ | |
| 602 | 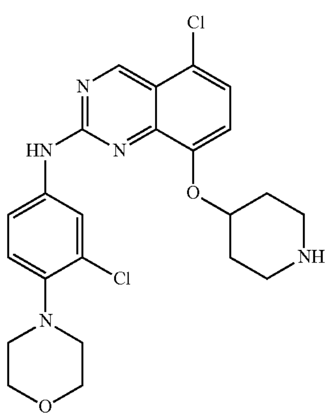 | 5-chloro-N-(3-chloro-4-morpholinophenyl)-8-(piperidin-4-yloxy)quinazolin-2-amine | 474.1, 2.96 | Example 32 Steps 1 to 4 | ++++ | | ++++ | |

TABLE 3-continued

| Cmpd | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 603 | 4-(5-chloro-8-(piperidin-4-yloxy)quinazolin-2-ylamino)-N-isopropylbenzenesulfonamide | 476.1, 2.82 | Example 32 Steps 1 to 4 | ++++ | | ++++ | |
| 604 | 4-(5-chloro-8-(piperidin-4-yloxy)quinazolin-2-ylamino)-N-cyclopropylbenzamide | 438.1, 2.6 | Example 32 Steps 1 to 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|------|-----------|------|------|------|------|------|------|------|
| 605 | 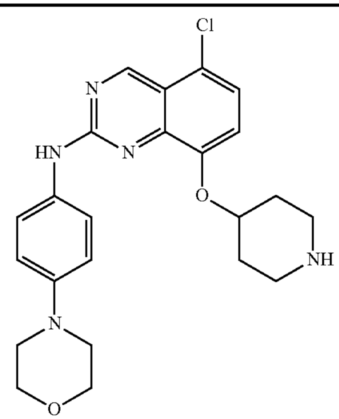 | 5-chloro-N-(4-morpholinophenyl)-8-(piperidin-4-yloxy)quinazolin-2-amine | 440.1, 2.1 | Example 32 Steps 1 to 4 | ++++ | | +++ | |
| 606 | 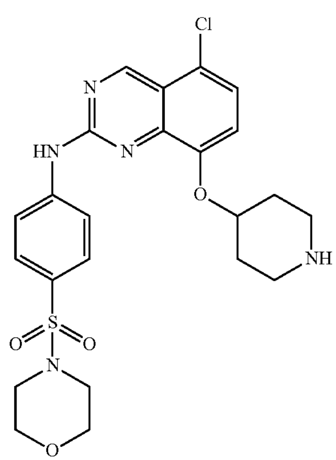 | 5-chloro-N-(4-(morpholinosulfonyl)phenyl)-8-(piperidin-4-yloxy)quinazolin-2-amine | 504, 2.8 | Example 32 Steps 1 to 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 607 | 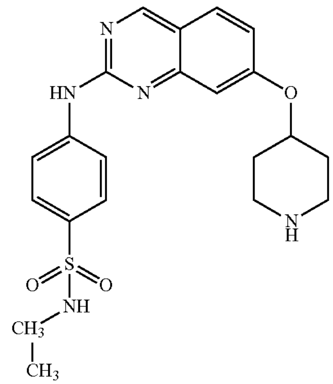 | N-isopropyl-4-(7-(piperidin-4-yloxy)quinazolin-2-ylamino)benzenesulfonamide | 442, 2.1 | Example 32 Steps 1 to 4 | ++++ | | ++++ | |
| 608 | 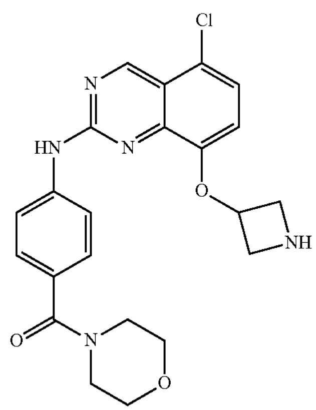 | (4-(8-(azetidin-3-yloxy)-5-chloroquinazolin-2-ylamino)phenyl)(morpholino)methanone | 440.2, 2.4 | Example 32 Steps 1 to 4 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 609 | 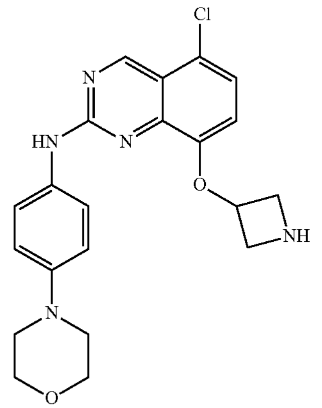 | 8-(azetidin-3-yloxy)-5-chloro-N-(4-morpholinophenyl)quinazolin-2-amine | 412.1, 2.01 | Example 32 Steps 1 to 4 | ++++ | | +++ | |
| 610 | 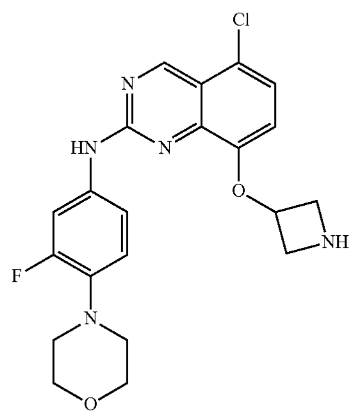 | 8-(azetidin-3-yloxy)-5-chloro-N-(3-fluoro-4-morpholinophenyl)quinazolin-2-amine | 430.1, 2.54 | Example 32 Steps 1 to 4 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 611 | 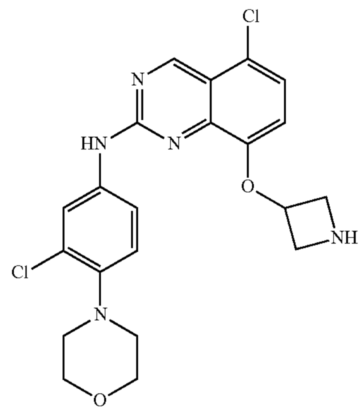 | 8-(azetidin-3-yloxy)-5-chloro-N-(3-chloro-4-morpholinophenyl)quinazolin-2-amine | 446.1, 2.9 | Example 32 Steps 1 to 4 | ++++ | | ++++ | |
| 612 | 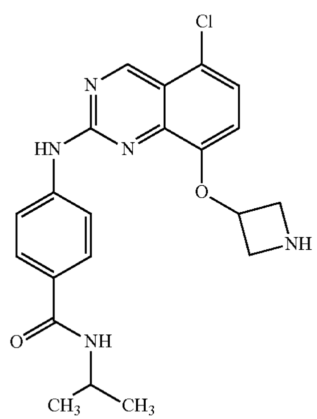 | 4-(8-(azetidin-3-yloxy)-5-chloroquinazolin-2-ylamino)-N-isopropylbenzamide | 412.2, 2.49 | Example 32 Steps 1 to 4 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 613 | 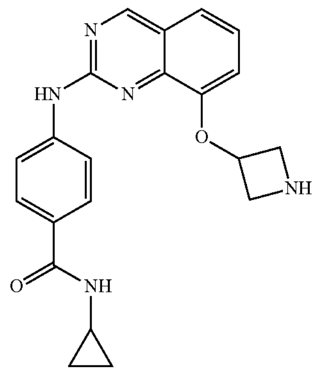 | 4-(8-(azetidin-3-yloxy)-5-chloroquinazolin-2-ylamino)-N-cyclopropylbenzamide | 410.1, 2.4 | Example 32 Steps 1 to 4 | ++++ | | ++++ | |
| 614 | 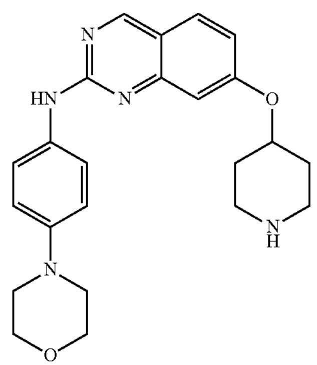 | N-(4-morpholinophenyl)-7-(piperidin-4-yloxy)quinazolin-2-amine | 406.2, 1.7 | Example 42 and Example 32 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 615 | 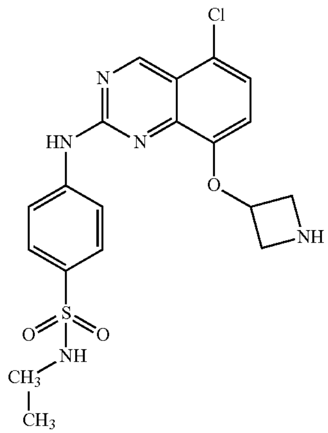 | 4-(8-(azetidin-3-yloxy)-5-chloroquinazolin-2-ylamino)-N-isopropylbenzenesulfonamide | 448.1, 2.72 | Example 32 Steps 1 to 4 | ++++ | | ++++ | |
| 616 | 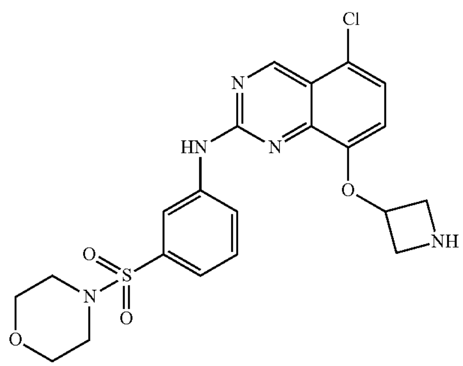 | 8-(azetidin-3-yloxy)-5-chloro-N-(3-(morpholinosulfonyl)phenyl)quinazolin-2-amine | 476.1, 2.6 | Example 32 Steps 1 to 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 617 | 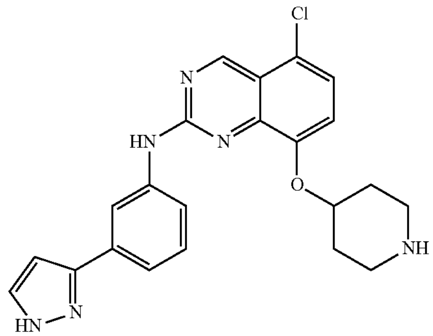 | N-(3-(1H-pyrazol-3-yl)phenyl)-5-chloro-8-(piperidin-4-yloxy)quinazolin-2-amine | 421.2, 2.7 | Example 32 Steps 1 to 4 | ++++ | | +++ | |
| 618 | 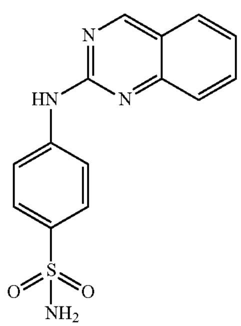 | 4-(quinazolin-2-ylamino)benzenesulfonamide | 301.1, 2.53 | Example 36 | ++++ | | +++ | |

TABLE 3-continued

| Cmpd | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|
| 619 | 7-(1-isopropylpiperidin-4-yloxy)-N-(4-morpholinophenyl)-6-(thiazol-2-yl)quinazolin-2-amine | 531.2, 2.2 | | ++++ | | ++++ | |
| 620 | 6-bromo-7-(1-isopropylpiperidin-4-yloxy)-N-(4-morpholinophenyl)quinazolin-2-amine | 526.2, 2.20 | | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 621 | 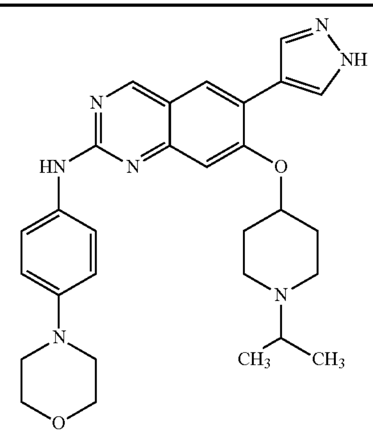 | 7-(1-isopropylpiperidin-4-yloxy)-N-(4-morpholinophenyl)-6-(1H-pyrazol-4-yl)quinazolin-2-amine | 514.3, 1.9 | | ++++ | | ++++ | |
| 622 | 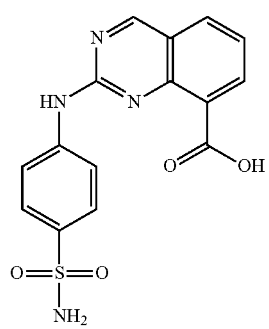 | 2-(4-sulfamoylphenylamino)quinazoline-8-carboxylic acid | | | +++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 623 | 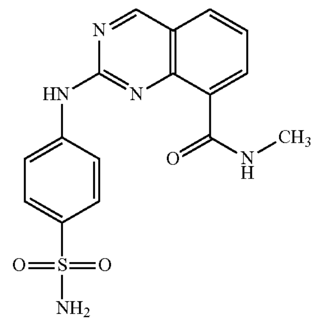 | N-methyl-2-(4-sulfamoylphenylamino)quinazoline-8-carboxamide | | | + | ++++ | | |
| 624 | 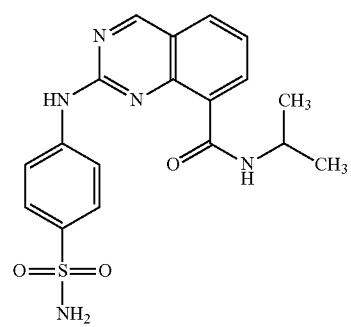 | N-isopropyl-2-(4-sulfamoylphenylamino)quinazoline-8-carboxamide | | | ++++ | ++++ | | |
| 625 | 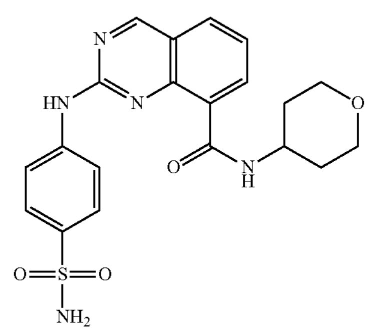 | 2-(4-sulfamoylphenylamino)-N-(tetrahydro-2H-pyran-4-yl)quinazoline-8-carboxamide | | | + | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 626 | 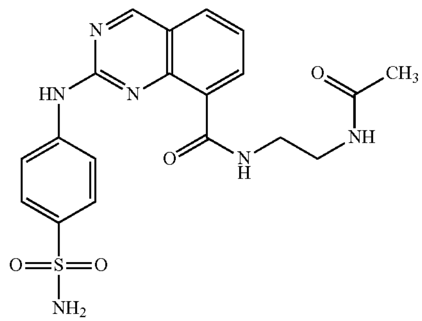 | N-(2-acetamidoethyl)-2-(4-sulfamoylphenylamino)quinazoline-8-carboxamide | | | + | +++ | | |
| 627 | 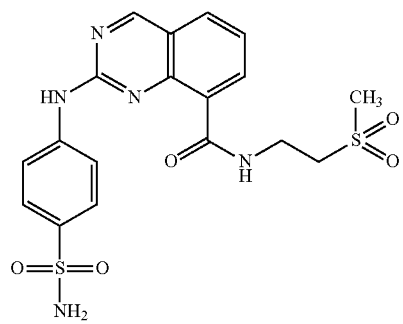 | N-(2-(methylsulfonyl)ethyl)-2-(4-sulfamoylphenylamino)quinazoline-8-carboxamide | | | + | +++ | | |
| 628 | 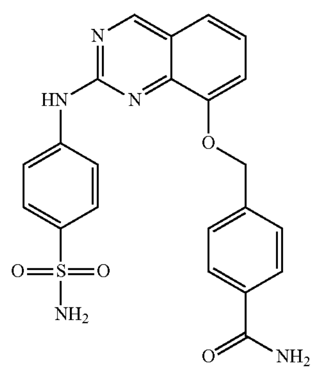 | 4-((2-(4-sulfamoylphenylamino)quinazolin-8-yloxy)methyl)benzamide | 450, 3.64 | Similar to Example 1 | ++++ | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 629 | 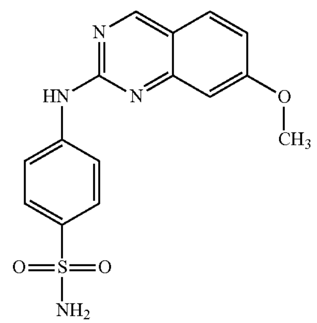 | 4-(7-methoxyquinazolin-2-ylamino)benzenesulfonamide | 331, 2.51 | Similar to Example 4 | ++++ | ++++ | | |
| 630 | 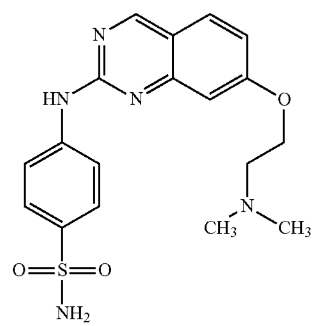 | 4-(7-(2-(dimethylamino)ethoxy)quinazolin-2-ylamino)benzenesulfonamide | 388, 1.76 | Similar to Example 4 | ++++ | +++ | | |
| 631 | 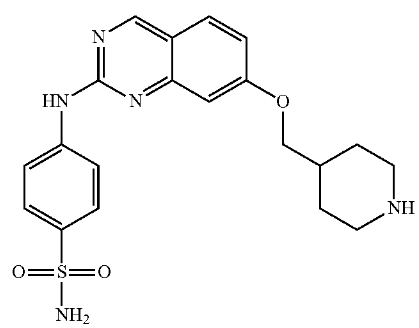 | 4-(7-(piperidin-4-ylmethoxy)quinazolin-2-ylamino)benzenesulfonamide | 414, 2.58 | Similar to Example 4 | ++++ | ++++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 632 | 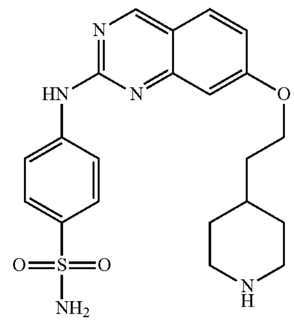 | 4-(7-(2-(piperidin-4-yl)ethoxy)quinazolin-2-ylamino)benzenesulfonamide | 428, 2.75 | Similar to Example 4 | ++++ | ++++ | | |
| 633 | 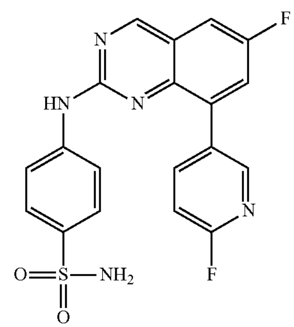 | 4-(6-fluoro-8-(6-fluoropyridin-3-yl)quinazolin-2-ylamino)benzenesulfonamide | 414, 4.38 | Similar to Example 24 | + | +++ | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 634 | 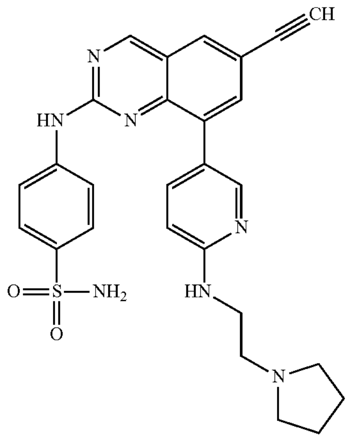 | 4-(6-ethynyl-8-(6-(2-(pyrrolidin-1-yl)ethylamino)pyridin-3-yl)quinazolin-2-ylamino)benzenesulfonamide | 514, 2.18 | Example 24 followed by SNAR reaction | ++++ | | ++++ | |
| 635 | 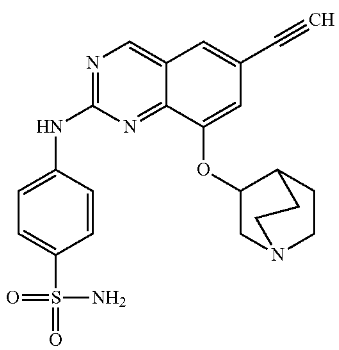 | 4-(6-ethynyl-8-(quinuclidin-3-yloxy)quinazolin-2-ylamino)benzenesulfonamide | 450, 2.39 | Similar to Example 9 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 636 | 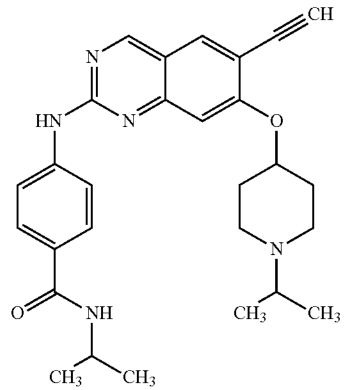 | 4-(6-ethynyl-7-(1-isopropylpiperidin-4-yloxy)quinazolin-2-ylamino)-N-isopropylbenzamide | 472, 2.65 | Example 27 | ++++ | | ++++ | |
| 637 | 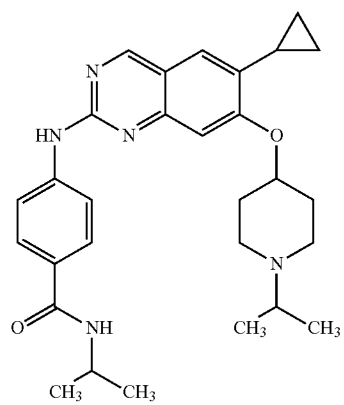 | 4-(6-cyclopropyl-7-(1-isopropylpiperidin-4-yloxy)quinazolin-2-ylamino)-N-isopropylbenzamide | 488, 2.64 | Example 27 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 638 | 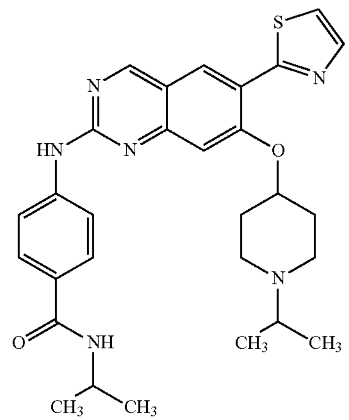 | N-isopropyl-4-(7-(1-isopropylpiperidin-4-yloxy)-6-(thiazol-2-yl)quinazolin-2-ylamino)benzamide | 531, 2.60 | Example 27 | +++ | | ++++ | |
| 639 | 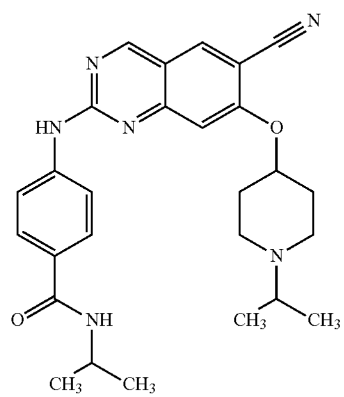 | 4-(6-cyclopropyl-7-(1-isopropylpiperidin-4-yloxy)quinazolin-2-ylamino)-N-isopropylbenzamide | 473, 2.53 | Example 27 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 640 | 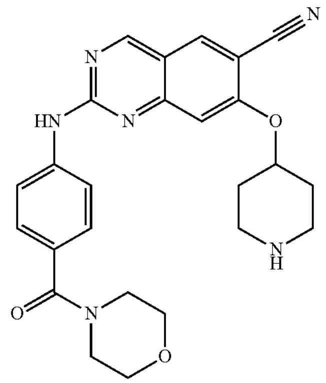 | 2-(4-(morpholine-4-carbonyl)phenylamino)-7-(piperidin-4-yloxy)quinazoline-6-carbonitrile | 459, 2.11 | Example 27 | ++++ | | ++++ | |
| 641 | 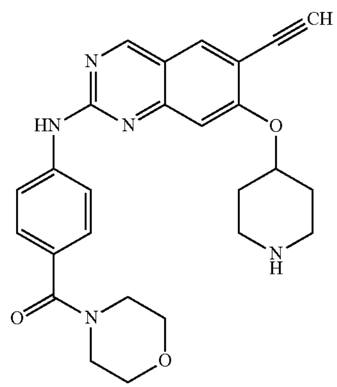 | (4-(6-ethynyl-7-(piperidin-4-yloxy)quinazolin-2-ylamino)phenyl)morpholino)methanone | 458, 2.18 | Example 27 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 642 | 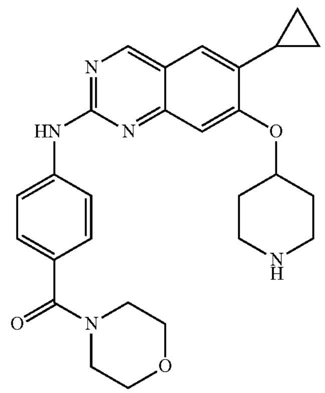 | (4-(6-cyclopropyl-7-(piperidin-4-yloxy)quinazolin-2-ylamino)phenyl)(morpholino)methanone | 474, 2.24 | Example 27 | ++++ | | ++++ | |
| 643 | 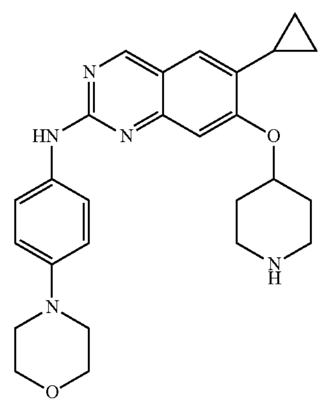 | 6-cyclopropyl-N-(4-morpholinophenyl)-7-(piperidin-4-yloxy)quinazolin-2-amine | 446, 2.12 | Example 27 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 644 | 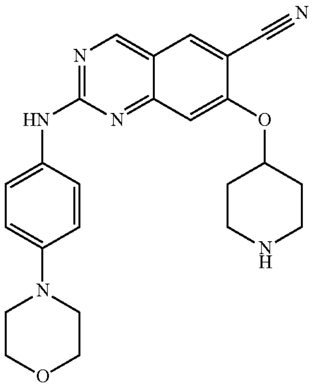 | 2-(4-morpholinophenylamino)-7-(piperidin-4-yloxy)quinazoline-6-carbonitrile | 431, 1.84 | Example 27 | +++ | | ++++ | |
| 645 | 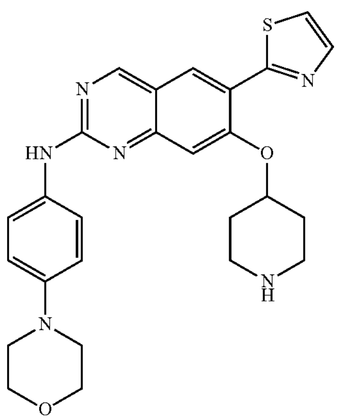 | N-(4-morpholinophenyl)-7-(piperidin-4-yloxy)-6-(thiazol-2-yl)quinazolin-2-amine | 489, 2.05 | Example 27 | ++++ | ++++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 646 | 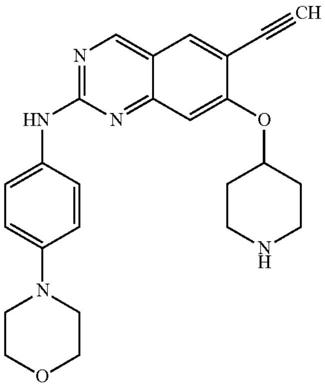 | 6-ethynyl-N-(4-morpholinophenyl)-7-(piperidin-4-yloxy)quinazolin-2-amine | 430, 2.04 | Example 27 | ++++ | ++++ | ++++ | |
| 647 | 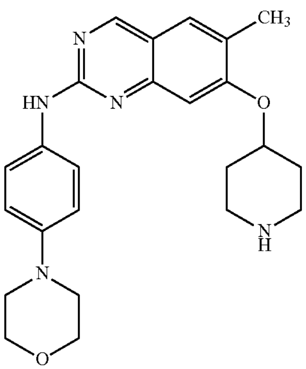 | 6-methyl-N-(4-morpholinophenyl)-7-(piperidin-4-yloxy)quinazolin-2-amine | 420, 1.91 | Example 27 | ++++ | ++++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 648 | 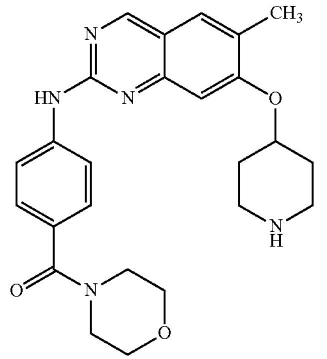 | (4-(6-methyl-7-(piperidin-4-yloxy)quinazolin-2-ylamino)phenyl)(morpholino)methanone | 448, 1.96 | Example 27 | ++++ | ++++ | ++++ | |
| 649 | 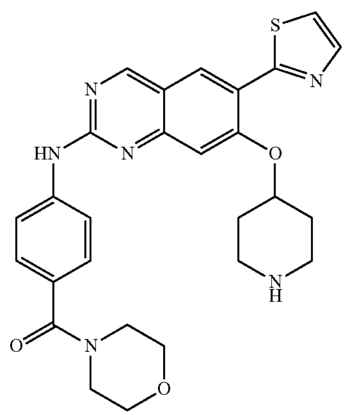 | morpholino(4-(7-(piperidin-4-yloxy)-6-(thiazol-2-yl)quinazolin-2-ylamino)phenyl)methanone | 517, 2.21 | Example 27 | ++++ | ++++ | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 650 | 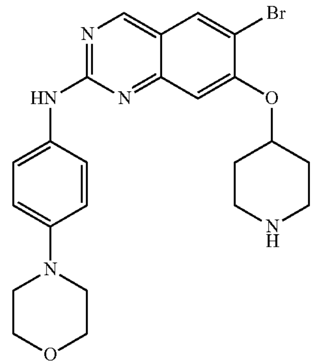 | 6-bromo-N-(4-morpholinophenyl)-7-(piperidin-4-yloxy)quinazolin-2-amine | 484/486 2.02 | Example 27 | +++ | | ++++ | |
| 651 | 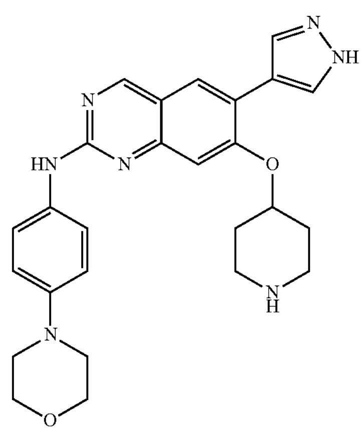 | N-(4-morpholinophenyl)-6-(1H-pyrazol-4-yl)-7-(piperidin-4-yloxy)quinazolin-2-amine | 472, 1.55 | Example 27 | ++++ | | | ++++ |

TABLE 3-continued

| Cmpd | Name | Structure | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 652 | 6-(isoxazol-4-yl)-N-(4-morpholinophenyl)-7-(piperidin-4-yloxy)quinazolin-2-amine | 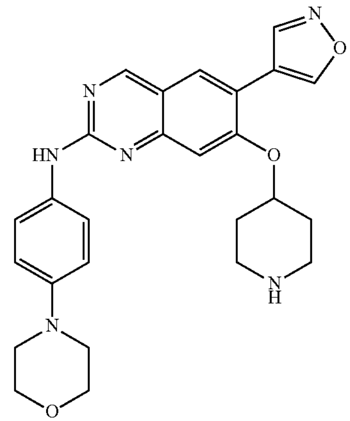 | 473, 1.68 | Example 27 | ++++ | ++++ | | ++++ |
| 653 | 7-(1-methylpiperidin-4-yloxy)-N-(4-morpholinophenyl)-6-(thiazol-2-yl)quinazolin-2-amine | 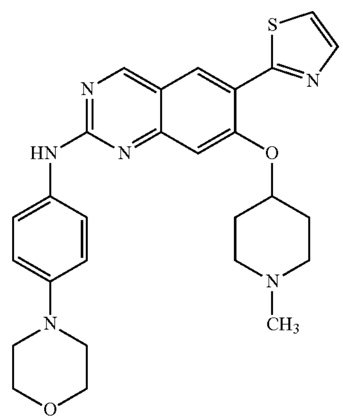 | 503, 1.97 | Example 27 | ++++ | ++++ | | ++++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 654 | 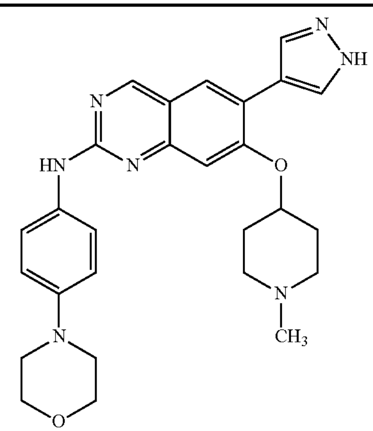 | 7-(1-methylpiperidin-4-yloxy)-N-(4-morpholinophenyl)-6-(1H-pyrazol-4-yl)quinazolin-2-amine | 486, 1.73 | Example 27 | ++++ | | | ++++ |
| 655 | 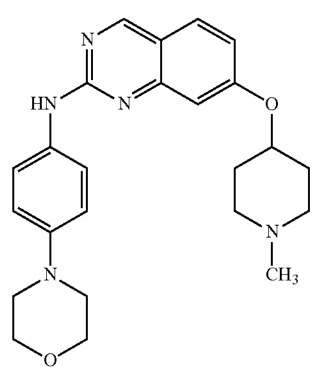 | 7-(1-methylpiperidin-4-yloxy)-N-(4-morpholinophenyl)quinazolin-2-amine | 420, 1.72 | Example 37 | ++++ | | | ++++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 656 | 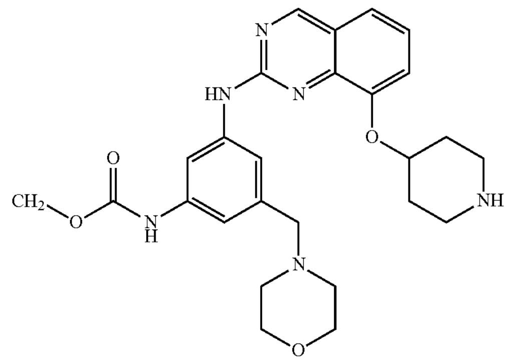 | methyl 3-(morpholinomethyl)-5-(8-(piperidin-4-yloxy)quinazolin-2-ylamino)phenylcarbamate | 493.2 | Example 2 | ++++ | | | ++++ |
| 657 | 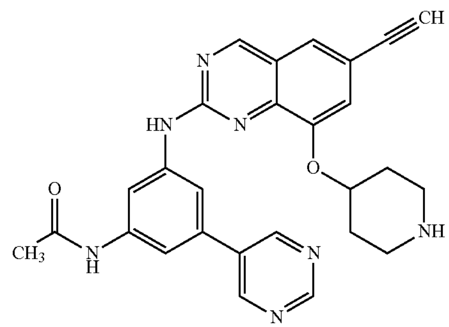 | N-(3-(6-ethynyl-8-(piperidin-4-yloxy)quinazolin-2-ylamino)-5-(pyrimidin-5-yl)phenyl)acetamide | 480.0, 2.05 | Example 23 step 2, using 3-acetamido-5-iodoaniline; step 3d using pyrimidine-5-boronic acid; step 3a; step 4 | ++++ | | | ++++ |
| 658 | 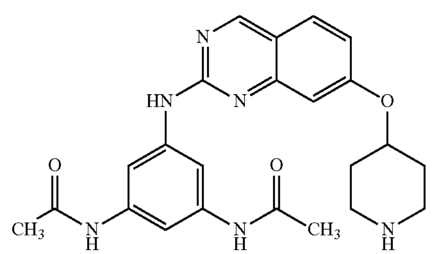 | N,N'-(5-(7-(piperidin-4-yloxy)quinazolin-2-ylamino)-1,3-phenylene)diacetamide | 435, 1.68 | Example 37 | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 659 | 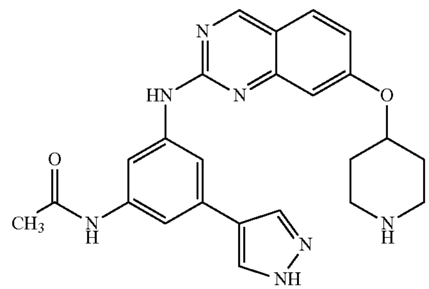 | N-(3-(7-(piperidin-4-yloxy)quinazolin-2-ylamino)-5-(1H-pyrazol-4-yl)phenyl)acetamide | 444, 1.73 | Example 37 | ++++ | | | ++++ |
| 660 | 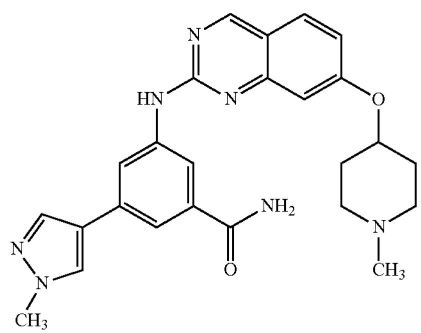 | 3-(1-methyl-1H-pyrazol-4-yl)-5-(7-(1-methylpiperidin-4-yloxy)quinazolin-2-ylamino)benzamide | 458.1, 1.78 | Example 42 and Example 32 | ++++ | | | ++++ |
| 661 | 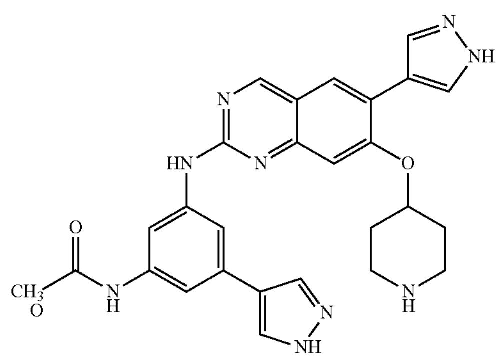 | methyl 3-(7-(piperidin-4-yloxy)-6-(1H-pyrazol-4-yl)quinazolin-2-ylamino)-5-(1H-pyrazol-4-yl)phenylcarbamate | 526, 1.79 | Example 303, 306 | ++++ | | | ++++ |

TABLE 3-continued

| Cmpd | Structure | Name | LC/MS (M + 1(m/z), Rt(min)) | Synthetic method | PDK1 IC50 | CPEC50 A2780 | CPEC50 PC3 | CPEC50 PC3MM |
|---|---|---|---|---|---|---|---|---|
| 662 | 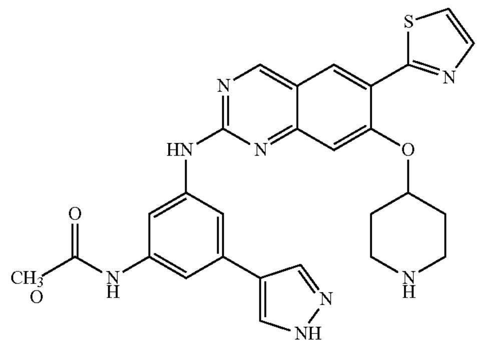 | methyl 3-(7-(piperidin-4-yloxy)-6-(thiazol-2-yl)quinazolin-2-ylamino)-5-(1H-pyrazol-4-yl)phenylcarbamate | 543, 2.03 | Example 303, 306 | ++++ | | | ++++ |
| 663 | 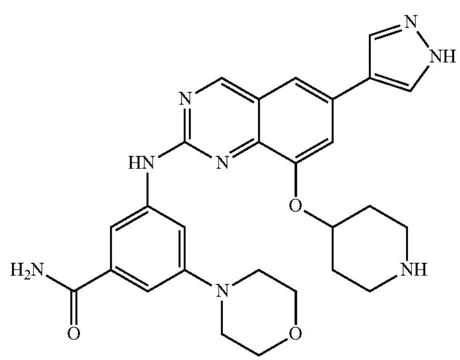 | 3-morpholino-5-(8-(piperidin-4-yloxy)-6-((1H-pyrazol-4-yl)quinazolin-2-ylamino)benzamide | 515.1, 1.79 | Example 23 step 2, using 3-carboxamido-5-morpholinoaniline; step 3d, using N-Boc-4-pyrazole-boronic acid | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 664 | 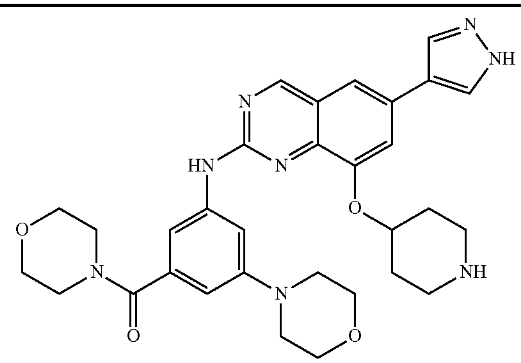 | morpholino(3-morpholino-5-(8-(piperidin-4-yloxy)-6-(1H-pyrazol-4-yl)quinazolin-2-ylamino)phenyl)methanone | 585.1, 1.90 | Example 23 step 2, using 3-morpholinocarboxamide-5-morpholinoaniline; step 3d, using N-Boc-4-pyrazole-boronic acid | ++++ | | | +++ |
| 665 | 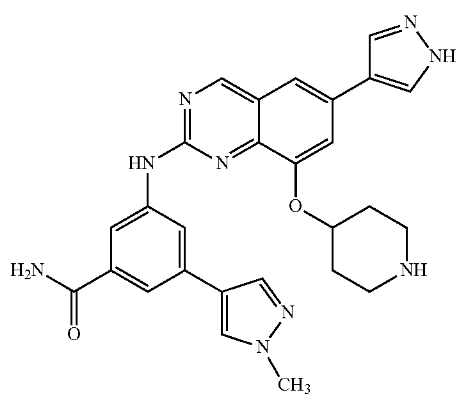 | 3-(1-methyl-1H-pyrazol-4-yl)-5-(8-(piperidin-4-yloxy)-6-(1H-pyrazol-4-yl)quinazolin-2-ylamino)benzamide | 510.1, 1.83 | Example 23 step 2, using 3-carboxamido-5-(1-methyl)pyrazol-4-ylaniline; step 3d, using N-Boc-4-pyrazole-boronic acid; step 4 | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 666 | 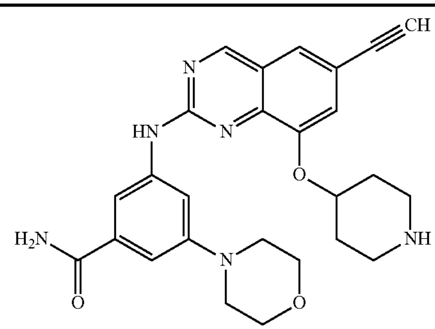 | 3-(6-ethynyl-8-(piperidin-4-yloxy)quinazolin-2-ylamino)-5-morpholinobenzamide | 473.0, 1.98 | Example 23 step 2, using 3-carboxamido-5-morpholinoaniline; step 3a | ++++ | | | +++ |
| 667 | 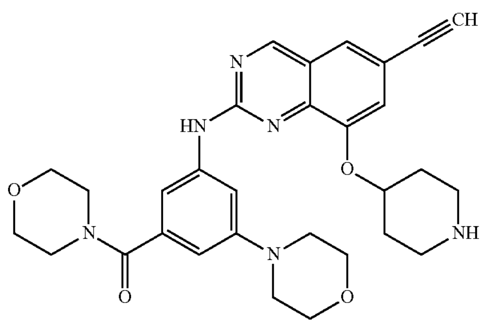 | (3-(6-ethynyl-8-(piperidin-4-yloxy)quinazolin-2-ylamino)-5-morpholinophenyl)(morpholino)methanone | 543.1, 2.11 | Example 23 step 2, using 3-morpholinocarboxamido-5-morpholinoaniline; step 3a | ++++ | | | ++++ |
| 668 | 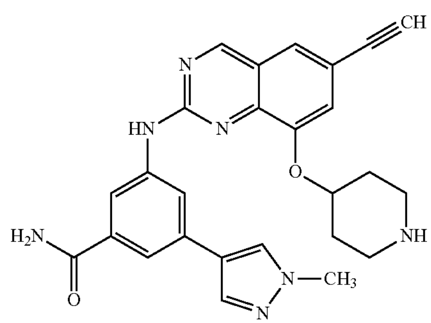 | 3-(6-ethynyl-8-(piperidin-4-yloxy)quinazolin-2-ylamino)-5-(1-methyl-1H-pyrazol-4-yl)benzamide | 468.1, 2.01 | Example 23 step 2, using 3-carboxamido-5-(1-methyl)pyrazol-4-ylaniline; step 4 | ++++ | | | ++++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 669 | 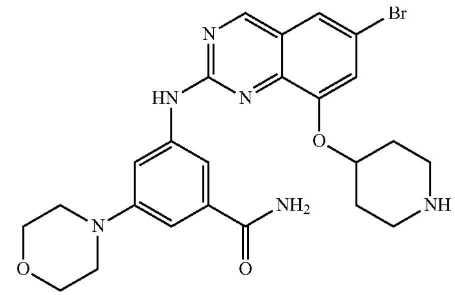 | 3-(6-bromo-8-(piperidin-4-yloxy)quinazolin-2-ylamino)-5-morpholinobenzamide | 528.9, 2.03 | Example 23 step 2, using 3-carboxamido-5-morpholinoaniline | ++++ | | | +++ |
| 670 | 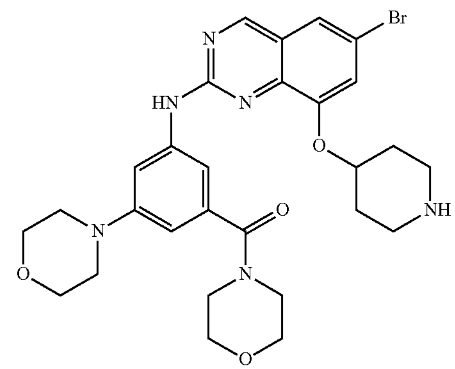 | (3-(6-bromo-8-(piperidin-4-yloxy)quinazolin-2-ylamino)-5-morpholinophenyl)(morpholino)methanone | 599.0, 2.16 | Example 23 step 2, using 3-morpholinocarboxamide-5-morpholinoaniline | ++++ | | | ++++ |
| 671 | 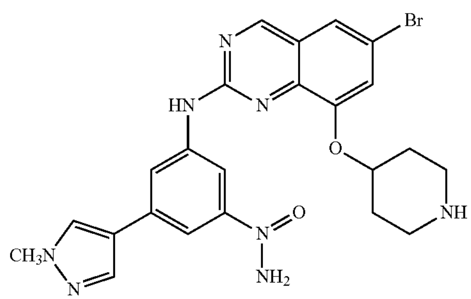 | 3-(6-bromo-8-(piperidin-4-yloxy)quinazolin-2-ylamino)-5-(1-methyl-1H-pyrazol-4-yl)benzamide | 523.9, 2.07 | Example 23 step 2, using 3-carboxamido-5-(1-methyl)pyrazol-4-ylaniline; step 4 | ++++ | | | ++++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 672 | 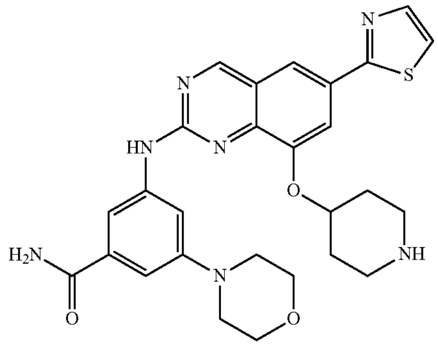 | 3-morpholino-5-(8-(piperidin-4-yloxy)-6-(thiazol-2-yl)quinazolin-2-ylamino)benzamide | 532.1, 2.09 | Example 23 step 2, using 3-carboxamido-5-morpholinoaniline; step 3c | ++++ | | | +++ |
| 673 | 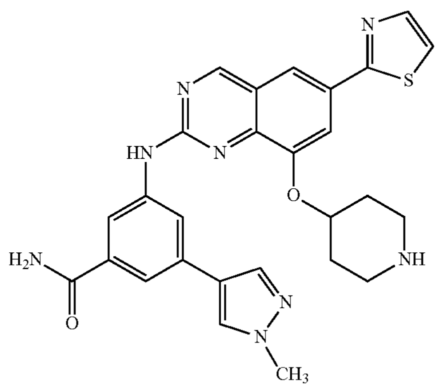 | 3-(1-methyl-1H-pyrazol-4-yl)-5-(8-(piperidin-4-yloxy)-6-(thiazol-2-yl)quinazolin-2-ylamino)benzamide | 527.2, 2.13 | Example 23 step 2, using 3-carboxamido-5-(1-methyl)pyrazol-4-ylaniline; step 3c | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 674 | 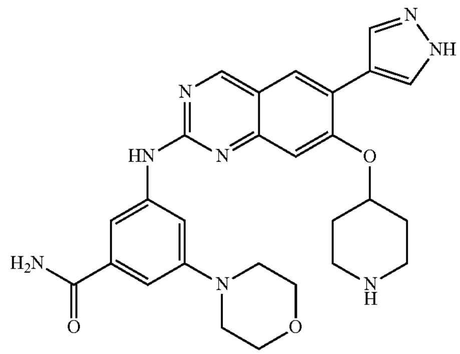 | 3-morpholino-5-(7-(piperidin-4-yloxy)-6-(1H-pyrazol-4-yl)quinazolin-2-ylamino)benzamide | 515, 1.77 | Example 27 | ++++ | | | +++ |
| 675 | 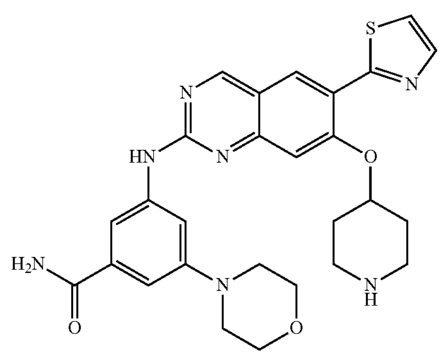 | 3-morpholino-5-(7-(piperidin-4-yloxy)-6-(thiazol-2-yl)quinazolin-2-ylamino)benzamide | 532, 1.94 | Example 27 | ++++ | | | +++ |

TABLE 3-continued

| Cmpd | Structure | Name | LC/MS (M + 1(m/z), Rt(min)) | Synthetic method | PDK1 IC₅₀ | CPEC₅₀ A2780 | CPEC₅₀ PC3 | CPEC₅₀ PC3MM |
|---|---|---|---|---|---|---|---|---|
| 676 | 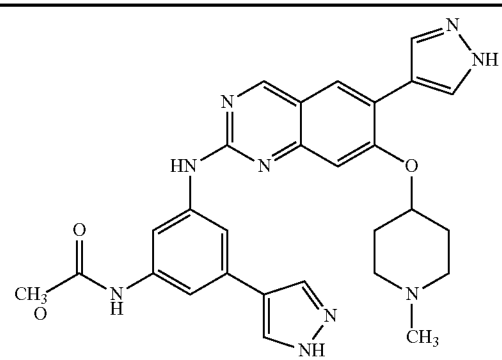 | methyl 3-(7-(1-methylpiperidin-4-yloxy)-6-(1H-pyrazol-4-yl)quinazolin-2-ylamino)-5-(1H-pyrazol-4-yl)phenylcarbamate | 540, 1.83 | Example 27 | ++++ | | | ++++ |
| 677 | 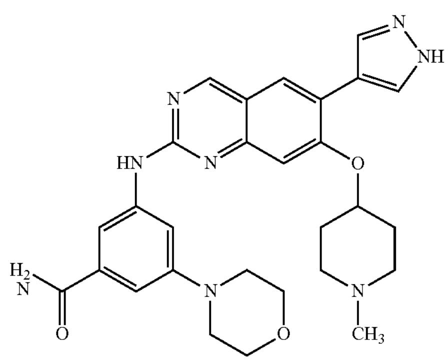 | 3-(7-(1-methylpiperidin-4-yloxy)-6-(1H-pyrazol-4-yl)quinazolin-2-ylamino)-5-morpholinobenzamide | 529, 1.72 | Example 27 | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 678 | 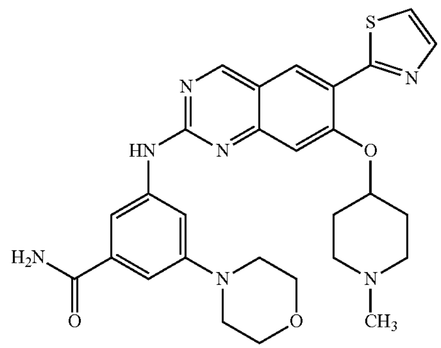 | 3-(7-(1-methylpiperidin-4-yloxy)-6-(thiazol-2-yl)quinazolin-2-ylamino)-5-morpholinobenzamide | 546, 1.90 | Example 27 | ++++ | | | ++++ |
| 679 | 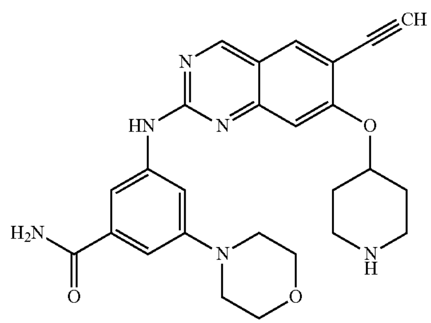 | 3-(6-ethynyl-7-(piperidin-4-yloxy)quinazolin-2-ylamino)-5-morpholinobenzamide | 473, 1.86 | Example 27 | ++++ | | | +++ |
| 680 | 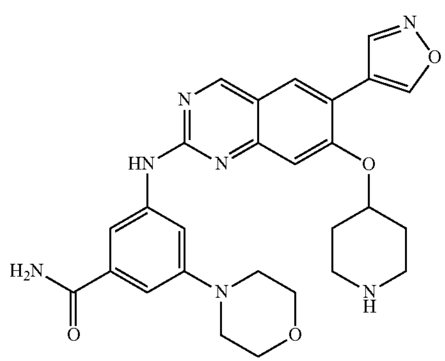 | 3-(6-(isoxazol-4-yl)-7-(piperidin-4-yloxy)quinazolin-2-ylamino)-5-morpholinobenzamide | 516, 1.85 | Example 27 | ++++ | | | +++ |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 681 | 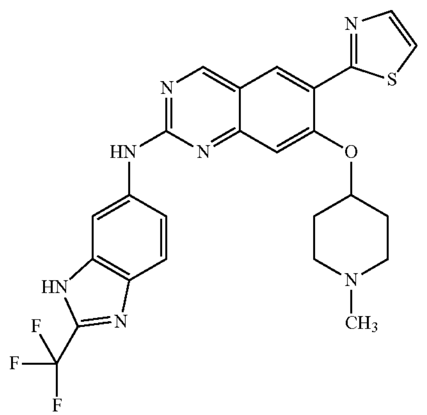 | 7-(1-methylpiperidin-4-yloxy)-6-(thiazol-2-yl)-N-(2-(trifluoromethyl)-1H-benzo[d]imidazol-6-yl)quinazolin-2-amine | 526.1, 2.2 | Example 27 | ++++ | | | +++ |
| 682 | 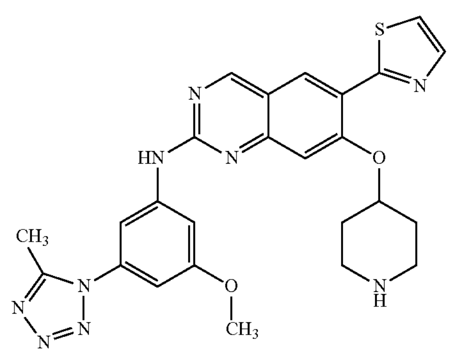 | N-(3-methoxy-5-(5-methyl-1H-tetrazol-1-yl)phenyl)-7-(piperidin-4-yloxy)-6-(thiazol-2-yl)quinazolin-2-amine | 516, 2.21 | Similar to Example 53 | ++++ | | | ++++ |

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 683 | 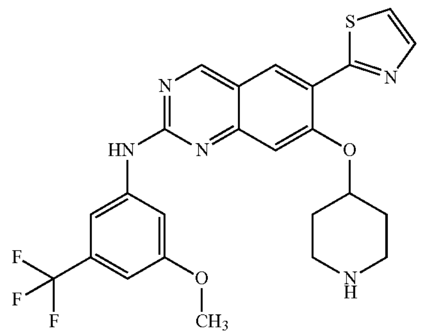 | N-(3-methoxy-5-(trifluoromethyl)phenyl)-7-(piperidin-4-yloxy)-6-(thiazol-2-yl)quinazolin-2-amine | 502, 2.58 | Similar to Example 53 | | | | |
| 684 | 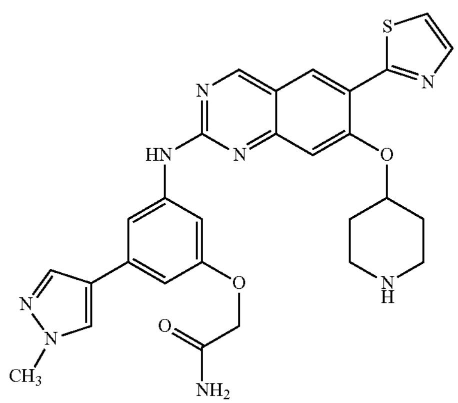 | 2-(3-(1-methyl-1H-pyrazol-4-yl)-5-(7-(piperidin-4-yloxy)-6-(thiazol-2-yl)quinazolin-2-ylamino)phenoxy)acetamide | 557, 1.99 | Similar to Example 53 | | | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 685 | 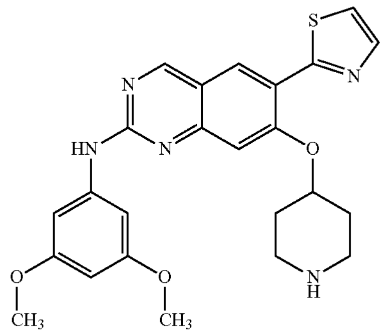 | N-(3,5-dimethoxyphenyl)-7-(piperidin-4-yloxy)-6-(thiazol-2-yl)quinazolin-2-amine | 464, 2.2 | Similar to Example 53 | | | | |
| 686 | 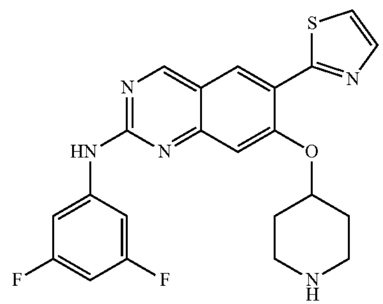 | N-(3,5-difluorophenyl)-7-(piperidin-4-yloxy)-6-(thiazol-2-yl)quinazolin-2-amine | 440, 2.42 | Similar to Example 53 | | | | |
| 687 | 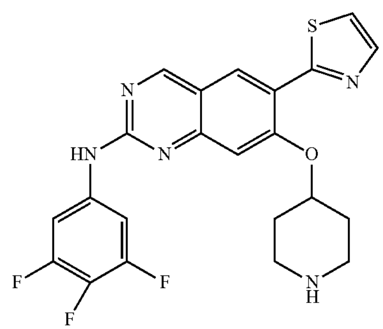 | 7-(piperidin-4-yloxy)-6-(thiazol-2-yl)-N-(3,4,5-trifluorophenyl)quinazolin-2-amine | 458, 2.47 | Similar to Example 53 | | | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 688 | 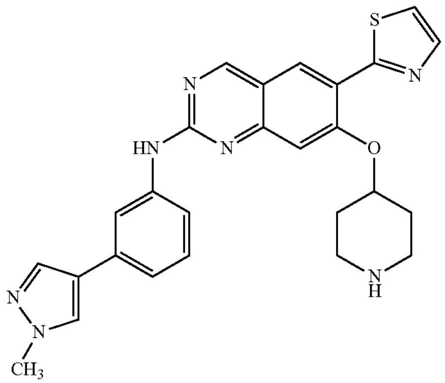 | N-(3-(1-methyl-1H-pyrazol-4-yl)phenyl)-7-(piperidin-4-yloxy)-6-(thiazol-2-yl)quinazolin-2-amine | 484.2, 2.55 | Example 27 | | | | |
| 689 | 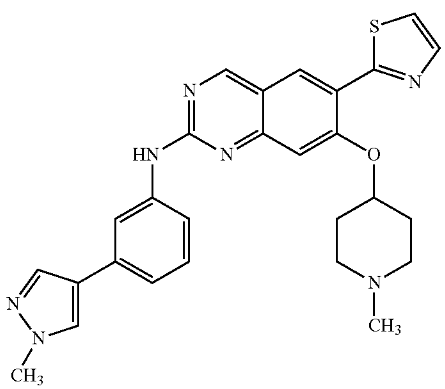 | N-(3-(1-methyl-1H-pyrazol-4-yl)phenyl)-7-(1-methylpiperidin-4-yloxy)-6-(thiazol-2-yl)quinazolin-2-amine | 498.2, 2.6 | Example 27 | | | | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 690 | 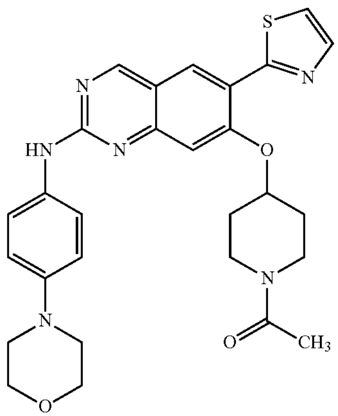 | 1-(4-(2-(4-morpholinophenylamino)-6-(thiazol-2-yl)quinazolin-7-yloxy)piperidin-1-yl)ethanone | 531, 2.18 | Example 27 | ++++ | | | ++++ |
| 691 | 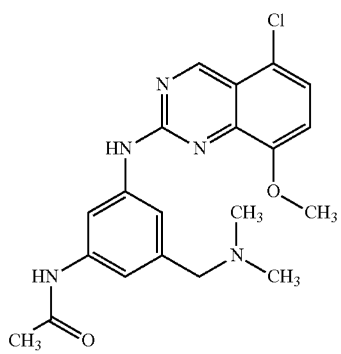 | N-(3-(5-chloro-8-methoxyquinazolin-2-ylamino)-5-((dimethylamino)methyl)phenyl)acetamide | 400.2, 2.12 | Similar to Example 49 | ++++ | | +++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 692 | 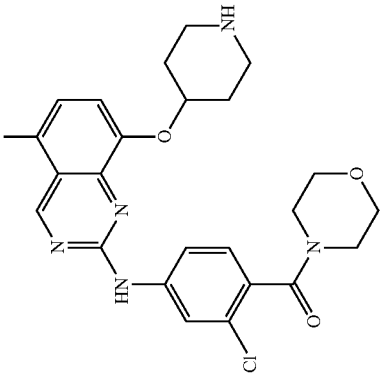 | (2-chloro-4-(5-chloro-8-(piperidin-4-yloxy)quinazolin-2-ylamino)phenyl)(morpholino)methanone | 502.2, 2.29 | Similar to Example 48 | ++++ | | ++++ | |
| 693 | 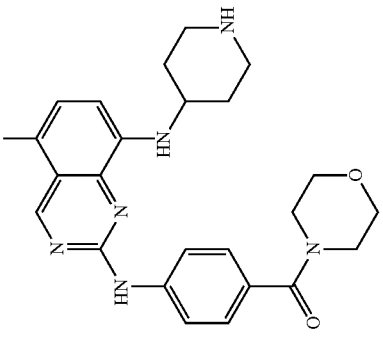 | (4-(5-chloro-8-(piperidin-4-ylamino)quinazolin-2-ylamino)phenyl)(morpholino)methanone | 467.2, 2.27 | Similar to example 50 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 694 | 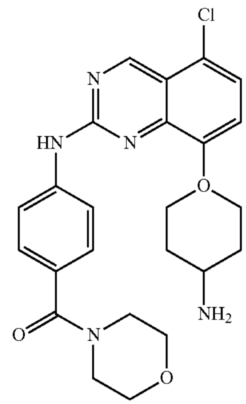 | (4-(8-(4-aminopiperidin-1-yl)-5-chloroquinazolin-2-ylamino)phenyl)(morpholino)methanone | 467.2, 2.10 | Similar to example 50 | ++++ | | ++++ | |
| 695 | 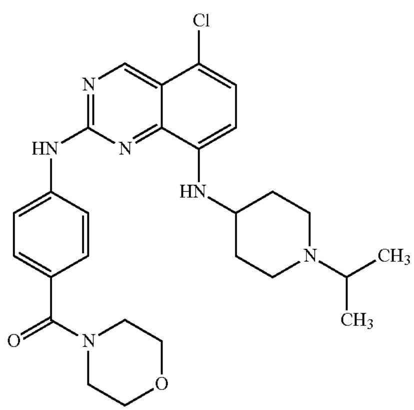 | (4-(5-chloro-8-(1-isopropylpiperidin-4-ylamino)quinazolin-2-ylamino)phenyl)(morpholino)methanone | 509.2, 2.38 | Similar to example 50 | ++++ | | +++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 696 | 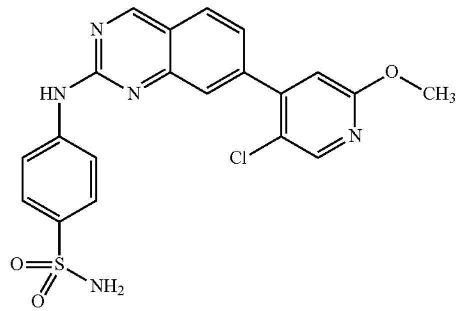 | 4-(7-chloro-2-methoxypyridin-4-yl)quinazolin-2-ylamino)benzenesulfonamide | 442.1 | Similar to example 29 | + | +++ | | |
| 697 | 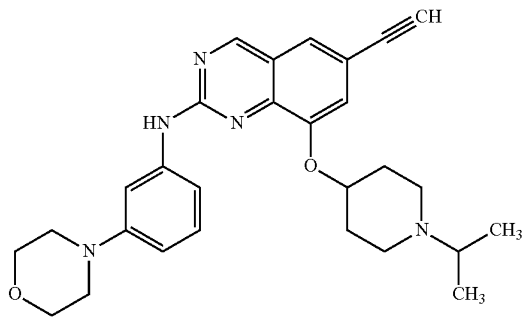 | 6-ethynyl-8-(1-isopropylpiperidin-4-yloxy)-N-(3-morpholinophenyl)quinazolin-2-amine | 472.2, 2.23 | Similar to example 22 | ++++ | | ++++ | |
| 698 | 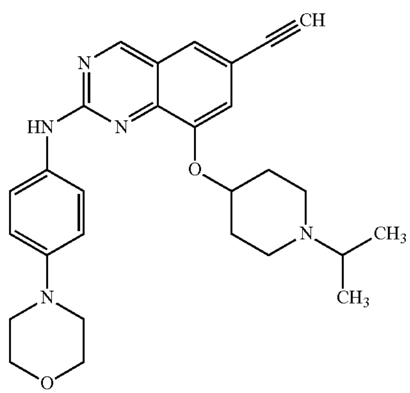 | 6-ethynyl-8-(1-isopropylpiperidin-4-yloxy)-N-(4-morpholinophenyl)quinazolin-2-amine | 472.2, 2.06 | Similar to example 22, using 4-morpholinoaniline in place of 3-morpholinoaniline | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 699 | 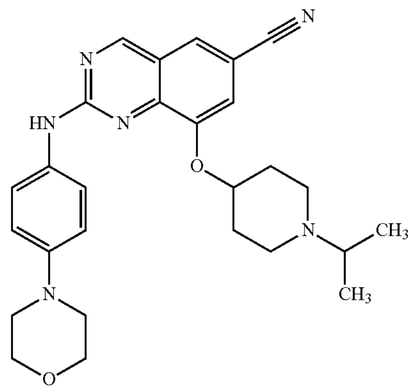 | 8-(1-isopropylpiperidin-4-yloxy)-2-(4-morpholinophenylamino)quinazoline-6-carbonitrile | 473.2, 2.02 | Similar to example 22 step 1 using 4-morpholinoaniline in place of 3-morpholinoaniline | ++++ | | ++++ | |
| 700 | 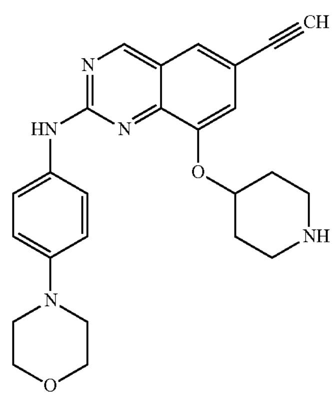 | 6-ethynyl-N-(4-morpholinophenyl)-8-(piperidin-4-yloxy)quinazolin-2-amine | 430.1, 2.00 | Example 23, steps 1, 2, 3a, and 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 701 | 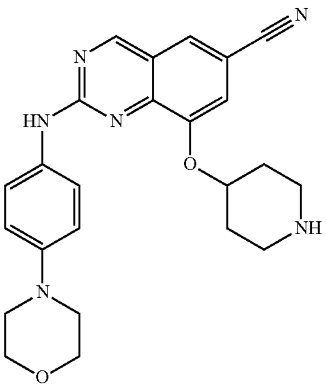 | 2-(4-morpholinophenylamino)-8-(piperidin-4-yloxy)quinazoline-6-carbonitrile | 431.1, 1.92 | Example 23, steps 1, 2, 3b, and 4 | ++++ | | ++++ | |
| 702 | 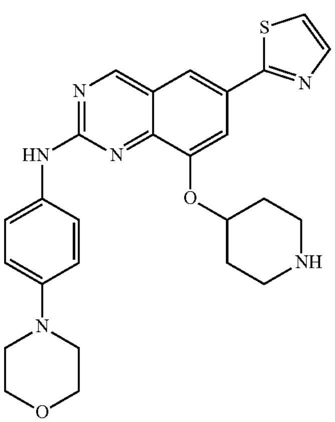 | N-(4-morpholinophenyl)-8-(piperidin-4-yloxy)-6-(thiazol-2-yl)quinazolin-2-amine | 489.1, 2.02 | Example 23, steps 1, 2, 3c, and 4 | ++++ | | ++++ | |

TABLE 3-continued
| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 703 | 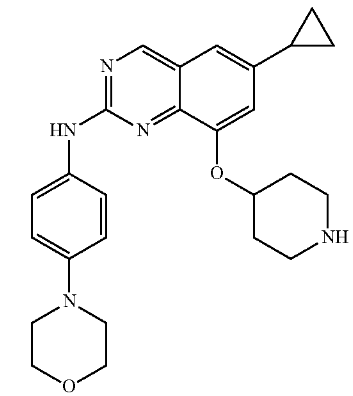 | 6-cyclopropyl-N-(4-mropholinophenyl)-8-(piperidin-4-yloxy)quinazolin-2-amine | 446.2, 2.05 | Example 23, steps 1, 2, 3d, and 4 | ++++ | | ++++ | |
| 704 | 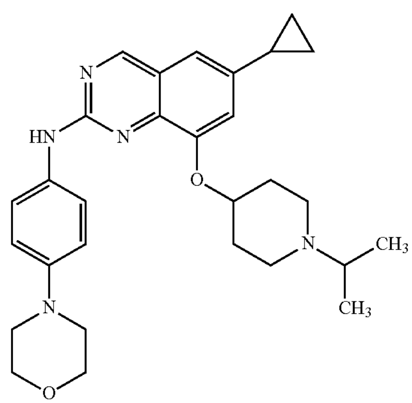 | 6-cyclopropyl-8-(1-isopropylpiperidin-4-yloxy)-N-(4-morpholinophenyl)quinazolin-2-amine | 488.3, 2.14 | Example 23, steps 1, 2, 3d, and 4 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 705 | 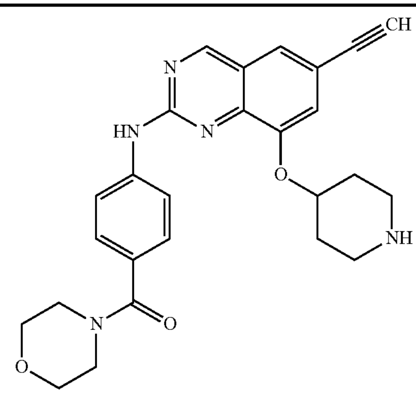 | (4-(6-ethynyl-8-(piperidin-4-yloxy)quinazolin-2-yl)aminophenyl)(morpholino)methanone | 458.2, 2.03 | Example 23, steps 1, 2, 3a, 4, using (4-aminophenyl)(morpholino)methanone in place of 4-morpholinoaniline | +++ | | ++++ | |
| 706 | 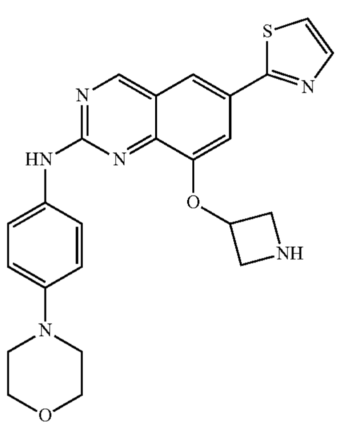 | 8-(azetidin-3-yloxy)-N-(4-morpholinophenyl)-6-(thiazol-2-yl)quinazolin-2-amine | 461.1, 1.93 | Example 23 steps 1, 2, 3c, and 4, using N-tert-butyl 3-hydroxy-1-azetidine carboxylate in place of N-tert-butyl 4-hydroxy-1-piperidine carboxylate | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 707 | 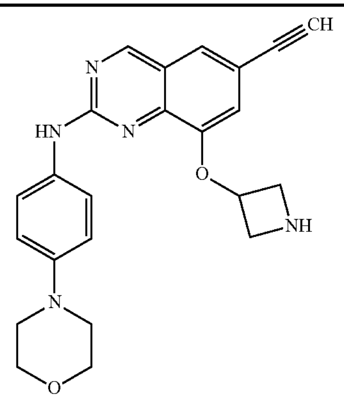 | 8-(azetidin-3-yloxy)-6-ethynyl-N-(4-morpholinophenyl)quinazolin-2-amine | 402.2, 1.89 | Example 23, steps 1, 2, 3a, and 4, using N-tert-butyl 3-hydroxy-1-azetidine carboxylate in place of N-tert-butyl 4-hydroxy-1-piperidine carboxylate | ++++ | | ++++ | |
| 708 | 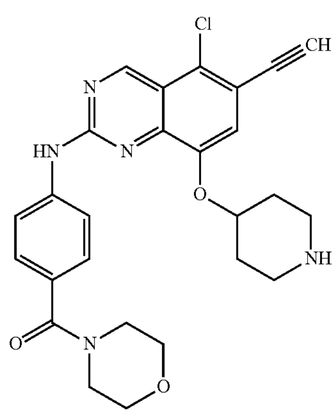 | (4-(5-chloro-6-ethynyl-8-(piperidin-4-yloxy)quinazolin-2-ylamino)phenyl)(morpholino)methanone | 492.2, 2.26 | Example 9 using 6-bromo-2,5-dichloro-8-methoxyquinazoline in place of 1b, then analogous to 23a | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|------|-----------|------|------------------------------|------------------|----------------|-------------------|-----------------|-------------------|
| 709 | 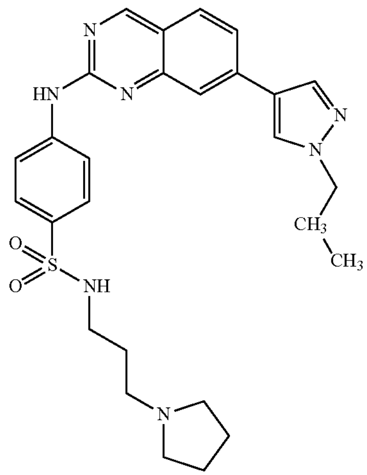 | 4-(7-(1-isobutyl-1H-pyrazol-4-yl)quinazolin-2-ylamino)-N-(3-(pyrrolidin-1-yl)propyl)benzenesulfonamide | 534, 3.05 | Example 25 | ++++ | | ++++ | |
| 710 | 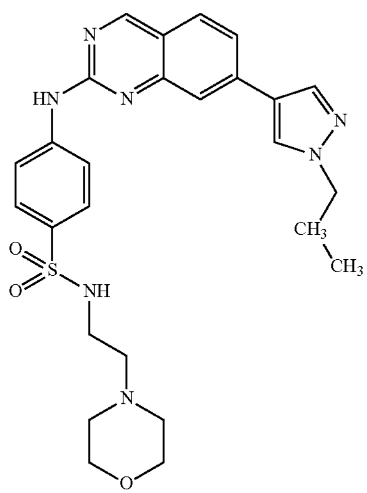 | 4-(7-(1-isobutyl-1H-pyrazol-4-yl)quinazolin-2-ylamino)-N-(2-morpholinoethyl)benzenesulfonamide | 536, 2.88 | Example 25 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 711 | 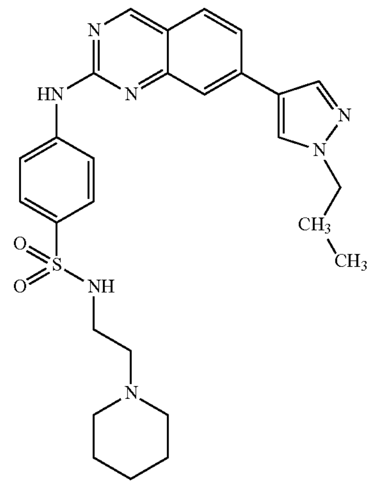 | 4-(7-(1-isobutyl-1H-pyrazol-4-yl)quinazolin-2-ylamino)-N-(2-(piperidin-1-yl)ethyl)benzenesulfonamide | 534, 3.01 | Example 25 | ++++ | | ++++ | |
| 712 | 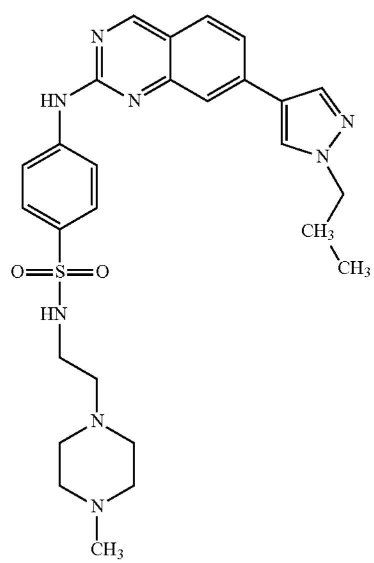 | 4-(7-(1-isobutyl-1H-pyrazol-4-yl)quinazolin-2-ylamino)-N-(2-(4-methylpiperazin-1-yl)ethyl)benzenesulfonamide | 549, 2.62 | Example 25 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 713 | 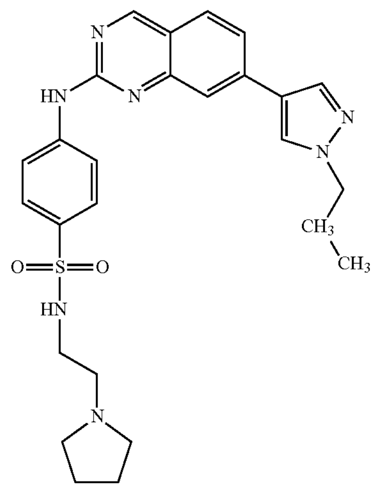 | 4-(7-(1-isobutyl-1H-pyrazol-4-yl)quinazolin-2-ylamino)-N-(2-(pyrrolidin-1-yl)ethyl)benzenesulfonamide | 520, 2.97 | Example 25 | ++++ | | ++++ | |
| 714 | 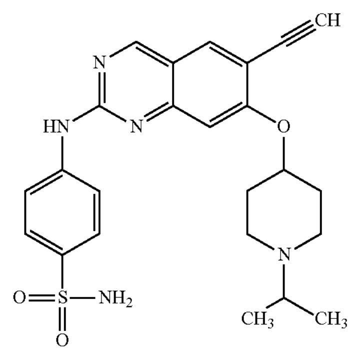 | 4-(6-ethynyl-7-(1-isopropylpiperidin-4-yloxy)quinazolin-2-ylamino)benzenesulfonamide | 466, 3.20 | Example 27 | ++++ | | ++++ | |

TABLE 3-continued

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 715 | 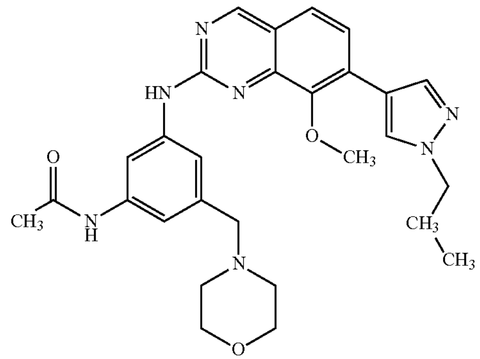 | N-(3-(7-(1-isobutyl-1H-pyrazol-4-yl)-8-methoxyquinazolin-2-ylamino)-5-(morpholinomethyl)phenyl)acetamide | 530.2, 2.12 | Example 5, then Example 9 step 3, Example 35, step 2 and 4 | ++++ | | | ++++ |
| 716 | 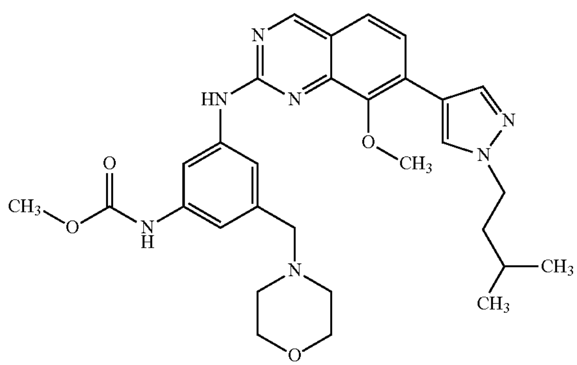 | methyl 3-(7-(1-isopentyl-1H-pyrazol-4-yl)-8-methoxyquinazolin-2-ylamino)-5-(morpholinomethyl)phenyl carbamate | 560.2, 2.51 | Example 5, then Example 9 step 3, Example 35, step 2 and 4 | ++++ | | | ++++ |

TABLE 4

| Cmpd | Structure | Name | LC/MS (M + 1(m/z), Rt(min)) | Synthetic method | PDK1 IC$_{50}$ | CPEC$_{50}$ A2780 | CPEC$_{50}$ PC3 | CPEC$_{50}$ PC3MM |
|---|---|---|---|---|---|---|---|---|
| 717. | 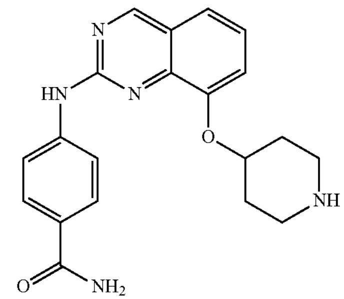 | 4-(8-(piperidin-4-yloxy)quinazolin-2-ylamino)benzamide | | Example 20, steps 2 and 3, using 4-aminoacetanilide in place of (4-aminophenyl)(morpholino)methanone | ++++ | ++++ | | ++++ |
| 718. | 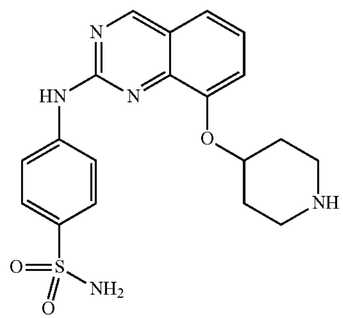 | 4-(8-(piperidin-4-yloxy)quinazolin-2-ylamino)benzenesulfonamide | | Example 20, steps 2 and 3, using sulfanilamide in place of (4-aminophenyl)(morpholino)methanone | ++++ | ++++ | ++++ | ++++ |
| 719. | 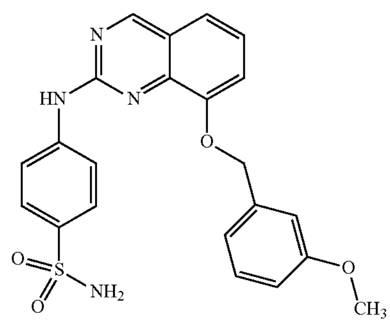 | 4-(8-(3-methoxybenzyloxy)quinazolin-2-ylamino)benzenesulfonamide | | | + | ++++ | | + |

TABLE 4-continued

| | Name | Structure | | | |
|---|---|---|---|---|---|
| 720. | 4-(8-(benzo[c][1,2,5]-oxadiazol-5-ylmethoxy)quinazolin-2-ylamino)benzenesulfonamide | | + | + | +++ |
| 721. | (S)-4-(8-(pyrrolidin-3-yloxy)quinazolin-2-ylamino)benzenesulfonamide | | ++++ | ++++ | +++ |
| 722. | 4-(8-(quinuclidin-3-yloxy)quinazolin-2-ylamino)benzenesulfonamide | | ++++ | ++++ | +++ |

TABLE 4-continued
| | | | | | |
|---|---|---|---|---|---|
| 723. | (S)-4-(8-(1-methylpyrrolidin-3-yloxy)quinazolin-2-ylamino)benzenesulfonamide 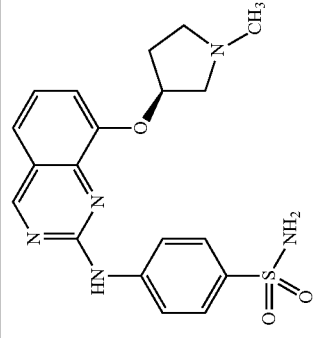 | +++ | +++ | +++ | +++ |
| 724. | 4-(8-(1-methylpiperidin-4-yloxy)quinazolin-2-ylamino)benzenesulfonamide 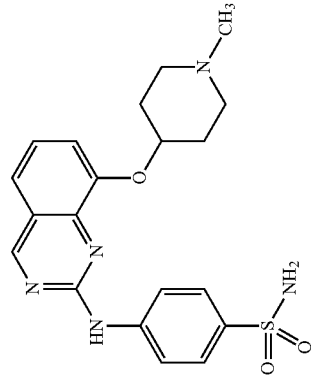 | +++ | +++ | +++ | +++ |
| 725. | 4-(8-(1-isopropylpiperidin-4-yloxy)quinazolin-2-ylamino)benzenesulfonamide 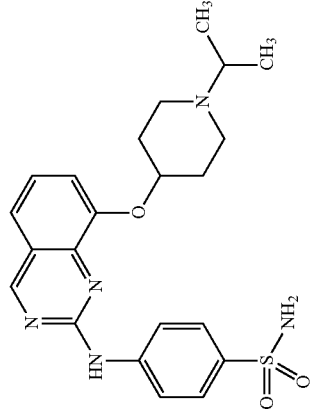 | +++ | +++ | +++ | +++ |

TABLE 4-continued

| | | | | |
|---|---|---|---|---|
| 726. | (R)-4-(8-(pyrrolidin-3-yloxy)quinazolin-2-ylamino)benzenesulfonamide | ++++ | ++++ | ++++ |
| 727. | (R)-4-(8-(1-methylpyrrolidin-3-yloxy)quinazolin-2-ylamino)benzenesulfonamide | ++++ | ++++ | ++++ |
| 728. | 8-(cyclopentyloxy)-N-cyclopropylquinazolin-2-amine | + | + | +++ |
| 729. | 8-(cyclopentyloxy)-N-(2,5-difluorobenzyl)quinazolin-2-amine | + | + | +++ |

| | | | |
|---|---|---|---|
| 730. | 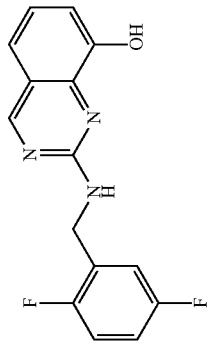 | 2-(2,5-difluorobenzyl-amino)quinazolin-8-ol | + + +++ + |
| 731. | 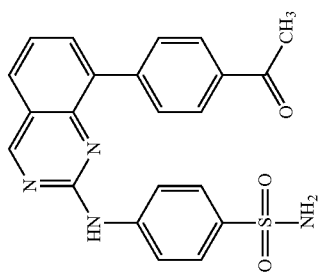 | 4-(8-(4-acetyl-phenyl)quinazolin-2-ylamino)benzene-sulfonamide | +++ ++++ +++ +++ |
| 732. | 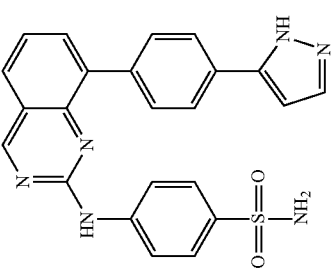 | 4-(8-(4-(1H-pyrazol-5-yl)phenyl)quinazolin-2-ylamino)benzene-sulfonamide | ++++ ++++ ++++ +++ |

| | | | |
|---|---|---|---|
| 733. | 4-(8-(1-methylpiperidin-3-yloxy)quinazolin-2-ylamino)benzenesulfonamide | 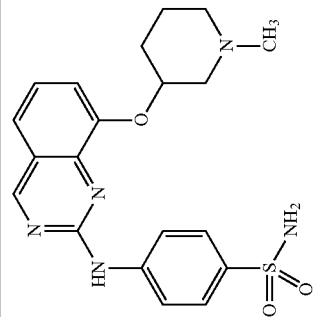 | ++++ ++++ ++++ |
| 734. | 3-(2-(4-sulfamoylphenyl-amino)quinazolin-8-yl)benzamide | 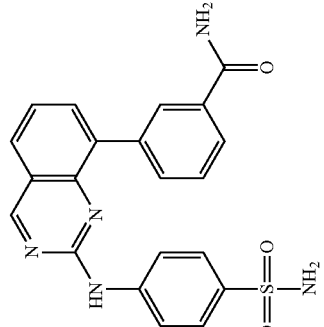 | ++++ ++++ ++++ |
| 735. | 4-(8-(3-(methysulfonyl)phenyl)quinazolin-2-ylamino)benzenesulfonamide | 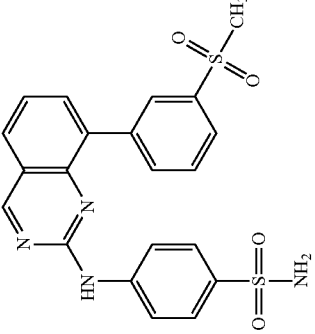 | ++++ ++++ ++++ |

TABLE 4-continued
| | | | |
|---|---|---|---|
| 736. | 4-(8-(3-(methylsulfonamido)phenyl)quinazolin-2-ylamino)benzenesulfonamide | 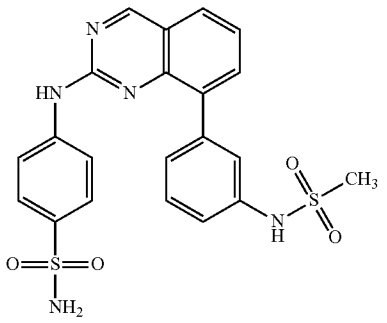 | +++ +++ +++ |
| 737. | N-(3-(2-(4-sulfamoylphenylamino)quinazolin-8-yl)phenyl)acetamide | 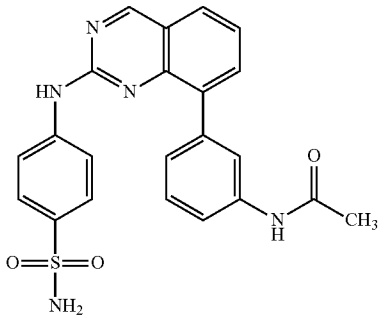 | +++ +++ +++ |
| 738. | 3-(2-(4-sulfamoylphenylamino)quinazolin-8-yl)benzenesulfonamide | 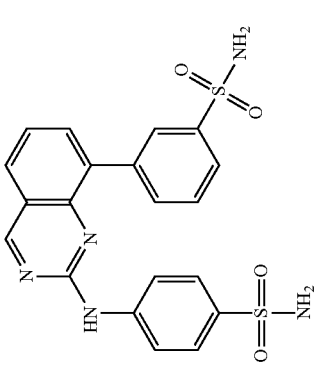 | +++ +++ +++ |

TABLE 4-continued

| | | | | |
|---|---|---|---|---|
| 739. | 4-(8-(benzo[d][1,3]dioxol-5-yl)quinazolin-2-ylamino)benzenesulfonamide | ++++ | ++++ | ++++ |
| 740. | 4-(2-(4-sulfamoylphenyl-amino)quinazolin-8-yl)benzamide | ++++ | ++++ | +++ |
| 741. | 4-(8-(2-fluoropyridin-4-yl)-quinazolin-2-ylamino)benzenesulfonamide | ++++ | ++++ | ++++ |

TABLE 4-continued
| 742. | 4-(8-(pyridin-3-yl)quinazolin-2-ylamino)benzenesulfonamide | 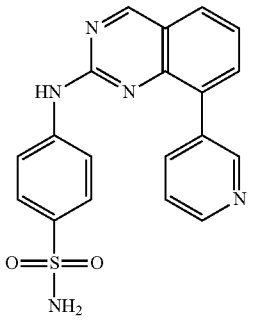 | ++++ | +++ | ++++ |
| 743. | 4-(8-(pyridin-4-yl)quinazolin-2-ylamino)benzenesulfonamide | 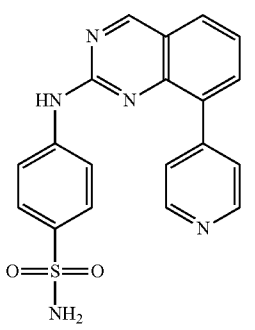 | ++++ | +++ | ++++ |
| 744. | (S)-4-(8-(quinuclidin-3-yloxy)quinazolin-2-ylamino)benzenesulfonamide | 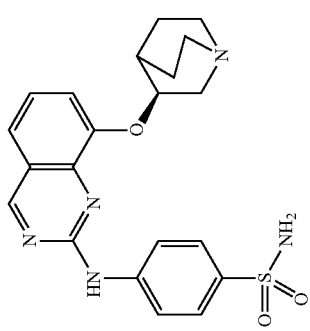 | ++++ | ++++ | ++++ |

TABLE 4-continued
| | | | |
|---|---|---|---|
| 745. | 4-(8-(2-(2-methoxyethylamino)pyridin-4-yl)quinazolin-2-ylamino)benzenesulfonamide | 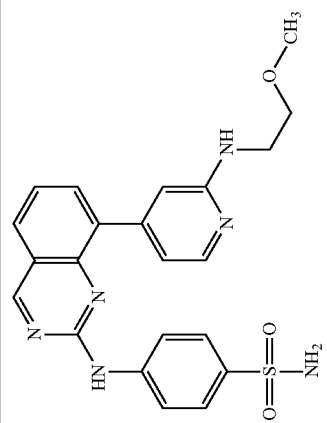 | +++ +++ +++ |
| 746. | N-(2-(4-(2-(4-sulfamoylphenylamino)quinazolin-8-yl)pyridin-2-ylamino)ethyl)acetamide | 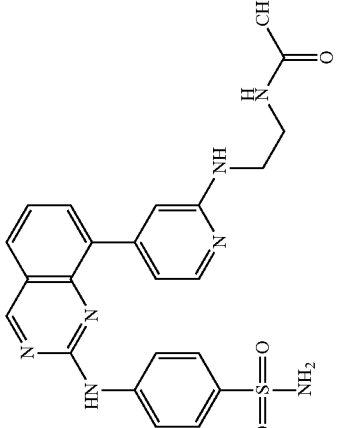 | +++ +++ +++ |
| 747. | 4-(8-(2-(2-(pyrrolidin-1-yl)ethylamino)pyridin-4-yl)quinazolin-2-ylamino)benzenesulfonamide | 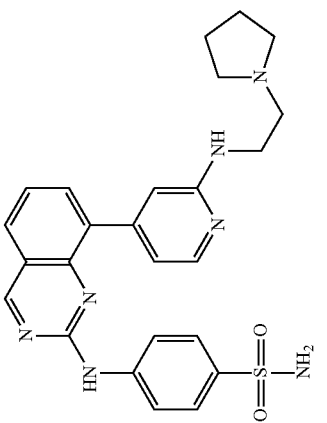 | +++ +++ +++ |

TABLE 4-continued

| | | | | |
|---|---|---|---|---|
| 748. | 4-(8-(isoxazol-4-yl)quinazolin-2-ylamino)benzene-sulfonamide | ++++ | ++++ | ++++ |
| 749. | 4-(8-(8-methyl-8-azabicyclo[3.2.1]octan-3-yloxy)quinazolin-2-ylamino)benzene-sulfonamide | ++++ | ++++ | +++ |
| 750. | 4-(7-(piperidin-4-yloxy)quinazolin-2-ylamino)benzene-sulfonamide | ++++ | ++++ | +++ |

TABLE 4-continued
| | | | | |
|---|---|---|---|---|
| 751. | 4-(8-(1H-pyrazol-yl)quinazolin-2-ylamino)benzene-sulfonamide |  | ++++ | ++++ | ++++ |
| 752. | 4-(8-(2-morpholinopyridin-4-yl)quinazolin-2-ylamino)benzene-sulfonamide | 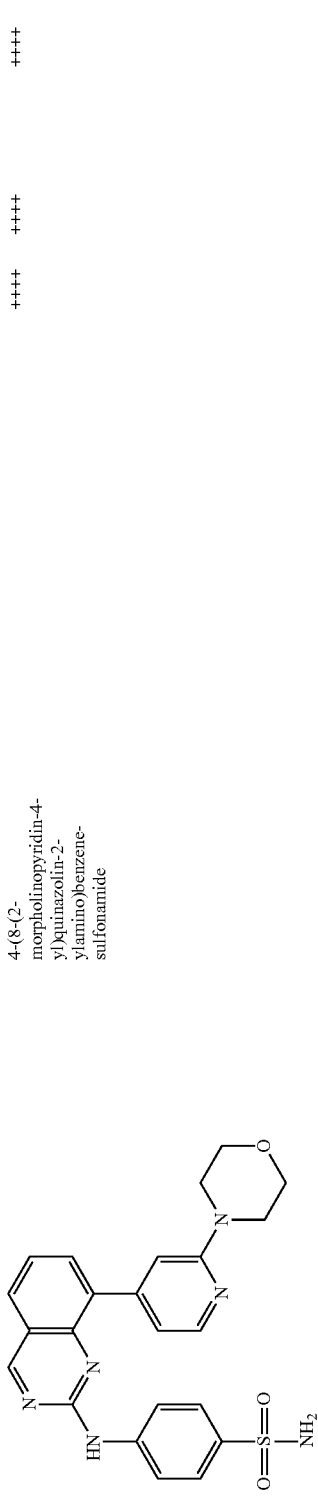 | ++++ | ++++ | ++++ |
| 753. | 4-(8-(2-(4-methylpiperazin-1-yl)pyridin-4-yl)quinazolin-2-ylamino)benzene-sulfonamide |  | ++++ | ++++ | ++++ |

TABLE 4-continued

| | | | | |
|---|---|---|---|---|
| 754. | [structure] | | ++++ | ++++ | ++++ |
| 755. | 4-(8-(2-(3-oxopiperazin-1-yl)pyridin-4-yl)quinazolin-2-ylamino)benzenesulfonamide | [structure] | ++++ | ++++ | ++++ |
| 756. | 4-(8-(2-aminopyridin-4-yl)quinazolin-2-ylamino)benzenesulfonamide | [structure] | ++++ | ++++ | ++++ |

TABLE 4-continued

| | | | |
|---|---|---|---|
| 757. | 4-(8-phenylquinazolin-2-ylamino)benzenesulfonamide | ++++ | ++++ | ++++ |
| 758. | 4-(7-(pyridin-4-yl)quinazolin-2-ylamino)benzenesulfonamide | ++++ | ++++ | ++++ |
| 759. | 2-fluoro-4-(2-(4-sulfamoylphenylamino)quinazolin-7-yl)benzamide | ++++ | +++ | ++++ |

TABLE 4-continued
| | | | | |
|---|---|---|---|---|
| 760. | 4-(8-(pyrrolidine-1-carbonyl)quinazolin-2-ylamino)benzenesulfonamide | 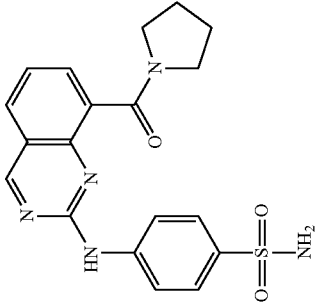 | ++++ +++ | ++++ |
| 761. | N-(2-methoxyethyl)-2-(4-sulfamoylphenyl-amino)quinazoline-8-carboxamide | 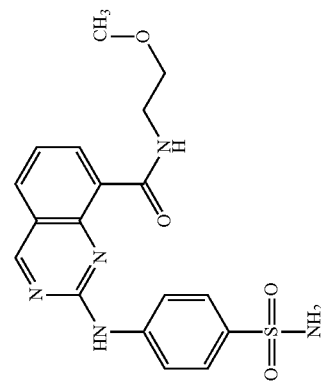 | ++++ ++++ | +++ |
| 762. | N-(2-(pyrrolidin-1-yl)ethyl)-2-(4-sulfamoylphenyl-amino)quinazoline-8-carboxamide | 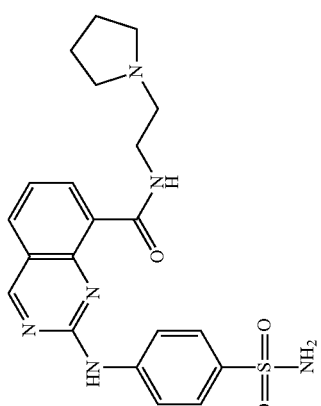 | ++++ ++++ | +++ |

TABLE 4-continued
| | | | | | |
|---|---|---|---|---|---|
| 763. | 4-(7-(1-methylpiperidin-4-yloxy)quinazolin-2-ylamino)benzenesulfonamide | 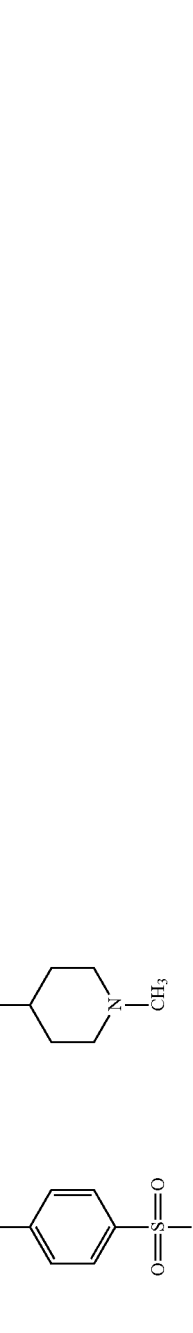 | ++++ | ++++ | ++++ | ++++ |
| 764. | 4-(7-(4-(2-methoxyethyl)piperazine-1-carbonyl)quinazolin-2-ylamino)benzenesulfonamide | 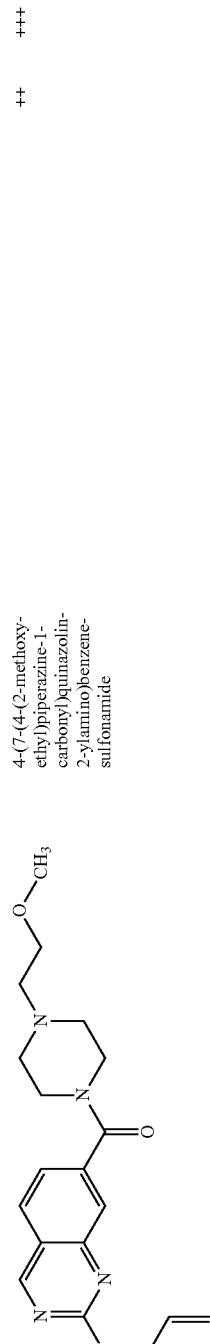 | ++ | ++ | +++ | ++ |
| 765. | 4-(8-(5-chloro-2-methoxypyridin-4-yl)quinazolin-2-ylamino)benzenesulfonamide | 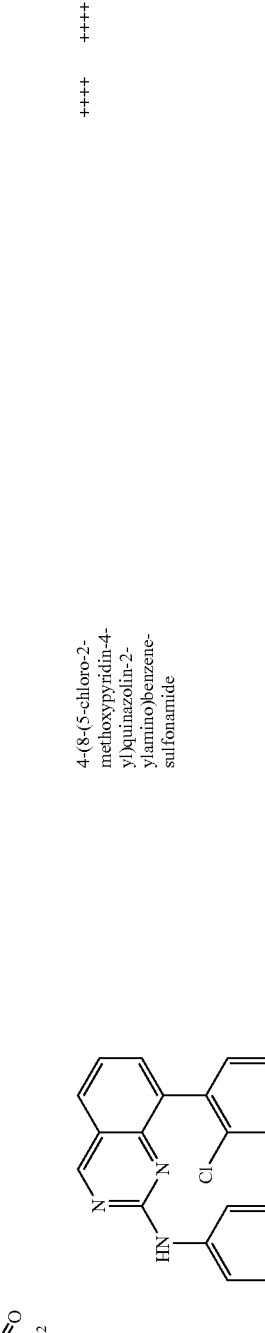 | ++++ | ++++ | ++++ | +++ |

TABLE 4-continued
| | | | | |
|---|---|---|---|---|
| 766. | 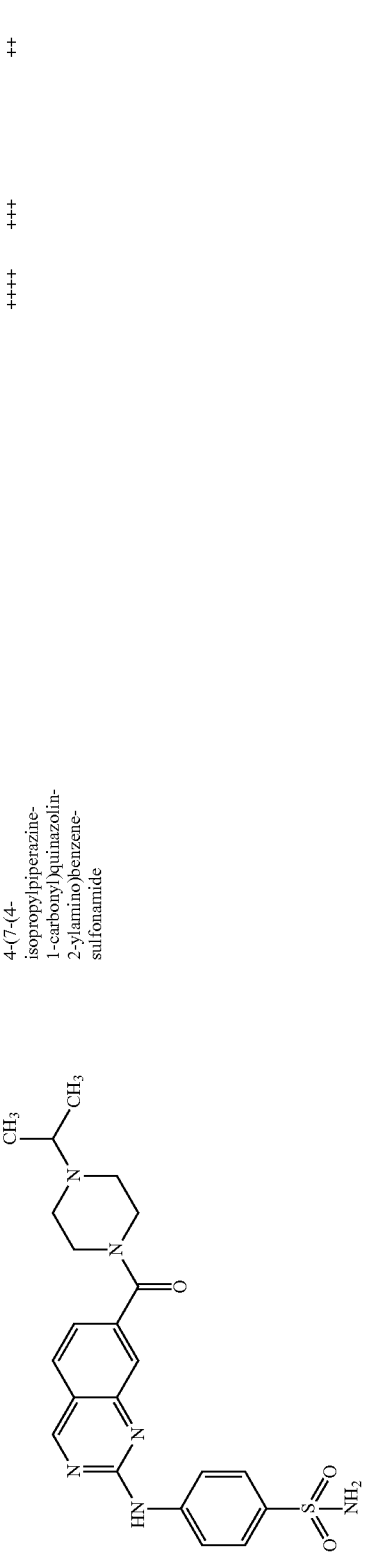 4-(7-(4-isopropylpiperazine-1-carbonyl)quinazolin-2-ylamino)benzene-sulfonamide | ++++ | +++ | ++ |
| 767. | 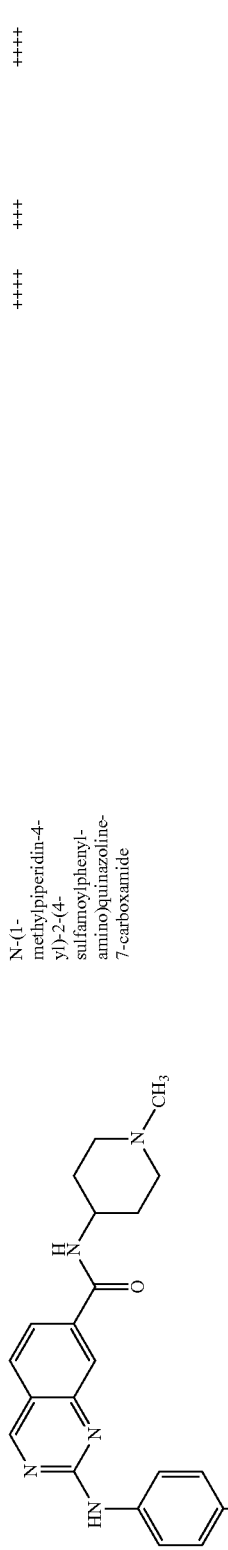 N-(1-methylpiperidin-4-yl)-2-(4-sulfamoylphenyl-amino)quinazoline-7-carboxamide | ++++ | +++ | +++ |
| 768. |  4-(8-(morpholine-4-carbonyl)quinazolin-2-ylamino)benzene-sulfonamide | +++ | +++ | +++ |

TABLE 4-continued

| | | | | | |
|---|---|---|---|---|---|
| 769. | [structure] | 4-(8-(4-methylpiperazine-1-carbonyl)quinazolin-2-ylamino)benzene-sulfonamide | +++ | +++ | ++++ |
| 770. | [structure] | | ‡ | ‡‡ | ‡ |
| 771. | [structure] | N-(4-(morpholino-sulfonyl)phenyl)-8-(piperidin-4-yloxy)quinazolin-2-amine | ++++ | ++++ | ++++ |

TABLE 4-continued
| | | | | | |
|---|---|---|---|---|---|
| 772. | 8-(1-isopropylpiperidin-4-yloxy)-N-(4-(morpholinosulfonyl)-phenyl)quinazolin-2-amine |  | +++ | +++ | +++ |
| 773. | N-(3-(morpholinosulfonyl)phenyl)-8-(piperidin-4-yloxy)quinazolin-2-amine | 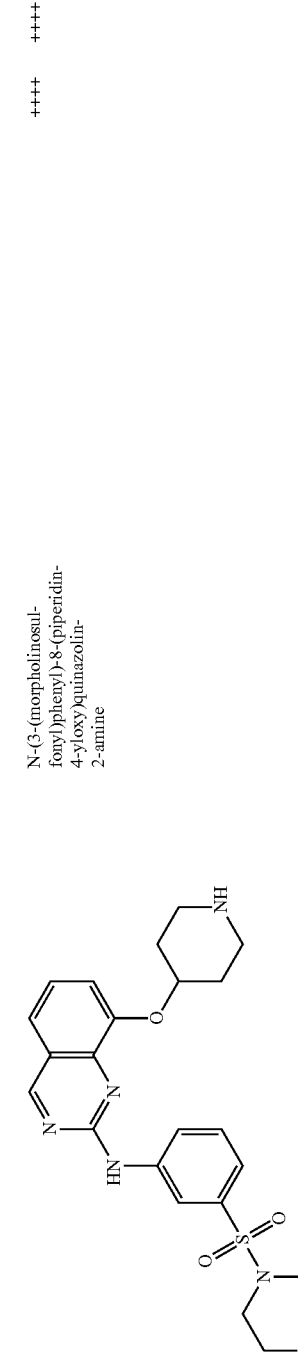 | +++ | +++ | +++ |
| 774. | 8-(1-isopropylpiperidin-4-yloxy)-N-(3-(morpholinosulfonyl)phenyl)quinazolin-2-amine | 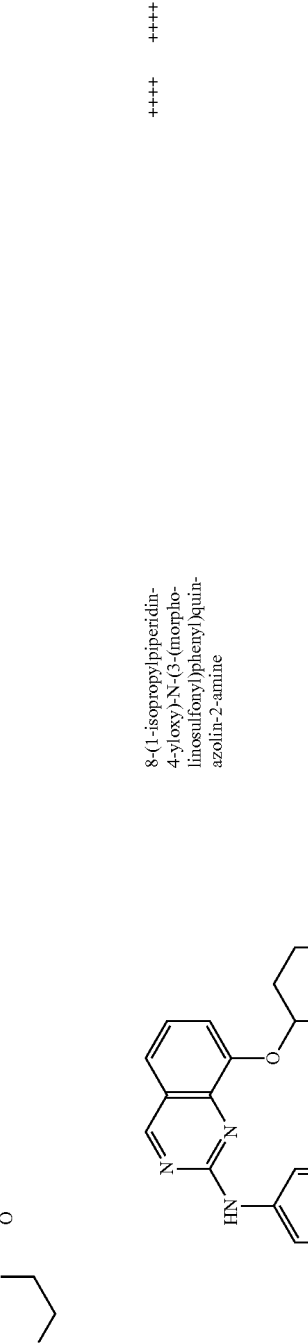 | +++ | +++ | +++ |

TABLE 4-continued
| | | | | |
|---|---|---|---|---|
| 775. | N-(3-(4-methylpiperazin-1-ylsulfonyl)phenyl)-8-(piperidin-4-yloxy)quinazolin-2-amine | ++++ | +++ | ++++ |
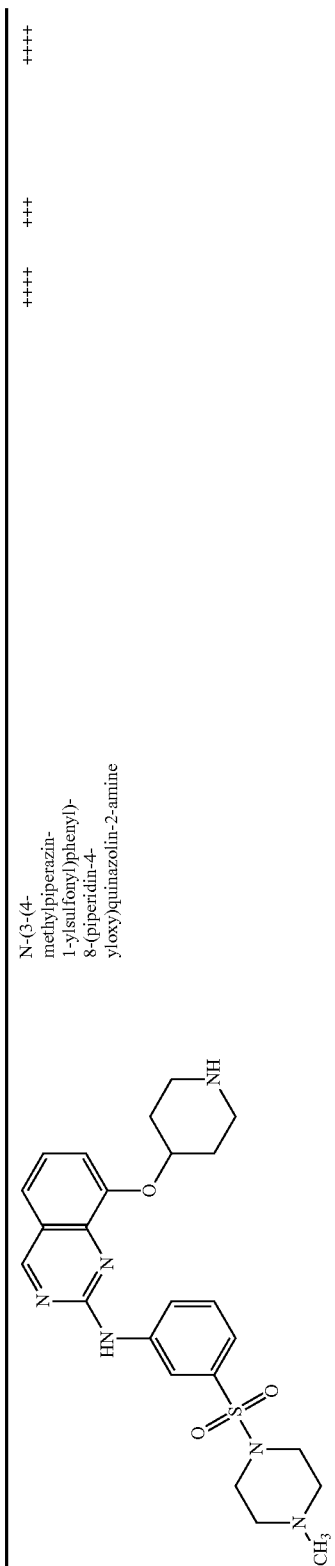
| | | | | |
|---|---|---|---|---|
| 776. | N-isopropyl-3-(8-(piperidin-4-yloxy)quinazolin-2-ylamino)benzenesulfonamide | ++++ | +++ | ++++ |
| | | | | |
|---|---|---|---|---|
| 777. | N-(2-methoxyethyl)-3-(8-(piperidin-4-yloxy)quinazolin-2-ylamino)benzenesulfonamide | ++++ | +++ | ++++ |

TABLE 4-continued
| | | | | | |
|---|---|---|---|---|---|
| 778. | N-(4-(4-methylpiperazin-1-ylsulfonyl)phenyl)-8-(piperidin-4-yloxy)-quinazolin-2-amine 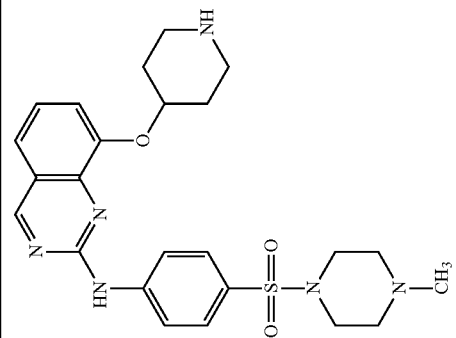 | ++++ | ++++ | ++++ | ++++ |
| 779. | N-isopropyl-4-(8-(piperidin-4-yloxy)quinazolin-2-ylamino)benzenesulfonamide 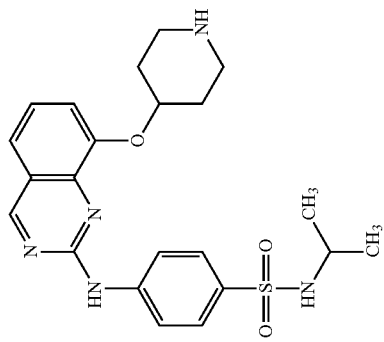 | ++++ | ++++ | ++++ | ++++ |

TABLE 4-continued
| 780. | N-(2-methoxyethyl)-4-(8-(piperidin-4-yloxy)quinazolin-2-ylamino)benzenesulfonamide | 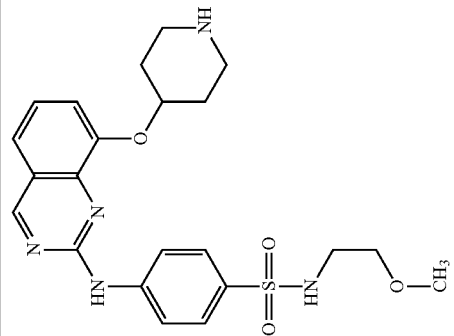 | ++++ | ++++ | ++++ | ++++ |
| 781. | N-cyclopropyl-4-(8-(piperidin-4-yloxy)quinazolin-2-ylamino)benzenesulfonamide | 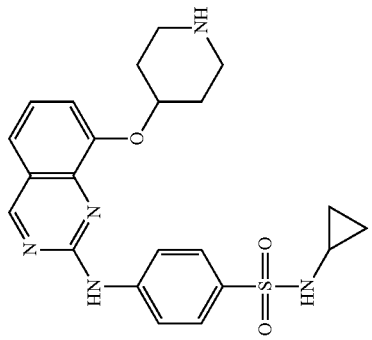 | ++++ | ++++ | ++++ | ++++ |

TABLE 4-continued

| | | | | |
|---|---|---|---|---|
| 782. | 3-(2-4-sulfamoylphenyl-amino)quinazolin-7-yl)benzamide | ++++ | +++ | +++ |
| 783. | 4-(2-(4-sulfamoylphenyl-amino)quinazolin-7-yl)benzamide | ++++ | +++ | +++ |
| 784. | 2-(2-(4-sulfamoylphenyl-amino)quinazolin-7-yl)benzamide | ++++ | +++ | +++ |

TABLE 4-continued
| | | | |
|---|---|---|---|
| 785. | 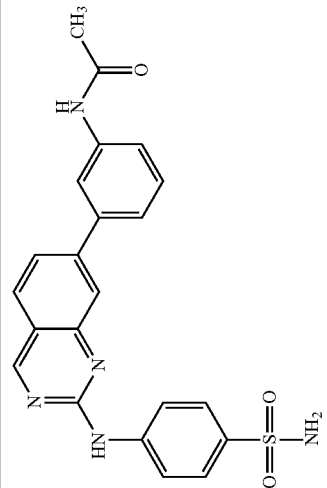 N-(3-(2-(4-sulfamoyl)phenyl-amino)quinazolin-7-yl)phenyl)-acetamide | +++ | +++ |
| 786. | 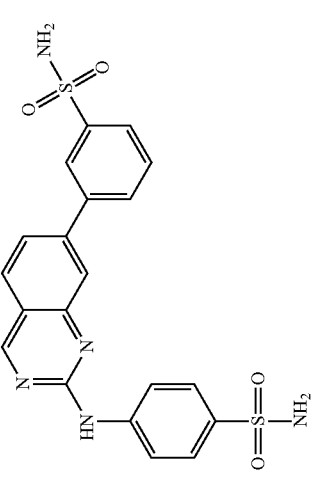 3-(2-(4-sulfamoyl)phenyl-amino)quinazolin-7-yl)benzene-sulfonamide | ++++ | ++++ | +++ |
| 787. | 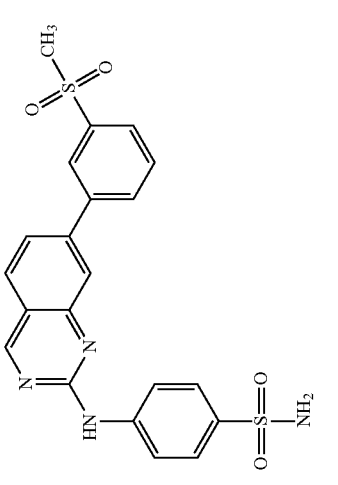 4-(7-(3-(methyl-sulfonyl)phenyl)quinazolin-2-ylamino)benzene-sulfonamide | ++++ | ++++ |

TABLE 4-continued

| # | Name | Structure | Activity |
|---|------|-----------|----------|
| 788. | 4-(7-(3-methyl-sulfonamidophenyl)quin-azolin-2-ylamino)benzene-sulfonamide | | ++  ++ |
| 789. | 4-(7-(6-aminopyridin-3-yl)quinazolin-2-ylamino)benzene-sulfonamide | | ++++  ++++  ++++ |
| 790. | 5-(2-(4-sulfamoylphenylamino)-quinazolin-7-yl)-picolinamide | | ++++  +++  +++ |

TABLE 4-continued

| # | Structure | Name | | | |
|---|---|---|---|---|---|
| 791. | | 4-(7-(benzo[d][1,3]dioxol-5-yl)quinazolin-2-ylamino)benzenesulfonamide | + | +++ | + |
| 792. | | 4-(7-(1H-pyrazol-4-yl)quinazolin-2-ylamino)benzenesulfonamide | ++++ | ++++ | +++ |
| 793. | | 4-(7-(pyridin-3-yl)quinazolin-2-ylamino)benzenesulfonamide | ++++ | ++++ | +++ |

TABLE 4-continued

| # | Name | Structure | | | |
|---|---|---|---|---|---|
| 794. | 4-(7-(1-isopropylpiperidin-4-yloxy)quinazolin-2-ylamino)benzene-sulfonamide | | +++ | +++ | +++ |
| 795. | 4-(7-hydroxy-8-(1-isopropylpiperidin-4-yl)quinazolin-2-ylamino)benzene-sulfonamide | | +++ | +++ | +++ |
| 796. | 4-(8-(1-isopropylpiperidin-4-yloxy)quinazolin-2-ylamino)-N-methylbenzamide | | +++ | +++ | +++ |

TABLE 4-continued

| | | | | | |
|---|---|---|---|---|---|
| 797. | N-isopropyl-4-(8-(1-isopropylpiperidin-4-yloxy)quinazolin-2-ylamino)benzamide | ++++ | ++++ | ++++ | ++++ |
| 798. | 4-(7-(4-methylpiperazine-1-carbonyl)quinazolin-2-ylamino)benzenesulfonamide | ± | ± | ++ | ± |
| 799. | 4-(7-(1-methyl-1H-pyrazol-4-yl)quinazolin-2-ylamino)benzenesulfonamide | ++++ | ++++ | ++++ | ++++ |

TABLE 4-continued

| | | | | | |
|---|---|---|---|---|---|
| 800. | 4-(7-(2-fluoropyridin-3-yl)quinazolin-2-ylamino)benzenesulfonamide | | ++++ | ++++ | ++++ |
| 801. | 4-(7-(5-methoxypyridin-3-yl)quinazolin-2-ylamino)benzenesulfonamide | | ++++ | +++ | +++ |
| 802. | 4-(7-(4-(morpholine-4-carbonyl)phenyl)quinazolin-2-ylamino)benzenesulfonamide | | ++++ | +++ | +++ |

TABLE 4-continued
| | | | | |
|---|---|---|---|---|
| 803. | N-(piperidin-3-yl)-2-(4-sulfamoylphenyl-amino)quinazoline-8-carboxamide |  | ++++ | +++ | ++++ |
| 804. | (R)-4-(8-(3-(dimethyl-amino)pyrrolidine-1-carbonyl)quinazolin-2-ylamino)benzene-sulfonamide |  | ++++ | +++ | ++++ |
| 805. | N-(piperidin-4-yl)-2-(4-sulfamoylphenyl-amino)quinazoline-8-carboxamide |  | ++++ | +++ | ++++ |

TABLE 4-continued
| | | | |
|---|---|---|---|
| 806. | (S)-4-(8-(3-(dimethyl-amino)pyrrolidine-1-carbonyl)quinazolin-2-ylamino)benzene-sulfonamide | 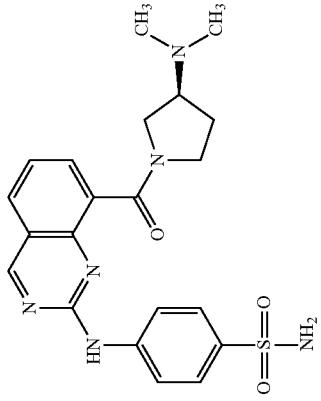 | +++ +++ ++++ |
| 807. | (R)-N-(quinuclidin-3-yl)-2-(4-sulfamoyl-phenylamino)quinazoline-8-carboxamide | 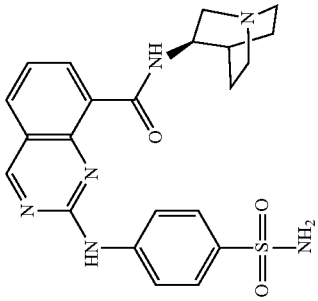 | +++ +++ +++ |
| 808. | 4-(8-(3-oxopiperazine-1-carbonyl)quinazolin-2-ylamino)benzene-sulfonamide | 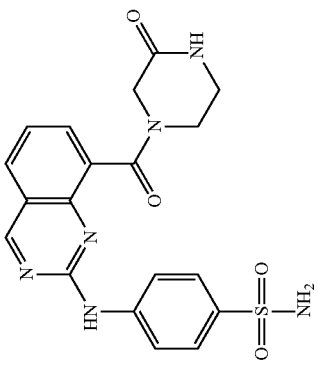 | ++++ +++ +++ |

TABLE 4-continued

| | | | | |
|---|---|---|---|---|
| 809. | (S)-N-(quinuclidin-3-yl)-2-(4-sulfamoylphenyl-amino)quinazoline-8-carboxamide | | +++ | ++++ |
| 810. | 4-(8-(piperidin-4-yloxy)quinazolin-2-ylamino)-N-(2-(pyrrolidin-1-yl)ethyl)benzenesulfonamide | ++++ | ++++ | ++++ |

| | | | | |
|---|---|---|---|---|
| 811. | 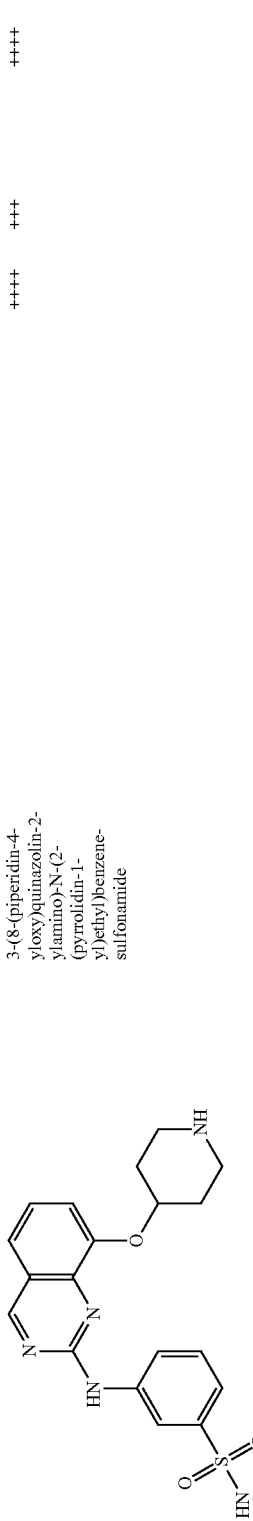 3-(8-(piperidin-4-yloxy)quinazolin-2-ylamino)-N-(2-(pyrrolidin-1-yl)ethyl)benzenesulfonamide | ++++ | +++ | ++++ |
| 812. |  N-cyclopropyl-3-(8-(piperidin-4-yloxy)quinazolin-2-ylamino)benzenesulfonamide | ++++ | ++++ | ++++ |
| 813. |  4-(7-(1H-indazol-6-yl)quinazolin-2-ylamino)benzenesulfonamide | ++++ | +++ | ++++ |

TABLE 4-continued

| | | | | |
|---|---|---|---|---|
| 814. | 4-(7-(2-methoxypyrimidin-5-yl)quinazolin-2-ylamino)benzenesulfonamide | ++++ | ++++ | ++++ |
| 815. | 4-(7-(1H-indazol-6-ylamino)quinazolin-2-ylamino)benzenesulfonamide | ++++ | ++++ | ++++ |
| 816. | 4-(8-(1-isobutylpiperidin-4-yloxy)quinazolin-2-ylamino)benzenesulfonamide | ++++ | ++++ | ++++ |

TABLE 4-continued

| | | | | |
|---|---|---|---|---|
| 817. | 4-(8-(1-ethylpiperidin-4-yloxy)quinazolin-2-ylamino)benzene-sulfonamide | ++++ | ++++ | ++++ |
| 818. | 4-(8-(1-isopropylazetidin-3-yloxy)quinazolin-2-ylamino)benzene-sulfonamide | ++++ | ++++ | ++++ |
| 819. | 4-(8-(azetidin-3-yloxy)quinazolin-2-ylamino)benzene-sulfonamide | ++++ | ++++ | +++ |

TABLE 4-continued

| | | | | |
|---|---|---|---|---|
| 820. | 4-(7-(pyrrolidine-1-carbonyl)quinazolin-2-ylamino)benzenesulfonamide | ++++ | ++++ | ++++ |
| 821. | 4-(8-(6-aminopyridin-3-yl)quinazolin-2-ylamino)benzenesulfonamide | ++++ | ++++ | ++++ |
| 822. | 4-(8-(3-(4-methylpiperazine-1-carbonyl)phenyl)-quinazolin-2-ylamino)benzenesulfonamide | ++++ | ++++ | ++++ |

TABLE 4-continued

| | | | | | |
|---|---|---|---|---|---|
| 823. | 4-(8-(2-aminopyrimidin-5-yl)quinazolin-2-ylamino)benzenesulfonamide | | ++++ | ++++ | ++++ |
| 824. | 4-(8-(4-(4-methyl-piperazine-1-carbonyl)phenyl)quinazolin-2-ylamino)benzenesulfonamide | | ++++ | ++++ | ++++ |
| 825. | 4-(8-(6-(2-methoxyethyl-amino)pyridin-3-yl)quinazolin-2-ylamino)benzenesulfonamide | | ++++ | ++++ | ++++ |

TABLE 4-continued
| | | | | |
|---|---|---|---|---|
| 826. | 4-(8-(6-morpholinopyridin-3-yl)quinazolin-2-ylamino)benzenesulfonamide | 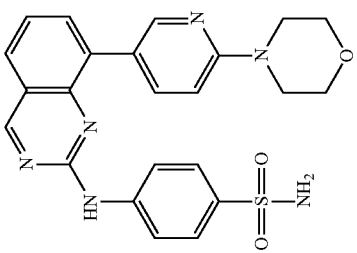 | ++++ | ++++ | ++++ |
| 827. | 4-(8-(6-(4-methylpiperazin-1-yl)pyridin-3-yl)-quinazolin-2-ylamino)benzenesulfonamide | 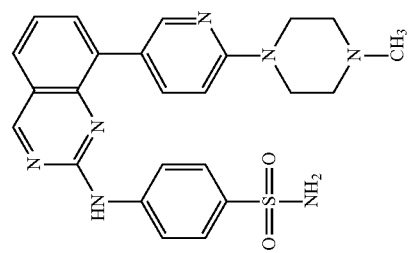 | ++++ | ++++ | ++++ |

| | | | | |
|---|---|---|---|---|
| 828. | 4-(8-(6-(3-oxopiperazin-1-yl)pyridin-3-yl)quinazolin-2-ylamino)benzenesulfonamide | +++ | +++ | +++ |
| 829. | N-(2-(5-(2-(4-sulfamoylphenylamino)quinazolin-8-yl)pyridin-2-ylamino)ethyl)acetamide | +++ | +++ | +++ |
| 830. | 4-(8-(6-(2-(pyrrolidin-1-yl)ethylamino)pyridin-3-yl)-quinazolin-2-ylamino)benzenesulfonamide | +++ | +++ | +++ |

TABLE 4-continued

| | | | |
|---|---|---|---|
| 831. | [structure] | 4-(8-(6-(isopropylamino)pyridin-3-yl)quinazolin-2-ylamino)benzenesulfonamide | ++++ ++++ ++++ |
| 832. | [structure] | 4-(8-(6-(pyrrolidin-1-yl)pyridin-3-yl)quinazolin-2-ylamino)benzenesulfonamide | ++++ ++++ ++++ |
| 833. | [structure] | 4-(8-(2-oxo-1,2-dihydropyridin-4-yl)quinazolin-2-ylamino)benzenesulfonamide | ++++ ++++ ++++ |

TABLE 4-continued

| | | | | |
|---|---|---|---|---|
| 834. | | | +++ | +++ | +++ |
| 835. | 4-(8-(1-isobutylazetidin-3-yloxy)quinazolin-2-ylamino)benzenesulfonamide | | +++ | +++ | +++ |
| 836. | 4-(7-(2,6-difluoropyridin-3-yl)quinazolin-2-ylamino)benzenesulfonamide | | +++ | +++ | +++ |

TABLE 4-continued

| | | | | |
|---|---|---|---|---|
| 837. | 4-(7-(6-fluoropyridin-3-yl)quinazolin-2-ylamino)benzenesulfonamide | ++++ | ++++ | ++++ |
| 838. | N-(5-chloro-2-methlyphenyl)-2-(4-sulfamoylphenylamino)quinazoline-7-carboxamide | ++++ | ++++ | ++++ |
| 839. | N-(3-carbamoyl-4-methylthiophen-2-yl)-2-(4-sulfamoylphenylamino)quinazoline-7-carboxamide | ++++ | ++++ | ++++ |

| | | | |
|---|---|---|---|
| 840. | 4-(7-(1-oxo-1,2,3,4-tetrahydroisoquinolin-6-yl)quinazolin-2-ylamino)benzenesulfonamide |  | ++++ ++++ +++ ++++ |
| 841. | 4-(8-(1-ethylazetidin-3-yloxy)quinazolin-2-ylamino)benzenesulfonamide | 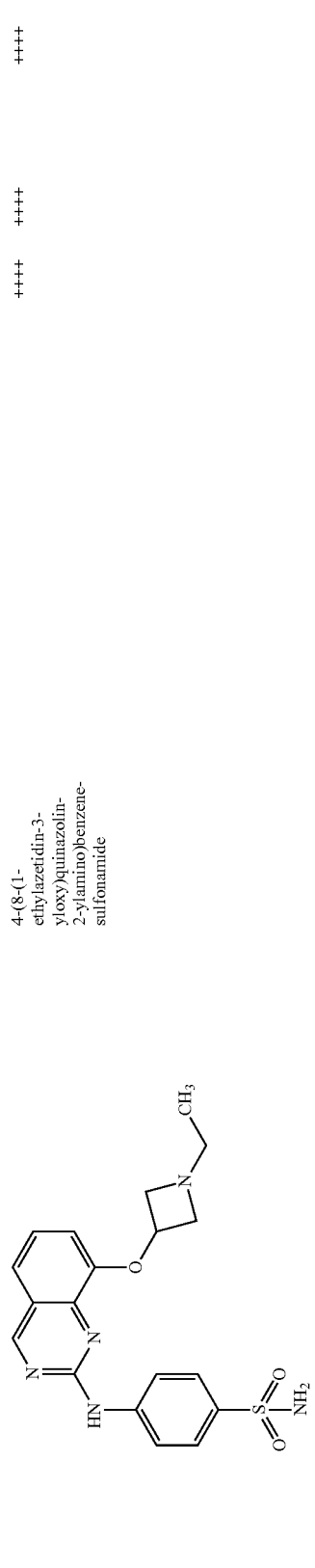 | ++++ ++++ +++ ++++ |
| 842. | N-(2-carbamoyl-5-methylphenyl)-2-(4-sulfamoylphenyl-amino)quinazoline-7-carboxamide |  | ++++ ++++ +++ ++++ |

TABLE 4-continued

| | | | | | |
|---|---|---|---|---|---|
| 843. | 4-(7-(1-methylpiperidin-4-ylamino)quinazolin-2-ylamino)benzenesulfonamide | ++++ | ++++ | ++++ | ++++ |
| 844. | 4-(7-(2-oxo-1,2-dihydropyrimidin-5-yl)quinazolin-2-ylamino)benzenesulfonamide | ++++ | +++ | ++++ | ++++ |
| 845. | 4-(7-bromo-8-(piperidin-4-yloxy)quinazolin-2-ylamino)benzenesulfonamide | ++++ | ++++ | ++++ | ++++ |

TABLE 4-continued

| | Structure | Name | | | | | |
|---|---|---|---|---|---|---|---|
| 846. | (structure) | 4-(6-bromo-8-(piperidin-4-yloxy)quinazolin-2-ylamino)benzenesulfonamide | Similar to example 1 | ++++ | ++++ | ++++ | ++++ |
| 847. | (structure) | 4-(6-bromo-8-(quinuclidin-3-yloxy)quinazolin-2-ylamino)benzenesulfonamide | Similar to example 1 | ++++ | ++++ | ++++ | ++++ |
| 848. | (structure) | 4-(7-(1,3,5-trimethyl-1H-pyrazol-4-yl)quinazolin-2-ylamino)benzenesulfonamide | | ++++ | ++++ | ++++ | ++++ |

TABLE 4-continued
| | | | |
|---|---|---|---|
| 849. | 4-(7-(1-isobutyl-1H-pyrazol-4-yl)quinazolin-2-ylamino)benzenesulfonamide | 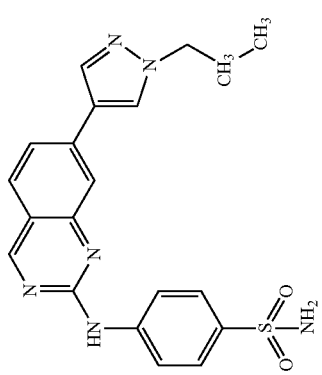 | +++ +++ +++ +++ |
| 850. | 4-(7-(2-(pyrrolidin-1-yl)ethylamino)pyridin-4-yl)quinazolin-2-ylamino)benzenesulfonamide | 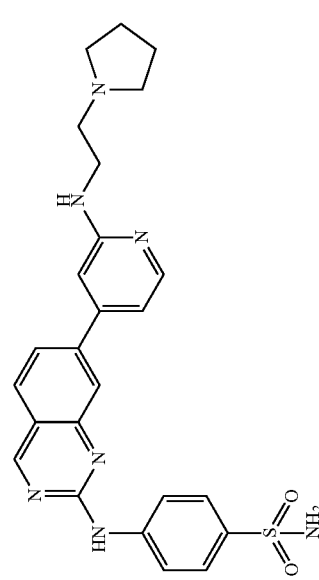 | +++ +++ ++ +++ |
| 851. | 4-(7-(2-(pyrrolidin-1-yl)pyridin-4-yl)quinazolin-2-ylamino)benzenesulfonamide | 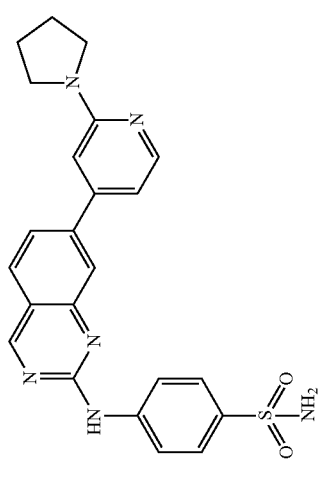 | +++ +++ ++ +++ |

| | | |
|---|---|---|
| 852. | 4-(7-(2-morpholinopyridin-4-yl)quinazolin-2-ylamino)benzenesulfonamide 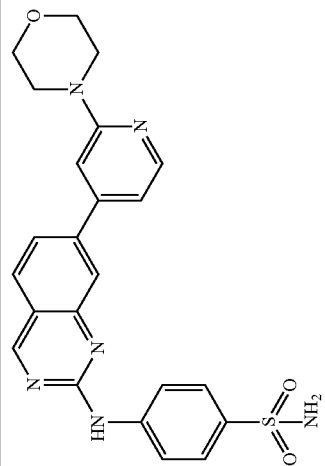 | ++++ ++++ |
| 853. | 4-(8-(piperidin-4-yloxy)-7-(pyridin-3-yl)quinazolin-2-ylamino)benzenesulfonamide 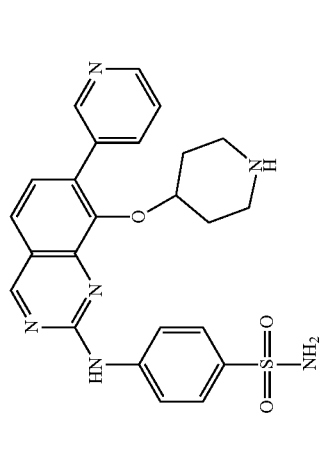 | ++++ ++++ |
| 854. | 4-(8-(piperidin-4-yloxy)-2-(4-sulfamoylphenyl-amino)quinazolin-7-yl)benzamide 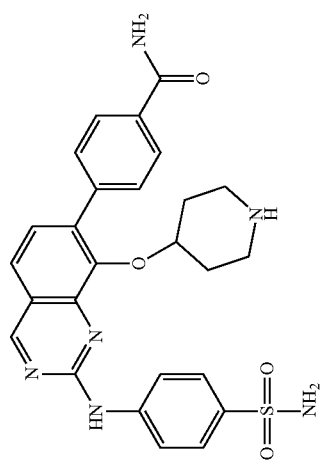 | ++++ +++ |

TABLE 4-continued
| | | | |
|---|---|---|---|
| 855. | 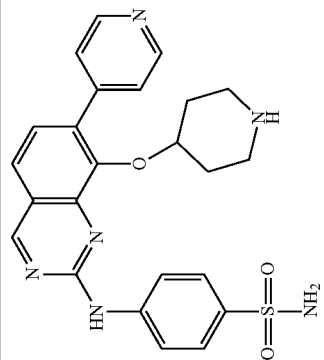 | 4-(8-(piperidin-4-yloxy)-7-(pyridin-4-yl)quinazolin-2-ylamino)benzenesulfonamide | ++++ +++ |
| 856. | 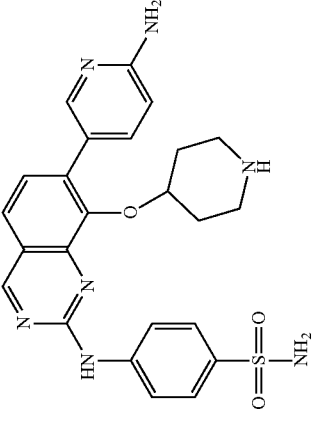 | 4-(7-(6-aminopyridin-3-yl)-8-(piperidin-4-yloxy)quinazolin-2-ylamino)benzenesulfonamide | ++++ ++++ |
| 857. | 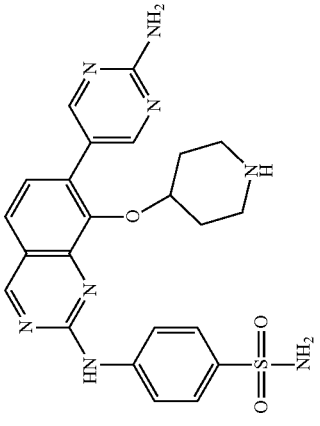 | 4-(7-(2-aminopyrimidin-5-yl)-8-(piperidin-4-yloxy)quinazolin-2-ylamino)benzenesulfonamide | ++++ +++ |

TABLE 4-continued
| | | | | |
|---|---|---|---|---|
| 858. | 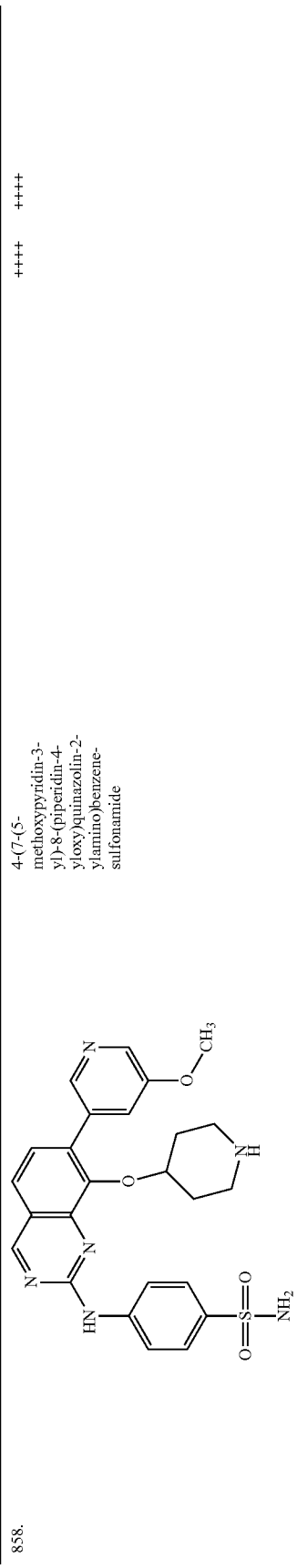 | 4-(7-(5-methoxypyridin-3-yl)-8-(piperidin-4-yloxy)quinazolin-2-ylamino)benzenesulfonamide | +++ | ++++ |
| 859. |  | 4-(8-(piperidin-4-yloxy)-7-(1H-pyrazol-4-yl)quinazolin-2-ylamino)benzenesulfonamide | +++ | ++++ |
| 860. | 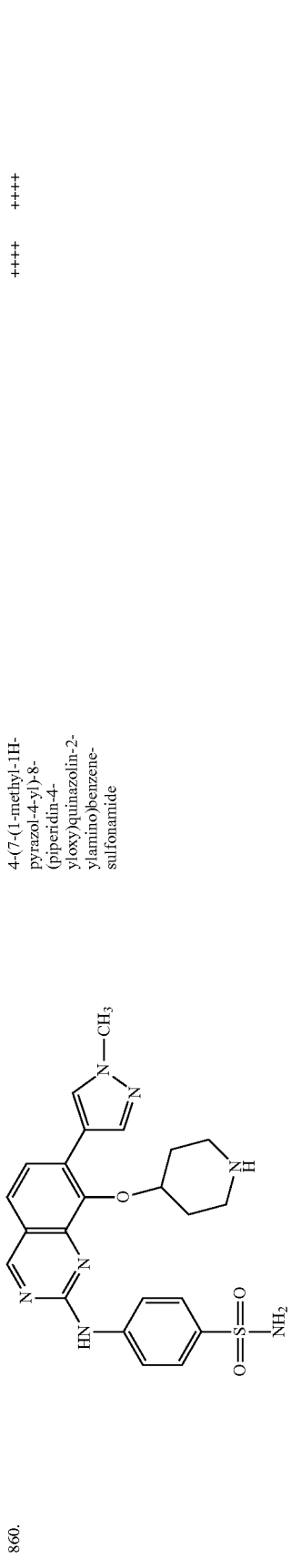 | 4-(7-(1-methyl-1H-pyrazol-4-yl)-8-(piperidin-4-yloxy)quinazolin-2-ylamino)benzenesulfonamide | +++ | ++++ |

TABLE 4-continued

| | Name | Structure | | |
|---|---|---|---|---|
| 861. | 4-(7-(oxazol-2-yl)-8-(piperidin-4-yloxy)quinazolin-2-ylamino)benzenesulfonamide | | ++++ | ++++ |
| 862. | 4-(8-(piperidin-4-yloxy)-7-(thiazol-2-yl)quinazolin-2-ylamino)benzenesulfonamide | | ++++ | ++++ |
| 863. | 4-(8-(piperidin-4-yloxy)-7-(pyridin-2-yl)quinazolin-2-ylamino)benzenesulfonamide | | ++++ | ++++ |

TABLE 4-continued
| | | | |
|---|---|---|---|
| 864. | 4-(7-cyano-8-(piperidin-4-yloxy)quinazolin-2-ylamino)benzenesulfonamide | 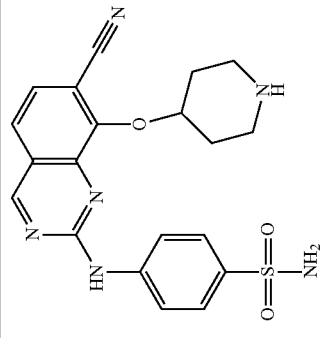 | ++++ ++++ |
| 865. | 4-(7-(3,5-dimethyl-1H-pyrazol-4-yl)quinazolin-2-ylamino)benzenesulfonamide | 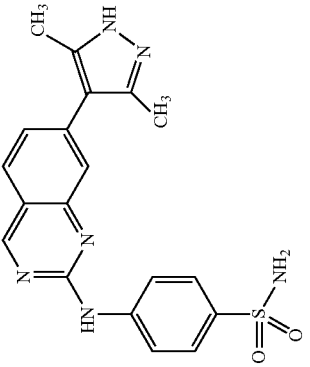 | ++++ ++++ |
| 866. | 4-(7-(isoxazol-4-yl)quinazolin-2-ylamino)benzenesulfonamide | 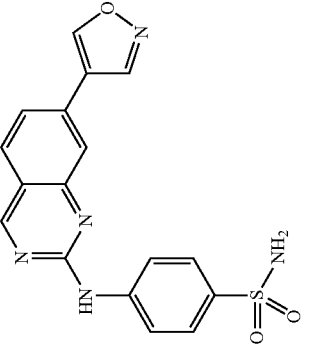 | ++++ ++++ |

TABLE 4-continued
| | | | | |
|---|---|---|---|---|
| 867. | 4-(7-(3,5-dimethylisoxazol-4-yl)quinazolin-2-ylamino)benzenesulfonamide | 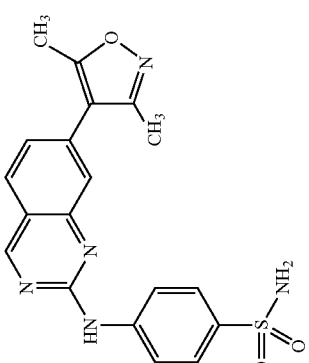 | +++ | ++++ | ++++ |
| 868. | N-(4-(morpholinosulfonyl)phenyl)-7-(1H-pyrazol-4-yl)quinazolin-2-amine | 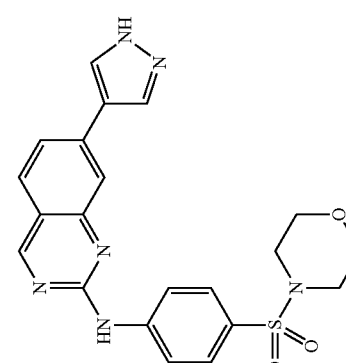 | +++ | ++++ | ++++ |
| 869. | 7-(1-methylpiperidin-4-yloxy)-N-(4-(morpholinosulfonyl)phenyl)quinazolin-2-amine | 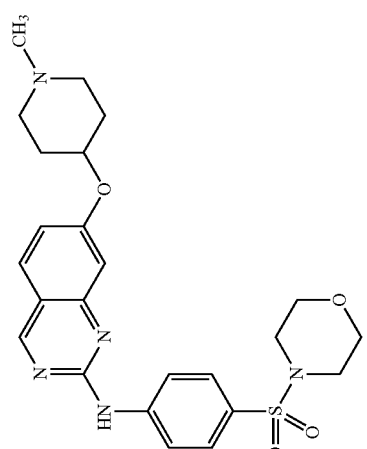 | +++ | ++++ | ++++ |

TABLE 4-continued
| | | | |
|---|---|---|---|
| 870. | 4-(7-hydroxy-8-(1-methylpiperidin-4-yl)quinazolin-2-ylamino)benzenesulfonamide | 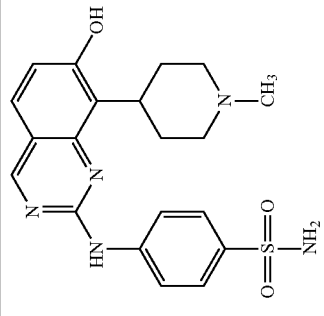 | ++++ ++++ |
| 871. | 4-(8-((4-methylpiperazin-1-yl)methyl)quinazolin-2-ylamino)benzenesulfonamide | 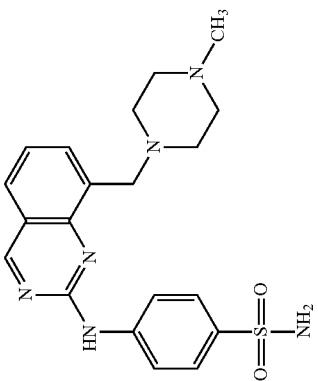 | ++++ ++++ |
| 872. | 4-(8-(morpholinomethyl)quinazolin-2-ylamino)benzenesulfonamide | 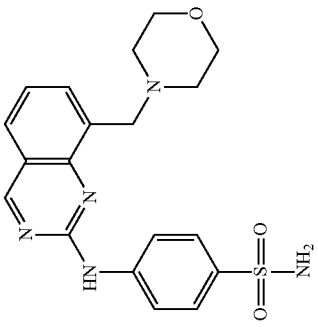 | ++++ ++++ |

TABLE 4-continued

| | | | |
|---|---|---|---|
| 873. | 4-(8-(4-fluorophenyl-amino)quinazolin-2-ylamino)benzene-sulfonamide | ++++ | ++++ |
| 874. | 7-(1-isopropyl-piperidin-4-yloxy)-N-(4-(morpholino-sulfonyl)phenyl)quinazolin-2-amine | ++++ | ++++ |
| 875. | 4-(7-(1-oxo-1,2,3,4-tetrahydroisoquinolin-6-yl)-8-(piperidin-4-yloxy)quinazolin-2-ylamino)benzene-sulfonamide | ++++ | +++ |

TABLE 4-continued
| | | | |
|---|---|---|---|
| 876. | 4-(7-(1-isobutyl-1H-pyrazol-4-yl)-8-(piperidin-4-yloxy)quinazolin-2-ylamino)benzenesulfonamide | 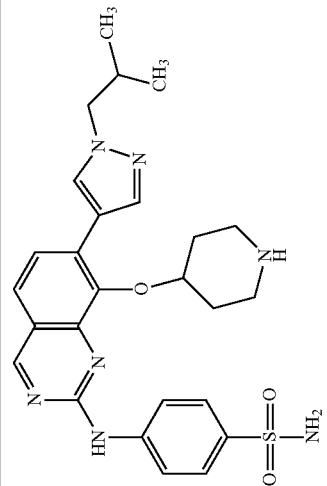 | ++++ ++++ |
| 877. | 4-(8-(piperidin-4-yloxy)-7-(pyrazin-2-yl)quinazolin-2-ylamino)benzenesulfonamide | 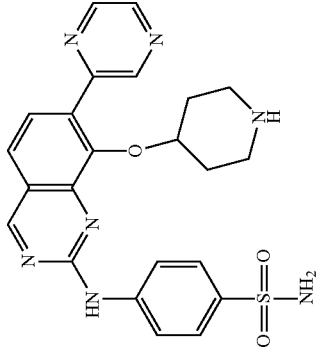 | ++++ ++++ |
| 878. | 4-(7-(6-(2-(pyrrolidin-1-yl)ethylamino)pyridin-3-yl)quinazolin-2-ylamino)benzenesulfonamide | 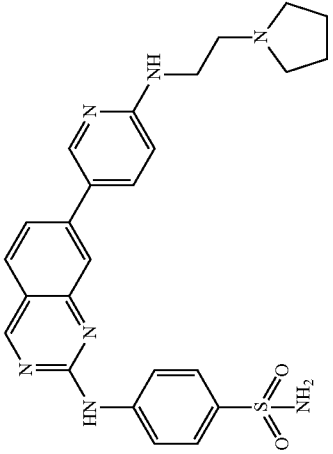 | ++++ ++++ |

TABLE 4-continued

| | | | |
|---|---|---|---|
| 879. | 4-(7-(6-(4-methyl-piperazin-1-yl)pyridin-3-yl)quinazolin-2-ylamino)benzene-sulfonamide | ++++ | ++++ |
| 880. | 4-(7-(6-(pyrrolidin-1-yl)pyridin-3-yl)quinazolin-2-ylamino)benzene-sulfonamide | ++++ | +++ |
| 881. | 4-(7-(6-morpholinopyridin-3-yl)quinazolin-2-ylamino)benzene-sulfonamide | ++++ | +++ |

TABLE 4-continued

| | | |
|---|---|---|
| 882. | 4-(7-(2-(4-methylpiperazin-1-yl)pyridin-4-yl)quinazolin-2-ylamino)benzenesulfonamide | ++++ ++++ |
| 883. | 4-(7-(1-isopentyl-1H-pyrazol-4-yl)quinazolin-2-ylamino)benzenesulfonamide | ++++ ++++ |
| 884. | 4-(6-fluoro-8-(1-oxo-1,2,3,4-tetrahydroisoquinolin-6-yl)quinazolin-2-ylamino)benzenesulfonamide | ++++ ++++ |

TABLE 4-continued

| | Name | Structure | | |
|---|---|---|---|---|
| 885. | 4-(8-(6-aminopyridin-3-yl)-6-fluoroquinazolin-2-ylamino)benzenesulfonamide | (structure) | ++++ | ++++ | ++++ |
| 886. | 4-(6-fluoro-2-(4-sulfamoylphenyl-amino)quinazolin-8-yl)benzamide | (structure) | ++++ | +++ | |
| 887. | 4-(8-(1-oxo-1,2,3,4-tetrahydroisoquinolin-6-yl)quinazolin-2-ylamino)benzenesulfonamide | (structure) | ++++ | +++ | |

TABLE 4-continued

| | | | | |
|---|---|---|---|---|
| 888. | 4-(6-fluoro-8-(6-(4-methylpiperazin-1-yl)pyridin-3-yl)quinazolin-2-ylamino)benzenesulfonamide | ++++ | ++++ | ++++ |
| 889. | 4-(6-fluoro-8-(6-(3-oxopiperazin-1-yl)pyridin-3-yl)quinazolin-2-ylamino)benzenesulfonamide | ++++ | ++++ | |

TABLE 4-continued
| | | | |
|---|---|---|---|
| 890. | 4-(6-fluoro-8-(6-(pyrrolidin-1-yl)-pyridin-3-yl)-quinazolin-2-ylamino)benzene-sulfonamide | 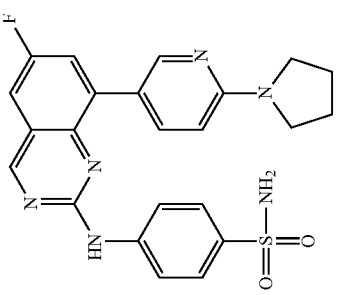 | +++ +++ +++ |
| 891. | N-(2-(5-(6-fluoro-2-(4-sulfamoylphenyl-amino)quinazolin-8-yl)pyridin-2-ylamino)ethyl)acetamide | 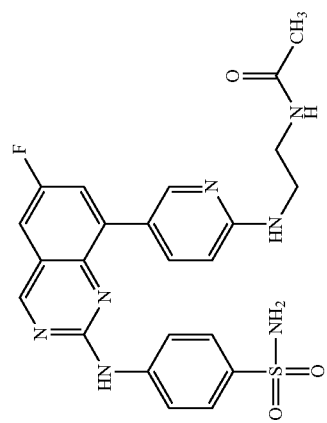 | +++ +++ +++ |
| 892. | 4-(6-fluoro-8-(6-(2-(pyrrolidin-1-yl)ethylamino)pyridin-3-yl)quinazolin-2-ylamino)benzene-sulfonamide | 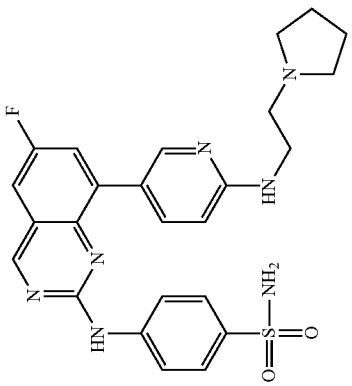 | ++++ ++++ ++++ |

TABLE 4-continued

| | | | | |
|---|---|---|---|---|
| 893. | 4-(6-fluoro-8-(6-(2-methoxyethyl-amino)pyridin-3-yl)quinazolin-2-ylamino)benzene-sulfonamide | ++++ | ++++ | ++++ |
| 894. | 4-(6-fluoro-8-(6-morpholinopyridin-3-yl)quinazolin-2-ylamino)benzene-sulfonamide | ++++ | ++++ | +++ |
| 895. | 4-(8-(pyridin-3-ylamino)quinazolin-2-ylamino)benzene-sulfonamide | ++++ | +++ | +++ |

TABLE 4-continued
| | | | |
|---|---|---|---|
| 896. | 4-(8-((3-oxopiperazin-1-yl)methyl)quinazolin-2-ylamino)benzenesulfonamide | 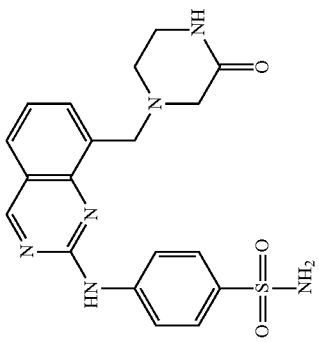 | ++++ ++++ |
| 897. | 4-(8-((isopropylamino)methyl)quinazolin-2-ylamino)benzenesulfonamide | 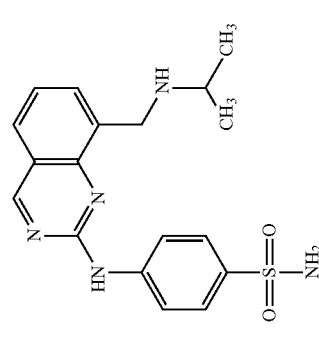 | ++++ ++++ |
| 898. | 4-(7,8-bis(1-methyl-1H-pyrazol-4-yl)quinazolin-2-ylamino)benzenesulfonamide | 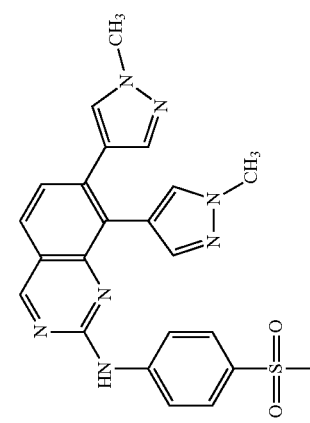 | ++++ ++++ |

TABLE 4-continued

| | | | |
|---|---|---|---|
| 899. | 4-(7,8-di(pyridin-3-yl)quinazolin-2-ylamino)benzenesulfonamide | +++ | ++++ |
| 900. | 4-(7,8-bis(6-aminopyridin-3-yl)quinazolin-2-ylamino)benzenesulfonamide | +++ | ++++ |
| 901. | 4-(8-((benzylamino)methyl)quinazolin-2-ylamino)benzenesulfonamide | +++ | ++++ |

TABLE 4-continued
| | | | | |
|---|---|---|---|---|
| 902. | 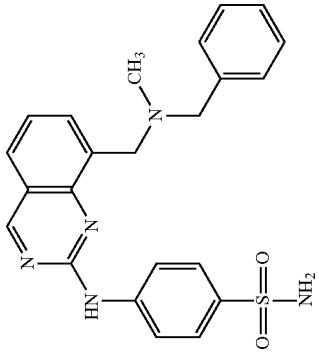 | 4-(8-((benzyl-amino)methyl)quin-azolin-2-ylamino)benzene-sulfonamide | +++ | ++++ |
| 903. | 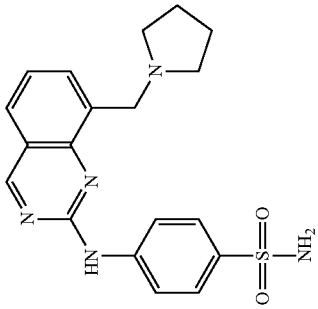 | 4-(8-(pyrrolidin-1-ylmethyl)quinazolin-2-ylamino)benzene-sulfonamide | +++ | ++++ |
| 904. | 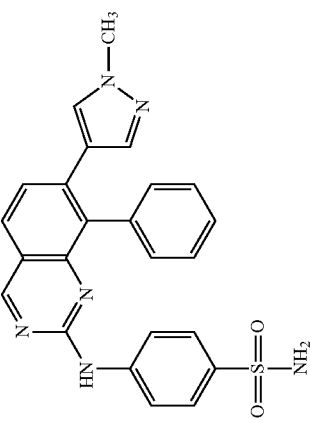 | 4-(7-(1-methyl-1H-pyrazol-4-yl)-8-phenylquinazolin-2-ylamino)benzene-sulfonamide | +++ | ++++ |

TABLE 4-continued

| | | | | |
|---|---|---|---|---|
| 905. | [structure] | 4-(8-(6-aminopyridin-3-yl)-7-(1-methyl-1H-pyrazol-4-yl)quinazolin-2-ylamino)benzenesulfonamide | ++++ | ++++ | ++++ |
| 906. | [structure] | 4-(7-(1-methyl-1H-pyrazol-4-yl)-8-(4-(4-methylpiperazine-1-carbonyl)phenyl)quinazolin-2-ylamino)benzenesulfonamide | ++++ | ++++ | ++++ |
| 907. | [structure] | 4-(8-(6-fluoropyridin-3-yl)-7-(1-methyl-1H-pyrazol-4-yl)quinazolin-2-ylamino)benzenesulfonamide | ++++ | ++++ | ++++ |

| | | | | |
|---|---|---|---|---|
| 908. | 4-(8-(6-(2-methoxy-ethylamino)pyridin-3-yl)-7-(1-methyl-1H-pyrazol-4-yl)quinazolin-2-ylamino)benzene-sulfonamide 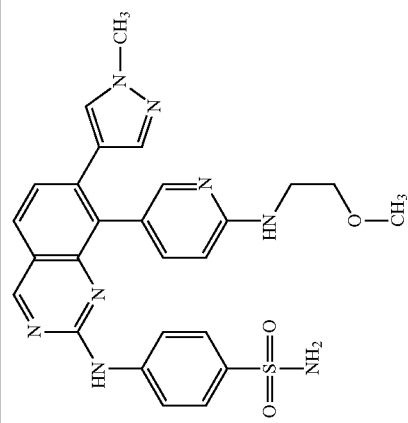 | +++ | +++ | +++ |
| 909. | 4-(7-(1-methyl-1H-pyrazol-4-yl)-8-(6-morpholinopyridin-3-yl)quinazolin-2-ylamino)benzene-sulfonamide 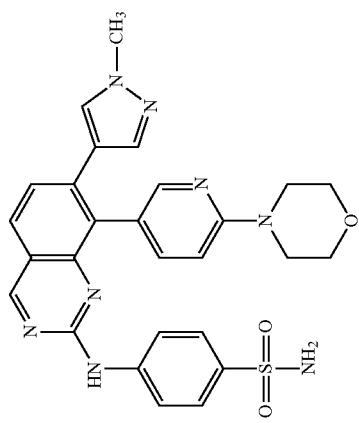 | +++ | +++ | +++ |

TABLE 4-continued

| | | | | | |
|---|---|---|---|---|---|
| 910. | [structure] | 4-(7-(1-methyl-1H-pyrazol-4-yl)-8-(6-(4-methylpiperazin-1-yl)pyridin-3-yl)quinazolin-2-ylamino)benzenesulfonamide | +++ | +++ | +++ |
| 911. | [structure] | 4-(7-phenyl-8-(piperidin-4-yloxy)quinazolin-2-ylamino)benzenesulfonamide | +++ | +++ | +++ |
| 912. | [structure] | 4-(7,8-bis(6-fluoropyridin-3-yl)quinazolin-2-ylamino)benzenesulfonamide | +++ | +++ | +++ |

TABLE 4-continued
| 913. | 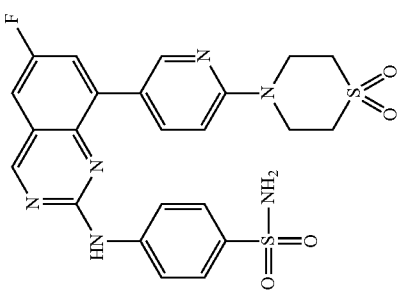 | | ++++ | ++++ | ++++ |
| 914. | 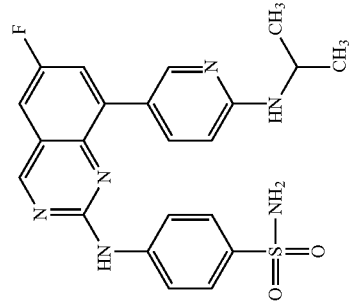 | 4-(6-fluoro-8-(6-(isopropylamino)pyridin-3-yl)quinazolin-2-ylamino)benzenesulfonamide | ++++ | ++++ | ++++ |

TABLE 4-continued
| | | | |
|---|---|---|---|---|
| 915. | 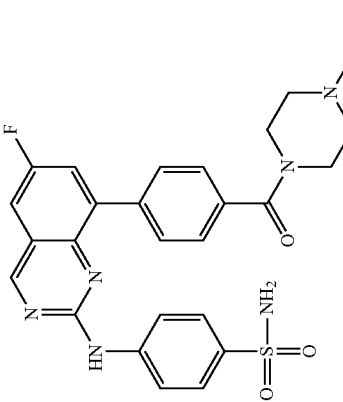 | 4-(6-fluoro-8-(4-(4-methylpiperazine-1-carbonyl)phenyl)quinazolin-2-ylamino)benzenesulfonamide | ++++ | ++++ | ++++ |
| 916. | 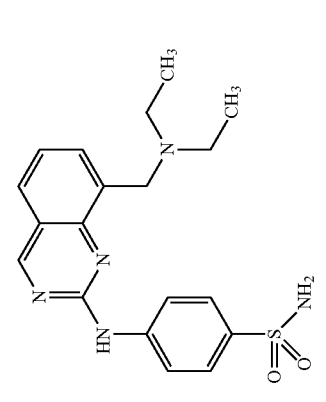 | 4-(8-((diethylamino)methyl)quinazolin-2-ylamino)benzenesulfonamide | ++++ | ++++ | ++++ |
| 917. | 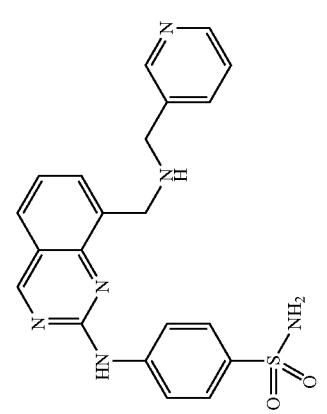 | 4-(8-((pyridin-3-ylmethylamino)methyl)quinazolin-2-ylamino)benzenesulfonamide | ++++ | ++++ | ++++ |

TABLE 4-continued
| | | | |
|---|---|---|---|
| 918. | 4-(8-((2-(1H-imidazol-5-yl)ethylamino)methyl)-quinazolin-2-ylamino)-benzenesulfonamide | 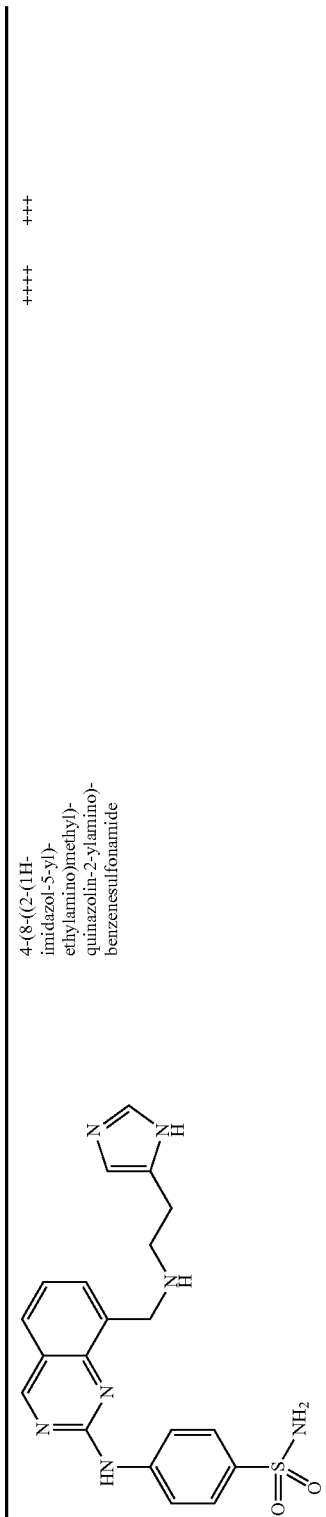 | ++++ +++ |
| 919. | 1-((2-(4-sulfamoylphenylamino)-quinazolin-8-yl)methyl)-piperidine-4-carboxamide | 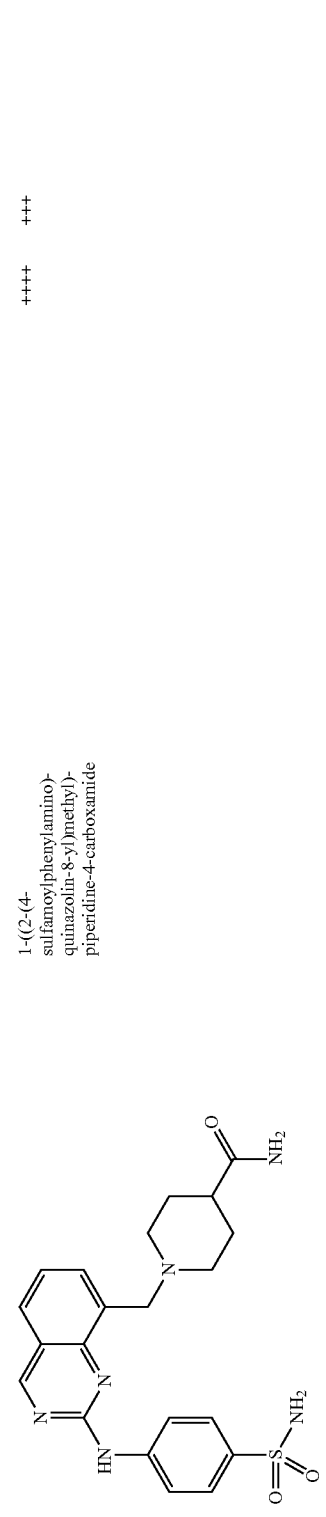 | +++ +++ |
| 920. | 4-(8-((tetrahydro-2H-pyran-4-ylamino)methyl)quinazolin-2-ylamino)benzene-sulfonamide |  | +++ +++ |

TABLE 4-continued
| | | | |
|---|---|---|---|
| 921. | 4-(8-((cyclohexylamino)methyl)quinazolin-2-ylamino)benzenesulfonamide | 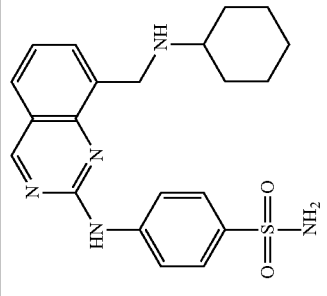 | ++++ ++++ |
| 922. | 4-(8-(((tetrahydrofuran-2-yl)methylamino)methyl)-quinazolin-2-ylamino)-benzenesulfonamide | 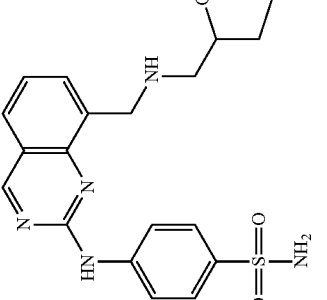 | ++++ ++++ |
| 923. | 4-(8-((3,4-dihydroisoquinolin-2(1H)-yl)methyl)-quinazolin-2-ylamino)-benzenesulfonamide | 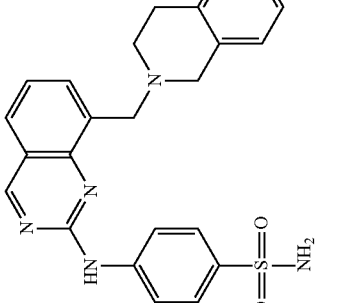 | ++++ ++++ |

TABLE 4-continued
| | | | | |
|---|---|---|---|---|
| 924. | 4-(8-((4-acetylpiperazin-1-yl)methyl)quinazolin-2-ylamino)benzenesulfonamide | 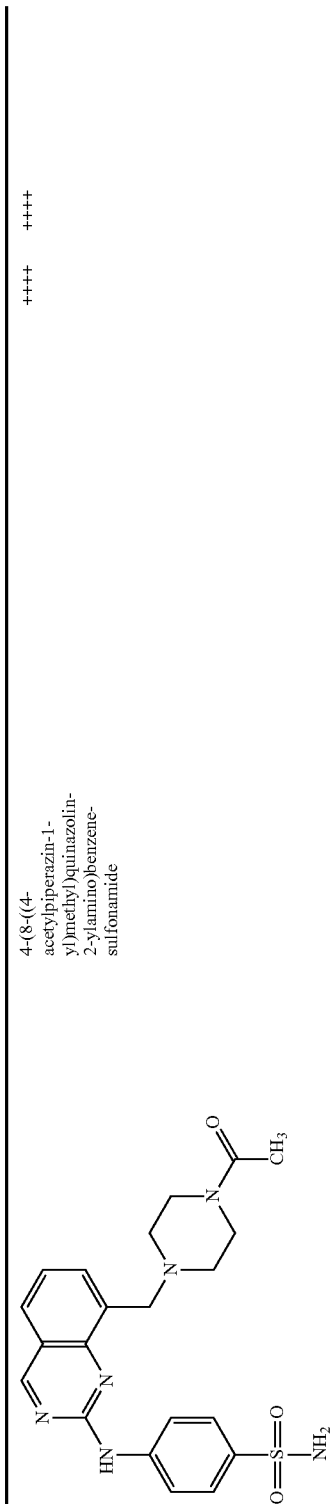 | ++++ | ++++ |
| 925. | 4-(8-((4-isopropylpiperazin-1-yl)methyl)quinazolin-2-ylamino)benzenesulfonamide |  | ++++ | ++++ |
| 926. | 4-(6-chloro-8-(1-methyl-1H-pyrazol-4-yl)quinazolin-2-ylamino)benzenesulfonamide |  | ++++ | +++ |

TABLE 4-continued

| | | | |
|---|---|---|---|
| 927. | 4-(6-chloro-8-(6-(2-(pyrrolidin-1-yl)ethylamino)pyridin-3-yl)quinazolin-2-ylamino)benzenesulfonamide | | ++++ ++++ ++++ |
| 928. | 4-(6-chloro-8-(6-(3-methylenepiperazin-1-yl)pyridin-3-yl)quinazolin-2-ylamino)benzenesulfonamide | | ++++ ++++ ++++ |

TABLE 4-continued
| | | | | |
|---|---|---|---|---|
| 929. | 4-(8-(6-amino-5-(trifluoromethyl)pyridin-3-yl)quinazolin-2-ylamino)benzenesulfonamide | 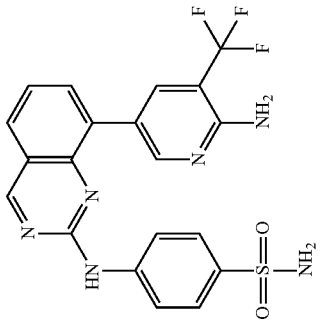 | +++ | +++ |
| 930. | 4-(8-(6-amino-4-(trifluoromethyl)pyridin-3-yl)quinazolin-2-ylamino)benzenesulfonamide | 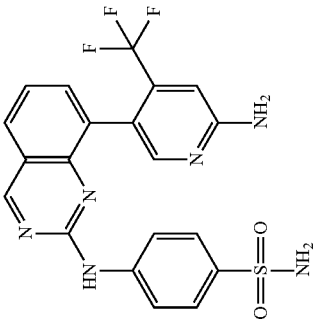 | +++ | +++ |
| 931. | 4-(8-(1-methyl-1H-pyrazol-4-yl)quinazolin-2-ylamino)benzenesulfonamide | 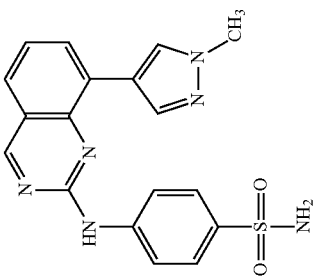 | +++ | - |

TABLE 4-continued

| | | | |
|---|---|---|---|
| 932. | (E)-4-(2-(2-(1-isobutyl-1-isobutyl-1H-pyrazol-4-yl)phenyl)guanidino)benzenesulfonamide | +++ | +++ |
| 933. | 4-(7-(6-amino-5-(trifluoromethyl)pyridin-3-yl)-8-(piperidin-4-yloxy)quinazolin-2-ylamino)benzenesulfonamide | +++ | +++ |
| 934. | 4-(7-(6-amino-4-(trifluoromethyl)pyridin-3-yl)-8-(piperidin-4-yloxy)quinazolin-2-ylamino)benzenesulfonamide | +++ | +++ |

TABLE 4-continued
| | | | |
|---|---|---|---|
| 935. | 4-(8-((2-(pyrrolidin-1-yl)ethylamino)methyl)quinazolin-2-ylamino)benzenesulfonamide |  | +++ +++ |
| 936. | (S)-4-(8-(3-(dimethylamino)pyrrolidin-1-yl)methyl)quinazolin-2-ylamino)benzenesulfonamide |  | +++ +++ |
| 937. | 4-(8-((1-methylpiperidin-4-ylamino)methyl)quinazolin-2-ylamino)benzenesulfonamide |  | +++ +++ |

TABLE 4-continued

| | Name | | |
|---|---|---|---|
| 938. | (R)-4-(8-((3-(dimethylamino)-pyrrolidin-1-yl)methyl)-quinazolin-2-ylamino)-benzenesulfonamide | +++ | +++ |
| 939. | 4-(7-(2-fluoro-6-methylpyridin-3-yl)-quinazolin-2-ylamino)-benzenesulfonamide | +++ | +++ |
| 940. | 2-(4-fluorophenylamino)-8-(1-isopropylpiperidin-4-yl)quinazolin-7-ol | +++ | +++ |

TABLE 4-continued

| | | | |
|---|---|---|---|
| 941. | 4-(8-(5-(pyrrolidin-1-ylmethyl)pyridin-3-yl)-quinazolin-2-ylamino)-benzenesulfonamide | +++ | +++ |
| 942. | 4-(8-(5-(morpholino-methyl)pyridin-3-yl)-quinazolin-2-ylamino)-benzenesulfonamide | +++ | +++ |
| 943. | 4-(8-(5-((4-methylpiperazin-1-yl)methyl)pyridin-3-yl)quinazolin-2-ylamino)benzene-sulfonamide | +++ | +++ |

TABLE 4-continued
| | | | |
|---|---|---|---|
| 944. | 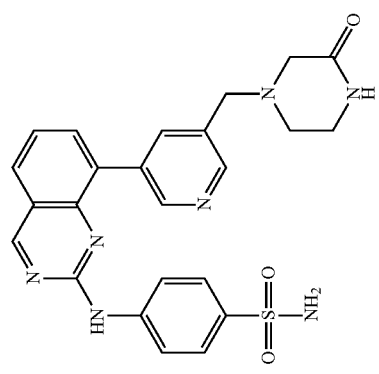 | 4-(8-(5-((3-oxopiperazin-1-yl)methyl)pyridin-3-yl)quinazolin-2-ylamino)benzenesulfonamide | +++ | +++ |
| 945. | 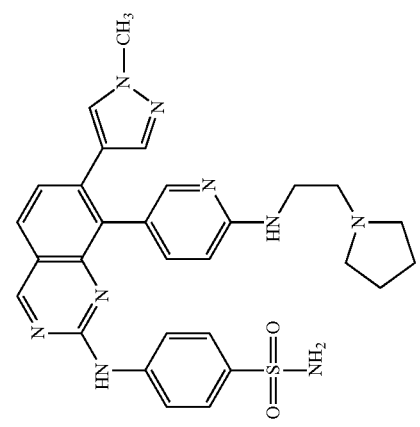 | 4-(7-(1-methyl-1H-pyrazol-4-yl)-8-(6-(2-(pyrrolidin-1-yl)ethylamino)pyridin-3-yl)quinazolin-2-ylamino)benzenesulfonamide | +++ | +++ |

TABLE 4-continued

| | | | |
|---|---|---|---|
| 946. | 4-(8-(5-((isopropylamino)methyl)pyridin-3-yl)quinazolin-2-ylamino)benzenesulfonamide | +++ | +++ |
| 947. | 1-((5-(2-(4-sulfamoylphenylamino)-quinazolin-8-yl)pyridin-3-yl)methyl)piperidine-4-carboxamide | +++ | +++ |

TABLE 4-continued
| | | |
|---|---|---|
| 948. | 4-(8-(5-((tetrahydro-2H-pyran-4-ylamino)methyl)-pyridin-3-yl)quinazolin-2-ylamino)benzene-sulfonamide  | ++++ ++++ |
| 949. | 4-(8-(5-((4-acetylpiperazin-1-yl)methyl)pyridin-3-yl)quinazolin-2-ylamino)benzene-sulfonamide  | ++++ +++ |

| | | | |
|---|---|---|---|
| 950. | 4-(8-(5-((methyl(tetrahydro-2H-pyran-4-yl)amino)methyl)pyridin-3-yl)-quinazolin-2-ylamino)-benzenesulfonamide | 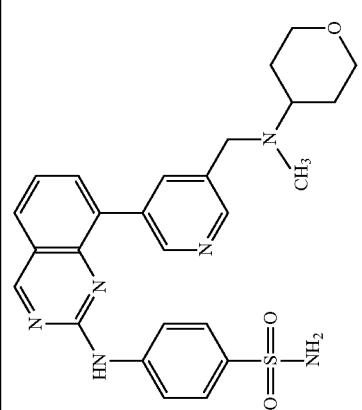 | +++ +++ |
| 951. | (R)-4-(8-(6-(3-(dimethylamino)-pyrrolidin-1-yl)-pyridin-2-yl)-quinazolin-2-ylamino)-benzenesulfonamide | 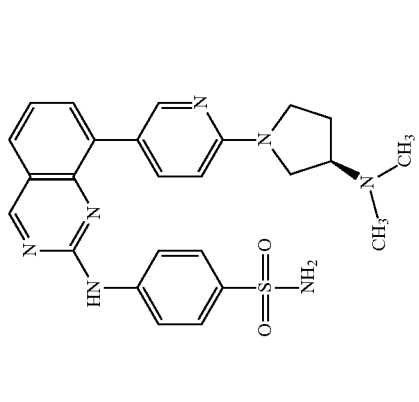 | +++ +++ |

TABLE 4-continued

| | | | |
|---|---|---|---|
| 952. | (S)-4-(8-(6-(3-(dimethylamino)-pyrrolidin-1-yl)-pyridin-3-yl)-quinazolin-2-ylamino)-benzenesulfonamide | +++ | +++ |
| 953. | 4-(8-(6-(2-morpholinoethylamino)-pyridin-3-yl)quinazolin-2-ylamino)benzene-sulfonamide | +++ | +++ |

TABLE 4-continued
| | Name | | Activity |
|---|---|---|---|
| 954. | 4-(8-(6-(2-(diethylamino)-ethylamino)pyridin-3-yl)quinazolin-2-ylamino)benzene-sulfonamide 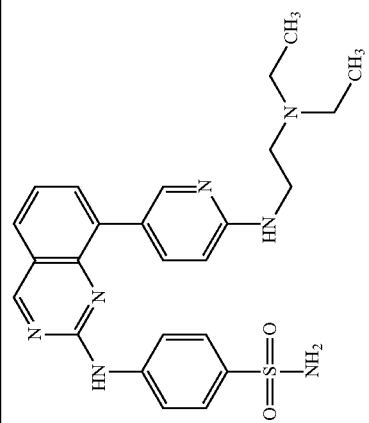 | +++ | +++ |
| 955. | 4-(8-(6-(1-methylpiperidin-4-ylamino)pyridin-3-yl)quinazolin-2-ylamino)benzene-sulfonamide 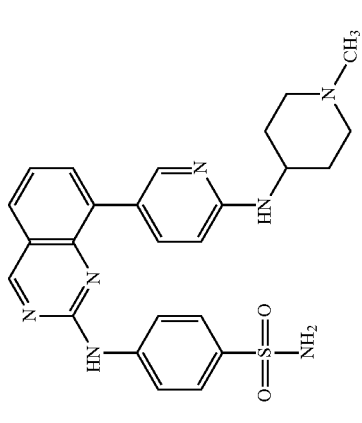 | +++ | +++ |

TABLE 4-continued

| # | Structure | Name | | |
|---|---|---|---|---|
| 956. | 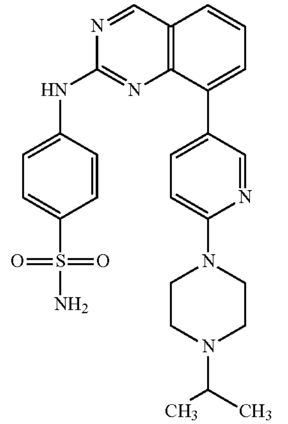 | 4-(8-(6-(4-isopropylpiperazin-1-yl)pyridin-3-yl)quinazolin-2-ylamino)benzenesulfonamide | +++ | +++ |
| 957. | 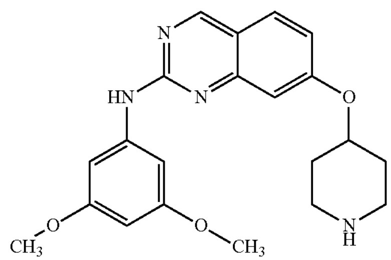 | N-(3,5-dimethoxyphenyl)-7-(piperidin-4-yloxy)quinazolin-2-amine | +++ | +++ |
| 958. | 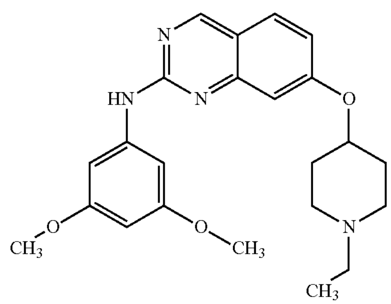 | N-(3,5-dimethoxyphenyl)-7-(1-ethylpiperidin-4-yloxy)quinazolin-2-amine | +++ | +++ |

TABLE 4-continued
| | | | |
|---|---|---|---|
| 959. | N-(4-chlorophenyl)-7-(1-isopropylpiperidin-4-yloxy)quinazolin-2-amine | 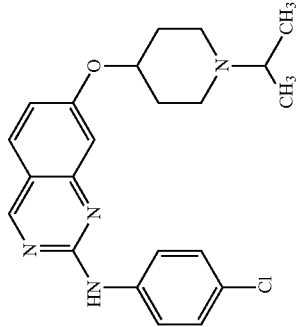 | +++ +++ |
| 960. | 2-(4-chlorophenylamino)-8-(1-isopropylpiperidin-4-yl)quinolin-7-ol | 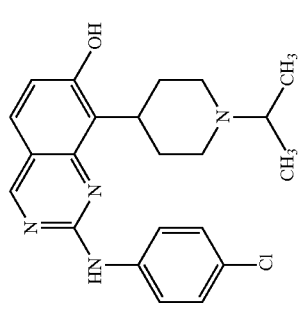 | +++ +++ |
| 961. | N-isopropyl-4-(7-(1-isopropylpiperidin-4-yloxy)quinazolin-2-ylamino)benzenesulfonamide | 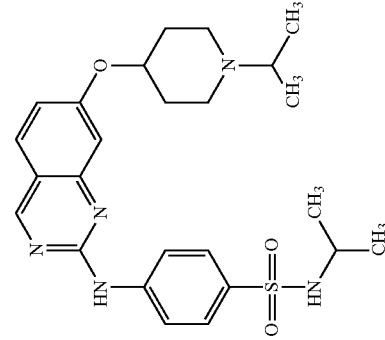 | +++ +++ |

| | | | |
|---|---|---|---|
| 962. | 5-(2-(4-sulfamoylphenylamino)-quinazolin-8-yl)nicotinic acid | 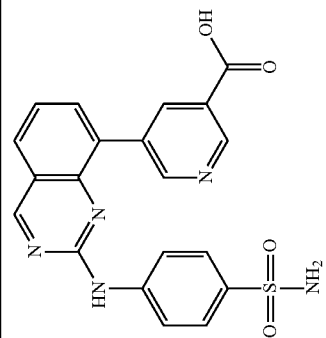 | +++  +++ |
| 963. | 4-(8-(6-(2-(pyrrolidin-1-yl)-ethylamino)pyridin-3-yl)-6-(trifluoromethyl)-quinazolin-2-ylamino)-benzenesulfonamide | 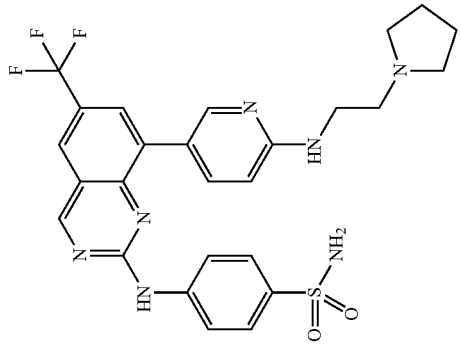 Example 17 | ++++  ++++ |

TABLE 4-continued

| | Structure | Name | Method | Activity |
|---|---|---|---|---|
| 964. | | 4-(8-(6-(4-methylpiperazin-1-yl)pyridin-3-yl)-6-(trifluoromethyl)quinazolin-2-ylamino)benzenesulfonamide | Example 17, using N-methylpiperazine in place of 1-(2-aminoethyl)-pyrrolidine | +++ |
| 965. | | 4-(8-(6-(3-oxopiperazin-1-yl)pyridin-3-yl)-6-(trifluoromethyl)quinazolin-2-ylamino)benzenesulfonamide | Example 17, using piperazin-2-one in place of 1-(2-aminoethyl)-pyrrolidine | ++++ |

| | | | | |
|---|---|---|---|---|
| 966. | 2-(4-(8-(1-isopropylpiperidin-4-yloxy)quinazolin-2-ylamino)phenyl)-N-methylacetamide 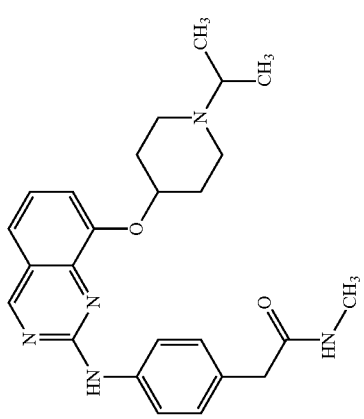 | 544.1, 2.16 | Example 18 | ++++ ++++ |
| 967. | N-isopropyl-2-(4-(8-(1-isopropylpiperidin-4-yloxy)quinazolin-2-ylamino)phenyl)-acetamide 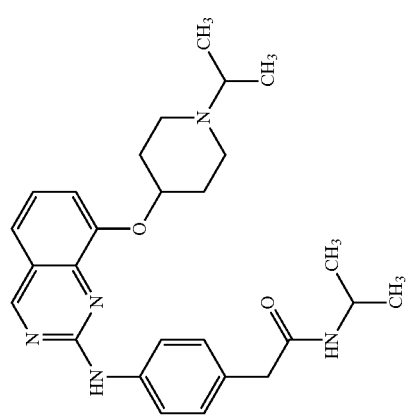 | | Example 18 step 2, using 2-(4-aminophenyl)-N-isopropylacetamide in place of 2-(4-aminophenyl)-N-methylacetamide | ++++ ++++ |

TABLE 4-continued

| | | | |
|---|---|---|---|
| 968. | [structure] | 8-(1-isopropylpiperidin-4-yloxy)-N-(4-morpholinophenyl)-quinazolin-2-amine | Example 18 step 2, using 4-morpholinoaniline in place of 2-(4-aminophenyl)-N-methylacetamide | +++ | +++ |
| 969. | [structure] | N-(4-(8-(1-isopropylpiperidin-4-yloxy)quinazolin-2-ylamino)phenyl)-acetamide | Example 18 step 2, using 4-aminoacetanilide in place of 2-(4-aminophenyl)-N-methylacetamide | +++ | +++ |
| 970. | [structure] | 2-(4-(8-(1-isopropylpiperidin-4-yloxy)quinazolin-2-ylamino)phenyl)-acetamide | Example 18 step 2, using 2-(4-aminophenyl)-acetamide in place of 2-(4-aminophenyl)-N-methylacetamide | +++ | +++ |

TABLE 4-continued

| | | | |
|---|---|---|---|
| 971. | 4-(8-(6-(3-(isopropylamino)propylamino)pyridin-3-yl)quinazolin-2-ylamino)benzenesulfonamide | [structure] | +++ +++ +++ |
| 972. | 4-(8-(6-(3-(pyrrolidin-1-yl)propylamino)pyridin-3-yl)quinazolin-2-ylamino)benzenesulfonamide | [structure] | +++ +++ +++ |
| 973. | (S)-4-(8-(6-((1-ethylpyrrolidin-2-yl)methylamino)pyridin-2-ylamino)-benzenesulfonamide | [structure] | +++ +++ +++ |

TABLE 4-continued

| | | | |
|---|---|---|---|---|
| 974. | (R)-4-(8-(6-((1-ethylpyrrolidin-2-yl)methylamino)pyridin-3-yl)quinazolin-2-ylamino)benzenesulfonamide | +++ | +++ |
| 975. | 4-(8-(6-((1-methylpiperidin-4-yl)methylamino)pyridin-3-yl)quinazolin-2-ylamino)benzenesulfonamide | +++ | +++ |
| 976. | (R)-4-(8-(5-(3-(dimethylamino)pyrrolidine-1-carbonyl)pyridin-3-yl)quinazolin-2-ylamino)benzenesulfonamide | +++ | ++ |

TABLE 4-continued

| # | Structure | Name | | |
|---|---|---|---|---|
| 977. | 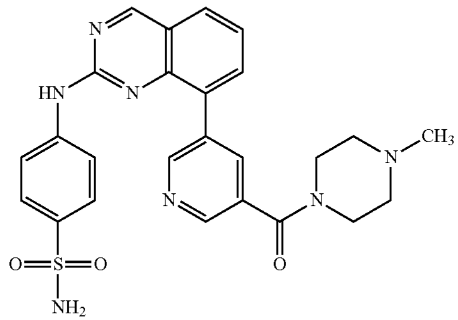 | 4-(8-(5-(4-methylpiperazine-1-carbonyl)pyridin-3-yl)quinazolin-2-ylamino)benzene-sulfonamide | +++ | ++ |
| 978. | 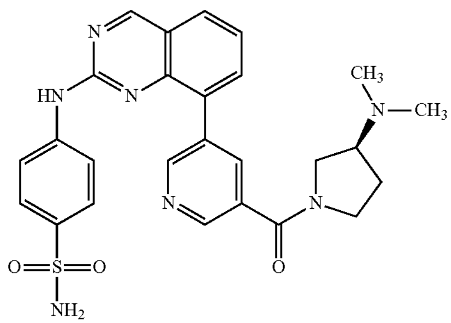 | (S)-4-(8-(5-(3-(dimethylamino)-pyrrolidine-1-carbonyl)pyridin-3-yl)quinazolin-2-ylamino)benzene-sulfonamide | +++ | ++ |
| 979. | 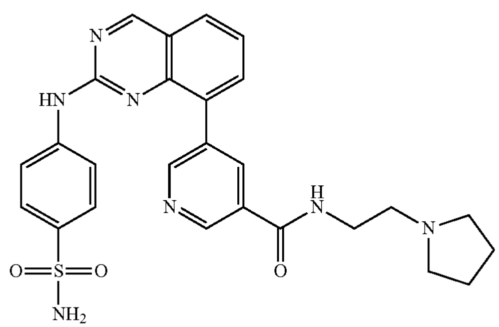 | N-(2-(pyrrolidin-1-yl)ethyl)-5-(2-(4-sulfamoylphenylamino)-quinazolin-8-yl)-nicotinamide | +++ | ++ |

TABLE 4-continued
| | | | |
|---|---|---|---|
| 980. |  4-(8-(5-(4-(dimethylamino)-piperidine-1-carbonyl)-pyridin-3-yl)quinazolin-2-ylamino)benzene-sulfonamide | ++++ | +++ |
| 981. |  N-(1-methylpiperidin-4-yl)-5-(2-(4-sulfamoylphenyl-amino)quinazolin-8-yl)-nicotinamide | ++++ | +++ |
| 982. |  N-((1-methylpiperidin-4-yl)methyl)-5-(2-(4-sulfamoylphenylamino)-quinazolin-8-yl)-nicotinamide | ++++ | +++ |

TABLE 4-continued
| | | | |
|---|---|---|---|
| 983. | 4-(8-(5-(3-oxopiperazine-1-carbonyl)pyridin-3-yl)quinazolin-2-ylamino)benzenesulfonamide | 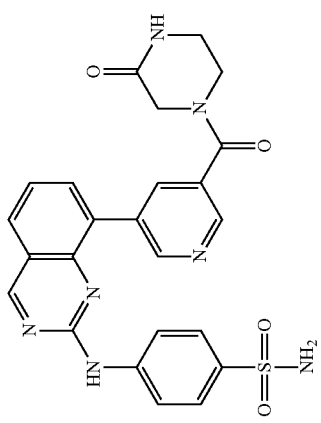 | +++ +++ |
| 984. | 4-(8-(5-(morpholine-4-carbonyl)pyridin-3-yl)quinazolin-2-ylamino)benzenesulfonamide | 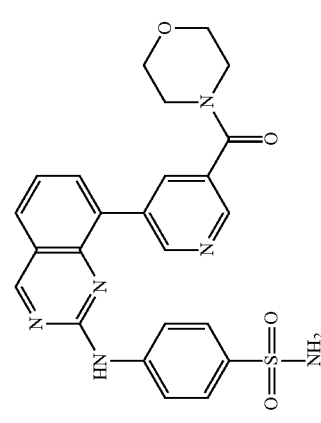 | +++ +++ |
| 985. | 4-(8-(4-(4-methylpiperazin-1-yl)phenyl)quinazolin-2-ylamino)benzenesulfonamide | 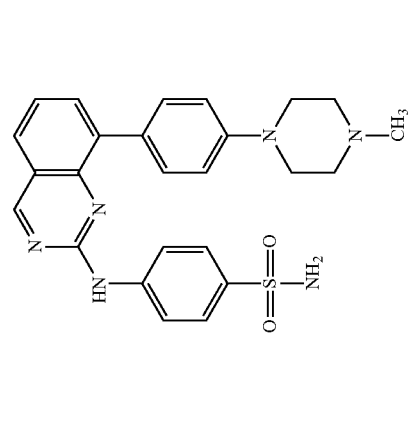 | +++ +++ |

TABLE 4-continued
| | | | |
|---|---|---|---|
| 986. | 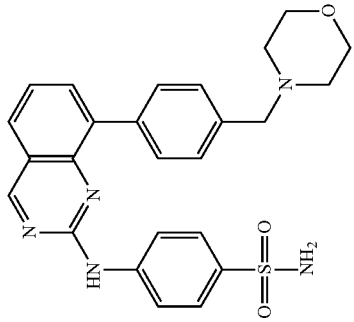 4-(8-(4-(mopholinomethyl)-phenyl)quinazolin-2-ylamino)benzene-sulfonamide | +++ | +++ |
| 987. | 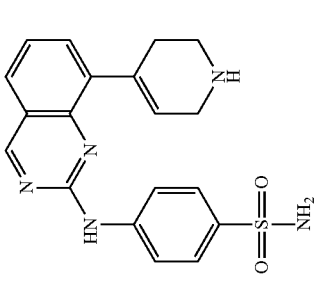 4-(8-(1,2,3,6-tetrahydropyridin-4-yl)quinazolin-2-ylamino)benzene-sulfonamide | +++ | +++ |
| 988. | 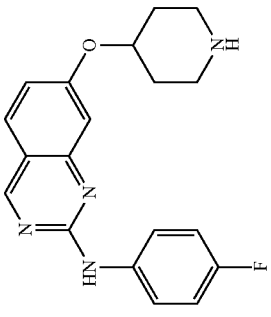 N-(4-fluorophenyl)-7-(piperidin-4-yloxy)-quinazolin-2-amine | +++ | +++ |

TABLE 4-continued
| | | | |
|---|---|---|---|
| 989. | N-(4-fluorophenyl)-7-(1-isopropylpiperidin-4-yloxy)quinazolin-2-amine |  | +++ +++ |
| 990. | 1-(4-(7-(1-isopropylpiperidin-4-yloxy)quinazolin-2-ylamino)phenyl)-N-methylmethanesulfonamide | 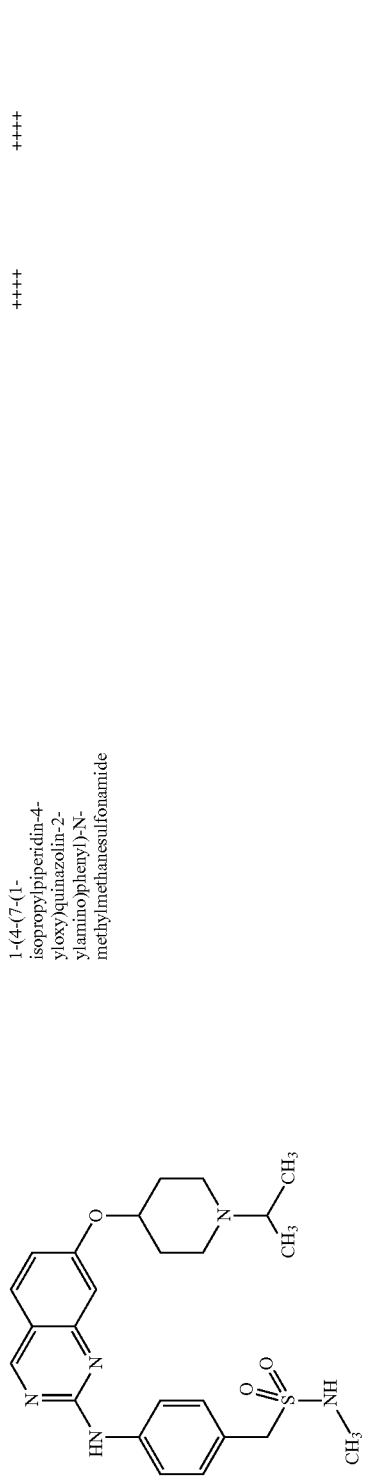 | +++ +++ |
| 991. | 7-(1-isobutyl-1H-pyrazol-4-yl)-N-(4-morpholinophenyl)quinazolin-2-amine | 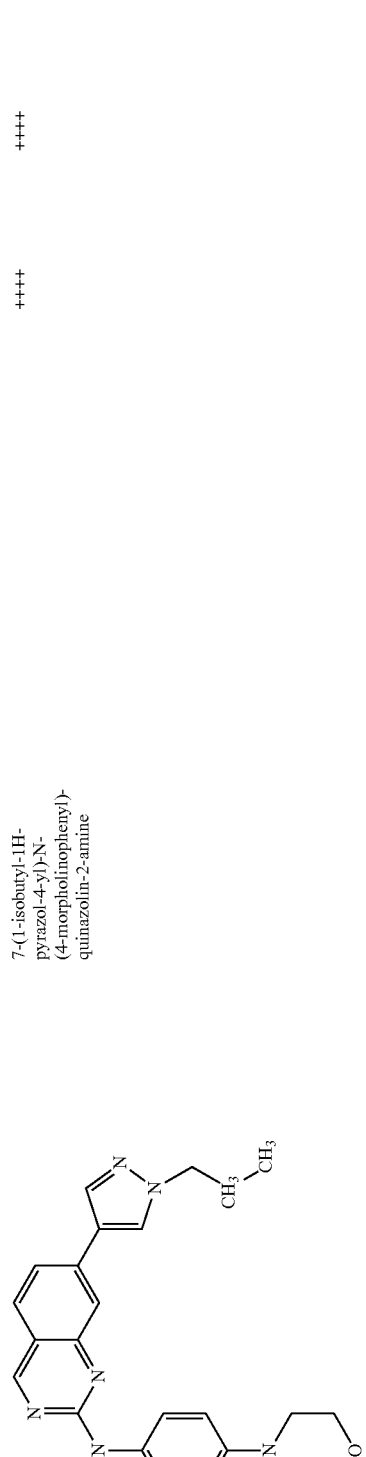 | +++ +++ |

| | | | |
|---|---|---|---|
| 992. | N-(4-(8-(1-isopropylpiperidin-4-yloxy)quinazolin-2-ylamino)phenyl)-pyrrolidine-1-carboxamide 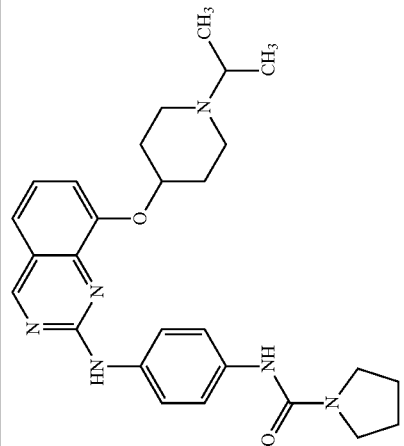 | Example 13, using 2-chloro-8-(1-isopropyl-piperidin-4-yloxy)-quinazoline in place of 2-chloro-8-methoxyquinazoline and N-(4-aminophenyl)-pyrrolidine-1-carboxamide in place of 3,5-dimethoxyaniline | +++ +++ |
| 993. | N-isopropyl-4-(8-(6-(2-(pyrrolidin-1-yl)-ethylamino)pyridin-3-yl)quinazolin-2-ylamino)benzamide 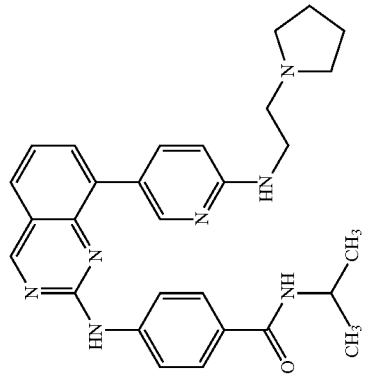 | | +++ +++ |

| | | | |
|---|---|---|---|
| 994. | N-(4-fluorophenyl)-8-(6-(2-(pyrrolidin-1-yl)ethylamino)pyridin-3-yl)quinazolin-2-amine | 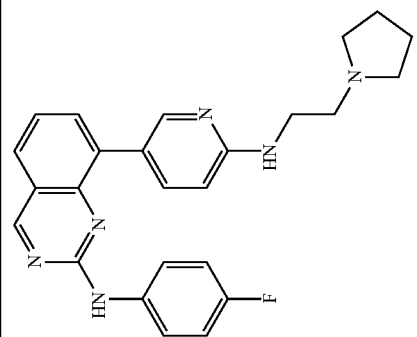 | ++++ ++++ |
| 995. | N-(4-chorophenyl)-8-(6-(2-(pyrrolidin-1-yl)ethylamino)pyridin-3-yl)quinazolin-2-amine | 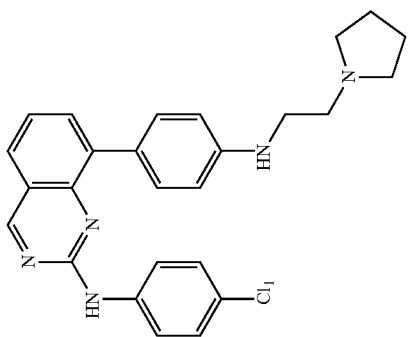 | ++++ ++++ |

TABLE 4-continued
| 996. | N-(4-morpholinophenyl)-8-(6-(2-(pyrrolidin-1-yl)ethylamino)pyridin-3-yl)quinazolin-2-amine | 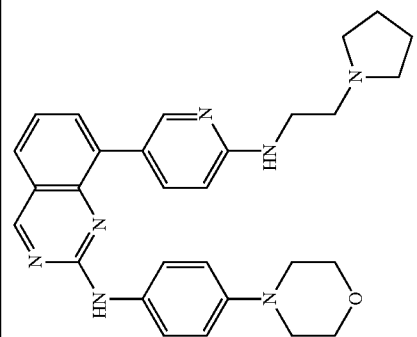 | +++ | +++ |
| 997. | 8-(6-(2-(pyrrolidin-1-yl)ethylamino)pyridin-3-yl)-N-(4-(trifluoromethyl)phenyl)quinazolin-2-amine | 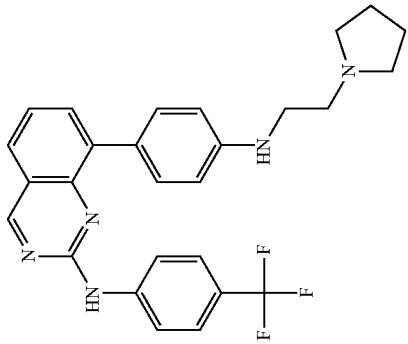 | +++ | +++ |

TABLE 4-continued
| | | | | |
|---|---|---|---|---|
| 998. | N-methyl-1-(4-(8-(6-(2-(pyrrolidin-1-yl)-ethylamino)pyridin-3-yl)quinazolin-2-ylamino)phenyl)-methanesulfonamide | 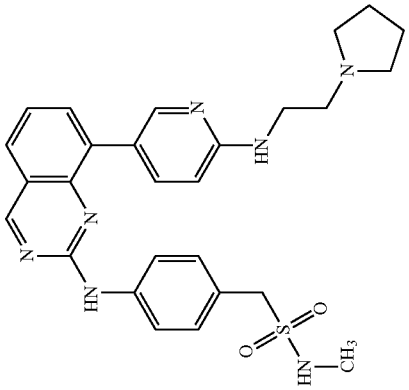 | +++ | +++ |
| 999. | N-(4-fluorophenyl)-8-(6-(4-methylpiperazin-1-yl)pyridin-3-yl)-quinazolin-2-amine | 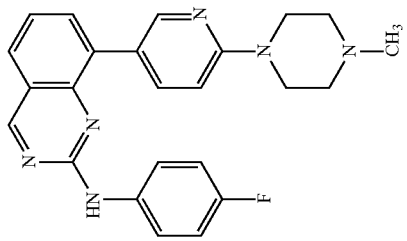 | +++ | +++ |

TABLE 4-continued

| | | | |
|---|---|---|---|
| 1000. | 5-(8-(6-(2-(pyrrolidin-1-yl)ethylamino)pyridin-3-yl)quinazolin-2-ylamino)-1H-benzo[d]imidazol-2(3H)-one | +++ | +++ |
| 1001. | N-(2-methyl-5-(8-(6-(2-(pyrrolidin-1-yl)ethylamino)pyridin-3-yl)quinazolin-2-ylamino)phenyl)-methanesulfonamide | +++ | +++ |
| 1002. | 2-(3-(8-(1-isopropylpiperidin-4-yloxy)quinazolin-2-ylamino)phenyl)-acetamide | +++ | ++ Example 18 step 2, using 2-(3-aminophenyl)-acetamide in place of 2-(4-aminophenyl)-N-methylacetamide |

TABLE 4-continued

| # | Structure | Name | Synthesis | Activity |
|---|---|---|---|---|
| 1003. | | 2-(3-(8-(1-isopropylpiperidin-4-yloxy)quinazolin-2-ylamino)phenyl)-N-methylacetamide | Example 18 step 2, using 2-(3-aminophenyl)-N-methylacetamide in place of 2-(4-aminophenyl)-N-methylacetamide | ++++ / +++ |
| 1004. | | 2-(3-(8-(1-isopropylpiperidin-4-yloxy)quinazolin-2-ylamino)phenyl)-N-(3-(2-(methylamino)-2-oxoethyl)phenyl)acetamide | Example 16 step 2, using 2-(4-aminophenyl)-N-(3-(2-(methylamino)-2-oxoethyl)phenyl)acetamide in place of 2-(4-aminophenyl)-N-methylacetamide | ++++ / +++ |
| 1005. | | N-isopropyl-2-(3-(8-(1-isopropylpiperidin-4-yloxy)quinazolin-2-ylamino)phenyl)acetamide | Example 18 step 2, using 2-(3-aminophenyl)-N-isopropylacetamide in place of 2-(4-aminophenyl)-N-methylacetamide | ++++ / +++ |
| 1006. | | 8-(1-isopropylpiperidin-4-yloxy)-N-(3-morpholinophenyl)quinazolin-2-amine | Example 18 step 2, using 3-morpholinoaniline in place of 2-(4-aminophenyl)-N-methylacetamide | ++++ / +++ |

TABLE 4-continued

| | | | |
|---|---|---|---|
| 1007. | 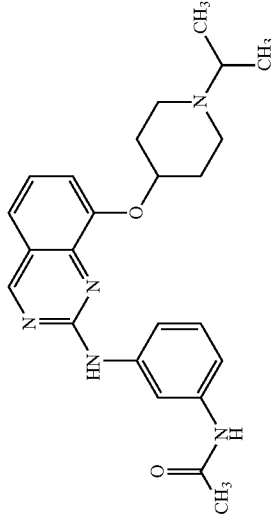 N-(3-(8-(1-isopropylpiperidin-4-yloxy)quinazolin-2-ylamino)phenyl)-acetamide | Example 18 step 2, using 3-aminoacetanilide in place of 2-(4-aminophenyl)-N-methylacetamide | +++ +++ |
| 1008. | 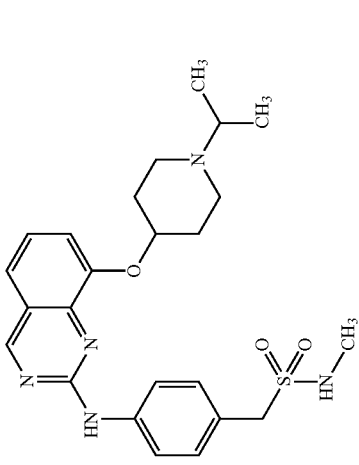 1-(4-(8-(1-isopropylpiperidin-4-yloxy)quinazolin-2-ylamino)phenyl)-N-methylmethane-sulfonamide | Example 18 step 2, using 1-(4-aminophenyl)-N-methyl-methanesulfonamide in place of 2-(4-aminophenyl)-N-methylacetamide | +++ +++ |
| 1009. | 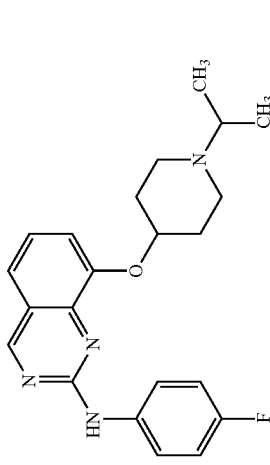 N-(4-fluorophenyl)-8-(1-isopropylpiperidin-4-yloxy)quinazolin-2-amine | Example 13, using 2-chloro-8-(1-isopropylpiperidin-4-yloxy)quinazoline in place of 2-chloro-8-methoxyquinazoline and 4-fluoroaniline in place of 3,5-dimethoxy-aniline | +++ ++ |

TABLE 4-continued

| | | | |
|---|---|---|---|
| 1010. | 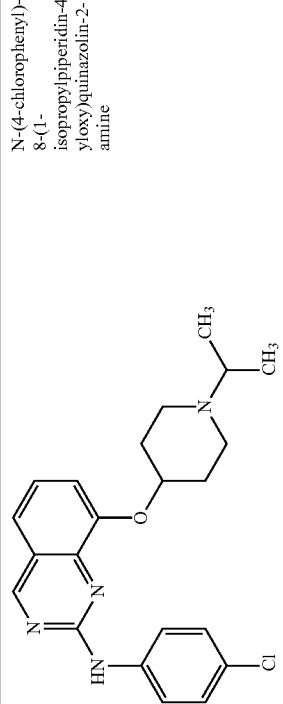 | N-(4-chlorophenyl)-8-(1-isopropylpiperidin-4-yloxy)quinazolin-2-amine | Example 13, using 2-chloro-8-(1-isopropylpiperidin-4-yloxy)quinazoline in place of 2-chloro-8-methoxyquinazoline and 4-chloroaniline in place of 3,5-dimethoxyaniline | ++++ | ++++ |
| 1011. | 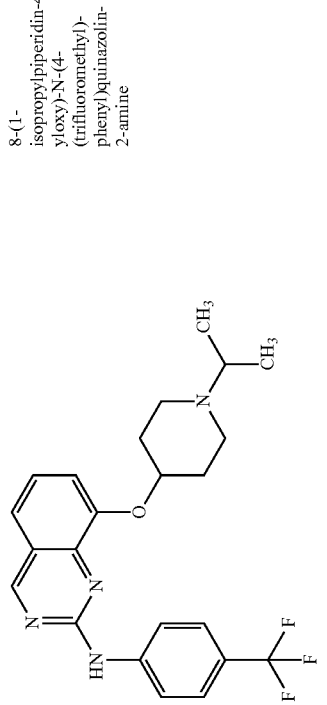 | 8-(1-isopropylpiperidin-4-yloxy)-N-(4-(trifluoromethyl)phenyl)quinazolin-2-amine | Example 13, using 2-chloro-8-(1-isopropylpiperidin-4-yloxy)quinazoline in place of 2-chloro-8-methoxyquinazoline and 4-trifluoromethyl-aniline in place of 3,5-dimethoxyaniline | ++++ | ++++ |
| 1012. | 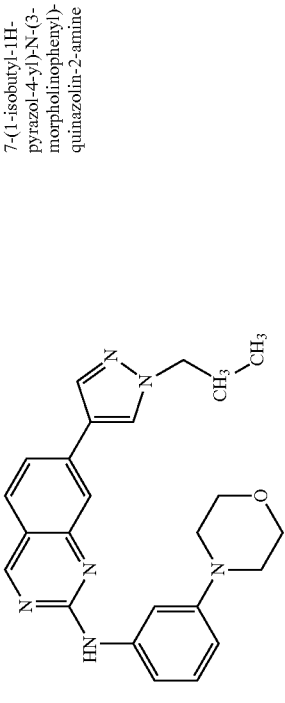 | 7-(1-isobutyl-1H-pyrazol-4-yl)-N-(3-morpholinophenyl)-quinazolin-2-amine | | +++ | +++ |

TABLE 4-continued

| | | | |
|---|---|---|---|
| 1013. | 3-chloro-N1-(7-(1-isopropylpiperidin-4-yloxy)quinazolin-2-yl)benzene-1,4-diamine | +++ | +++ |
| 1014. | N-(2-methyl-4-(7-(piperidin-4-yloxy)-quinazolin-2-ylamino)-phenyl)acetamide | +++ | +++ |
| 1015. | 4-(6-ethynyl-8-(1-isopropylpiperidin-4-yloxy)quinazolin-2-ylamino)benzene-sulfonamide | +++ Example 9 | +++ |

TABLE 4-continued
| | | | |
|---|---|---|---|
| 1016. | N-isopropyl-4-(8-(6-(2-(pyrrolidin-1-yl)ethylamino)pyridin-3-yl)quinazolin-2-ylamino)benzenesulfonamide | 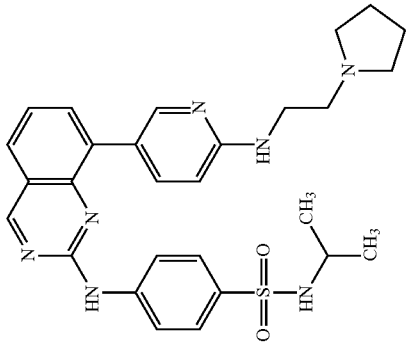 | +++ +++ +++ |
| 1017. | N-(2,4-difluorophenyl)-8-(6-(2-(pyrrolidin-1-yl)ethylamino)pyridin-3-yl)quinazolin-2-amine | 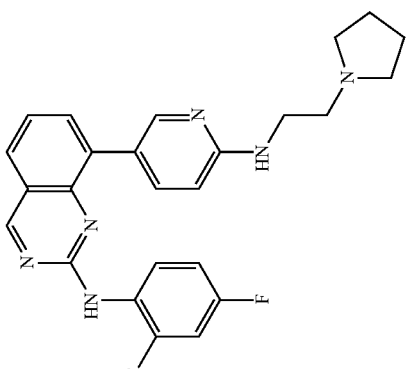 | +++ +++ +++ |

| | | |
|---|---|---|
| 1018. | N-(3,4-difluorophenyl)-8-(6-(2-(pyrrolidin-1-yl)ethylamino)pyridin-3-yl)quinazolin-2-amine | ++++ ++++ 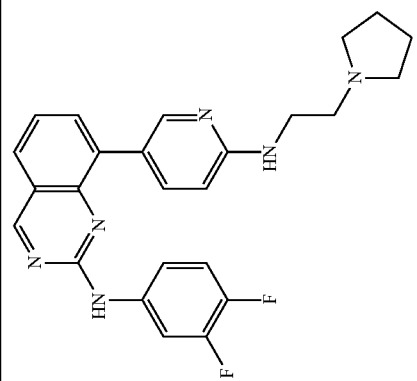 |
| 1019. | 2-(4-(8-(6-(2-(pyrrolidin-1-yl)ethylamino)pyridin-3-yl)quinazolin-2-ylamino)phenyl)ethanol | ++++ ++++ 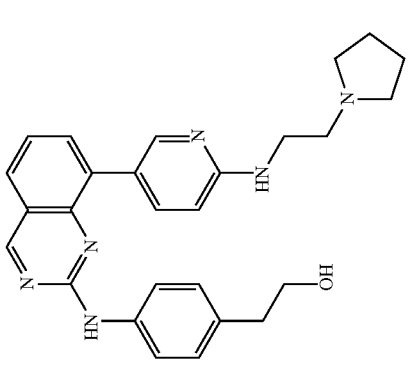 |

TABLE 4-continued
| 1020. | N-(3-fluorophenyl)-8-(6-(2-(pyrrolidin-1-yl)ethylamino)pyridin-3-yl)quinazolin-2-amine | 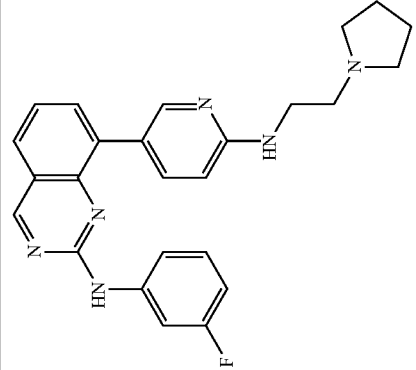 | ++++ | ++++ |
| 1021. | N-(3-(4-methyl-4H-1,2,4-triazol-3-yl)phenyl)-8-(6-(2-(pyrrolidin-1-yl)ethylamino)pyridin-3-yl)quinazolin-2-amine | 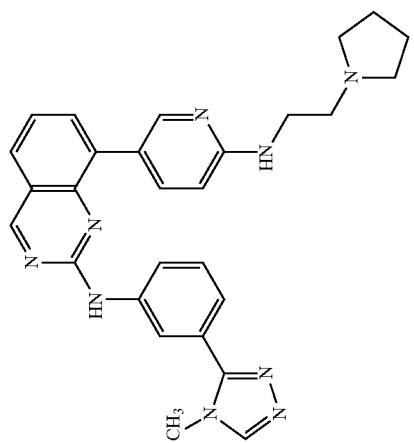 | ++++ | ++++ |

TABLE 4-continued
| 1022. | N-(3-morpholinophenyl)-8-(6-(2-(pyrrolidin-1-yl)ethylamino)pyridin-3-yl)quinazolin-2-amine | ++++ | ++++ |
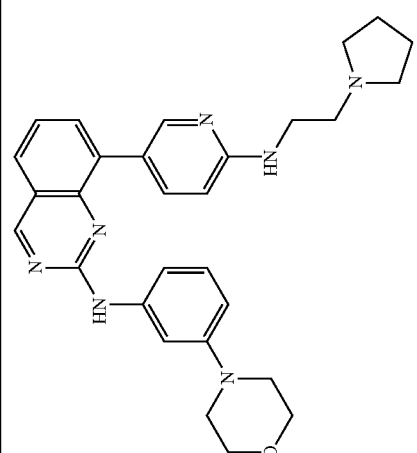
| 1023. | 8-(6-(2-(pyrrolidin-1-yl)ethylamino)pyridin-3-yl)-N-(3-(trifluoromethyl)phenyl)quinazolin-2-amine | ++++ | ++++ |
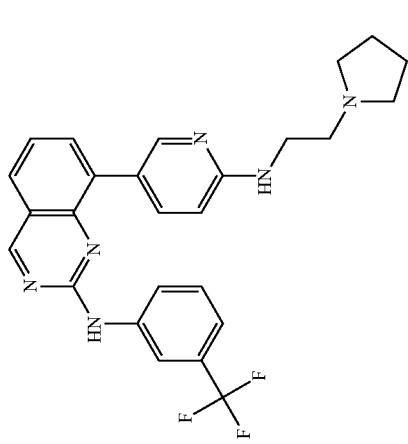

TABLE 4-continued

| | Name | | |
|---|---|---|---|
| 1024. | N-(2-chloro-4-(8-(6-(2-(pyrrolidin-1-yl)ethylamino)pyridin-3-yl)quinazolin-2-ylamino)phenyl)-acetamide | +++ | +++ |
| 1025. | 7-(1-isobutyl-1H-pyrazol-4-yl)-N-(4-(4-methylpiperazin-1-yl)phenyl)quinazolin-2-amine | +++ | +++ |
| 1026. | N-(5-(7-hydroxy-8-(1-isopropylpiperidin-4-yl)quinazolin-2-ylamino)-2-methylphenyl)methanesulfonamide | +++ | +++ |

TABLE 4-continued

| | | | |
|---|---|---|---|
| 1027. | N-(2-methyl-4-(8-(6-(2-(pyrrolidin-1-yl)-ethylamino)pyridin-3-yl)quinazolin-2-ylamino)phenyl)-acetamide | ++++ | ++++ |
| 1028. | N-(4-(methylsulfonyl)-phenyl)-8-(6-(2-(pyrrolidin-1-yl)-ethylamino)pyridin-3-yl)quinazolin-2-amine | ++++ | +++ |

TABLE 4-continued
| | | | |
|---|---|---|---|
| 1029. | 8-(6-(4-methylpiperazin-1-yl)pyridin-3-yl)-N-(4-(morpholinosulfonyl)phenyl)quinazolin-2-amine | 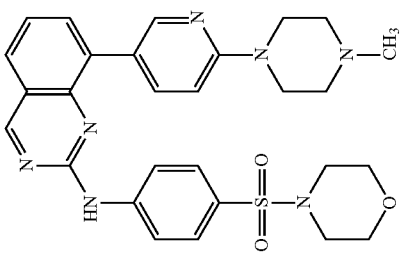 | ++++ +++ |
| 1030. | 2-(4-fluoro-3-methylphenylamino)-8-(1-isopropylpiperidin-4-yl)quinazolin-7-ol | 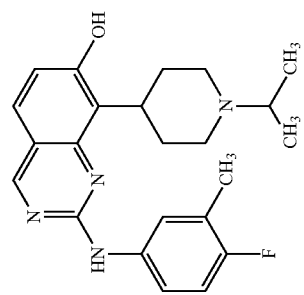 | +++ +++ |

| Cmpd | Structure | Name | LC/MS (M + 1(m/z), Rt(min)) | PDK1 BV11261 | CPEC50 A2780 | CPEC50 PC3 | CPEC50 PC3 MM |
|---|---|---|---|---|---|---|---|
| 1031 | 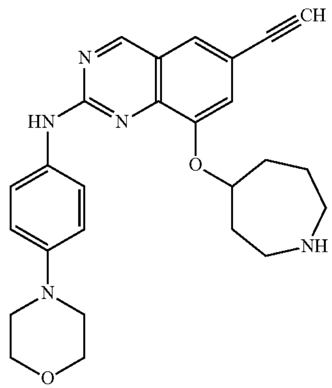 | 8-(azepan-4-yloxy)-6-ethynyl-N-(4-morpholinophenyl)quinazolin-2-amine | 444, 2.05 | ++++ | | ++++ | |
| 1032 | 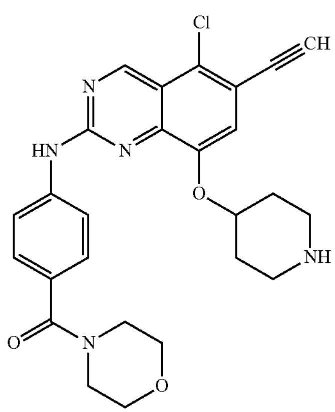 | (4-(5-chloro-6-ethynyl-8-(piperidin-4-yloxy)quinazolin-2-ylamino)phenyl)(morpholino)methanone | 492.2, 2.26 | ++++ | | ++++ | |

TABLE 4-continued

| | | | |
|---|---|---|---|
| 1033 | (4-(5-chloro-8-methoxy-7-(1-methyl-1H-pyrazol-4-yl)quinazolin-2-ylamino)phenyl)-(morpholino)methanone | 479.2, 3.4 | ++++ ++++ |
| 1034 | 4-(5-chloro-8-methoxy-7-(1-methyl-1H-pyrazol-4-yl)quinazolin-2-ylamino)-N-isopropylbenzamide | 451.1, 3.78 | ++++ ++++ |

TABLE 4-continued
| | | | |
|---|---|---|---|
| 1035 | 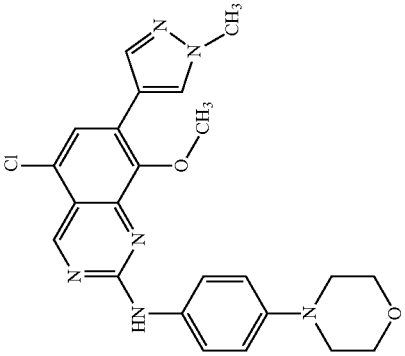 | 5-chloro-8-methoxy-7-(1-methyl-1H-pyrazol-4-yl)-N-(4-morpholinophenyl)-quinazolin-2-amine | 451.2, 2.89 | +++ | ++++ |
| 1036 | 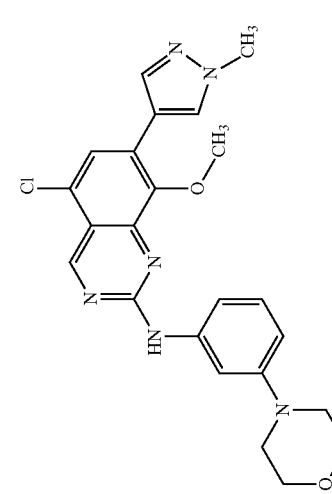 | 5-chloro-8-methoxy-7-(1-methyl-1H-pyrazol-4-yl)-N-(3-morpholinophenyl)-quinazolin-2-amine | 451.2, 3.46 | +++ | ++++ |
| 1037 | 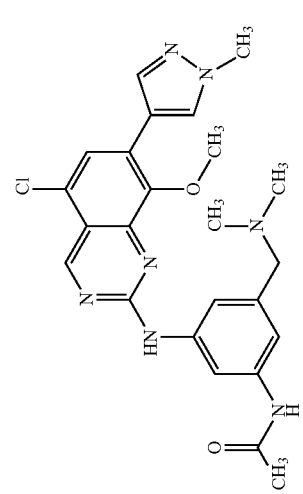 | N-(3-(5-chloro-8-methoxy-7-(1-methyl-1H-pyrazol-4-yl)quinazolin-2-ylamino)-5-((dimethylamino)methyl)phenyl)-acetamide | 480.2, 2.5 | +++ | +++ |

TABLE 4-continued
| | | | |
|---|---|---|---|
| 1038 | 4-(5-chloro-8-methoxy-7-(1-methyl-1H-pyrazol-4-yl)-quinazolin-2-ylamino)-N-cyclopropylbenzamide | 449.2, 3.5 | ++++ |
| 1039 | 4-(6-ethynyl-7-(1-oxo-1,2,3,4-tetrahydroisoquinolin-6-yl)quinazolin-2-ylamino)-N-isopropylbenzamide | 476, 3.32 | ++++ |
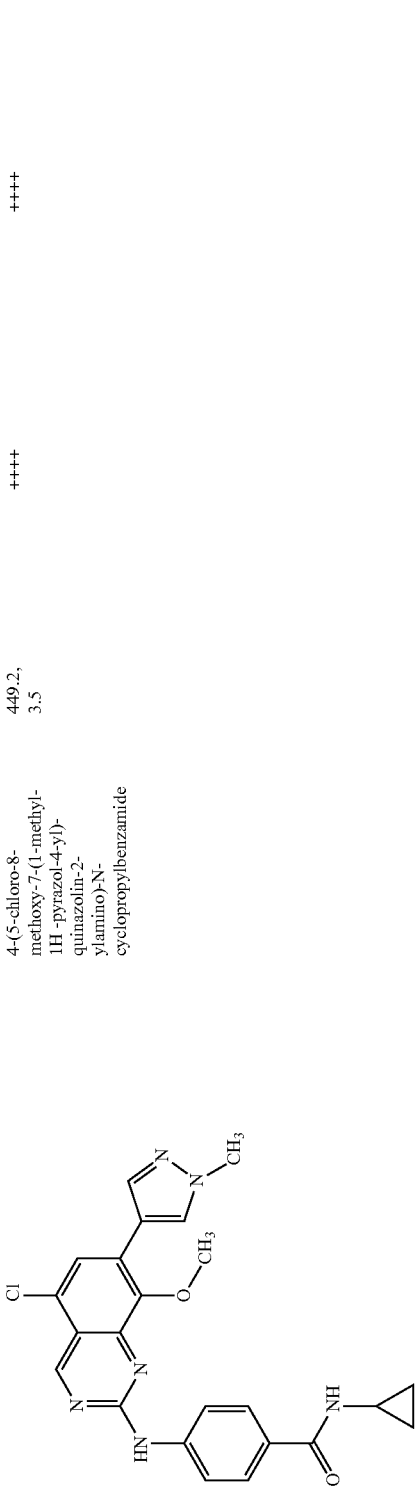
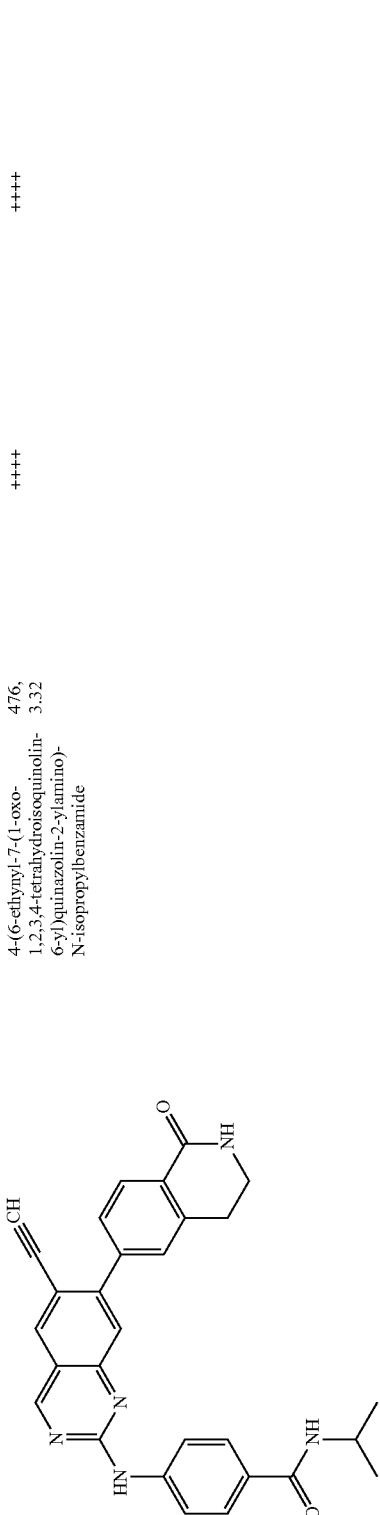

TABLE 4-continued

| | | | | |
|---|---|---|---|---|
| 1040 | N-isopropyl-4-(7-(1-oxo-1,2,3,4-tetrahydroisoquinolin-6-yl)quinazolin-2-ylamino)benzamide | 452, 3.10 | ++++ | +++ |
| 1041 | 6-(6-ethynyl-2-(4-(morpholine-4-carbonyl)phenylamino)quinazolin-7-yl)-3,4-dihydroisoquinolin-1(2H)-one | 504, 3.02 | ++++ | +++ |
| 1042 | methyl 3-(7-(1-isopentyl-1H-pyrazol-4-yl)-8-methoxyquinazolin-2-ylamino)-5-(morpholinomethyl)phenylcarbamate | | ++++ | ++++ |

TABLE 4-continued

| | | |
|---|---|---|
| 1043 | N-(3-(7-(1-isobutyl-1H-pyrazol-4-yl)-8-methoxyquinazolin-2-ylamino)-5-(morpholinomethyl)phenyl)acetamide | ++++ |

The Compounds in Tables 1-4 were named using AutoNom 2000 (Automatic Nomenclature) for ISIS/Base or ChemDraw v. 10, implementing IUPAC standardized nomenclature. Superscripted characters are denoted by asterisks (*) before and after the character.

Further provided are compounds of Formula I and mixtures thereof where any asymmetric carbon atom(s) can have either the R or S configuration. Substituents at a double bond or a ring of the compounds of formula I may be present in either the cis (—Z—) or trans (—E—) configurations. The compounds may thus be present as mixtures of isomers, diastereomers, and enantiomers or may be present as pure isomers. In some embodiments, the compounds are enantiomerically pure where only one enantiomer is present. In other embodiments, the compound may be present as a mixture of enantiomers which includes more of one enantiomer than it does of the other.

Other embodiments provide methods for inhibiting PDK1 in a subject. More particularly, the present invention provides a method of inhibiting PDK1 comprising administering to a human or animal subject, a quinazoline compound as described herein. Such methods include administering a compound of Formula I, II or III to the subject.

The present invention further provides compositions including: a compound of Formula I, II or III and a pharmaceutically acceptable carrier or excipient.

Further methods of the invention are provided wherein compositions described herein are used for the treatment of cancer and reduction of tumor growth. In particular, the quinazoline compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma. More particularly, the quinazoline compound of the invention is administered for the treatment of cancers of the prostate, lung, colon, or breast. In one such embodiment, the quinazoline compound is administered to a subject in need thereof. In some such embodiments, the administration of the compound has an inhibiting effect upon tumor cell growth.

In accordance with another embodiment of the present invention, a therapeutic composition for inhibiting tumor cell growth in a subject is provided. Such compositions include an effective amount of a compound of the invention (i.e., a compound of Formula I, II or III) and at least one pharmaceutically acceptable carrier. In such embodiments, the composition is effective at inhibiting the growth of one or more mammalian tumor cells.

Pharmaceutical compositions that include the compounds described herein may include additives such as excipients. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more of these. Other suitable pharmaceutically acceptable excipients are described in Remington: The Science And Practice Of Pharmacy, Lippincott Williams & Wilkins; Baltimore, Md., 21st ed. (May 28, 2005), which is hereby incorporated herein by reference in its entirety and for all purposes as if fully set forth herein.

Pharmaceutical compositions that include the compounds of the invention may be in any form suitable for the intended method of administration, including, for example, as a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more of these. The liquid carrier may include other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, but are not limited to, soybean oil, coconut oil, olive oil, safflower oil, cottonseed oil, and the like. For parenteral administration, the carrier may be an oily ester such as ethyl oleate, isopropyl myristate, and the like. Compositions of the present invention may also be in the form of microparticles, microcapsules, and the like, as well as combinations of any two or more of these.

The compounds and combinations of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form may include, in addition to a compound of the present invention, stabilizers, preservatives, excipients, and the like. Preferred lipids include phospholipids and phosphatidyl cholines (lecithins), both natural and synthetic. Methods of forming liposomes are known in the art. See, for example, Prescott, Ed., *Methods in Cell Biology*, Volume XIV, Academic Press, New York, N.W., p. 33 et seq (1976).

Controlled release delivery systems may also be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, poly(phosphoesters), polyamides, polyurethanes, poly(imidocarbonates) and poly(phosphazenes).

The compounds of the invention may be administered enterally, orally, parenterally, sublingually, by inhalation spray, rectally, or topically in dosage unit formulations that include conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdermal, rectal, and the like. Topical administration may also include the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will, therefore, melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also include, as is normal practice, additional substances other than inert diluents, e.g., lubricating agents such as magnesium stearate. In the case of capsules, tablets, and pills, the dosage forms may also include buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

Effective amounts of the compounds of the invention generally include any amount sufficient to detectably treat the disorders described herein.

Successful treatment of a subject in accordance with the invention may result in a reduction or alleviation of symptoms in a subject afflicted with a medical or biological disorder. For example, treatment may halt the further progression of the disorder, or may prevent or retard development of the disorder.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and severity of the particular disease undergoing therapy. The therapeutically effective amount for a given situation can be readily determined by routine experimentation and is within the skill and judgment of the ordinary clinician.

DEFINITIONS

As used above and elsewhere herein the following terms and abbreviations have the meanings defined below:

AcH Acetic Acid
ATP Adenosine triphosphate
BCG *Mycobacterium bovis bacillus* Calmette-Guerin
Bn Benzyl
BSA Bovine Serum Albumin
DCM Dichloromethane
DIEA N,N-diisopropyl-ethylamine
EDC 1-(3-Dimethylaminopropyl)3-ethylcarbodiimide hydrochloride
FHA Filamentous haemaglutinin
GCMS Gas Chromatography/Mass Spectroscopy
*H. Pylori Helicobacter Pylori*
HBr Hydrogen Bromide
HPLC High Performance Liquid Chromatography
$IC_{50}$ value The concentration of an inhibitor that causes a 50% reduction in a measured activity.
IFN Interferon
IL Interleukin
IMS Immunomagnetic separation
IPV Inactivated polio virus
LCMS Liquid Chromatography/Mass Spectroscopy
LPS Lipid polysaccharide
MAb or mAb Monoclonal Antibody
MeOH Methanol
MW Molecular Weight
NMR Nuclear magnetic resonance
OMV Outer membrane vesicle
PBMC Peripheral blood mononuclear cells
Rt Room temperature (25° C.)
tBOK Potassium Tertiary Butoxide
TEA Triethylamine
OTf Triflate
THF Tetrahydrofuran
TLC Thin Layer Chromatography and/or Tender Loving Care
TMS Trimethylsilyl
TNF- Tumour necrosis factor-alpha Reference to "quinazolines" (as pertaining to quinazolines of the present invention), indicates compounds having the general structure of Formula I, II or III as described herein. In some embodiments, the quinazolines include the compounds listed in Tables 1-5, infra.

"Modulating" refers to inducing or suppressing.

A "disease associated with cellular proliferation" includes, but is not limited to cancers, for example cancers of the prostate, lung, colon and breast, neuro-fibromatosis, atherosclerosis, pulmonary fibrosis, arthritis, psoriasis, glomerulonephritis, restenosis, proliferative diabetic retinopathy (PDR), hypertrophic scar formation, inflammatory bowel disease, transplantation rejection, angiogenesis, and endotoxic shock.

The term "effective amount" is an amount necessary or sufficient to realize a desired biological effect. For example, an effective amount of a compound to treat a disorder may be an amount necessary to cause reduction or alleviation of symptoms in a subject afflicted with a medical or biological disorder. For example, treatment may halt the further progression of the disorder, or may prevent or retard development of the disorder. The effective amount may vary, depending, for example, upon the condition treated, weight of the subject and severity of the disease. One of skill in the art can readily determine the effective amount empirically without undue experimentation.

As used herein "an effective amount for treatment" refers to an amount sufficient to palliate, ameliorate, stabilize, reverse, slow or delay progression of a condition such as a disease state.

A "subject" or "patient" is meant to describe a human or vertebrate animal including a dog, cat, horse, cow, pig, sheep, goat, monkey, rat, mouse, and other mammals.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The compounds of the present invention can be used in the form of salts as in "pharmaceutically acceptable salts" derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-napthalenesulfonate, oxalate, pamoate, pectinate, sulfate, 3-phenylpropionate, picrate, pivalate, propionate, succinate, tartrate, thiocyanate, p-toluenesulfonate and undecanoate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained. The terms used in the claims are defined below.

"Alkyl" refers to saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

"Alkyl interrupted with —O—, —S—, —SO—, —SO2-, —NH—, carbonyl, carbonylamino, or aminocarbonyl" refers to a C2-10 alkyl group in which an —O—, —S—, —SO—, —SO2—, —NH—, carbonyl, carbonylamino, or aminocarbonyl is inserted between the carbon atoms of the alkyl group. For example, an ethylene radical interrupted with —O— is —C—O—C—. An ethylene radical interrupted with carbonyl is —C—C(=O)—C—.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —NRC(O)alkyl, —NRC(O) substituted alkyl, —NRC(O)cycloalkyl, —NRC(O) substituted cycloalkyl, —NRC(O)cycloalkenyl, —NRC(O) substituted cycloalkenyl, —NRC(O)alkenyl, —NRC(O) substituted alkenyl, —NRC(O)alkynyl, —NRC(O) substituted alkynyl, —NRC(O)aryl, —NRC(O) substituted aryl, —NRC(O)heteroaryl, —NRC(O) substituted heteroaryl, —NRC(O)heterocyclic, and —NRC(O) substituted heterocyclic wherein R is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —$NH_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —SO₂-substituted cylcoalkyl, —SO₂-cycloalkenyl, —SO₂-substituted cycloalkenyl, —SO₂-aryl, —SO₂-substituted aryl, —SO₂-heteroaryl, —SO₂-substituted heteroaryl, —SO₂-heterocyclic, and —SO₂-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Aminocarbonyl" refers to the group —C(O)NR¹⁰R¹¹ where R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR¹⁰R¹¹ where R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonylamino" refers to the group —NRC(O)NR¹⁰R¹¹ where R is hydrogen or alkyl and R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonylamino" refers to the group —NRC(S)NR¹⁰R¹¹ where R is hydrogen or alkyl and R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR¹⁰R¹¹ where R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO₂NR¹⁰R¹¹ where R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO₂NR¹⁰R¹¹ where R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylamino" refers to the group —NR—SO₂NR¹⁰R¹¹ where R is hydrogen or alkyl and R¹⁰ and R¹¹ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkyenyl, heteroaryl, substituted heteroaryl, heterocyclic, and substituted heterocyclic and where R¹⁰ and R¹¹ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkyenyl, aryl, substituted aryl, heteroaryl, substituted heteroaryl, heterocyclic and substituted heterocyclic are as defined herein.

"Amidino" refers to the group —C(=NR$^{12}$)R$^{10}$R$^{11}$ where R$^{10}$, R$^{11}$, and R$^{12}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{10}$ and R$^{11}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified, for example, by vinyl, allyl, and but-3-en-1-yl.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to a vinyl (unsaturated) carbon atom.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy substitution is not attached to an acetylenic carbon atom.

"Carbonyl" refers to the divalent group —C(O)— which is equivalent to —C(=O)—.

"Carboxyl" or "carboxy" refers to —COOH or salts thereof

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the group —NR—C(O)O-alkyl, substituted —NR—C(O)O-alkyl, —NR—C(O)O-alkenyl, —NR—C(O)O-substituted alkenyl, —NR—C(O)

O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic wherein R is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, substituted —O—C(O)O-alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH$_2$.

"Substituted guanidino" refers to —NR$^{13}$C(=NR$^{13}$)N(R$^{13}$)$_2$ where each R$^{13}$ is independently selected from the group consisting of hydrogen, alkyl, substituted alkyl, aryl, substituted aryl, heteroaryl, substituted heteroaryl, heterocyclic, and substituted heterocyclic and two R$^{13}$ groups attached to a common guanidino nitrogen atom are optionally joined together with the nitrogen bound thereto to form a heterocyclic or substituted heterocyclic group, provided that at least one R$^{13}$ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or unsaturated group having a single ring or multiple condensed rings, including fused bridged and spiro ring systems, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spirocycloalkyl" refers to divalent cyclic groups from 3 to 10 carbon atoms having a cycloalkyl ring with a spiro union (the union formed by a single atom which is the only common member of the rings) as exemplified by the following structure:

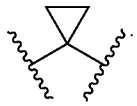

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cylcoalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cylcoalkyl, —OSO$_2$-cycloalkenyl, —OSO$_2$-substituted cycloalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Thiol" refers to the group —SH.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein.

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to individually disclose methyl, ethyl, C$_3$ alkyl (propyl and isopropyl), C$_4$ alkyl, C$_5$ alkyl, and C$_6$ alkyl.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moeity such as pyrazoles, imidazoles, benzimidazoles, triazoles, and tetrazoles.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "protected" or a "protecting group" with respect to hydroxyl groups, amine groups, and sulfhydryl groups refers to forms of these functionalities which are protected from undesirable reaction with a protecting group known to those skilled in the art such as those set forth in Protective Groups in Organic Synthesis, Greene, T. W., John Wiley & Sons, New York, N.Y., (1st Edition, 1981) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, benzyl or dibenzyl, amides such as, formamide, acetamide, trifluoroacetamide, and benzamide; imides, such as phthalimide, and dithiosuccinimide; and others. In some embodiments, a protecting group for amines is a benzyl group. Examples of protected sulfhydryl groups include, but are not limited to, thioethers such as S-benzyl thioether, and S-4-picolyl thioether; substituted S-methyl derivatives such as hemithio, dithio and aminothio acetals; and others.

Quinazoline compounds of Formula I, II or III may exhibit the phenomenon of tautomerism, and the formula drawings within this specification can represent only one of the possible tautomeric forms. It is to be understood that the invention encompasses any tautomeric form which possesses immunomodulatory activity and is not to be limited merely to any one tautomeric form utilized within the formula drawings.

Quinazolines of Formula I, II or III also may exist in solvated as well as unsolvated forms such as, for example, hydrated forms. The invention encompasses both solvated and unsolvated forms which possess immunomodulatory activity.

The invention also includes isotopically-labeled quinazoline compounds, that are structurally identical to those disclosed above, except that one or more atom is/are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, tautomers thereof, prodrugs thereof, and pharmaceutically acceptable salts of the compounds and of the prodrugs that contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

The compounds of the invention are useful in pharmaceutical compositions for human or veterinary use where inhibition of PDK1 is indicated, for example, in the treatment of cellular proliferative diseases such as tumor and/or cancerous cell growth mediated by PDK1. In particular, the compounds are useful in the treatment of human or animal (e.g., murine) cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma. In some preferred embodiments, the compounds of the invention are used to treat cancers of the prostate, lung, colon, and breast.

In other aspects, the invention provides methods for manufacture of PDK1 inhibitor compounds. It is further contemplated that, in addition to the compounds of Formulas I-III, intermediates, and their corresponding methods of syntheses are included within the scope of the embodiments.

In further embodiments, the present invention provides for compounds of Formula I, II, or III for inhibition of Cdk1 and/or Cdk2. Another embodiment provides a method of treating cancer responsive to inhibition of Cdk1, comprising administering a compound of Formula I, II, or III. Another embodiment provides a method of treating cancer responsive to inhibition of Cdk2, comprising administering a compound of Formula I, II, or III.

In further embodiment, the invention provides methods of inhibiting phosphorylation of Akt comprising administering a compound of Formula I, II, or III to a human in need thereof. Another embodiment provides a method of treating cancer responsive to inhibition of phosphorylation of Akt, comprising administering a compound of Formula I, II, or III. Another embodiment provides a method of inhibiting phosphorylation of Akt comprising contacting a cell with a compound of Formula I, II, or III.

In further embodiments, the invention provides methods of inhibiting PDK1 comprising orally administering a compound of Formula I, II, or III to a human in need thereof. In a more particular embodiment the human is suffering from cancer. In a more particular embodiment the cancer is responsive to treatment with a compound that inhibits phosphorylation of PDK1. In another embodiment the compound is orally bioavailable.

In some embodiments of the methods of inhibiting PDK1 using a PDK1 inhibitor compound described herein, the $IC_{50}$ value of the compound is less than or equal to about 1 mM with respect to PDK1. In other such embodiments, the $IC_{50}$ value is less than or equal to about 100 μM, is less than or equal to about 25 μM, is less than or equal to about 10 μM, is less than or equal to about 1 μM, is less than or equal to about 0.1 μM, is less than or equal to about 0.050 μM, or is less than or equal to about 0.010 μM.

In one embodiment, a method of reducing PDK1 activity in a human or animal subject is provided. In the method, a compound of the any of the aforementioned embodiments is administered in an amount effective to reduce PDK1 activity.

In some embodiments of the method of inhibiting PDK1 using a PDK1 inhibitor compound of the embodiments, the $IC_{50}$ value of the compound is between about 1 nM to about 10 nM. In other such embodiments, the $IC_{50}$ value is between about 10 nM to about 50 nM, between about 50 nM to about 100 nM, between about 100 nM to about 1 μM, between about 1 μM to about 25 μM, or is between about 25 μM to about 100 μM.

Another embodiment provides methods of treating a PDK1-mediated disorder. In one method, an effective amount of a PDK1 inhibitor compound is administered to a patient (e.g., a human or animal subject) in need thereof to mediate (or modulate) PDK1 activity. In other such embodiments the PDK1-mediated disorder is cancer.

Still another embodiment provides methods of treating diseases characterized by "abnormal cellular proliferation." The term "abnormal cellular proliferation" includes, for example, any disease or disorder characterized by excessive or pathologically elevated cell growth such as is characteristic of various cancers and non-cancer proliferative disorders.

Example cancers include, for example, lung cancer, bronchial cancer, prostate cancer, breast cancer, pancreatic cancer, colon cancer, rectal cancer, colorectal cancer, thyroid cancer, liver cancer, intrahepatic bile duct cancer, hepatocellular cancer, gastric cancer, glioma/glioblastoma, endometrial cancer, melanoma, kidney cancer, renal pelvic cancer, urinary bladder cancer; uterine corpus cancer; uterine cervical cancer, ovarian cancer, multiple myeloma, esophageal cancer, acute myelogenous leukemia, chronic myelogenous leukemia, lymphocytic leukemia, myeloid leukemia, brain cancer, oral cavity cancer, and pharyngeal cancer, laryngeal cancer, small intestinal cancer, non-Hodgkin lymphoma, and villous colon adenoma.

Example non-cancer proliferative disorders include neurofibromatosis, atherosclerosis, pulmonary fibrosis, arthritis, psoriasis, glomerulonephritis, restenosis, proliferative diabetic retinopathy (PDR), hypertrophic scar formation, inflammatory bowel disease, transplantation rejection, angiogenesis, and endotoxic shock.

In some embodiments, the invention provides pharmaceutical compositions including at least one compound of Formula I, II, or III, together with one or more pharmaceutically acceptable carriers suitable for administration to a human or animal subject, either alone or together with other agents, for example, anticancer agents.

In further embodiments, the invention provides methods of treating human or animal subjects suffering from a cellular proliferative disease, such as cancer. In some such embodiments, the invention provides methods of treating a human or animal subject in need of such treatment, comprising administering to the subject a therapeutically effective amount of a compound of Formula I, II, or III, either alone or in combination with other anticancer agents.

In particular, compositions will either be formulated together as a combination therapeutic or administered separately. Anticancer agents for use with the preferred embodiments include, but are not limited to, one or more of the following set forth below:

A. Kinase Inhibitors

Kinase inhibitors for use as anticancer agents in conjunction with the compositions of the preferred embodiments include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec® (imatinib).

B. Anti-Estrogens

Estrogen-targeting agents for use in anticancer therapy in conjunction with the compositions of the preferred embodiments include Selective Estrogen Receptor Modulators (SERMs) including tamoxifen, toremifene, raloxifene; aromatase inhibitors including Arimidex® or anastrozole; Estrogen Receptor Downregulators (ERDs) including Faslodex® or fulvestrant.

C. Anti-Androgens

Androgen-targeting agents for use in anticancer therapy in conjunction with the compositions of the preferred embodiments include flutamide, bicalutamide, finasteride, aminoglutethamide, ketoconazole, and corticosteroids.

D. Other Inhibitors

Other inhibitors for use as anticancer agents in conjunction with the compositions of the preferred embodiments include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade® (U.S. Pat. No. 5,780,454), XL-784; and cyclooxygenase 2 (COX-2) inhibitors including nonsteroidal antiinflammatory drugs I (NSAIDs).

E. Cancer Chemotherapeutic Drugs

Particular cancer chemotherapeutic agents for use as anticancer agents in conjunction with the compositions of the preferred embodiments include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, gemcitabine (Gemzar® or difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents

Alkylating agents for use in conjunction with the compositions of the preferred embodiments for anticancer therapeutics include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan, irofluven (acylfulvene), penclomedine, pyrazoloacridine (PD-115934); O6-benzylguanine, decitabine (5-aza-2-deoxycytidine), brostallicin, mitomycin C (MitoExtra), TLK-286 (Telcyta®), temozolomide, trabectedin (U.S. Pat. No. 5,478,932), AP-5280 (Platinate formulation of Cisplatin), porfiromycin, and clearazide (mechlorethamine).

G. Chelating Agents

Chelating agents for use in conjunction with the compositions of the preferred embodiments for anticancer therapeutics include tetrathiomolybdate (WO 01/60814); RP-697, Chimeric T84.66 (cT84.66), gadofosveset (Vasovist®), deferoxamine, and bleomycin optionally in combination with electroporation (EPT).

H. Biological Response Modifiers

Biological response modifiers, such as immune modulators, for use in conjunction with the compositions of the preferred embodiments for anticancer therapeutics include staurosporine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexalen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 6,083,505, 5,352,784, 5,494,916, 5,482,936, 5,346,905, 5,395,937, 5,238,944, and 5,525,612) or 2,4-diaminoimidazoquinolines (WO 06/31878); and SMIPs, including benzazoles, anthraquinones, thiosemicarbazones, and tryptanthrins (WO 04/87153, WO 04/64759, and WO 04/60308).

I. Cancer Vaccines:

Anticancer vaccines for use in conjunction with the compositions of the preferred embodiments include Avicine® (*Tetrahedron Lett.* 26:2269-70 (1974)); oregovomab (OvaRex®); Theratope® (STn-KLH); Melanoma Vaccines; GI-4000 series (GI-4014, GI-4015, and G14016), which are directed to five mutations in the Ras protein; Glio Vax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy:

Anticancer agents for use in conjunction with the compositions of the preferred embodiments also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sima-027 (RNAi-based therapeutic targeting VEGFR-1 mRNA).

The foregoing may be better understood by reference to the following Examples that are presented for illustration and not to limit the scope of the inventive concepts. The Example compounds and their analogs are easily synthesized by one skilled in the art from procedures described herein, as well as in patents or patent applications listed herein which are all hereby incorporated by reference in their entireties and for all purposes as if fully set forth herein.

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millennium chromatography system with a 2695 Separation Module (Milford, Mass.). The analytical columns were reversed phase Phenomenex Luna C18-5µ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on one of two LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

GCMS analysis is performed on a Hewlett Packard instrument (HP6890 Series gas chromatograph with a Mass Selective Detector 5973; injector volume: 1 µL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis was performed on some of the compounds with a Varian 300 MHz NMR (Palo Alto, Calif.). The spectral reference was either TMS or the known chemical shift of the solvent. Some compound samples were run at elevated temperatures (e.g., 75° C.) to promote increased sample solubility.

The purity of some of the compounds is assessed by elemental analysis (Desert Analytics, Tucson, Ariz.).

Melting points are determined on a Laboratory Devices Mel-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

Example 1

Preparation of 3-(8-(1-Methylpiperidin-4-yloxy)quinazolin-2-ylamino)benzenesulfonamide

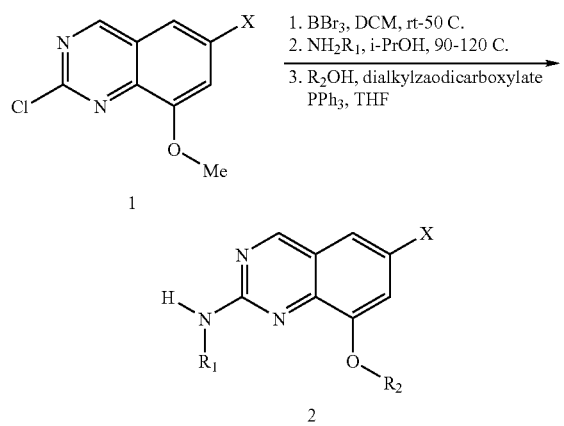

1a: X = H, 1b: X = Br

Step 1. Preparation of 2-Chloroquinazolin-8-ol

To a 0.55M solution of 2-chloro-8-methoxyquinazoline in DCM was added boron tribromide (2.2 eq. of a 1.0 M solution in DCM) over 5 minutes at 0° C. The reaction mixture was stirred at ambient temperature for 22 hours, and then cooled to −5° C. for 30 minutes. The precipitate was collected by vacuum filtration and then stirred in ice water for 30 minutes. The solid was collected by vacuum filtration and rinsed with 2-propanol. The off-white solid was dried in a desiccator to give the desired product in 79% yield. ES/MS m/z 181 (MH$^+$).

Step 2. Preparation of 3-(8-Hydroxyquinazolin-2-ylamino)benzenesulfonamide

To a 0.3 M solution of 2-chloroquinazolin-8-ol in 2-propanol was added sulfanilamide (1.0 eq). The reaction was stirred at 90° C. for 14 hours. The hydrochloride was collected by vacuum filtration and then stirred in aqueous sodium bicarbonate. The solid was collected by vacuum filtration and rinsed with water. The off-white solid was dried in a desiccator to give the desired product in 93% yield. ES/MS m/z 317 (MH$^+$).

Step 3. Preparation of 3-(8-(1-Methylpiperidin-4-yloxy)quinazolin-2-ylamino)benzenesulfonamide To a 0.3M solution of triphenylphosphine (1.5 eq) in THF was added di-tert-butylazodicarboxylate (1.5 eq). The mixture was stirred 15 minutes at ambient temperature. 4-Hydroxy-1-methylpiperidine (4.5 eq) was added. The mixture was stirred 15 minutes at ambient temperature. 3-(8-Hydroxyquinazolin-2-ylamino)benzenesulfonamide (1.0 eq) was added. The mixture was stirred an additional 1 hour. The crude mixture was concentrated, purified by RPHPLC, and lyophilized to give the desired product in 24.2% yield ES/MS m/z 414 (MH$^+$).

Example 2

Step 1. Preparation of 2-chloro-8-methoxyquinazoline

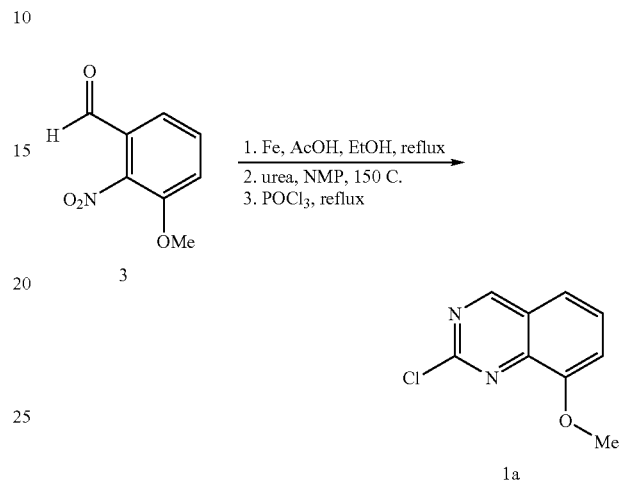

Step 1. Preparation of 2-amino-3-methoxybenzaldehyde

Iron powder (40 g) was slowly added to a stirred solution of 3-methoxy-2-nitrobenzaldehyde (1) (70 g, 386 mmole) in AcOH gal. (100 mL) and EtOH abs. (400 mL). The reaction was cooled using an ice bath followed by addition of con. HCL (1 mL). The reaction became exothermic. After stabilization of the reaction temperature, the reaction was heated to reflux. The reaction reached completion after ca. 20 minutes according to LCMS. The reaction mixture was cooled to RT and filtered. The filtrate was evaporated to a thick brown syrup. The dark residue was dissolved in EtOAc (500 mL) and water (200 mL). The mixture was basified with NaOH 6M to ca. pH 10. The mixture was filtered over celite and the layers separated. The organic layer was washed with NaHCO$_3$ (2×100 mL), water (2×100 mL), brine (100 mL), dried (Na$_2$SO$_4$), filtered and evaporated to a dark amber oil. The oil was dried in vacuo to give 95% pure product 2-amino-3-methoxybenzaldehyde in 64% yield (37.2 g, 246 mmole).

Step 2. Preparation of 8-methoxyquinazolin-2-ol

Solid 2-amino-3-methoxybenzaldehyde (37.2 g, 0.246 mole), urea (158 g, 2.5 mole) and catalytic NH$_4$OAc (1 g) were thoroughly mixed together in a roundbottom flask. The solid mixture was heated in a 160° C. bath. The solids quickly melted and stirring was commenced. After about 15 minutes, solids start to precipitate from the hot solution. After adding NMP (150 mL) to dissolve the solids, the reaction was heated with stirring for an additional 30-45 minutes until complete as judged by LCMS. The hot reaction mixture was poured into vigorously stirred water (400 mL). The reaction flask was washed out with water (3×100 mL) and EtOAc (4×50 mL). After stirring ca. 30 minutes, mixture was filtered to collect the light solid precipitate. The solid filter cake was washed with portions of water and EtOAc to give a white solid. The solid was dried on the frit and in vacuo to give the product in 99% purity and 95% yield (41 g, 233 mmole).

Step 3. Preparation of 2-chloro-8-methoxyquinazoline

Neat POCl₃ (400 mL) was added to 8-methoxyquinazolin-2-ol (5.0 g, 28.4 mmole) with stirring and cooling over an ice bath under argon. After ca. 1 minute, the reaction was removed from the ice bath and stirred at RT for ca. 20 minutes until a fine yellow suspension was formed. The reaction, fitted with a reflux condenser, was heated in an oil bath at 140-145° C. After about 1 hour, the reaction turned clear and colorless. LCMS showed that the reaction was complete. The POCl₃ was evaporated under reduced pressure, and dried in vacuo. After 12 hours, the residue was partitioned between EtOAc (300 mL) and sat. NaHCO₃ (200 mL). The mixture was stirred cautiously watching gas evolution until the pH reached ~8. The layers were separated and the organic layer was washed with NaHCO₃ (2×100 mL), water with 5% brine (2×100 mL), brine (100 mL), dried (Na₂SO₄), filtered and evaporated to a yellow solid. The crude product was purified by flash chromatography eluting with 50% EtOAc/Hexane and finishing with 100% EtOAc to produce a white solid after evaporating the correct fractions. The pure 2-chloro-8-methoxyquinazoline was isolated in 89% yield (4.9 g, 25.3 mmole).

Example 3

Step 1. Preparation of 6-bromo-2-chloro-8-methoxyquinazoline

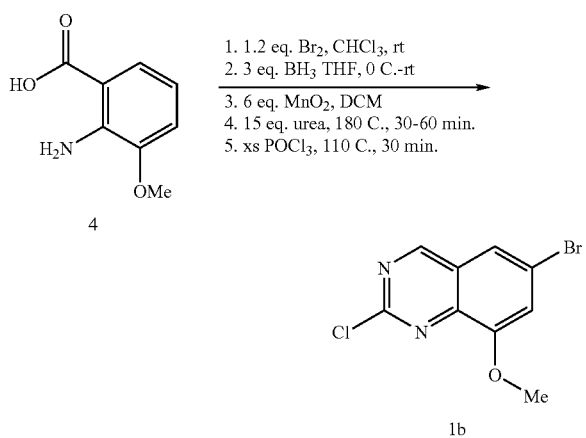

Step 1. Preparation of 2-amino-5-bromo-3-methoxybenzoic acid

To a 0.24 M chloroform solution of 2-amino-3-methoxybenzoic acid (4, 11.87 g, 71.7 mmol) at 0° C. was added bromine (1.08 eq. 0.31 M) in chloroform dropwise. The mixture was warmed to room temperature and stirred under argon for 16 hours. The resulting precipitate was collected by filtration and washed thoroughly with chloroform. The crude material was dried in vacuo to give the title as an HBr salt in 99% yield. ES/MS m/z 248/250 (MH⁺).

Step 2. Preparation of (2-amino-5-bromo-3-methoxyphenyl)methanol

To a 0.24 M THF suspension 2-amino-5-bromo-3-methoxybenzoic acid (71.7 mmol) at 0° C. was added borane THF solution (1 M, 220 mL, 220 mmol). The mixture was stirred under argon at room temperature for 66 hours. The reaction was quenched by adding ethanol (15 mL) at 0° C. and stirred for 15 minutes. The mixture was poured into water and extracted with dichloromethane. The organic extracts were combined, washed with brine, dried with sodium sulfate and concentrated in vacuo to give crude material as a white solid (10.16 g, 62% yield). ES/MS m/z 230/232 (MH⁺).

Step 3. Preparation of 2-amino-5-bromo-3-methoxybenzaldehyde

To a 0.15 M chloroform solution of (2-amino-5-bromo-3-methoxyphenyl)methanol (10.16 g, 43.96 mmol) was added manganese dioxide (19.9 g, 280.5 mmol). The mixture was stirred under argon at room temperature for 16 hours. The resulting mixture was filtered through celite and washed with dichloromethane. The filtrate was concentrated to dryness and used in next step. ES/MS m/z 228/230 (MH⁺).

Step 4. Preparation of 6-bromo-8-methoxyquinazolin-2-ol

The mixture of 2-amino-5-bromo-3-methoxybenzaldehyde (43.96 mmol, crude material from step 3) and urea (35 g, 583 mmol) from the previous step was heated to 180° C. under argon for 1 hour. Water (300 mL) was added after cooling to room temperature. The solid was collected by filtration and air dried to give 12.45 g of powder. ES/MS m/z 254/256 (MH⁺).

Step 5. Preparation of 6-bromo-2-chloro-8-methoxyquinazoline

A suspension of 6-bromo-8-methoxyquinazolin-2-ol (43.96 mmol) in POCl₃ (120 mL) was heated to 110° C. for 30 minutes The mixture was cooled to room temperature, evaporated POCl₃ and partitioned between water and dichloromethane. The organic portion was concentrated to give a crude material which was purified by column chromatography (silica gel, eluted with 2% MeOH in dichloromethane) to yield pure material as a yellow solid in 30% yield (3 steps, 3.62 g). ES/MS m/z 272/274 (MH⁺).

Example 4

Preparation of 3-(7-(1-Methylpiperidin-4-yloxy)quinazolin-2-ylamino)benzenesulfonamide

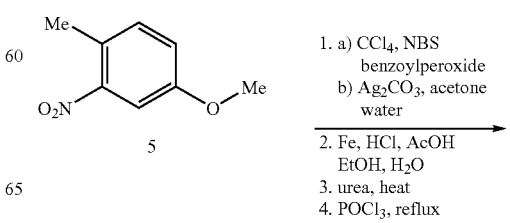

-continued

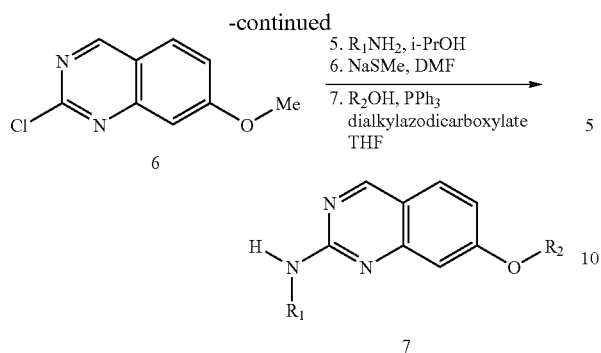

Step 1. Preparation of 4-methoxy-2-nitrobenzaldehyde

Compound 5 (20.43 g, 0.122 mol, 1.0 eq) was dissolved in 480 ml of $CCl_4$ under Ar. NBS (48.94 g, 0.275 mol, 2.2 eq) was added to the solution as a solid in one portion followed by addition of benzoyl peroxide (0.67 g, 2.76 mmol). The reaction mixture was stirred under reflux conditions for 4.5 hours. The $^1H$ NMR of an aliquot showed ~90% conversion of starting material to dibromo derivative.

The reaction mixture was cooled to RT, and concentrated. $CCl_4$ was chased twice with acetone. The residue was taken into acetone (1 L) and $Ag_2CO_3$ (37.1 g, 0.135 mol, 1.1 eq) was added followed by addition of water (100 mL). The reaction mixture was left stirring at RT overnight. TLC (EtOAc: Hexanes=3:7) showed a new spot. The reaction mixture was filtered though celite, and the filter cake was washed with acetone and the filtrate was concentrated. 340 mL of $H_2O$ was added to the crude and the product was extracted with EtOAc (800 mL, 400 mL). The emulsion that formed was filtered through celite and the layers were separated. The organic layer was washed with brine, dried over $Na_2SO_4$, and concentrated to give 8.27 g of crude material, which was purified by column chromatography (EtOAc/Hexanes) giving 14.7 g (67% yield) of pure compound.

Step 2. Preparation of 2-Formyl-5-methoxyaniline

A flask was charged with 4-methoxy-2-nitrobenzaldehyde (14.7 g, 81.2 mmol, 1.0 eq), EtOH (270 mL), glacial AcOH (270 mL), $H_2O$ (135 mL), degassed and filled with argon. Then Fe powder (325 mesh) (27.2 g, 0.49 mol, 6.0 eq) was added followed by addition of concentrated HCl (12.24 mL, 0.148 mol, 1.8 eq). After stirring the reaction mixture for 1 hour at 60-65° C. (oil bath) TLC (EtOAc/Hex=4:6) showed that no starting material was left. The reaction mixture was cooled down to RT, diluted with 200 mL of $H_2O$ and neutralized with $Na_2CO_3$ to pH=7-8. The product was extracted into $CH_2Cl_2$. The emulsion that formed was filtered through celite, organic layer was washed with brine, dried over $Na_2SO_4$, concentrated giving 12.0 g (98% yield) of the title compound.

Step 3. Preparation of 2-Hydroxy-7-methoxyquinazoline

2-Formyl-5-methoxyaniline (11.93 g, 79.5 mmol, 1.0 eq) and urea (38.0 g, 0.636 mol, 8.0 eq) were mixed, ground into a fine powder and placed into a 1 L 2-neck flask equipped with a mechanical stirrer and an air condenser. The flask was placed into a preheated (160° C.) oil bath. The reaction mixture melted and was stirred at 170-180° C. for 1 hour until it solidified forming yellowish-brown solid. The reaction mixture was cooled to RT, crushed, mixed with 70 mL of $H_2O$ and stirred for ~1 hour at RT. The solid was filtered, washed with 150 mL of $H_2O$ and 20 mL of ice cold $Et_2O$. The yellow solid thus obtained was dried over $P_4O_{10}$ under high vacuum for several hours and the crude material (12.57 g) was used for the next step without purification.

Step 4. Preparation of 2-Chloro-7-methoxyquinazoline

The crude 2-Hydroxy-7-methoxyquinazoline (12.48 g) was mixed with 170 mL of $POCl_3$, and the reaction mixture was stirred under reflux conditions for 6 hours. $POCl_3$ was removed using a rotovap. The crude was mixed with ~500 mL of $CHCl_3$, stirred for 1 hour at RT, neutralized with $Na_2CO_3$ (pH 6-7) and the product was then extracted into chloroform. The emulsion that formed was filtered through celite, organic layer was washed with brine, dried over $Na_2SO_4$ and concentrated. The crude was purified by column chromatography (EtOAc/Hex) followed by recrystallization from EtOAc/Hex giving 4.4 g of pure compound 6 (the combined yield for two last steps is 29%).

Step 5. Preparation of 3-(7-Methoxyquinazolin-2-ylamino)benzenesulfonamide

To a 0.3 M solution of 2-chloro-7-methoxyquinazoline 6 in 2-propanol was added sulfanilamide (1.0 eq). The reaction was stirred at 90° C. for 20 hours. The hydrochloride was collected by vacuum filtration and then stirred in aqueous sodium bicarbonate. The solid was collected by vacuum filtration and rinsed with water. The off-white solid was dried in vacuum to give the desired product in 95% yield. ES/MS m/z 331 ($MH^+$).

Step 6. Preparation of 3-(7-Hydroxyquinazolin-2-ylamino)benzenesulfonamide

To a 0.02M solution of 3-(7-Methoxyquinazolin-2-ylamino)benzenesulfonamide in NMP was added sodium thiomethoxide (5.0 eq) at ambient temperature. The reaction was stirred at 80° C. for 3 hours. The solid was collected by vacuum filtration and was partitioned between ethyl acetate and water. Saturated ammonium hydrochloride was added to aqueous phase until the PH=6. Aqueous phase was extracted with ethyl acetate. The organic phase was washed with brine, dried over sodium sulfate and concentrated to give desired product in 85% yield. ES/MS m/z 317 ($MH^+$).

Step 7. 3-(7-(1-Methylpiperidin-4-yloxy)quinazolin-2-ylamino)benzenesulfonamide To a 0.2M solution of triphenylphosphine (1.5 eq) in THF was added di-tert-butylazodicarboxylate (1.5 eq). The mixture was stirred 15 minutes at ambient temperature. 4-Hydroxy-1-methylpiperidine (4.0 eq) was added, and the mixture was stirred 15 minutes at ambient temperature. 3-(7-Hydroxyquinazolin-2-ylamino)benzenesulfonamide (1.0 eq) was then added, and the mixture was stirred an additional 10 hours. The crude mixture was concentrated, purified by RPHPLC, and lyophilized to give the desired product 7 in 18% yield. ES/MS m/z 414 (MH+).

Example 5

Preparation of 7-bromo-2-chloroquinazolin-8-ol

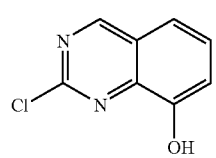

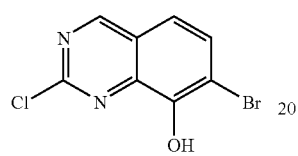

Solid NBS (1.09 g, 6.11 mmole) was added to a stirred solution of 2-chloroquinazolin-8-ol (1.10 g, 6.11 mmole) and diisopropyl amine (2.2 mL, 15.30 mmole) in CHCl₃ (60 mL) at −5° C. under argon. After stirring at −5 to 0° C. for 1 hour, LCMS showed that the reaction was complete. The reaction was evaporated to a residue which was dissolved in DMSO (5 mL) and purified by prep. HPLC. The pure product was obtained as a white solid in 51% yield (800 mg, 3.08 mmole).

Example 6

Preparation of tert-butyl 4-(7-bromo-2-chloro-quinazolin-8-yloxy)piperidine-1-carboxylate

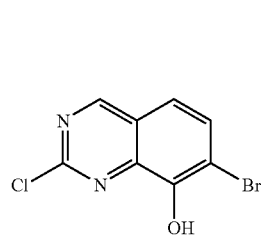

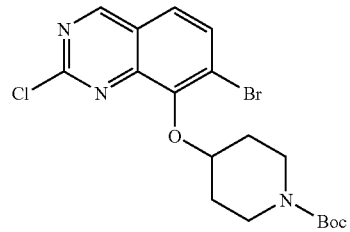

A solution of DEAD (404 mg, 2.32 mmole) in THF (0.5 mL) was added to a solution of 7-bromo-2-chloroquinazolin-8-ol (400 mg, 1.54 mmole), tert-butyl 4-hydroxypiperidine-1-carboxylate (621 mg, 3.09 mmole) and PPh₃ (610 mg, 2.32 mmole) in THF (5.5 mL) at RT. After 1.5 hours, silica gel was added to the reaction which was evaporated to dryness and loaded onto a flash column. The product was eluted with 25% EtOAc/hexane to give tert-butyl 4-(7-bromo-2-chloro-quinazolin-8-yloxy)piperidine-1-carboxylate in 80% yield (545 mg, 1.23 mmole).

Example 7

Preparation of tert-butyl 4-(7-bromo-2-(4-sulfa-moylphenylamino)quinazolin-8-yloxy)piperidine-1-carboxylate

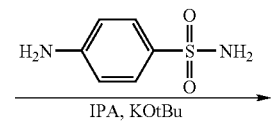

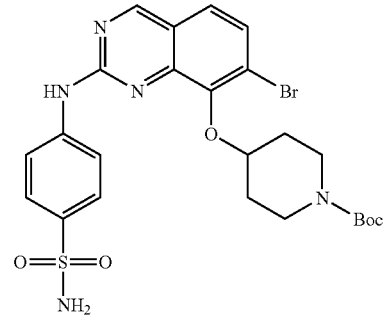

Solid KOtBu (442 mg, 3.95 mmole) was added to a solution of tert-butyl 4-(7-bromo-2-chloroquinazolin-8-yloxy)piperidine-1-carboxylate (500 mg, 1.13 mmole) and 4-aminobenzenesulfonamide (777 mg, 4.62 mmole) in IPA (15 mL). The reaction was sealed and heated to 105° C. with stirring. After 2.5 hours, AcOH was added to the reaction to pH 4 and the reaction was evaporated to a solid. The crude product was dissolved in DMSO (15 mL) and purified by prep. HPLC to give 241 mg of product in 37% yield (417 mmole).

Example 8

Preparation of 4-(7-(1-methyl-1H-pyrrol-3-yl)-8-(piperidin-4-yloxy)quinazolin-2-ylamino)benzene-sulfonamide

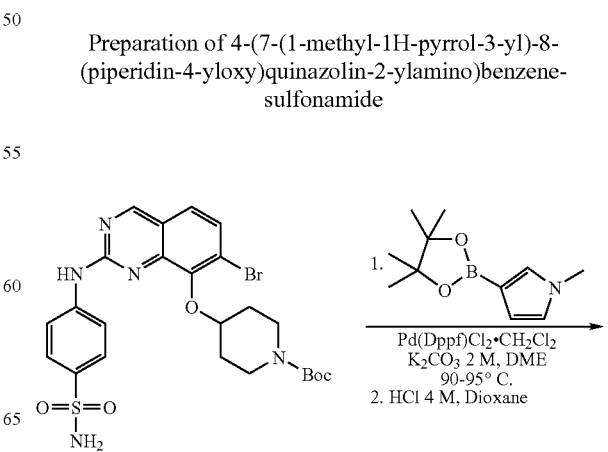

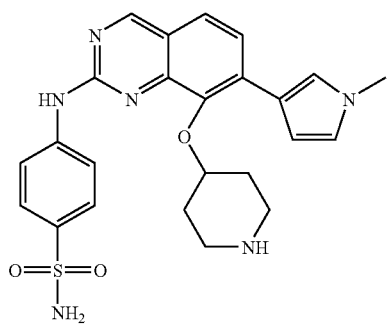

Example 9

Synthesis of 4-(6-ethynyl-8-(1-isopropylpiperidin-4-yloxy)quinazolin-2-ylamino)benzenesulfonamide (Compound 1015)

Step 1. Preparation of 6-bromo-2-chloroquinazolin-8-ol and 2,6-dibromoquinazolin-8-ol

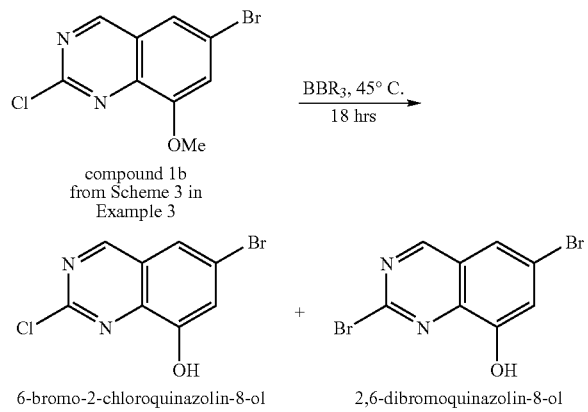

A 2M solution of $K_2CO_3$ (180 µL) was added to a mixture of tert-butyl 4-(7-bromo-2-(4-sulfamoylphenylamino)quinazolin-8-yloxy)piperidine-1-carboxylate (18 mg, 0.031 mmole), 1-methyl-3-(4,4,5,5-tetramethyl-1,3,2-dioxaborolan-2-yl)-1H-pyrrole (20 mg, 0.093 mmole) and palladium (4 mg, 0.005 mmole) in DME (0.6 mL). The reaction was sparged with argon, sealed and heated at 90-95° C. with stirring. After 90 minutes, LCMS showed that the reaction had reached completion. The Boc group was removed by adding 4M HCl (1.5 mL) in dioxane to the cooled reaction mixture. After 2 hours, the reaction was complete by LCMS. The reaction was filtered, evaporated, dissolved in DMSO (1 mL) and purified by prep. HPLC to give 3.4 mg of the pure product as a TFA salt.

To compound 1b (1.26 g, 4.6 mmol) suspended in dichloromethane (20 mL) at 0° C. was added dropwise a dichloromethane solution of borontribromide (1 M, 28 mL, 28 mmol). The mixture was heated to 45° C. for 18 hrs. The resulting suspension was cooled and concentrated to dryness. The residue was cooled in ice bath and saturated $NaHCO_3$ aq. was added. The solid was collected and air dried to give desired product mixture. Without further purification, this was used in the next step.

Step 2. Preparation of 6-bromo-2-chloro-8-(1-isopropylpiperidin-4-yloxy)quinazoline and 2,6-dibromo-8-(1-isopropylpiperidin-4-yloxy)quinazoline

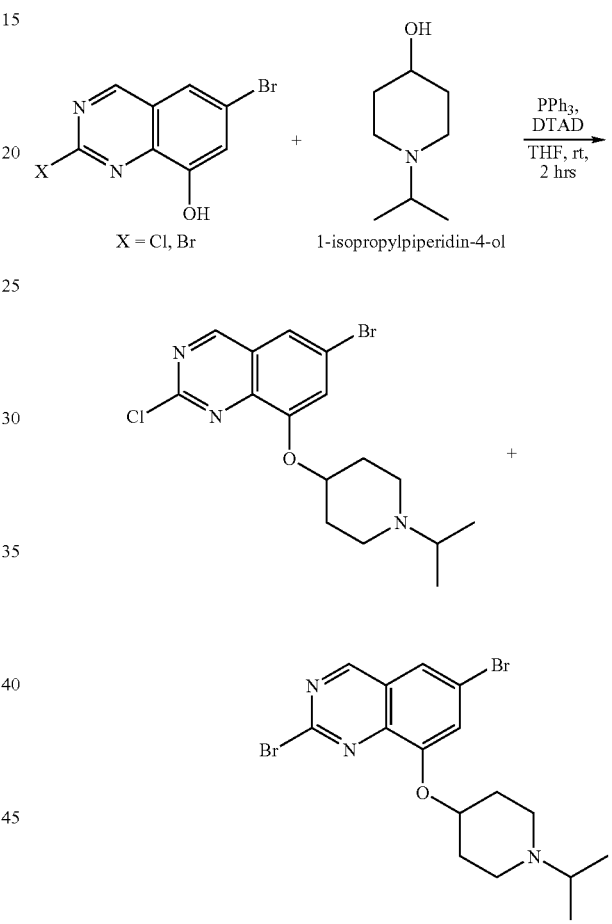

Triphenylphosphine (0.49 g, 1.86 mmol), di-t-butylazodicarboxylate (0.42 g, 1.86 mmol) and 1-isopropylpiperidin-4-ol (0.54 g, 3.74 mmol) were mixed in anhydrous THF (6 mL) and stirred at room temperature for 1.5 hrs. To this mixture was added the THF (5 mL) suspension of a mixture of 6-bromo-2-chloroquinazolin-8-ol and 2,6-dibromoquinazolin-8-ol (0.35 g). The reaction was stirred at room temperature for 2 hrs, worked up by pouring into water and extracted with EtOAc. The organic extracts were washed with brine, dried with sodium sulfate and concentrated in vacuo. The resulting residue was purified by column chromagraphy (silica gel, eluted with EtOAc/Hexanes 1:1 and DCM/MeOH 9:1) to give 0.25 g brown foam as desired product mixture. ES/MS m/z 384/386 (1:1) ($MH^+$ for 6-bromo-2-chloro-8-(1-isopropylpiperidin-4-yloxy)quinazoline) and 428/430/432 (1:2:1) ($MH^+$ for 2,6-dibromo-8-(1-isopropylpiperidin-4-yloxy)quinazoline).

Step 3. Preparation of 4-(6-bromo-8-(1-isopropylpip-eridin-4-yloxy)quinazolin-2-ylamino)benzene-sulfonamide

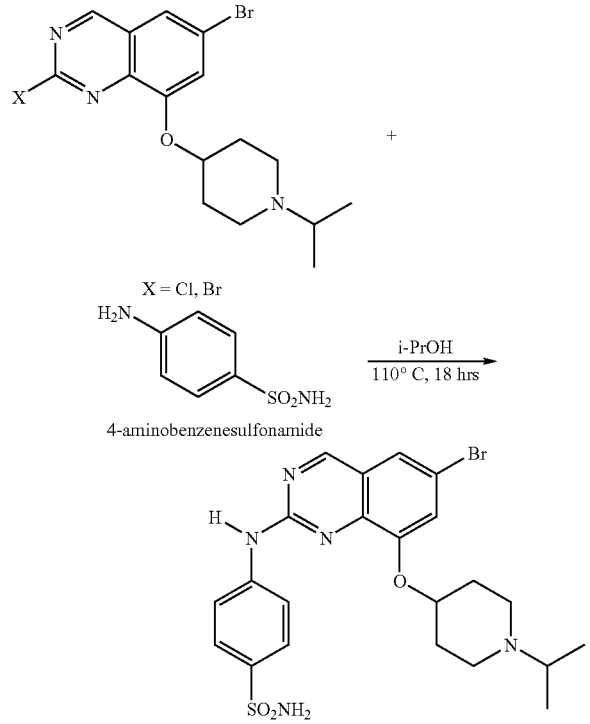

To the mixture of 6-bromo-2-chloro-8-(1-isopropylpiperi-din-4-yloxy)quinazoline and 2,6-dibromo-8-(1-isopropylpi-peridin-4-yloxy)quinazoline (0.15 g) in 1.5 mL of isopropanol was added 4-aminobenzenesulfonamide (81 mg, 0.47 mmol) and HCl in dioxane (4M, 100 µL). The mixture was heated to 100° C. for 15 hrs. Additional amount of 4-aminobenzenesulfonamide (0.2 g) was added and heating was continued at 120° C. for 18 hrs. The reaction was cooled to room temperature, diluted with NaHCO₃ (saturated aqueous) and extracted with EtOAc. The organic extracts were dried and concentrated to give a yellow foam containing desired product 4-(6-bromo-8-(1-isopropylpiperidin-4-yloxy) quinazolin-2-ylamino)benzenesulfonamide. ES/MS m/z 520/522 (MH$^+$).

Step 4. Preparation of 4-(6-ethynyl-8-(1-isopropylpi-peridin-4-yloxy)quinazolin-2-ylamino)benzene-sulfonamide

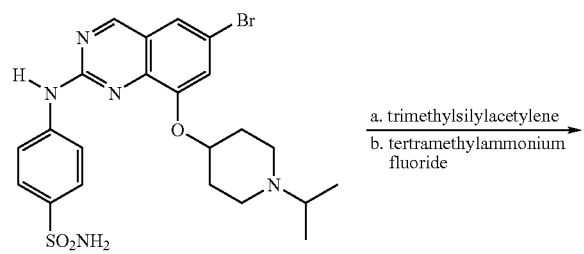

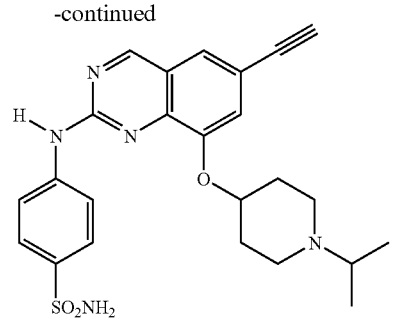

A mixture of 4-(6-bromo-8-(1-isopropylpiperidin-4-yloxy)quinazolin-2-ylamino)benzenesulfonamide (crude, ~50% purity), trimethylsilylacetylene (0.2 mL), CuI (16 mg), PdCl₂(dppf)₂ (32 mg), triethylamine (0.8 mL) and dimethylformamide (0.8 mL) was microwaved at 120° C. for 10 min. The resulting dark brown mixture was diluted with THF (0.8 mL). Tetramethylammonium fluoride (30 mg) was added and the mixture was stirred at room temperature for 18 hrs. The resulting mixture was diluted with water and extracted with EtOAc. The organic extracts were dried with sodium sulfate and concentrated to give a residue which was purified by reverse phase HPLC. The pure fraction was collected and lyophilized to yield desired product as a TFA salt. ES/MS m/z 466 (MH$^+$).

Example 10

Synthesis of 6-bromo-2-chloro-8-fluoroquinazoline

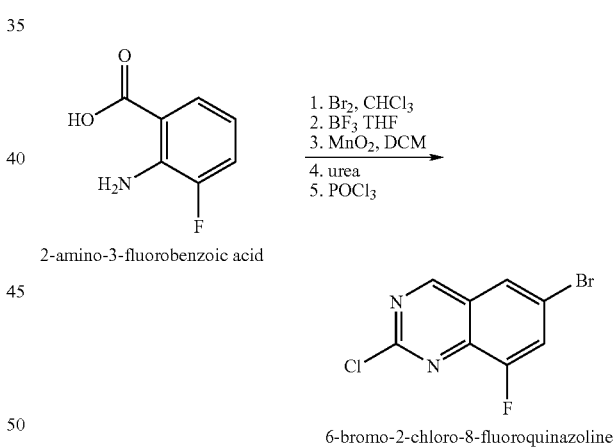

Step 1. To a suspension of 2-amino-3-fluorobenzoic acid (5 g, 32.2 mmol) in chloroform (200 mL) was added dropwise bromine (1.1 equiv.) in chloroform (125 mL) solution. The mixture was stirred at room temperature for 16 hrs. The resulting white solid was collected by filtration and washed thoroughly with methylene chloride until the filtrate was colorless. The solid was air-dried to give 9.6 g of white powder as HBr salt of 2-amino-5-bromo-3-fluorobenzoic acid (95% yield). ES/MS m/z 234/236 (MH$^+$).

Step 2. To the above intermediate (30.6 mmol) in THF (100 mL) at 0 C. was added boran tetrahydrofuran complex solution (1 M in THF, 129 mL, 4 equiv.). The mixture was stirred at room temperature for 40 hrs. The solvent was removed in vacuo and the excess reagent was quenched by addition of water (30 mL) slowly. The pH (~3) was adjusted by adding sodium bicarbonate (sat. aq.) to pH 7. Extracted with methylene chloride. The organic extracts were combined, washed with brine, dried with sodium sulfate and concentrated to give a crude material as white solide. ES/MS m/z 220/222 (MH+).

Step 3. To the above intermediate (30.6 mmol) in dichloromethane (450 mL) was added manganese dioxide (MnO₂, 22 g, 258 mmol). The mixture was stirred at room temperature under argon for 18 hrs. The mixture was filtered through celite pad and washed thoroughly with dichloromethane. The filtrated was concentrated in vacuo to give crude product (2-amino-5-bromo-3-fluorophenyl)methanol (5.6 g) which was used for the next step without further purification. ES/MS m/z 218/220 (MH+).

Step 4. A mixture of (2-amino-5-bromo-3-fluorophenyl)methanol (5.6 g, 23.7 mmol, obtained from step 3) and urea (21 g, 15 equiv.) was heated to 175° C. with vigorous stirring for 15 min. The reaction was cooled to room temperature and water was added. The solid was collected by filtration. Air-dried to give 2-hydroxyquinazoline as a light brown solid.

Step 5. To the above crude material was added phosphooxychloride (POCl₃, 20 mL) and heated to 110° C. for 30 min. The resulting mixture was cooled to room temperature and concentrated in vacuo to nearly dryness. Ice water was added and pH was adjusted to ~6 using sodium bicarbonate. Extraction with dichloromethane followed by drying with sodium sulfate and concentrated in vacuo yielded desired product 6-bromo-2-chloro-8-fluoroquinazoline as light brown powder (1.63 g).

Example 11

Synthesis of 6-bromo-2,8-dichloroquinazoline

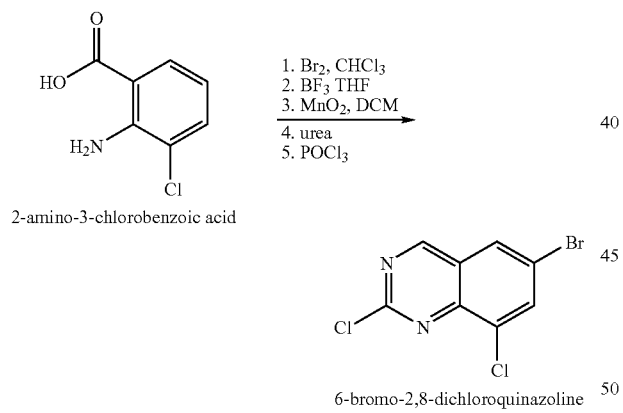

2-amino-3-chlorobenzoic acid 6-bromo-2,8-dichloroquinazoline

Step 1. To a suspension of 2-amino-3-chlorobenzoic acid (2 g, 11.6 mmol) in chloroform (120 mL) was added dropwise bromine (1.1 equiv.) in chloroform (12 mL) solution. The mixture was stirred at room temperature for 16 hrs. The resulting white solid was collected by filtration and washed thoroughly with methylene chloride until the filtrate was colorless. The solid was air-dried to give 3.35 g of white powder as HBr salt of 2-amino-5-bromo-3-chlorobenzoic acid (87% yield). ES/MS m/z 250/252 (MH+).

Step 2. To the above intermediate (3.35 g, 10.1 mol) in THF (40 mL) at 0° C. was added borane tetrahydrofuran complex solution (1 M in THF, 40 mL, 4 equiv.). The mixture was stirred at room temperature for 18 hrs. Additional borane tetrahydrofuran (20 mL) was added and continued reaction for another 24 hrs until the complete conversion of the starting material. The solvent was removed in vacuo and the excess reagent was quenched by addition of ethanol (20 mL) slowly. Water was added and the pH (~3) was adjusted by adding sodium bicarbonate (sat. aq.) to pH 7. Extracted with methylene chloride. The organic extracts were combined, washed with brine, dried with sodium sulfate and concentrated to give a crude material as white solide. ES/MS m/z 236/238 (MH+).

Step 3. To the above intermediate (10.1 mmol) in dichloromethane (80 mL) was added manganese dioxide (MnO₂, 6 g, 70 mmol). The mixture was stirred at room temperature under argon for 40 hrs. Additional manganese dioxide (6 g) was added and the reaction was continued for another 20 hrs until the complete conversion of the starting material. The mixture was filtered through celite pad and washed thoroughly with dichloromethane. The filtrated was concentrated in vacuo to give crude product (2-amino-5-bromo-3-chlorophenyl)methanol (3.3 g, orange solid) which was used for the next step without further purification. ES/MS m/z 234/236 (MH+).

Step 4. A mixture of (2-amino-5-bromo-3-chlorophenyl)methanol (3.3 g, obtained from step 3) and urea (10.5 g, 15 equiv.) was heated to 180° C. with vigorous stirring for 1 hr. The reaction was cooled to room temperature and water was added. The solid was collected by filtration. Air-dried to give 2-hydroxyquinazoline as a yellow powder (2.18 g, crude). ES/MS m/z 259/261 (MH+).

Step 5. To the above crude material was added phosphooxychloride (POCl₃, 25 mL) and heated to 130° C. for 30 min. The resulting mixture was cooled to room temperature and concentrated in vacuo to nearly dryness. Ice water was added and pH was adjusted to ~8 using sodium bicarbonate. Extraction with dichloromethane followed by drying with sodium sulfate and concentrated in vacuo yielded desired product 6-bromo-2,8-dichloroquinazoline as brown foam (1.4 g). This material was used in other chemical medications without further purification.

Example 12

Preparation of 3-(8-methoxyquinazolin-2-ylamino)benzamide

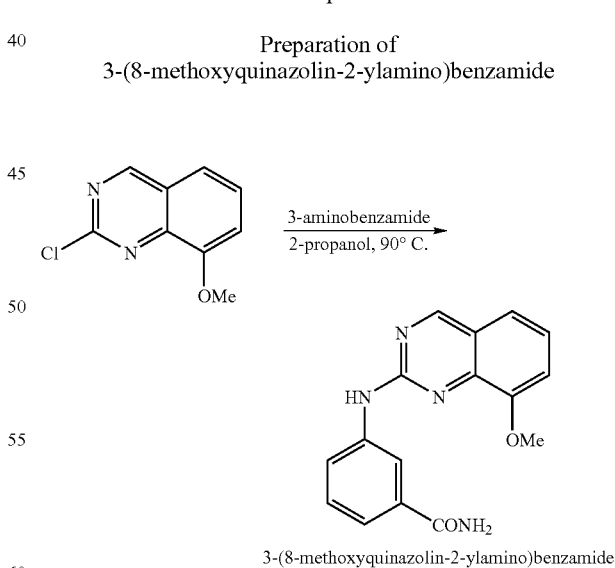

3-(8-methoxyquinazolin-2-ylamino)benzamide

To a 0.30 M solution of 2-chloro-8-methoxyquinazoline in 2-propanol was added 3-aminobenzamide (1.0 eq). The reaction was stirred at 90° C. for 14 h. The resulting solid was collected by vacuum filtration and triturated with additional 2-propanol. The yellow solid was dried in a desiccator to give the desired product as the hydrochloride. Alternatively, the

Example 13

Preparation of N-(3,5-dimethoxyphenyl)-8-methoxyquinazolin-2-amine

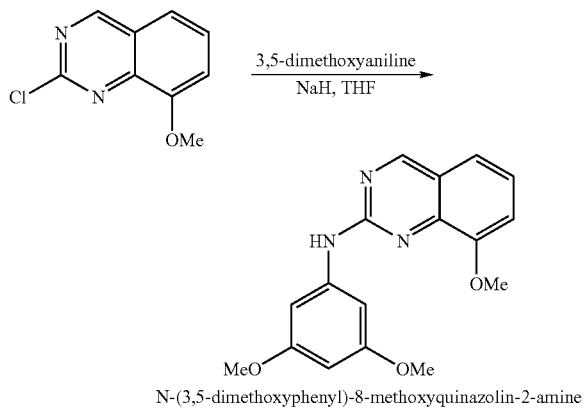

N-(3,5-dimethoxyphenyl)-8-methoxyquinazolin-2-amine

To a 0.40 M suspension of sodium hydride (2.0 eq) in THF was added 3,5-dimethoxyaniline (2.0 eq). The mixture was stirred for 10 min. 2-Chloro-8-methoxyquinazoline was added. The reaction was stirred for 2 h at ambient temperature and then quenched with water. The mixture was concentrated and purified by reverse-phase HPLC and lyophilized to give the desired product as the trifluoroacetic acid salt. ES/MS m/z 312 (MH$^+$).

Example 14

Preparation of 8-(2-aminoethoxy)-N-phenylquinazolin-2-amine (Compound 507)

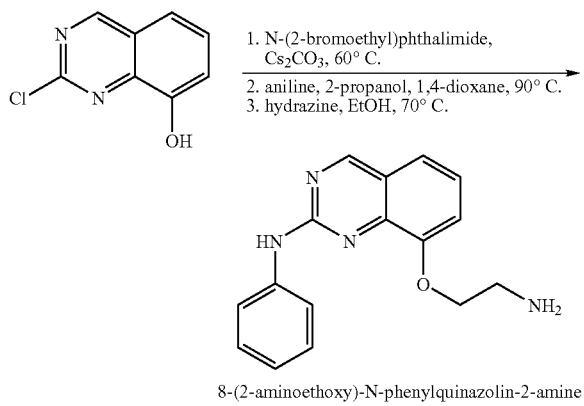

8-(2-aminoethoxy)-N-phenylquinazolin-2-amine

Step 1. Preparation of 8-O-alkylated intermediate

To a 0.20 M suspension of 2-chloroquinazolin-8-ol (1.0 eq) in THF was added cesium carbonate (4.0 eq). The mixture was stirred for 5 min at ambient temperature. N-(2-bromoethyl)phthalimide was added. The reaction was stirred for 24 h at 60 C. The mixture was diluted with THF and DCM, filtered, and concentrated. The crude material was purified by flash chromatography (1:1:1 hexanes:ethyl acetate:DCM) to give the desired product. ES/MS m/z 354 (MH$^+$).

Step 2. Preparation of 2-anilino intermediate

To a 0.20 M suspension of the product from Step 1 (1.0 eq) in 3:1 2-propanol: 1,4-dioxane was added aniline (1.0 eq). The mixture was stirred at 90 C. for 16 h and then concentrated to give the desired product as the hydrochloride salt. ES/MS m/z 411 (MH$^+$).

Step 3. Preparation of 8-(2-aminoethoxy)-N-phenylquinazolin-2-amine

To a 0.040 M suspension of the product from Step 2 (1.0 eq) in ethanol was added hydrazine (4.0 eq). The mixture was stirred at 70 C. for 3 h and then concentrated. The residue was re-dissolved in chloroform and washed with water. The organic phase was dried over sodium sulfate, filtered, and concentrated. The material could be purified by reverse-phase HPLC and lyophilized to give the desired product as the trifluoroacetic acid salt. ES/MS m/z 281 (MH$^+$).

Example 15

Preparation of 2,2-dimethyl-N1-(2-(2-(phenylamino)quinazolin-8-yloxy)ethyl)malonamide (Compound 508)

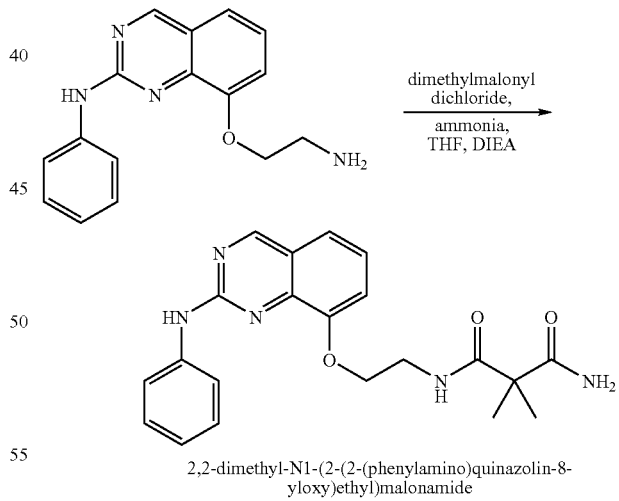

2,2-dimethyl-N1-(2-(2-(phenylamino)quinazolin-8-yloxy)ethyl)malonamide

To a 0.11M solution of dimethylmalonyl dichloride (2.0 eq) in THF was added a 0.5 M solution of ammonia in dioxane (3.5 eq). The mixture was stirred for 15 min at ambient temperature. Crude 591475 was added. After stirring for 5 min, DIEA (4.0 eq) was added; and the mixture was stirred for 30 min. Volatiles were removed under reduced pressure, and the crude residue was purified by reverse-phase HPLC and lyophilized to give the desired product as the trifluoroacetic acid salt. ES/MS m/z 394 (MH$^+$).

Example 16

Preparation of 4-(8-isopropoxyquinazolin-2-ylamino)-N-methylbenzamide (Compound 515)

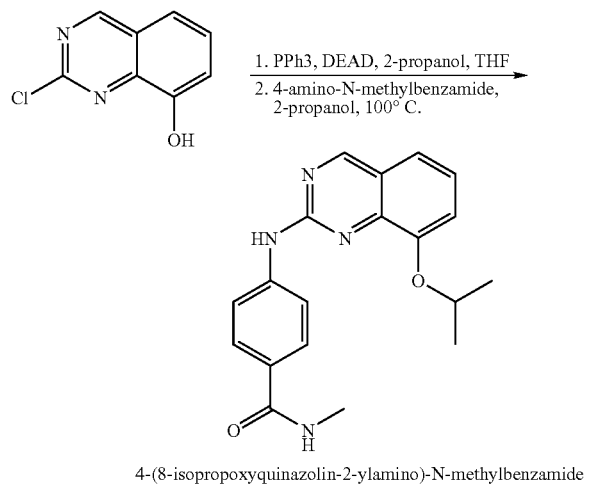

4-(8-isopropoxyquinazolin-2-ylamino)-N-methylbenzamide

Step 1. Preparation of 8-O-alkylated intermediate

To a 0.30 M solution of triphenylphosphine (1.5 eq) in THF was added diethylazodicarboxyate (1.5 eq). The mixture was stirred 15 min at ambient temperature. 2-Propanol (4.0 eq) was added. The mixture was stirred 15 min at ambient temperature. 2-Chloroquinazolin-8-ol (1.0 eq) was added. The mixture was stirred an additional 4 h. The crude mixture was concentrated, purified by flash chromatography (3:1 hexanes: ethyl acetate) to give the desired product. ES/MS m/z 223 (MH$^+$).

Step 2. Preparation of 4-(8-isopropoxyquinazolin-2-ylamino)-N-methylbenzamide To a 0.30 M solution of the product from Step 1 in 2-propanol was added 4-amino-N-methylbenzamide (1.0 eq). The reaction was stirred at 100° C. for 14 h. The mixture was concentrated and purified by reverse-phase HPLC and lyophilized to give the desired product as the trifluoroacetic acid salt. ES/MS m/z 337 (MH$^+$).

Example 17

Preparation of 4-(8-(6-(2-(pyrrolidin-1-yl)ethylamino)pyridin-3-yl)-6-(trifluoromethyl)quinazolin-2-ylamino)benzenesulfonamide (Compound 963)

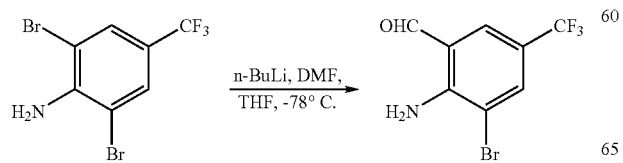

Step 1-Preparation of 2-Amino-3-bromo-5-(trifluoromethyl)benzaldehyde 2,6-Dibromo-4-(trifluoromethyl)aniline (3.19 g, 10.0 mmol, 1.00 eq) was dissolved in THF (50 mL) and cooled to −78° C. A 2.5 M solution of n-butyllithium in hexanes (8.40 mL, 21.0 mmol, 2.10 eq) was added dropwise over 15 min. The mixture was stirred at −78° C. for 1 h. A solution of DMF (1.03 mL, 14.0 mmol, 1.40 eq) in THF (5 mL) was added, and the mixture was stirred an additional 1 h at −78° C. The reaction was allowed to come to −15° C. over 30 min and then quenched with brine. The mixture was diluted with ethyl acetate, washed sequentially with water and brine, dried over sodium sulfate, filtered, and concentrated to give 1.74 g of the desired product as a pale yellow, crystalline solid. ES/MS m/z 268, 270 (MH$^+$).

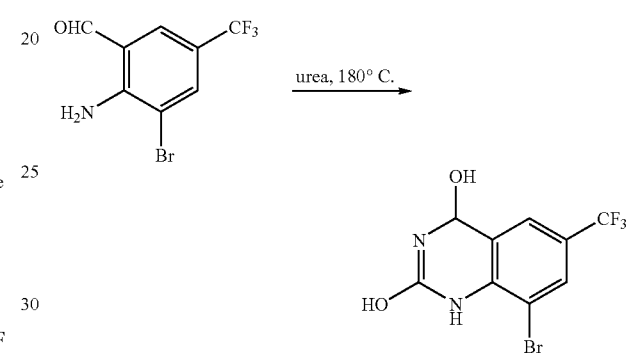

Step 2. Preparation of 8-bromo-6-(trifluoromethyl)-1,4-dihydroquinazoline-2,4-diol 2-Amino-3-bromo-5-(trifluoromethyl)benzaldehyde (1.74 g, 6.49 mmol, 1.00 eq) and urea (5.85 g, 97.4 mmol, 15.0 eq) were stirred at 190° C. for 3 h. The resulting solid was returned to ambient temperature, stirred in water (60 mL) for 20 min, and filtered. This was repeated for a total of three washes. The solid was dried in a desiccator to give 3.79 g of the desired product as an off-white solid. ES/MS m/z 311, 313 (MH$^+$).

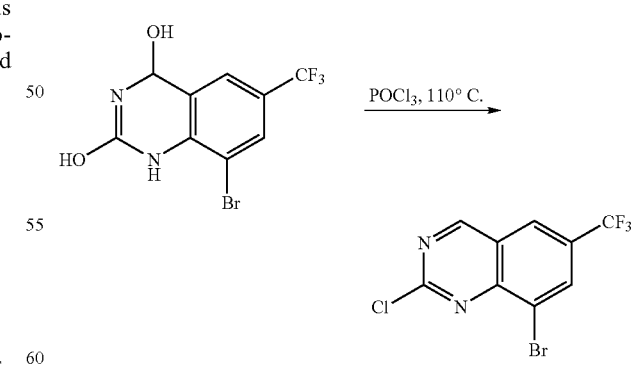

Step 3. Preparation of 8-Bromo-2-chloro-6-(trifluoromethyl)quinazoline

8-Bromo-6-(trifluoromethyl)-1,4-dihydroquinazoline-2,4-diol (3.79 g, 6.49 mmol, 1.00 eq). Phosphorus oxychloride (20 mL) was added. The mixture was stirred at 110° C. for 1.5 h. Volatiles were removed under reduced pressure. Ice water was added, and the pH was adjusted to 6-7 with aqueous sodium hydroxide and sodium bicarbonate. The precipitate was filtered off, rinsed with water, and dried under high vacuum. The crude material was triturated with THF. The mother liquor was concentrated to yield 332 mg of the desired product as an orange, crystalline solid. ES/MS m/z 313 (MH$^+$).

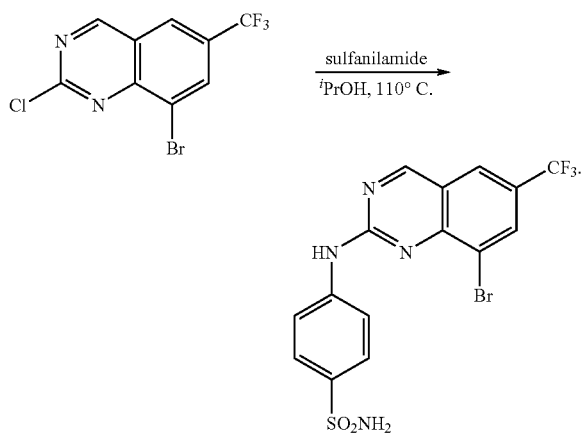

Step 4. Preparation of 4-(8-bromo-6-(trifluoromethyl)quinazolin-2-ylamino)benzenesulfonamide To a 0.30 M solution of 8-bromo-2-chloro-6-(trifluoromethyl)quinazoline in 2-propanol was added sulfanilamide (1.0 eq). The reaction was stirred at 110° C. for 14 h. The hydrochloride was collected by vacuum filtration and then stirred in aqueous sodium bicarbonate. The solid was collected by vacuum filtration and rinsed with water. The light yellow solid was dried in a desiccator to give 343 mg of the desired product. ES/MS m/z 447, 449 (MH$^+$).

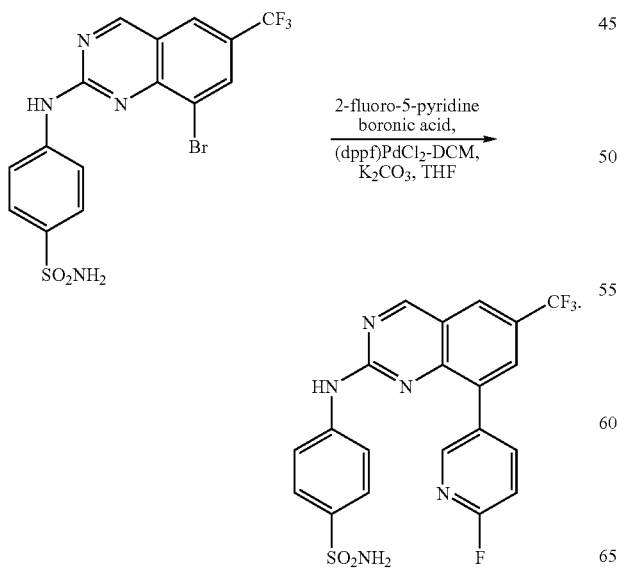

Step 5. Preparation of 4-(8-(6-fluoropyridin-3-yl)-6-(trifluoromethyl)quinazolin-2-ylamino)benzenesulfonamide To a 0.050 M solution of 4-(8-bromo-6-(trifluoromethyl)quinazolin-2-ylamino)benzenesulfonamide (1.0 eq) in DME was added 2-fluoro-5-pyridineboronic acid (3.0 eq), (dppf)Pd(II)Cl$_2$-CH$_2$Cl$_2$ (0.050 eq) and 2M aqueous potassium carbonate (8.0 eq). The mixture was microwaved at 120° C. for 10 min and then diluted with ethyl acetate and filtered through a pad of silica gel. The filtrate was concentrated to give the desired product which was used without further purification. ES/MS m/z 464 (MH$^+$).

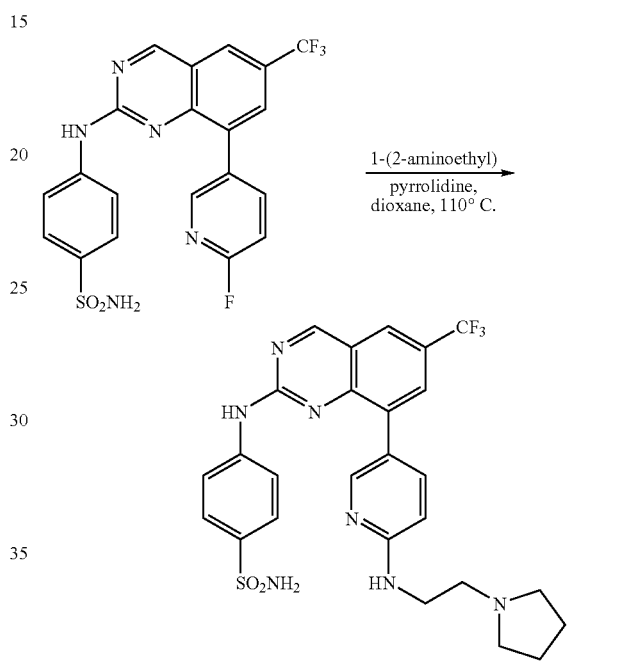

4-(8-(6-(2-(pyrrolidin-1-yl)ethylamino)pyridin-3-yl)-6-(trifluoromethyl)quinazolin-2-ylamino)benzenesulfonamide

Step 6. Preparation of 4-(8-(6-(2-(pyrrolidin-1-yl)ethylamino)pyridin-3-yl)-6-(trifluoromethyl)quinazolin-2-ylamino)benzenesulfonamide To a 0.25M solution of 4-(8-(6-fluoropyridin-3-yl)-6-(trifluoromethyl)quinazolin-2-ylamino)benzenesulfonamide (1.0 eq) in dioxane was added 1-(2-aminoethyl)pyrrolidine (3.0 eq). The mixture was stirred at 110° C. for 14 h and then concentrated and purified by reverse phase HPLC to give the desired compound as its TFA salt. ES/MS m/z 558 (MH$^+$).

Example 18

Synthesis of 2-(4-(8-(1-isopropylpiperidin-4-yloxy)quinazolin-2-ylamino)phenyl)-N-methylacetamide (Compound 969)

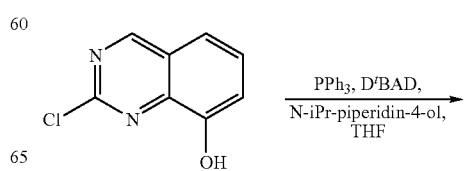

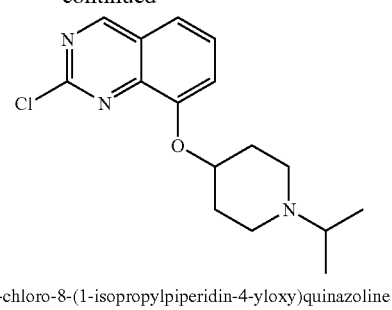

2-chloro-8-(1-isopropylpiperidin-4-yloxy)quinazoline

Step 1. Preparation of 2-Chloro-8-(1-isopropylpiperidin-4-yloxy)quinazoline

To a 0.30M solution of triphenylphosphine (1.5 eq) in THF was added di-tert-butylazodicarboxylate (1.5 eq). The mixture was stirred 15 min at ambient temperature. 4-Hydroxy-1-isopropylpiperidine (4.0 eq) was added. The mixture was stirred 15 min at ambient temperature. 2-Chloroquinazolin-8-ol (1.0 eq) was added. The mixture was stirred an additional 2 h. The crude mixture was concentrated, purified by flash chromatography (EtOAc then 90:10:1 DCM:MeOH:NH$_4$OH), and concentrated to give the desired product in 88% yield. ES/MS m/z 306 (MH$^+$).

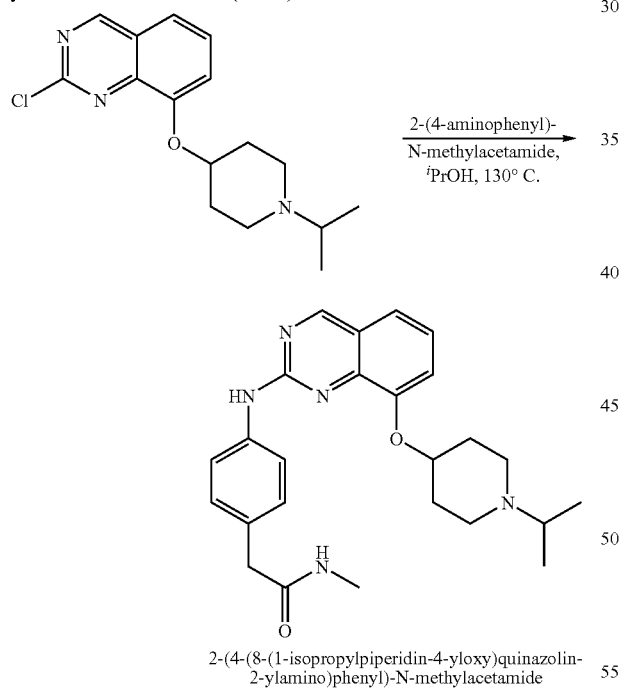

2-(4-(8-(1-isopropylpiperidin-4-yloxy)quinazolin-2-ylamino)phenyl)-N-methylacetamide

Step 2. Preparation of 2-(4-(8-(1-isopropylpiperidin-4-yloxy)quinazolin-2-ylamino)phenyl)-N-methylacetamide To a 0.50M solution of 2-chloro-8-(1-isopropylpiperidin-4-yloxy)quinazoline in 2-propanol was added 2-(4-aminophenyl)-N-methylacetamide (1.0 eq). The reaction was stirred at 130° C. for 14 h. The crude mixture was concentrated, purified by reverse-phase HPLC, and lyophilized to give the desired product as a TFA salt. ES/MS m/z 434 (MH$^+$).

Example 19

Preparation of 8-(1-isopropylpiperidin-4-yloxy)quinazolin-2-amine

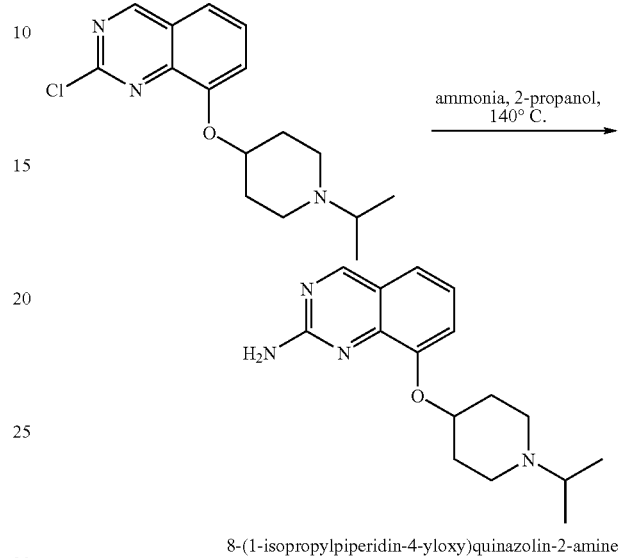

8-(1-isopropylpiperidin-4-yloxy)quinazolin-2-amine

Ammonia was bubbled into a 0.50M solution of 2-chloro-8-(1-isopropylpiperidin-4-yloxy)quinazoline (1.0 eq) in 2-propanol. The reaction was stirred at 140° C. for 4 d in a sealed vessel. The crude mixture was concentrated, purified by reverse-phase HPLC, and lyophilized to give the desired product as its trifluoroacetic acid salt. ES/MS m/z 287 (MH$^+$).

Example 20

Synthesis of morpholino(4-(8-(piperidin-4-yloxy)quinazolin-2-ylamino)phenyl)methanone (Compound 538)

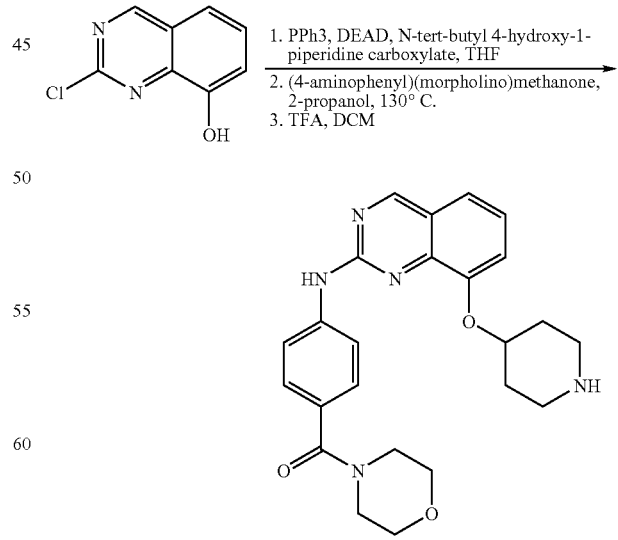

morpholino(4-(8-(piperidin-4-yloxy)quinazolin-2-ylamino)phenyl)methanone

Step 1. Preparation of 2-Chloro-8-(N-Boc-piperidin-4-yloxy)quinazoline

To a 0.30 M solution of triphenylphosphine (1.5 eq) in THF was added diethylazodicarboxylate (1.5 eq). The mixture was stirred 15 min at ambient temperature. N-Tert-butyl-4-Hydroxy-1-piperidine carboxylate (4.0 eq) was added. The mixture was stirred 15 min at ambient temperature. 2-Chloroquinazolin-8-ol (1.0 eq) was added. The mixture was stirred an additional 4 h. The crude mixture was concentrated, purified by flash chromatography (3:2 hexanes:EtOAc), and concentrated to give the desired product. ES/MS m/z 364 (MH$^+$).

Step 2. Displacement

To a 0.50M solution of 2-chloro-8-(1-isopropylpiperidin-4-yloxy)quinazoline in 2-propanol was added (4-aminophenyl)(morpholino)methanone (1.0 eq). The reaction was stirred at 130° C. for 14 h. The crude mixture was concentrated and used without further purification. ES/MS m/z 534 (MH$^+$).

Step 3. Preparation of morpholino(4-(8-(piperidin-4-yloxy)quinazolin-2-ylamino)phenyl)methanone The product from Step 2 was dissolved in enough 1:1 DCM:TFA to make a 0.20M solution. The mixture was stirred for 30 min at ambient temperature and concentrated. The crude product was purified by reverse-phase HPLC and lyophilized to give the desired product as its trifluoroacetic acid salt. ES/MS m/z 434 (MH$^+$).

Example 21

Preparation of 4-(8-(1-acetylpiperidin-4-yloxy)quinazolin-2-ylamino)benzenesulfonamide (Compound 539)

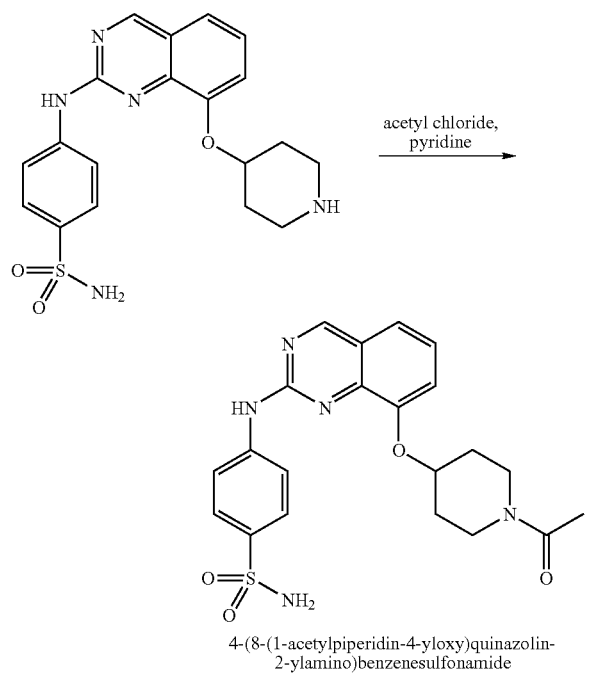

4-(8-(1-acetylpiperidin-4-yloxy)quinazolin-2-ylamino)benzenesulfonamide

To a 0.33M solution of 4-(8-(piperidin-4-yloxy)quinazolin-2-ylamino)benzenesulfonamide in pyridine was added acetyl chloride (1.5 eq). The reaction was stirred for 2 h at ambient temperature and quenched with water. The crude mixture was concentrated, purified by reverse-phase HPLC, and lyophilized to give the desired product as its trifluoroacetic acid salt. ES/MS m/z 442 (MH$^+$).

Example 22

Synthesis of 6-ethynyl-8-(1-isopropylpiperidin-4-yloxy)-N-(3-morpholinophenyl)quinazolin-2-amine (Compound 697)

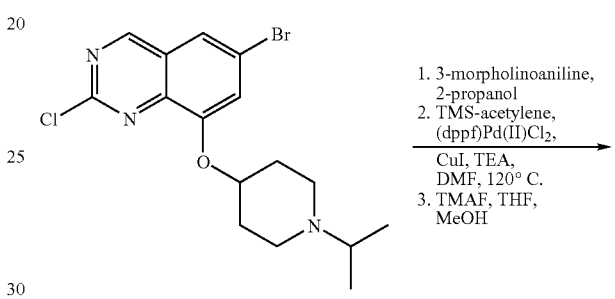

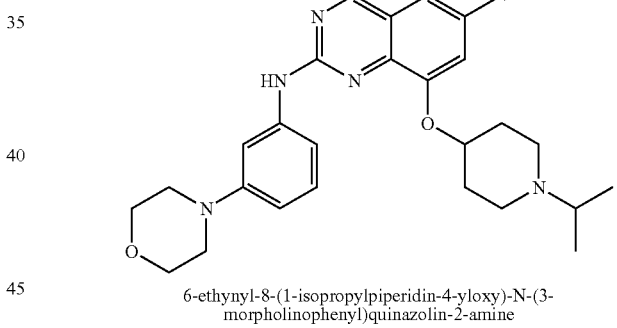

6-ethynyl-8-(1-isopropylpiperidin-4-yloxy)-N-(3-morpholinophenyl)quinazolin-2-amine

Step 1. Displacement of 2-chloro

To a 0.25M solution of 3-morpholinoaniline in 2-propanol was added 6-bromo-2-chloro-8-(1-isopropylpiperidin-4-yloxy)quinazoline (prepared by following Example 9, step 2). The mixture was stirred at 120° C. for 14 h, concentrated, and used without further purification. ES/MS m/z 526, 528 (MH$^+$).

Step 2-3. Preparation of 6-ethynyl-8-(1-isopropylpiperidin-4-yloxy)-N-(3-morpholinophenyl)quinazolin-2-amine The product of step 1 was subjected to subjected to Sonogashira and desilylation reaction (see the scheme above) to give the title compound. ES/MS m/z 306 (MH$^+$).

Example 23

Preparation of 6-ethynyl-N-(4-morpholinophenyl)-8-(piperidin-4-yloxy)quinazolin-2-amine (Compound 700)

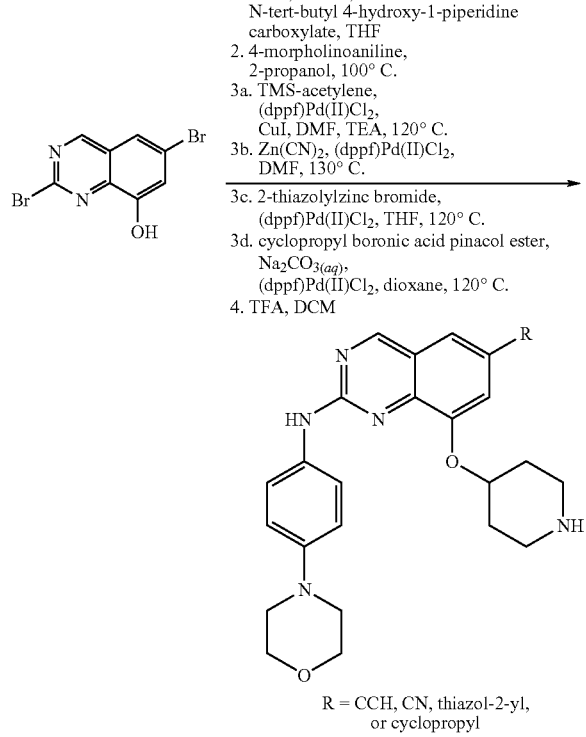

Step 1. Preparation of 2,6-dibromo-8-(N-Boc-piperidin-4-yloxy)quinazoline

To a 0.30M solution of triphenylphosphine (2.0 eq) in THF was added diethylazodicarboxylate (2.0 eq). The mixture was stirred 15 min at ambient temperature. N-Tert-butyl-4-Hydroxy-1-piperidine carboxylate (4.0 eq) was added. The mixture was stirred 15 min at ambient temperature. 2,6-Dibromo-8-hydroxyquinazoline (1.0 eq) was added. The mixture was stirred an additional 24 h. The crude mixture was concentrated, purified by flash chromatography (2:1 hexanes: EtOAc), and concentrated to give the desired product. ES/MS m/z 488 (MH$^+$).

Step 2. Displacement

To a 0.50M solution of 2,6-dibromo-8-(N-Boc-piperidin-4-yloxy)quinazoline in 2-propanol was added 4-morpholinoaniline (1.0 eq). The reaction was stirred at 100° C. for 14 h. The crude mixture was concentrated and used without further purification. ES/MS m/z 584, 586 (MH$^+$).

Step 3a. Sonogashira & Desilylation

The product from Step 2 was subjected to Sonogashira and desilylation reaction (see the scheme above) and carried on to Step 4 without purification. ES/MS m/z 530 (MH$^+$).

Step 3b. Cyanation

The product from Step 2 was subjected to cyanation reaction (see the scheme above) and carried on to Step 4 without purification. ES/MS m/z 531 (MH$^+$).

Step 3c. Negishi

The product from Step 2 was subjected to Negishi reaction (see the scheme above) and carried on to Step 4 without purification. ES/MS m/z 589 (MH$^+$).

Step 3d. Suzuki

To a 0.10M solution of the product from Step 2 (1.0 eq) in 1,4-dioxane was added cyclopropyl boronic acid pinacol ester (4.0 eq), [1,1'-bis(diphenylphosphino)ferrocene]dichloropalladium(II) complex with DCM (0.20 eq), and 2.0M aqueous sodium carbonate (7.0 eq). The reaction was microwaved at 140° C. for 10 min. The mixture was diluted with THF, filtered, concentrated, and carried on to Step 4 without purification. ES/MS m/z 488 (MH$^+$).

Step 4. Preparation of 6-ethynyl-N-(4-morpholinophenyl)-8-(piperidin-4-yloxy)quinazolin-2-amine The product from Step 3 was dissolved in enough 1:1 DCM:TFA to make a 0.20M solution. The mixture was stirred for 30 min at ambient temperature and concentrated. The crude product was purified by reverse-phase HPLC and lyophilized to give the desired product as its trifluoroacetic acid salt. ES/MS m/z 430 (MH$^+$).

Example 24

Synthesis of 4-(6-fluoro-8-(6-fluoropyridin-3-yl)quinazolin-2-ylamino)benzenesulfonamide (Compound 633)

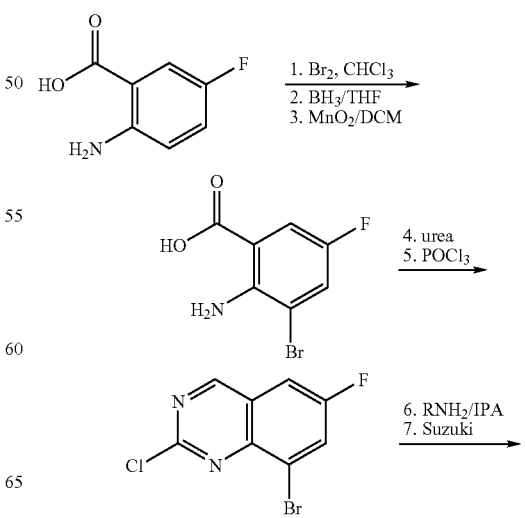

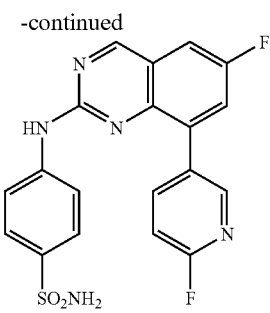

4-(6-fluoro-8-(6-fluoropyridin-3-yl)quinazolin-2-ylamino)
benzenesulfonamide

Step 1

To 2-Amino-5-fluorobenzoic acid (5 g, 32.2 mmol) in chloroform (90 mL) was added bromine (1.82 mL, 35.4 mmol) in chloroform (10 mL) solution dropwise via an additional funnel. The mixture was stirred at room temperature for 16 hrs. and LC/MS showed about 50% conversion of the starting material. Additional bromine (1.8 mL) was added to the reaction and continued stirring for another 24 hrs. The resulting white precipitate was collected by filtration, washed thoroughly with dichloromethane and air-dried to give 2-amino-3-bromo-5-fluorobenzoic acid as its HBr salt. ES/MS m/z 234/236 (MH+).

Step 2 (2-Amino-3-bromo-5-fluorophenyl)methanol

To a 0.5M suspension of 2-amino-3-bromo-5-fluorobenzoic acid in THF in an ice bath was slowly added borane (1.0M/THF, 3 eq). The reaction mixture was stirred at ambient temperature for 24 h. The mixture was recooled to 0° C. and quenched with methanol and concentrated to remove solvent. The residue was taken into ethyl acetate and organic phase was washed with water, saturated sodium bicarbonate, brine, dried over sodium sulfate and concentrated to give yellow solid in 90% yield. ES/MS m/z 220/222 (MH+).

Step 3. 2-Amino-3-bromo-5-fluorobenzaldehyde

Manganese (IV) oxide (5 eq) was added to a 0.2M solution of (2-amino-3-bromo-5-fluorophenyl)methanol in dichloromethane. The suspension was stirred at ambient temperature under Argon for 12 h. The reaction mixture was filtered through celite and filter cake was washed with dichloromethane. The combined filtrate was concentrated to give brown color solid. ES/MS m/z 218/220 (MH+).

Step 4. 8-Bromo-6-fluoroquinazolin-2-ol

Solid 8-bromo-6-fluoroquinazolin-2-ol (1 eq) and urea (14 eq) were thoroughly mixed together in a round bottom flask. The mixture was heated to 180° C. in an oil bath for 2.5 h. The reaction mixture was cooled to ambient temperature and water was added to the flask. Filtration gave yellow color solid, which was rinsed with ether and air dried. Yield: 62%. ES/MS m/z 243/245 (MH+).

Step 5. 8-Bromo-2-chloro-6-fluoroquinazoline

A 0.5M suspension of 8-bromo-6-fluoroquinazolin-2-ol in phosphorus oxychloride was heated to 110° C. in an oil bath. The suspension was turned to a brown color solution in 20 min. LCMS data showed that the reaction was complete after 1 h. The phosphorus oxychloride was removed by concentration. The residue was mixed with ice water, and adjusted pH to 7 by adding sodium bicarbonate. Reaction mixture was extracted with ethyl acetate. Combined organic phase was washed with water, brine, dried over sodium sulfate and concentrated to give desired product in 89% yield. ES/MS m/z 261/263 (MH+).

Step 6. 4-(8-Bromo-6-fluoroquinazolin-2-ylamino)benzensulfonamide

To a 0.4M suspension of 8-bromo-2-chloro-6-fluoroquinazoline in isopropanol was added 4-aminobenzensulfonamide (1 eq). The reaction mixture was heated to 120° C. in an oil bath for 2 days. LCMS showed that reaction was complete under the condition. Ethyl acetate was added to the reaction flask and the suspension was stirred at ambient temperature for 30 min and was filtered. Filter cake was rinsed with hexane and dried in vacuum to give product in 81% yield. ES/MS m/z 397/399 (MH+).

Step 7. Preparation of 4-(6-fluoro-8-(6-fluoropyridin-3-yl)quinazolin-2-ylamino)benzenesulfonamide Pd(dppf)$_2$Cl2CH2Cl2 (0.05 eq) was added to a 0.1M mixture of 4-(8-bromo-6-fluoroquinazolin-2-ylamino)benzensulfonamide (1 eq), 6-fluoropyridin-3-ylboronic acid (3 eq), potassium carbonate/water (2.0M, 2 eq) in DME. The mixture was microwaved at 120° C. for 20 min. Reaction mixture was diluted with ethyl acetate and washed with water, brine, dried and concentrated. The crude product was purified by RP HPLC. Lyophilization gave desired product 596148. ES/MS m/z 414 (MH+).

Example 25

Synthesis of 4-(7-(1-isobutyl-1H-pyrazol-4-yl)quinazolin-2-ylamino)-N-(3-(pyrrolidin-1-yl)propyl)benzenesulfonamide (Compound 709)

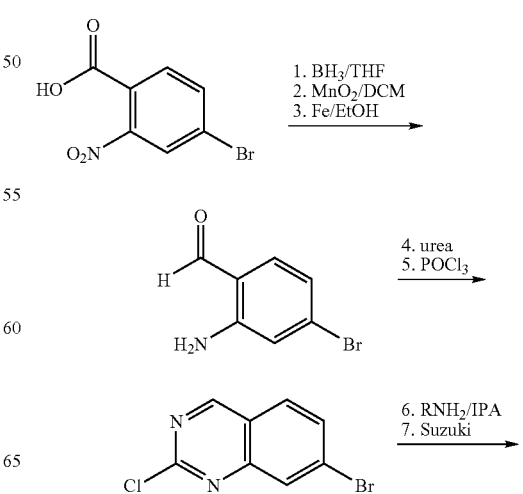

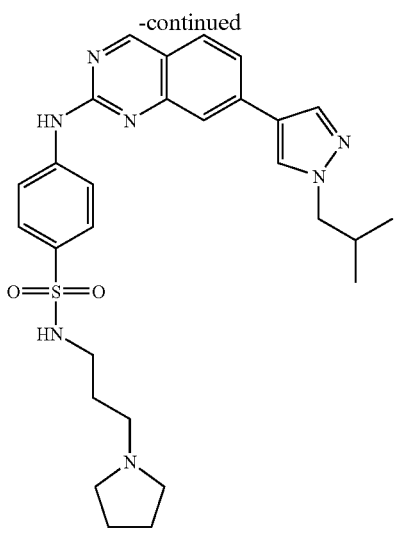

4-(7-(1-isobutyl-1H-pyrazol-4-yl)
quinazolin-2-ylamino)-N-(3-(pyrrolidin-1-yl)propyl)benzenesulfonamide Step 1. (4-Bromo-2-nitrophenyl)methanol To a 0.5M suspension of 4-bromo-2-nitrobenzoic acid in THF in an ice bath was slowly added borane (1.0M/THF, 4 eq). The reaction mixture was stirred at ambient temperature for 48 h. LCMS showed the reaction was complete. The mixture was recooled to 0° C. and quenched with methanol and concentrated to remove solvent. The residue was taken into ethyl acetate and organic phase was washed with water, saturated sodium bicarbonate, brine, dried over sodium sulfate and concentrated to give yellow solid in 95% yield.

Step 2. 4-Bromo-2-nitrobenzaldehyde

Manganese (IV) oxide (4 eq) was added to a 0.18M solution of (4-bromo-2-nitrophenyl)methanol in dichloromethane. The suspension was stirred at ambient temperature under Argon for 12 h. The reaction mixture was filtered through celite and filter cake was washed with dichloromethane. The combined filtrate was concentrated to give brown color solid in 78% yield.

Step 3. 2-Amino-4-bromobenzaldehyde

To a 0.2M solution of 4-bromo-2-nitrobenzaldehyde in acetic acid and ethanol (v/v 1:1) solvent system was added iron powder. The reaction mixture was stirred at ambient temperature under Argon for 1.5 h and LCMS showed the reaction was complete. Insoluble solid was filtered off and the filtrate was concentrated in vacuum. Residue was diluted with ethyl acetate and was washed with saturated sodium bicarbonate, brine, dried over sodium sulfate and concentrated. Crude product was purified by Biotage using 15% ethyl acetate in hexane to give desired product in 38% yield. ES/MS m/z 200/202 (MH$^+$).

Step 4. 7-Bromoquinazolin-2-ol

A mixture of 2-amino-4-bromobenzaldehyde (1 eq) and urea (14 eq) was heated to 180° C. in an oil bath under Argon for 1 h. Water was added to after cooling to ambient temperature. The solid was collected by filtration and air dried to give product in 95% yield. ES/MS m/z 225/227 (MH$^+$).

Step 5. 7-Bromo-2-chloroquinazoline

A 0.5M suspension of 7-bromoquinazolin-2-ol in phosphorus oxychloride was heated to 110° C. in an oil bath for 1 h. The mixture was cooled to room temperature. Volatiles were removed under reduced pressure. The residue was triturated with ice water. The solid was collected by filtration and air dried to give product in 65% yield. ES/MS m/z 243/245 (MH$^+$).

Step 6. 4-(7-Bromoquinazolin-2-ylamino)-N-(3-(pyrrolidin-1-yl)propyl)benzenesulfonamide To a 0.1M suspension of 7-bromo-2-chloroquinazoline in isopropanol was added 4-amino-N-(3-(pyrrolidin-1-yl)propyl)benzenesulfonamide (1.1 eq), followed by the addition of 4.0M HCl in dioxane (1.1 eq). The reaction mixture was heated to 120° C. in an oil bath for 1 h. LCMS showed that reaction was complete under the condition. Ethyl acetate was added to the reaction flask and the mixture was washed with saturated sodium bicarbonate, brine, dried over sodium sulfate and concentrated. Desired product was a yellow color solid. ES/MS m/z 490/492 (MH$^+$).

Step 7. Preparation of 4-(7-(1-isobutyl-1H-pyrazol-4-yl)quinazolin-2-ylamino)-N-(3-(pyrrolidin-1-yl)propyl)benzenesulfonamide Pd(dppf)2Cl2CH2Cl2 (0.05 eq) was added to a 0.05M mixture of 4-(7-bromoquinazolin-2-ylamino)-N-(3-(pyrrolidin-1-yl)propyl)benzenesulfonamide (eq), 1-isobutyl-4-(4,4,5,5-tetramethyl-1,3,2-dioxaborolan-2-yl)-1H-pyrazole (3 eq), 2.0M potassium carbonate/water (2 eq) in DME. The mixture was microwaved at 120° C. for 10 min Reaction mixture was diluted with ethyl acetate and washed with water, brine, dried and concentrated. The crude product was purified by RP HPLC. Lyophilization gave desired product. ES/MS m/z 534 (MH$^+$).

Example 26

Synthesis of 4-(6-ethynyl-7-(1-oxo-1,2,3,4-tetrahydroisoquinolin-6-yl)quinazolin-2-ylamino)-N-isopropylbenzamide

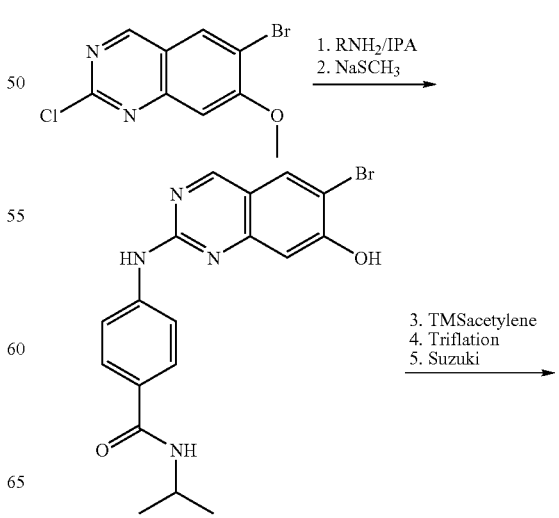

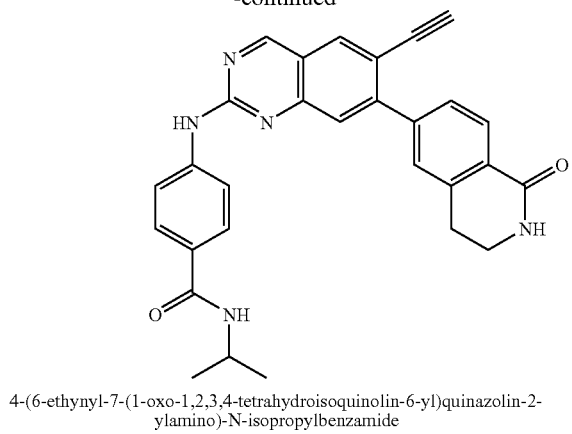

4-(6-ethynyl-7-(1-oxo-1,2,3,4-tetrahydroisoquinolin-6-yl)quinazolin-2-ylamino)-N-isopropylbenzamide

Step 1. 4-(6-Bromo-7-methoxyquinazolin-2-ylamino)-N-isopropylbenzamide

To a 0.25M suspension of 6-bromo-2-chloro-7-methoxyquinazoline in isopropanol was added 4-amino-N-isopropylbenzamide (1.0 eq). The reaction mixture was heated to 100° C. in an oil bath for 14 h. Reaction mixture was diluted with ethyl acetate and filtered to collect desired product. ES/MS m/z 415/417 (MH+).

Step 2. 4-(6-Bromo-7-hydroxyquinazolin-2-ylamino)-N-isopropylbenzamide

A 0.15M suspension of 4-(6-bromo-7-methoxyquinazolin-2-ylamino)-N-isopropylbenzamide (1.0 eq) and sodium thiomethoxide (4.0 eq) in DMF was heated to 80° C. in an oil bath for 12 h. The mixture was partitioned between ethyl acetate and water. The pH of aqueous phase was adjusted to 5 by adding saturated ammonium hydrochloride. Aqueous phase was extracted with ethyl acetate, and combined organic phase was washed with brine, dried over sodium sulfate, and concentrated to give desired product in 90% yield. ES/MS m/z 401/403 (MH+).

Step 3. 4-(7-Hydroxy-6-((trimethylsilyl)ethynyl)quinazolin-2-ylamino)-N-isopropylbenzamide To a 0.09M mixture of 4-(6-bromo-7-hydroxyquinazolin-2-ylamino)-N-isopropylbenzamide (0.17 mM), triethylamine (0.5 ml), Pd(dppf)2Cl2CH2Cl2 (0.1 eq), Copper(I) iodide (0.1 eq), in DMF was added trimethylsilylacetylene (10 eq). The suspension was microwaved at 120° C. for 20 min. Reaction mixture was diluted with ethyl acetate and was washed with water, brine, dried and concentrated to give crude product. ES/MS m/z 419 (MH+).

Step 4. 2-(4-(Isopropylcarbamoyl)phenylamino)-6-((trimethylsilyl)ethynyl)quinazolin-7-yltrifluoromethanesulfonate To a 0.15M solution of 4-(7-hydroxy-6-((trimethylsilyl)ethynyl)quinazolin-2-ylamino)-N-isopropylbenzamide in NMP were added N-phenyl-bis(trifluoromethanesulfonimide) (1.2 eq), and N,N-diisopropylethylamine (2.5 eq). The mixture was stirred at ambient temperature for 15 h. Solution was diluted with ethyl acetate and was washed with water, brine, dried over sodium sulfate and concentrated to give crude product. ES/MS m/z 551 (MH+).

Step 5. Preparation of 4-(6-ethynyl-7-(1-oxo-1,2,3,4-tetrahydroisoquinolin-6-yl)quinazolin-2-ylamino)-N-isopropylbenzamide A 2.0M solution of potassium carbonate (0.8 ml) was added to a mixture of 2-(4-(isopropylcarbamoyl)phenylamino)-6-((trimethylsilyl)ethynyl)quinazolin-7-yltrifluoromethanesulfonate (0.13 mmol), 6-(4,4,5,5-tetramethyl-1,3,2-dioxaboralan-2-yl)-3,4-dihydroisoquinolin-1(2H)-one (0.38 mmol), Pd(dppf)2Cl2Ch2Cl2 (0.01 mmol) in 1,2-dimethoxyethane (4 ml). The mixture was microwaved at 120° C. for 10 min. LCMS indicated formation of Suzuki product. Mixture was diluted with ethyl acetate, and was washed with water, brine, dried and concentrated. The oil residue was treated with tetramethylammonium fluoride (30 mg, 0.3 mmol) in THF (3 ml) at ambient temperature for 1 h. Solvent was removed under reduced pressure, and residue was diluted with ethyl acetate. Organic phase was washed with water, brine, dried and concentrated. The crude product was purified by RP HPLC. Lyophilization gave desired product 623995. ES/MS m/z 476 (MH+).

Example 27

Synthesis of 6-Ethynyl-N-(4-morpholinophenyl)-7-(piperidin-4-yloxy)quinazolin-2-amine (Compound 646)

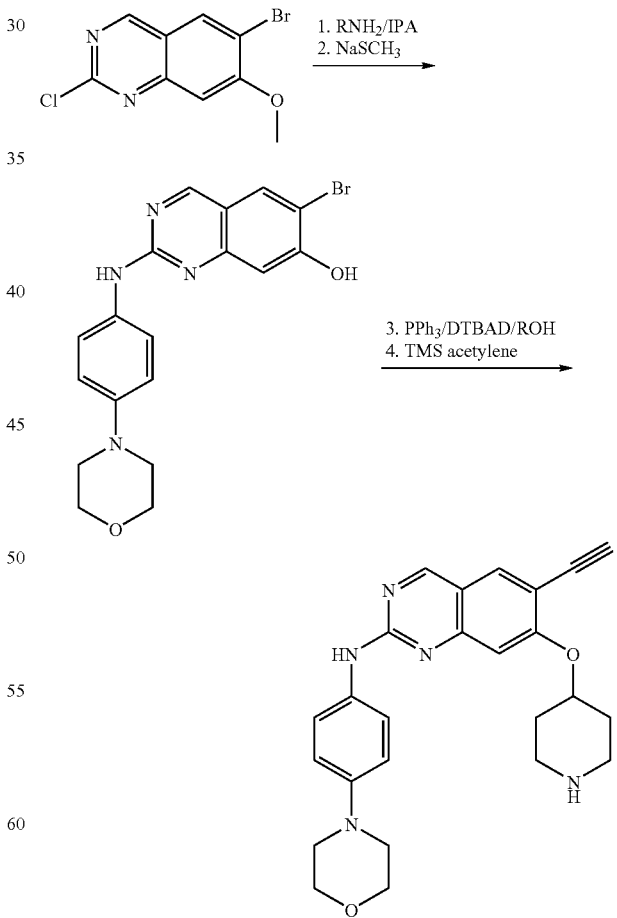

6-ethynyl-N-(4-morpholinophenyl)-7-(piperidin-4-yloxy)quinazolin-2-amine

879

Step 1. 6-Bromo-7-methoxy-N-(4-morpholinophenyl)quinazolin-2-amine

To a 0.12M suspension of 6-bromo-2-chloro-7-methoxyquinazoline (1.0 eq) in isopropanol was added 4-morpholinoaniline (1.0 eq). The reaction mixture was heated to 120° C. in an oil bath for 5 h. LCMS showed that reaction was complete under the condition. The reaction mixture was allowed to cool to room temperature and was filtered. The filter cake was rinsed with ethyl acetate and allowed air dry. Desired product was a brown solid as HCl salt. ES/MS m/z 415/417 (MH+).

Step 2. 6-Bromo-2-(4-morpholinophenylamino)quinazolin-7-ol

A 0.32M suspension of 6-bromo-7-methoxy-N-(4-morpholinophenyl)quinazolin-2-amine (1.0 eq) and sodium thiomethoxide (4.0 eq) in DMF was heated to 80° C. in an oil bath for 12 h. LCMS data indicated the reaction was complete. The mixture was partitioned between ethyl acetate and water. The insoluble solid was filtered off and was rinsed with ether and air dried to give product. ES/MS m/z 401/403 (MH+).

Step 3. tert-butyl 4-(6-bromo-2-(4-morpholinophenylamino)quinazolin-7-yloxy)piperidine-1-carboxylate To a 0.07M solution of triphenylphosphine (3.0 eq) in THF was added di-tert-butylazodicarboxylate (3.0 eq). The mixture was stirred for 15 min at ambient temperature. N-Boc-4-hydroxypiperidine (3.0 eq) was added, and the mixture was stirred at ambient temperature for another 15 min. 6-Bromo-2-(4-morpholinophenylamino)quinazolin-7-ol (1.0 eq, a 0.12M solution in THF) was added to reaction flask. The mixture was stirred an additional 15 h at ambient temperature. Solvent was removed under reduced pressure and the residue was purified by Biotage using 2% methanol in dichloromethane to give tert-butyl 4-(6-bromo-2-(4-morpholinophenylamino)quinazolin-7-yloxy)piperidine-1-carboxy. ES/MS m/z 584/586 (MH+).

Step 4. Preparation of 624175-6-Ethynyl-N-(4-morpholinophenyl)-7-(piperidin-4-yloxy)quinazolin-2-amine To a 0.05M mixture of tert-butyl 4-(6-bromo-2-(4-morpholinophenylamino)quinazolin-7-yloxy)piperidine-1-carboxylate (0.1 mmol), triethylamine (0.5 ml), Pd(dppf)2Cl2CH2Cl2 (0.1 eq), Copper(I) iodide (0.1 eq), in DMF was added trimethylsilylacetylene (10 eq). The suspension was microwaved at 120° C. for 25 min. Reaction mixture was diluted with ethyl acetate and was washed with water, brine, dried and concentrated. The oil residue was treated with tetramethylammonium fluoride (2.0 eq) in THF/methanol (1:1, 0.05M) at ambient temperature for 1 h. Solvent was removed under reduced pressure. The residue was taken into ethyl acetate and was washed with water, brine, dried and concentrated. The resulting dark oil was treated with 50% TFA in dichloromethane at ambient temperature for 1 h. LCMS indicated De-Boc was complete. Solvent was removed under reduced pressure. The crude product was purified by RP HPLC. Lyophilization gave desired product 624175. ES/MS m/z 430 (MH+).

880

Example 28

Preparation of 4-(8-(1-isobutylpiperidine-4-yloxy)quinazolin-2-ylamino)benzene sulfonamide The subject compound was prepared according to the general Scheme below:

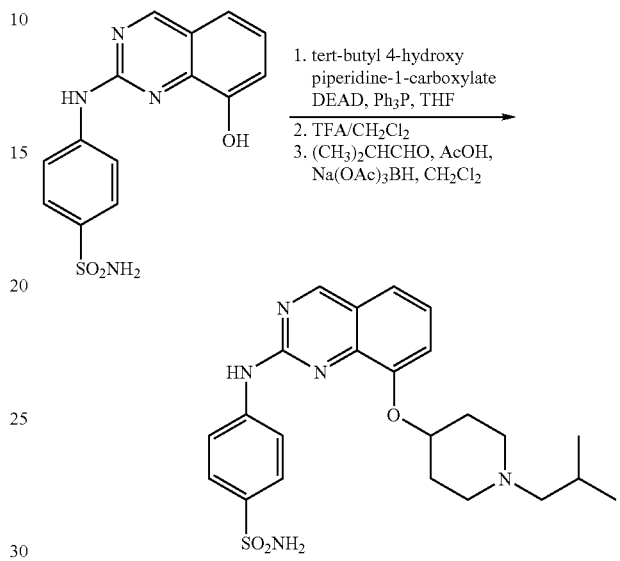

Step 1. Preparation of tert-butyl 4-(2-chloroquinazolin-8-yloxy)piperidine-1-carboxylate To a solution of triphenylphosphine (2 eq) in THF was added di-ethyl-azodicarboxylate (2 eq). The mixture was stirred 15 minutes at ambient temperature. tert-butyl-4-hydroxypiperidine-1-carboxylate (6 eq) was added. The mixture was stirred 15 minutes at ambient temperature. 4-(8-hydroxyquinazolin-2-ylamino)benzenesulfonamide (1.0 eq) was added. The mixture was stirred overnight at ambient temperature. The reaction goes to completion. The reaction mixture was concentrated and the oil was triturated the ether/hexane. A white solid crashed out. The solid was filtered to give tert-butyl 4-(2-chloroquinazolin-8-yloxy)piperidine-1-carboxylate in 90% yield ES/MS m/z 499 (MH+).

Step 2. Preparation of 4-(8-(piperidine-4-yloxy)quinazolin-2-ylamino)benzenesulfonamide To a solution of tert-butyl-(2-chloroquinazolin-8-yloxy)piperidine-1-carboxylate in methylenechloride was added 30% TFA/CH₂Cl₂ and the mixture was stirred for 1 h to give the TFA salt of 4-(8-(piperidine-4-yloxy)quinazolin-2-ylamino)benzenesulfonamide. The reaction mixture was concentrated to a solid to give the product in quantitative yield. ES/MS m/z 399 (MH+)

Step 3. Preparation of 4-(8-(1-isobutylpiperidine-4-yloxy)quinazolin-2-ylamino)benzenesulfonamide To a solution of the TFA salt of 4-(8-(piperidin-4-yloxy)quinazolin-2-ylamino)benzenesulfonamide in DCM was added isobutyraldehyde (2 eq) and a few drops of acetic acid. The mixture was stirred for 10 mins and to it was added sodiumtriacetoxyborohydride (1.5 eq) and the mixture was stirred for 1 h. The reductive amination went to completion, by LC/MS. The crude mixture was concentrated and purified on prep HPLC to give the product 4-(8-(1-isobutylpiperidine-4-yloxy)quinazolin-2-ylamino)benzenesulfonamide in 80% yield. ES/MS m/z 456.2 (MH+).

Example 29

Preparation of 4-(7-(6-morpholinopyridin-3-yl)quinazolin-2-ylamino-benzene sulfonamide (Compound 881)

The subject compound was prepared according to the general Scheme below:

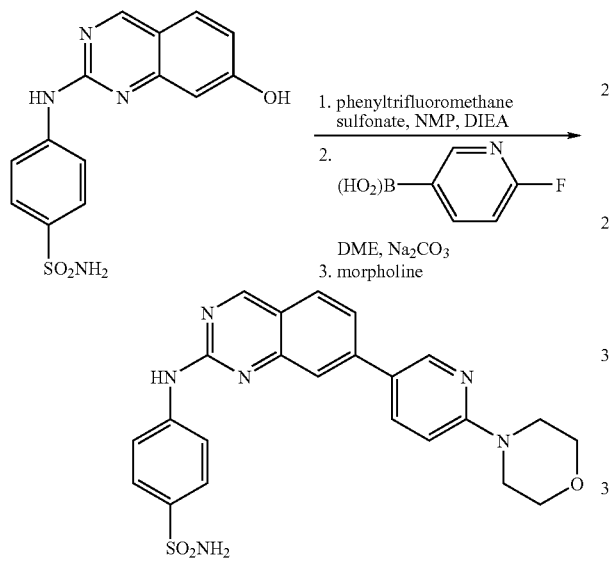

Step 1. Preparation of 2-(4-sulfamoylphenylamino)quinazolin-7-yltrifluoromethane sulfonate To a solution of 4-(7-hydroxyquinazolin-2-ylamino) benzenesulfonamide (1 eq) in NMP was added phenyltrifluoromethanesulfonate (1.2 eq) and DIEA (2.5 eq) and the reaction mixture was stirred over night at ambient temperature. The reaction mixture was then partitioned between ethyl acetate and water. The organic layers were washed with saturated sodium chloride and dried and concentrated. To the crude was added methylene chloride and few drops of methanol. The white solid hence formed was filtered to give 2-(4-sulfamoylphenylamino)quinazolin-7-yltrifluoromethane sulfonate in 80% yield. ES/MS m/z 447 (MH+).

Step 2. Preparation of 4-(7-(6-fluoropyridin3-yl)quinazolin-2-ylamino)benzenesulfonamide To a solution of 2-(4-sulfamoylphenylamino)quinazolin-7-yltrifluoromethane sulfonate (1 eq) in DME was added 2M sodium carbonate solution and 6-fluoropyridin-3-ylboronic acid (3 eq) and Pd(dppf)$_2$Cl$_2$.CH$_2$Cl$_2$ (0.05 eq) and the mixture was micro waved for 10 min at 120° C. The reaction mixture was then partitioned between ethyl acetate and water. The organic layer was concentrated to yield 4-(7-(6-fluoropyridin3-yl)quinazolin-2-ylamino)benzenesulfonamide. ES/MS m/z 396 (MH+).

Step 3. Preparation of 4-(7-(6-morpholinopyridin-3-yl)quinazolin-2-ylamino-benzene sulfonamide To 4-(7-(6-fluoropyridin3-yl)quinazolin-2-ylamino)benzenesulfonamide was added morpholine. The solution was heated at 80° C. for 3 h. SNAR goes to completion and the product was purified on prep HPLC to yield 4-(7-(6-morpholinopyridin-3yl)quinazolin-2ylamino-benzene sulfonamide in 50% yield. ES/MS m/z 463 (MH+).

Example 30

Preparation of N-methyl-2-(4-sulfamoylphenylamino)quinazoline-7-carboxamide

The subject compound was prepared according to the general Scheme below:

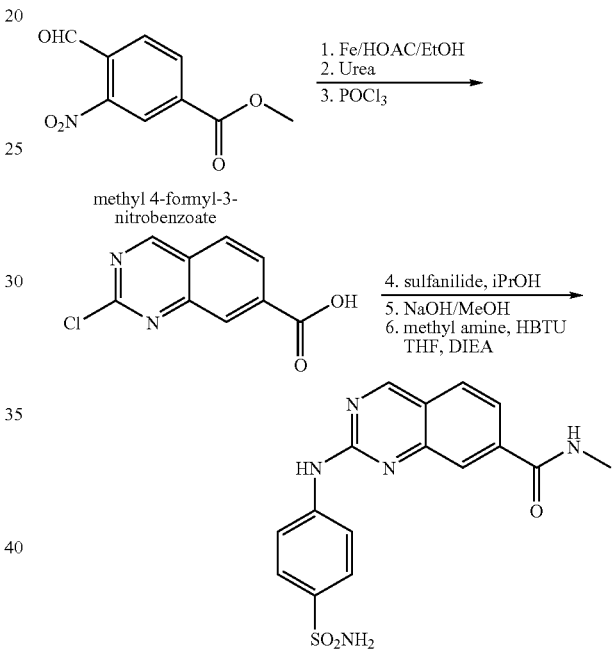

Step 1. Preparation of methyl 4-formyl-3-aminobenzoate

To a 1:1 mixture of ethanol and acetic acid was added methyl4-formyl-3-nitrobenzoate (1 eq) and Fe dust (3 eq) was added in portions. The reduction was complete in 1 h. The reaction mixture was filtered and then concentrated and partitioned between ethyl acetate and water. The organic layer was washed with saturated sodium bicarbonate and dried and concentrated to give methyl 4-formyl-3-aminobenzoate in 85% yield. ES/MS m/z 180 (MH+).

Step 2. Preparation of methyl 2-hydroxyquinazolin-7-carboxylate

To methyl 4-formyl-3-aminobenzoate (1 eq) was added urea (5 eq) and the mixture was heated to 145° C. for 16 h. To the crude was added water and the precipitated solid was filtered to give methyl 2-hydroxyquinazolin-7-carboxylate in quantitative yield. ES/MS m/z 205 (MH+).

Step 3. Preparation of methyl 2-chloroquinazolin-7-carboxylate

To 2-hydroxyquinazolin-7-carboxylate was added POCl₃ and the mixture was added heated to 100° C. for 20 min when the reaction went to completion. To the reaction mixture was added ice and water and the precipitated solid was filtered and dried on the high vacuum overnight to give methyl 2-chloroquinazolin-7-carboxylate in 60% yield. ES/MS m/z 223 (MH⁺).

Step 4. Preparation of methyl 2-(4-sulfamoylphenylamino)quinazolin-7-carboxylate To methyl 2-chloroquinazolin-7-carboxylate (1 eq) was added sulfanide (1 eq) and isopropanol and the mixture was heated to 90° C. for 2 h. The reaction went to completion. The reaction mixture was cooled to RT and filtered to give methyl 2-(4-sulfamoylphenyl amino)quinazolin-7-carboxylate in quantitative yield. ES/MS m/z/359 (MH⁺).

Step 5. Preparation of methyl 2-(4-sulfamoylphenylamino)quinazolin-7-carboxylic acid To 2-(4-sulfamoylphenyl amino)quinazolin-7-carboxylate was added 2N sodium hydroxide (4 eq) and methanol and the mixture was heated to 80° C. for 10 min. The saponification went to completion. The reaction mixture was concentrated and 1N HCl was added to precipitate methyl 2-(4-sulfamoylphenylamino)quinazolin-7-carboxylic acid as the HCl salt in quantitative yield. ES/MS m/z 344 (MH⁺).

Step 6. Preparation of N-methyl-2-(4-sulfamoylphenylamino)quinazoline-7-carboxamide To methyl 2-(4-sulfamoylphenylamino)quinazolin-7-carboxylic acid (1 eq) was added methylamine (2 eq) and DIEA (4 eq) and HBTU (2 eq) and the mixture was stirred at RT overnight. The coupling went to completion and the mixture was concentrated and partitioned between ethyl acetate and water. The organic layers were concentrated and purified on the prep HPLC to give N-methyl-2-(4-sulfamoylphenylamino)quinazoline-7-carboxamide in 50% yield. ES/MS m/z 358 (MH⁺).

Example 31

Preparation of 7-(piperidin-4-yloxy)-N-(3-(trifluoromethyl)phenyl)quinazolin-2-amine (Compound 569)

To tert-butyl 4-(2-(ethylsulfonyl)quinazolin-7-yloxy)piperidine-1-carboxylate (1 eq) was added 3-trifluoromethylaniline and the mixture was heated to 100° C. for 16 h. The formation of the product was confirmed by LC/MS. The mixture was then partitioned between ethyl acetate and water. The organic layer was purified on prep HPLC to give tert-butyl 4-(2-(ethylsulfonyl)quinazolin-7-yloxy)piperidine-1-carboxylate. To the concentrated pure fractions was added 30% TFA/DCM, and the mixture was stirred for 30 min. The deprotection went to completion and the 7-(piperidin-4-yloxy)-N-(3-(trifluoromethyl)phenyl)quinazolin-2-amine was isolated. ES/MS m/z 389 (MH⁺).

Preparation of 7-(1-isopropylpiperidin-4-yloxy)-N-(3-(trifluoromethyl)phenyl) quinazolin-2-amine (596754)

To 7-(piperidin-4-yloxy)-N-(3-(trifluoromethyl)phenyl)quinazolin-2-amine in DCM was added acetone (10 eq), a few drops of acetic acid and sodium triacetoxy borohydride (4 eq). The reaction mixture was stirred for 16 h at ambient temperature. The reductive amination went to completion to give 7-(1-isopropylpiperidin-4-yloxy)-N-(3-(trifluoromethyl)phenyl)quinazolin-2-amine. The mixture was then purified on prep HPLC to give 7-(1-isopropylpiperidin-4-yloxy)-N-(3-(trifluoromethyl)phenyl)quinazolin-2-amine. ES/MS m/z 431 (MH⁺).

Example 32

Preparation of 5-chloro-N-(4-morpholinophenyl)-8-(piperidin-4-yloxy)quinazolin-2-amine (Compound 605)

The subject compound was prepared according to the general Scheme below:

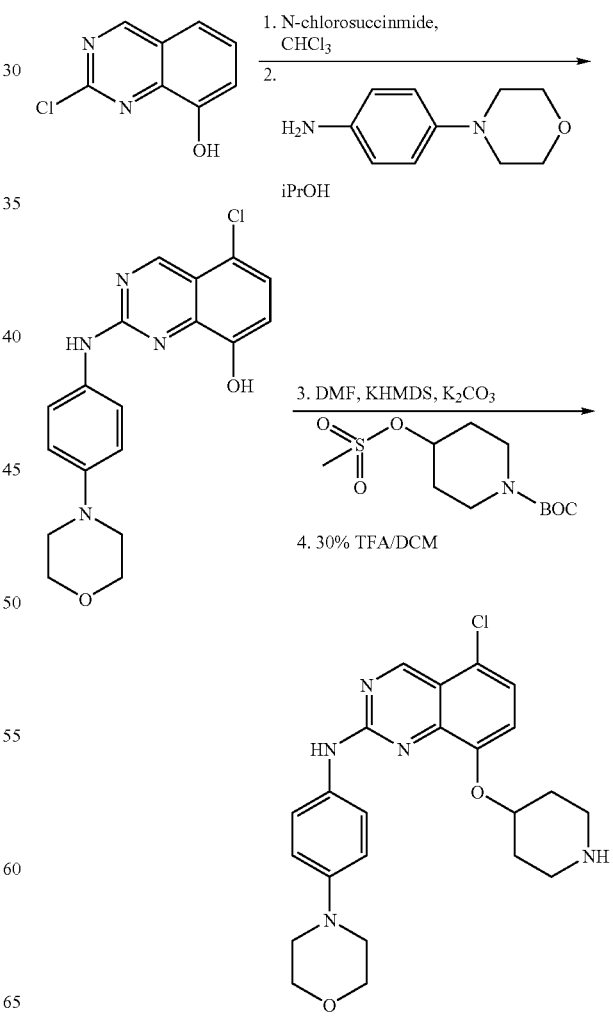

Step 1. Preparation of 2,5-dichloroquinazolin-8-ol

To a solution of 2-chloroquinazolin-8-ol (1 eq) in chloroform was added N-chlosuccinimide (1 eq) and the resulting mixture was heated to 40° C. for 2 h. The chlorination goes to completion giving 2,5-dichloroquinazolin-8-ol in 65% yield. 25% of the reaction was 2,7-dichloroquinazolin-8-ol and 15% of the reaction mixture was 2,5,8-trichloro quinazolin-8-ol. The reaction mixture was concentrated and the crude was purified by silica gel. The structures of the isomers were confirmed by $^1$H NMR and by LC/MS. ES/MS m/z 215 (MH$^+$).

Step 2. Preparation of 5-chloro-2-(4-morpholinophenylamino)quinazolin-8-ol

To a solution of isolated 2,5-dichloroquinazolin-8-ol (1 eq) in isopropanol was added 4-morpholinoaniline (1 eq) and the mixture was heated to 90° C. for 1 h. The SNAR went to completion by LC/MS and on concentration yielded 5-chloro-2-(4-morpholinophenylamino) quinazolin-8-ol in quantitative yield. ES/MS m/z 357 (MH$^+$).

3. Preparation of tert-butyl 4-(5-chloro-2-(4-morpholinophenylamino)quinazolin-8-yloxy)piperidin-1-carboxylate Step 3. The tert-butyl-4-(methylsulfonyloxy)piperidine-1-carboxylate used in this step was made as follows:
To tert-butyl 4-hydroxypiperidine-1-carboxylate (1 eq) in methylene chloride and triethyl amine (1.4 eq) at 0° C. was added methane sulfonyl chloride (1.4 eq) drop-wise. The reaction was brought to ambient temperature and was stirred for 1 h. The reaction mixture was washed with water and saturated sodium chloride solution. The organic layer was then dried with sodium sulfate and concentrated to yield tert-butyl-4-(methylsulfonyloxy)piperidine-1-carboxylate in quantitative yield. The product was confirmed by $^1$H NMR, and used without further purification.
To 5-chloro-2-(4-morpholinophenylamino)quinazolin-8-ol (1 eq) in DMF was added potassium carbonate (1.1 eq) and KHMDS (1.2 eq) and tert-butyl4-(methylsulfonyloxy)piperidine-1-carboxylate (1.5 eq). The reaction mixture was micro waved at 170° C. for 10 min. Formation of tert-butyl 4-(5-chloro-2-(4-morpholinophenylamino)quinazolin-8-yloxy)piperidin-1-carboxylate was confirmed by LC/MS. ES/MS m/z 540 (MH$^+$).

Step 4. Preparation of 5-chloro-N-(4-morpholinophenyl)-8-(piperidin-4-yloxy)quinazolin-2-amine The crude reaction mixture of tert-butyl 4-(5-chloro-2-(4-morpholinophenylamino) quinazolin-8-yloxy)piperidin-1-carboxylate was purified using prep HPLC and the purified fractions of the product was concentrated. To it was added a few drops of 30% TFA/DCM and the mixture was stirred for 30 min. The deprotection went to completion yielding 5-chloro-N-(4-morpholinophenyl)-8-(piperidin-4-yloxy) quinazolin-2-amine that was confirmed by LC/MS. ES/MS m/z 440 (MH$^+$).

Example 33

Preparation of 4-(7-methoxy-4-methylquinazolin-2-ylamino)enzenesulfonamide (Compound 583)

The subject compound was prepared according to the general Scheme below:

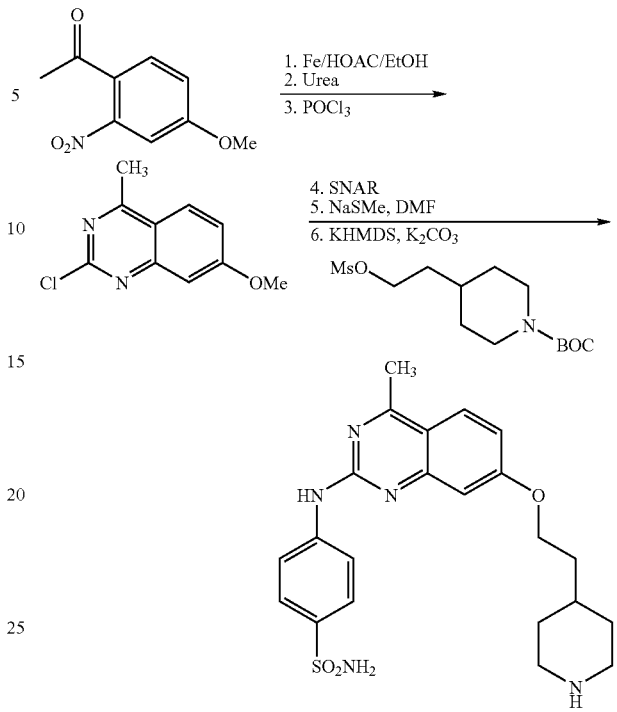

Step 1. Preparation of 1-(4-methoxy-2-aminophenyl)ethanone

To a 1:1 mixture of ethanol and acetic acid was added 1-(4-methoxy-2-nitrophenyl)ethanone (1 eq) and Fe dust (3 eq) was added in portions. The reduction was complete in 1 h. The reaction mixture was filtered and then concentrated and partitioned between ethyl acetate and water. The organic layer was washed with saturated sodium bicarbonate and dried and concentrated to give methyl 1-(4-methoxy-2-aminophenyl)ethanone in 85% yield. ES/MS m/z 196 (MH$^+$).

Step 2. Preparation of 7-methoxy-4-methylquinazolin-2-ol

To methyl 1-(4-methoxy-2-aminophenyl)ethanone (1 eq) was added urea (5 eq) and few mls of acetic acid the mixture was heated to 100° C. for 16 h. To the crude was added water and the precipitated solid was filtered to give methyl 7-methoxy-4-methylquinazolin-2-ol in quantitative yield. ES/MS m/z 191 (MH$^+$).

Step 3. Preparation of 2-chloro-7-methoxy-4-methylquinazoline

To 7-methoxy-4-methylquinazolin-2-ol was added POCl$_3$ and the mixture was added heated to 100° C. for 16 h when the reaction went to completion. To the reaction mixture was added ice and water and the precipitated solid was filtered and dried on the high vacuum overnight to give 2-chloro-7-methoxy-4-methylquinazoline in 60% yield. ES/MS m/z 209 (MH$^+$).

Step 4. Preparation of 4-(7-methoxy-4-methylquinazolin-2-ylamino)benzenesulfonamide To 2-chloro-7-methoxy-4-methylquinazoline (1 eq) in isopropanol was added sulfanilide (1 eq) and the mixture was heated to 90° C. for 16 h. The solid that precipitated was filtered and collected to give 4-(7-methoxy-4-methylquinazolin-2-ylamino)benzene sulfonamide. ES/MS m/z 345 (MH+).

Step 5. Preparation of 4-(7-hydroxy-4-methylquinazolin-2-ylamino)benzenesulfonamide To 2-chloro-7-methoxy-4-methylquinazoline in NMP was added sodium thiomethoxide (4 eq) and the mixture was added heated to 80° C. for 16 h when the reaction went to completion. To the reaction mixture was added water and ethyl acetate and ammonium chloride solution. The mixture was extracted with ethyl acetate and the organic layer was concentrated to give 4-(7-hydroxy-4-methylquinazolin-2-ylamino)benzenesulfonamide. ES/MS m/z 330 (MH+).

Step 6. Preparation of 4-(4-methyl-7-(2-(piperidin-4-yl)ethoxy)quinazolin-2-ylamino)benzene sulfonamide To 4-(7-hydroxy-4-methylquinazolin-2-ylamino)benzenesulfonamide (1 eq) in DMF was added potassium carbonate (1.1 eq) and KHMDS (1.2 eq) and tert-butyl 4-(2-(methylsulfonyloxy)ethyl)piperidine-1-carboxylate (1.5 eq). The reaction mixture was microwaved at 170° C. for 10 min. Formation of tert-butyl 4-(2-(4-methyl-2-(4-sulfamoylphenylamino)quinazolin-7-yloxy)ethyl)piperidine-1-carboxylate was confirmed by ¹H NMR and LC/MS.

The crude reaction mixture of tert-butyl 4-(2-(4-methyl-2-(4-sulfamoylphenylamino) quinazolin-7-yloxy)ethyl)piperidine-1-carboxylate was purified using prep HPLC and the purified fractions of the product was concentrated. To it was added a few drops of 30% TFA/DCM and the mixture was stirred for 30 min. The deprotection went to completion yielding 4-(4-methyl-7-(2-(piperidin-4-yl)ethoxy)quinazolin-2-ylamino)benzene sulfonamide that was confirmed by LC/MS. ES/MS m/z 442 (MH+).

Example 34

Preparation of (4-(5-chloro-8-methoxy-7-(1-methyl-1H-pyrazol-4-yl)quinazolin-2-ylamino)phenyl)(morpholino)methanone The subject compound was prepared according to the general Scheme below:

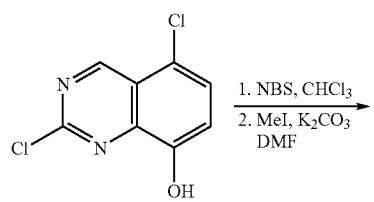

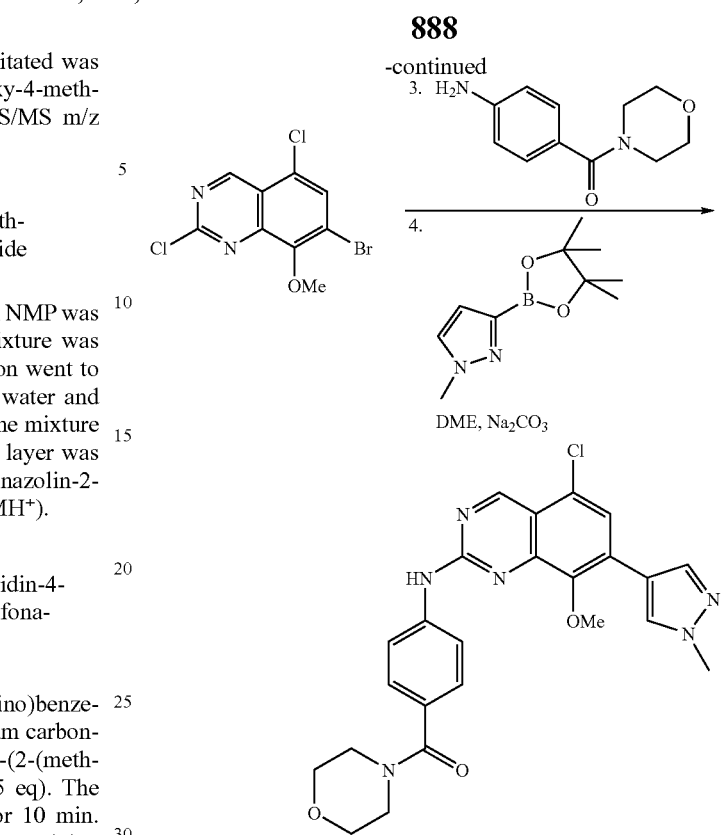

Step 1. Preparation of 7-bromo-2,5-dichloroquinazolin-8-ol

To 2,5-dichloroquinazolin-8-ol 91 eq) in chloroform was added NBS (1 eq) and the formation of 7-bromo-2,5-dichloroquinazolin-8-ol was instantaneous. The mixture was concentrated and confirmed by LC/MS. ES/MS m/z 294 (MH+).

Step 2. Preparation of 7-bromo-2,5-dichloro-8-methoxyquinazoline

To 7-bromo-2,5-dichloroquinazolin-8-ol (1 eq) was added methyl iodide (1 eq) and potassium carbonate (1 eq) and the mixture was stirred for 16 h at ambient temperature. Complete conversion to 7-bromo-2,5-dichloro-8-methoxyquinazoline was observed by HPLC. ES/MS m/z 308 (MH+).

Step 3. Preparation of (4-(7-bromo-5-chloro-8-methoxyquinazolin-2'-ylamino)phenyl) (morpholino) methanone To 7-bromo-2,5-dichloro-8-methoxyquinazoline (1 eq) was added (4-aminophenyl) (morpholino)methanone (1 eq) in isopropanol and the mixture was heated to 90° C. for 16 h. The solid formed was filtered to give (4-(7-bromo-5-chloro-8-methoxyquinazolin-2-ylamino)phenyl) (morpholino) methanone and was confirmed by LC/MS. ES/MS m/z 478 (MH+).

Step 4. Preparation of N-(5-chloro-8-methoxy-7-(1-methyl-1H-pyrazol-4-yl)quinazolin-2-yl)morpholine-4-carboxamide To (4-(7-bromo-5-chloro-8-methoxyquinazolin-2-ylamino)phenyl)(morpholino)methanone (1 eq) in DME and 2M sodium carbonate solution was added 1-methyl-3-(4,4,5,5-tetramethyl-1,3,2-dioxaborolan-2-yl)-1H-pyrazole (3 eq) and Pd(dppf)$_2$Cl$_2$.CH$_2$Cl$_2$ (0.05 eq) and the mixture was micro waved for 10 min at 120° C. The reaction mixture was then partitioned between ethyl acetate and water. The organic layer was concentrated and purified on prep HPLC to yield N-(5-chloro-8-methoxy-7-(1-methyl-1H-pyrazol-4-yl)quinazolin-2-yl)morpholine-4-carboxamide. ES/MS m/z 479 (MH$^+$).

Example 35

Preparation of 2-chloro-8-methoxy-4-methylquinazoline

The subject compound was prepared according to the general Scheme below:

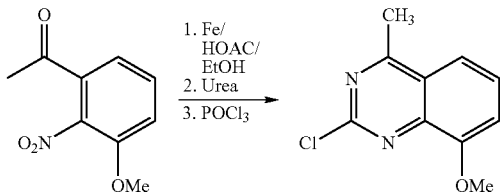

Step 1. Preparation of 3-methoxy-2-aminobenzaldehyde

To a 1:1 mixture of ethanol and acetic acid was added 3-methoxy-2-nitrobenzaldehyde (1 eq) and Fe dust (3 eq) was added in portions. The reduction was complete in 3 h. The reaction mixture was filtered and then concentrated and partitioned between ethyl acetate and water. The organic layer was washed with saturated sodium bicarbonate and dried and concentrated to give 2-amino-3-methoxybenzaldehyde in 85% yield. ES/MS m/z 151 (MH$^+$).

Step 2. Preparation of 8-methoxy-4-methylquinazolin-2-ol

To methyl 2-amino-3-methoxybenzaldehyde (1 eq) was added urea (5 eq) and few ml of acetic acid the mixture was heated to 100° C. for 16 h. To the crude was added water and the precipitated solid was filtered to give methyl 8-methoxy-4-methylquinazolin-2-ol in quantitative yield. ES/MS m/z 191 (MH$^+$).

Step 3. Preparation of 2-chloro-8-methoxy-4-methylquinazoline

To 8-methoxy-4-methylquinazolin-2-ol was added POCl$_3$ and the mixture was added heated to 100° C. for 16 h when the reaction went to completion. To the reaction mixture was added ice and water and the precipitated solid was filtered and dried on the high vacuum overnight to give 2-chloro-8-methoxy-4-methylquinazoline. ES/MS m/z 209 (MH$^+$).

Example 36

Preparation of 4-(quinazolin-2-ylamino)benzenesulfonamide (Compound 618)

To 2-(4-sulfamoylphenylamino)quinazolin-6-yltrifluoromethane sulfonate in DMF was added Pd(Ph$_3$)$_2$Cl$_2$ (0.02 eq) and formic acid (2 eq) followed by tributylamine (3 eq) and the mixture was heated to 110° C. for 3 h. Formation of the product was observed by LC/MS. The crude was purified on the prep to give 4-(quinazolin-2-ylamino)benzenesulfonamide. ES/MS m/z 301 (MH$^+$).

Example 37

Synthesis of N-(4-(morpholinosulfonyl)phenyl-7-(piperidin-4-yloxy)quinazolin-2-amine (Compound 332)

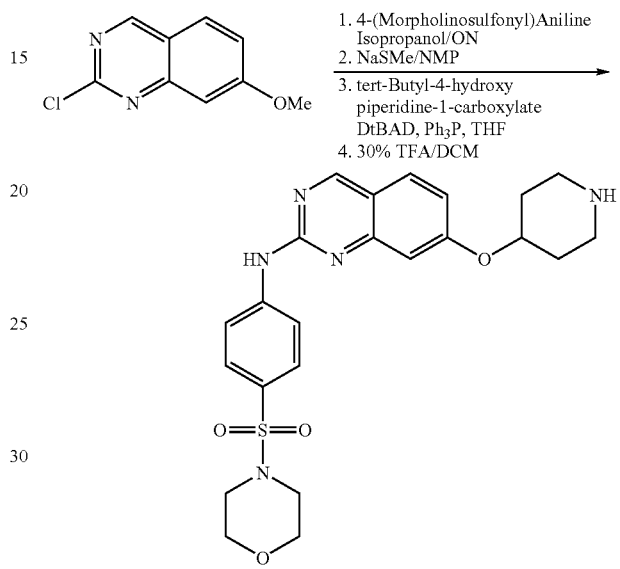

Step 1. Preparation of 7-methoxy-N-(4-(morpholinosulfonyl)phenyl)quinazolin-2-amine A mixture of 2-chloro-7-methoxyquinazoline (1 eq) and 4-(Morpholinosulfonyl) Aniline (1 eq) in 2-propanol was heated at 80° C. overnight. Product was precipitated in the reaction mixture. The precipitate was filtered, washed and dried under vacuum to provide 7-methoxy-N-(4-(morpholinosulfonyl)phenyl)quinazolin-2-amine as a yellow solid in 99% yield. ES/MS m/z 401.0 (MH$^+$).

Step 2. Preparation of 2-(4-(morpholinosulfonyl)phenylamino)quinazolin-7-ol

A mixture of 7-methoxy-N-(4-(morpholinosulfonyl)phenyl)quinazolin-2-amine (1 eq) and sodium thiomethoxide (4 eq) in NMP was heated at 80° C. for 4 h. Reaction mixture was diluted with water and acidified with 1N HCl. Compound was extracted with ethyl acetate. The organic layer was washed with satd. NaHCO$_3$, brine and dried over sodium sulfate. Filtration, evaporation and drying under vacuum provide 2-(4-(morpholinosulfonyl)phenylamino) quinazolin-7-ol as a light yellow viscous liquid in 99% yield. ES/MS m/z 387.0 (MH$^+$).

Step 3. Preparation of tert-butyl 4-(2-(4-(morpholinosulfonyl)phenylamino)quinazolin-7-yloxy) piperidine-1-carboxylate To a solution of triphenylphosphine (2 eq) in THF was added di-terbutylazodicarboxylate (2 eq). The mixture was stirred 15 minutes at ambient temperature under nitrogen atmosphere. To that was added tert-butyl-4-hydroxypiperidine-1-carboxylate (5 eq). The mixture was stirred 15 minutes at ambient temperature followed by addition of 2-(morpholinosulfonyl phenylamino) quinazolin-7-ol (1 eq). The mixture was stirred overnight at ambient temperature. The reaction mixture was concentrated and the residue was purified by flash column chromatography (50% EtOAc/Hexane) to provide product as a white solid in 80% yield. ES/MS m/z 570.1 (MH+).

Step 4. N-(4-(morpholinosulfonyl)phenyl-7-(piperidin-4-yloxy)quinazolin-2-amine

A solution of tert-butyl 4-(2-(4-(morpholinosulfonyl)phenylamino)quinazolin-7-yloxy) piperidine-1-carboxylate in 30% TFA/DCM was stirred for 30 min at ambient temperature. The solvent was evaporated and residue was purified by semi-prep HPLC to provide N-(4-(morpholinosulfonyl)phenyl-7-(piperidin-4-yloxy) quinazolin-2-amine in 80% yield. ES/MS m/z 470.1 (MH+).

Example 38
Synthesis of 7-(1-(2-fluoroethyl)piperidine-4-yloxy)-N-(4-(morpholinosulfonyl)phenyl)quinazolin-2-amine (Compound 333)

To a solution of N-(4-(morpholinosulfonyl)phenyl-7-(piperidin-4-yloxy) quinazolin-2-amine (1 eq) (See example 37, step 4) in DMF was added potassium carbonate (4 eq) and 1-fluoro-2-iodoethane (1.2 eq). The mixture was stirred overnight at ambient temperature. The reaction mixture was diluted with ethyl acetate and washed with water and brine. Dried over sodium sulfate, filtered, evaporated and purified by semi-preparative HPLC to provide 7-(1-(2-fluoroethyl)piperidine-4-yloxy)-N-(4-(morpholinosulfonyl)phenyl)quinazolin-2-amine as a yellow solid in 50% yield. ES/MS m/z 516.1 (MH+).

Example 39
Synthesis of 7-(1-methyl-1H-pyrazol-4-yl)-N-(4-(morpholinosulfonyl)phenyl)quinazolin-2-amine (Compound 317)

Step 1. Preparation of 2-(4-(morpholinosulfonyl)phenylamino)quinazolin-7-yltrifluoromethane sulfonate To a solution of 2-(4-(morpholinosulfonyl)phenylamino)quinazolin-7-ol (1 eq) (See example 37, step 2) in NMP was added phenyltrifluoromethanesulfonate (1.2 eq) and DIEA (2.5 eq) and the reaction mixture was stirred over night at ambient temperature. The reaction mixture was then partitioned between ethyl acetate and water. The organic layers were washed with saturated sodium chloride, dried and concentrated. The crude was purified by flash chromatography (60% EtOAc/Hexane) to provide product as a white solid in 70% yield. ES/MS m/z 519.0 (MH+).

Step 2. Preparation of 7-(1-methyl-1H-pyrazol-4-yl)-N-(4-(morpholinosulfonyl) phenyl)quinazolin-2-amine To a solution of 2-(4-(morpholinosulfonyl)phenylamino)quinazolin-7-yltrifluoromethane sulfonate (1 eq) in DME was added 2M sodium carbonate solution and 1-methyl-4-(4,4,5,5-tetramethyl-1,3,2-dioxaborolan-2-yl)-1H-pyrazole (3 eq) and Pd (dppf)$_2$Cl$_2$.CH$_2$Cl$_2$ (0.05 eq) and the mixture was micro waved for 10 min at 120° C. The reaction mixture was then partitioned between ethyl acetate and water. The organic layer was washed with brine, dried, concentrated and purified by semi-preparative HPLC to provide 7-(1-methyl-1H-pyrazol-4-yl)-N-(4-(morpholinosulfonyl)phenyl) quinazolin-2-amine in 60% yield. ES/MS m/z 551.1 (MH+).

Example 40
Synthesis of N$^7$-(1-methylpiperidin-4-yl)-N$^2$-(4-(morpholinosulfonyl)phenyl)quinazolin-2,7-diamine (Compound 348)

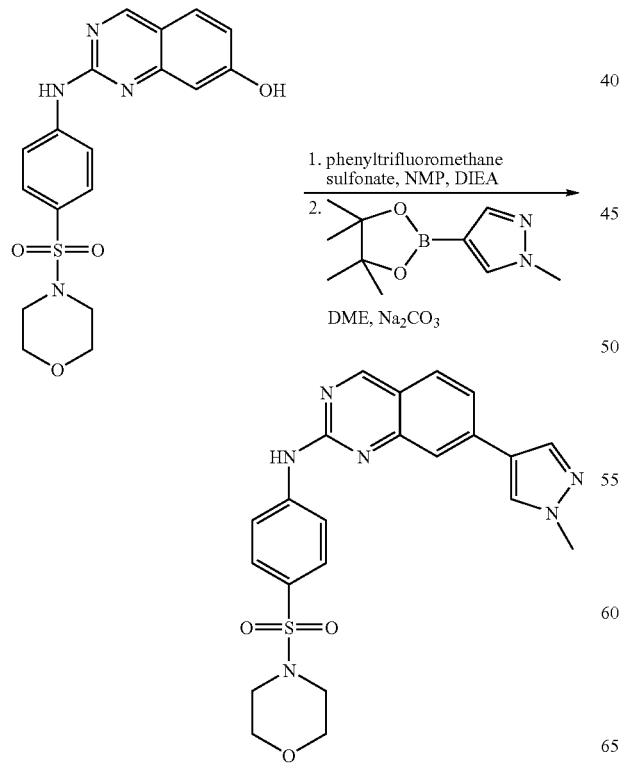

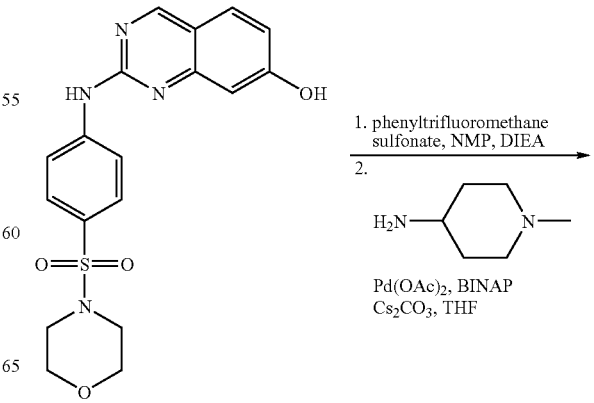

-continued

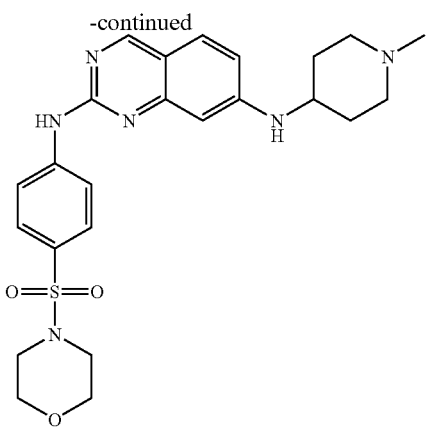

Step 1. Preparation of 2-(4-(morpholinosulfonyl) phenylamino)quinazolin-7-yltrifluoromethane sulfonate For preparation see example 39 step 1.

Step 2. Preparation of N⁷-(1-methylpiperidin-4-yl)-N²-(4-(morpholinosulfonyl)phenyl) quinazolin-2,7-diamine To a mixture of Pd(OAc)₂ (0.1 eq), CS₂CO₃ (1.75 eq) and BINAP (0.2 eq) in THF was purged nitrogen for 10 min. Then added to it was 2-(4-(morpholinosulfonyl)phenylamino) quinazolin-7-yltrifluoromethane sulfonate (1 eq) and 4-amino-1-methylpiperidine (4 eq). The reaction mixture was heated in sealed tube in oil bath for 3 h at 110° C. The reaction mixture was concentrated and purified by semi-prep HPLC to provide N⁷-(1-methylpiperidin-4-yl)-N²-(4-(morpholinosulfonyl)phenyl)quinazolin-2,7-diamine in 35% yield. ES/MS m/z 483.1 (MH⁺).

Example 41

Synthesis of Preparation of N-(4-fluoro-3-methylphenyl)-7-(1-isopropyl-piperidin-4-yloxy)-quinazolin-2-amine (Compound 327)

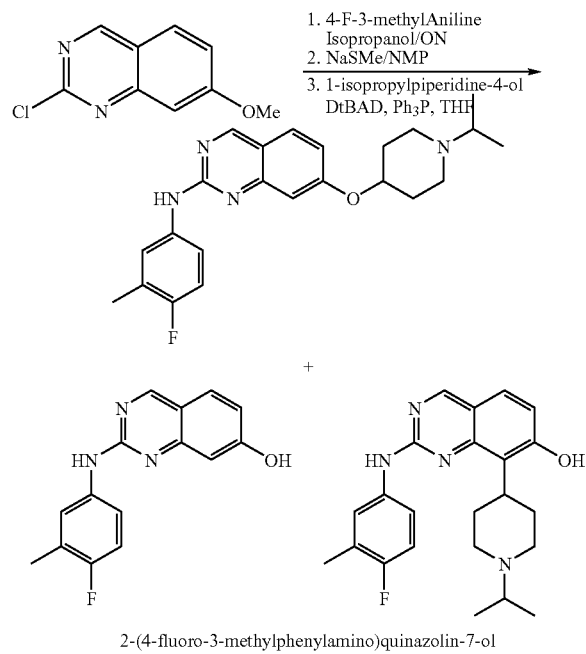

2-(4-fluoro-3-methylphenylamino)quinazolin-7-ol

-continued

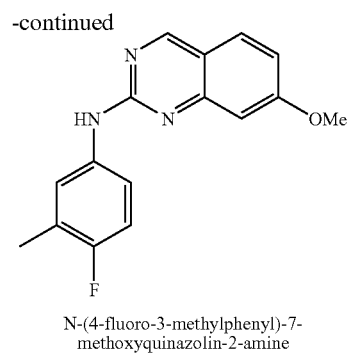

N-(4-fluoro-3-methylphenyl)-7-methoxyquinazolin-2-amine

Step 1. Preparation of N-(4-fluoro-3-methylphenyl)-7-methoxy quinazolin-2-amine

See example 37, step 1 for synthesis. ES/MS m/z 284.0 (MH⁺).

Step 2. Preparation of 2-(4-fluoro-3-methylphenylamino) quinazolin-7-ol

See example 37, step 2 for synthesis. ES/MS m/z 270.1 (MH⁺).

Step 3. Preparation of N-(4-fluoro-3-methylphenyl)-7-(1-isopropyl-piperidin-4-yloxy)-quinazolin-2-amine To a solution of triphenylphosphine (2 eq) in THF was added di-terbutylazodicarboxylate (2 eq). The mixture was stirred 15 minutes at ambient temperature under nitrogen atmosphere. To that was added 1-isopropylpiperidine-4-ol (5 eq). The mixture was stirred 15 minutes at ambient temperature followed by addition of 2-(4-fluoro-3-methylphenylamino) quinazolin-7-ol (1 eq). The mixture was stirred overnight at ambient temperature. The LC-MS of reaction mixture shows the presence of two product (2:1) with identical mass. The reaction mixture was concentrated and purified by semi-preparative HPLC to provide (N-(4-fluoro-3-methylphenyl)-7-(1-isopropyl-piperidin-4-yloxy)-quinazolin-2-amine as a major product ES/MS m/z 395.2 (MH⁺).

The other product was identified by NMR as 2-(4-fluoro-3-methylphenylamino)-8-(1-isopropyl-piperidin-4-yl)-quinazolin-7-ol). ES/MS m/z 395.2 (MH⁺).

Example 42

Synthesis of 5-(7-(piperidin-4-yloxy)-quinazolin-2-ylamino]-1H-benzo[d]imidazol-2(3H)-one (Compound 330)

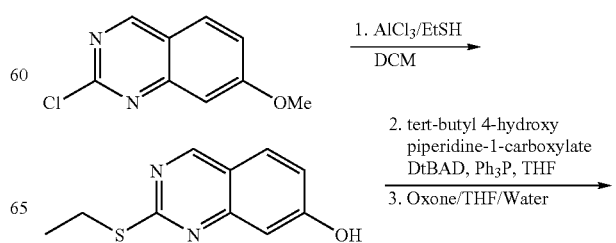

895
-continued

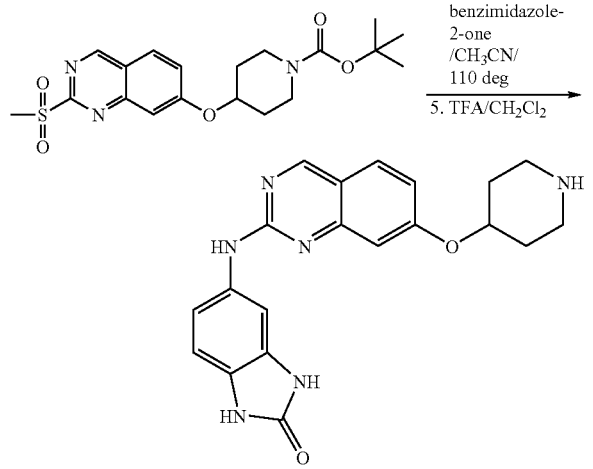

4. 5-amino-1,3-dihydro-benzimidazole-2-one /CH₃CN/ 110 deg
5. TFA/CH₂Cl₂

Step 1. Preparation of 2-(ethylthio)quinazolin-7-ol

To a solution of ethanthiol (30 ml) in DCM (50 ml) was added AlCl₃ (6 eq). The reaction mixture was cooled to 0° C. and stirred for 10 min under N₂ atmosphere. A solution of 2-chloro-7-methoxyquinazoline (1 eq) in DCM (20 ml) was added dropwise to it. The reaction mixture was warmed to room temperature and stirred for 2 h. The solvent was evaporated and residue was partitioned between EtOAc and satd. NaHCO3. The insoluble material was filtered, washed and dried to provide title product as a yellow solid (yield, 60%). The ethyl acetate layer was separated from basic layer, washed with brine and dried over sodium sulfate. Filtration, evaporation and drying under vacuum provide additional amount of product. (yield, 38%). ES/MS m/z 207.0 (MH⁺).

Step 2. Preparation of tert-butyl 4-(2-(ethylthio) quinazolin-7-yloxy)piperidine-1-carboxylate To a solution of triphenylphosphine (2 eq) in THF was added di-terbutylazodicarboxylate (2 eq). The mixture was stirred 15 minutes at ambient temperature under nitrogen atmosphere. To that was added tert-butyl-4-hydroxypiperidine-1-carboxylate (5 eq). The mixture was stirred 15 minutes at ambient temperature followed by addition of 2-(ethylthio) quinazolin-7-ol (1 eq). The mixture was stirred overnight at ambient temperature. The reaction mixture was concentrated and purified by flash column chromatography (10% EtOAc/Hexane) to provide product as a white solid in 90% yield. ES/MS m/z 390.1 (MH⁺).

Step 3. Preparation of tert-butyl 4-(2-(ethylsulfonyl) quinazolin-7-yloxy)piperidine-1-carboxylate To a solution of tert-butyl 4-(2-(ethylthio) quinazolin-7-yloxy)piperidine-1-carboxylate (1 eq) in THF (5 ml) was added a solution of oxone in water (5 ml) at 0° C. The reaction mixture was stirred for 30 min at 0° C. then warmed to room temperature and stirred for 4 h. The reaction was quenched with satd. sodium thiosulfate solution and basified with 1N NaOH. The product was extracted from basic layer with DCM. The DCM extracts were combined together, washed with brine and dried over sodium sulfate. The purification by flash column chromatography (70% EtOAc/Hexane) provide pure product in 60% yield. ES/MS m/z 422.0 (MH⁺).

Step 4. Preparation of tert-butyl 4-(2-(2-oxo-2,3-dihydro-1H-benzo[d]imidazol-5-ylamino) quinazolin-7-yloxy)piperidine-1-carboxylate A solution of tert-butyl 4-(2-(ethylsulfonyl) quinazolin-7-yloxy)piperidine-1-carboxylate (1 eq) and 5-amino-1,3-dihydro-benzimidazole-2-one (5 eq) in acetonitrile was heated in sealed tube at 110° C. for 48 h. The product was filtered, washed and dried. A brown solid, yield 50%. ES/MS m/z 477.5 (MH⁺).

Step 5. Preparation of 5-(7-(piperidin-4-yloxy)-quinazolin-2-ylamino]-1H-benzo[d]imidazol-2(3H)-one A solution of crude tert-butyl 4-(2-(2-oxo-2,3-dihydro-1H-benzo[d]imidazol-5-ylamino) quinazolin-7-yloxy)piperidine-1-carboxylate in 30% TFA/DCM was stirred at room temperature for 30 min. The solvent was evaporated and crude was purified by semi-prep HPLC to provide pure product in 30% yield ES/MS m/z 377.1 (MH⁺).

Example 43

Synthesis of 4-(7-aminoquinazolin-2-ylamino]-benzenesulfonamide (Compound 315)

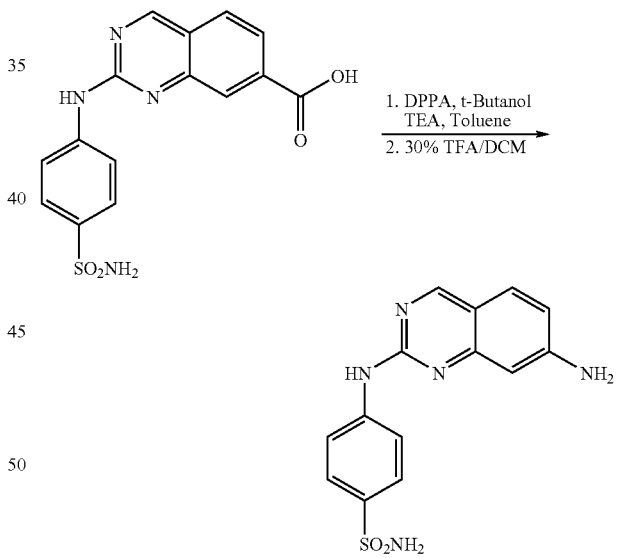

1. DPPA, t-Butanol TEA, Toluene
2. 30% TFA/DCM

Step 1. Preparation of tert-butyl 2-(4-sulfamoylphenylamino) quinazolin-7-yl) carbamate To 2-(4-sulfamoylphenylamino) quinazoline-7-carboxylic acid (1 eq) in toluene was added diphenylphosphorylazide (1.2 eq), tert-butanol (10 eq) and triethylamine (2 eq). The reaction mixture was heated at 70° C. for 30 min then 100° C. for overnight. The reaction mixture was concentrated and purified by semi-prep HPLC to provide pure product as a yellow solid in 35% yield. ES/MS m/z 416.0 (MH⁺).

Step 2. Preparation of 4-(7-aminoquinazolin-2-ylamino]-benzenesulfonamide

A solution of tert-butyl 2-(4-sulfamoylphenylamino) quinazolin-7-ylcarbamate in 30% TFA/DCM was stirred at room temperature for 30 min. The solvent was evaporated and crude was purified by semi-prep HPLC to provide 4-(7-aminoquinazolin-2-ylamino]-benzenesulfonamide. ES/MS m/z 316.0 (MH+).

Example 45

Synthesis of N-(2-(4-sulfamoylphenylamino) quinazolin-7-yl)acetamide (Compound 316)

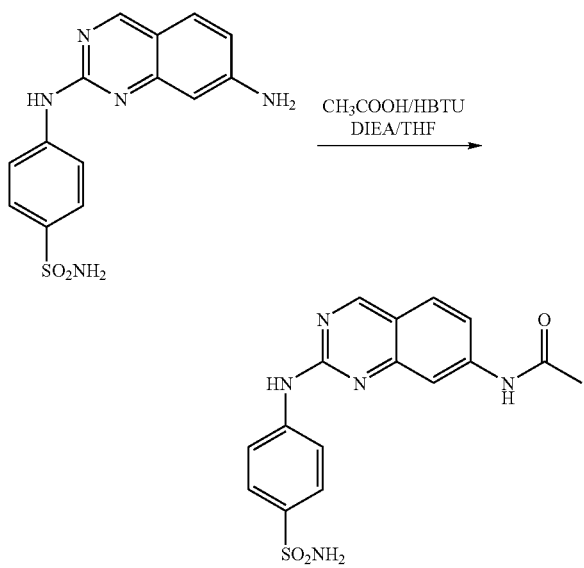

To a solution of 4-(7-aminoquinazolin-2-ylamino]-benzenesulfonamide (1 eq) (For synthesis see example 43) in THF was added acetic acid (5 eq), HBTU (4 eq) and DIEA (10 eq). The reaction mixture was stirred at room temperature for 48 h. The reaction does not go to completion. Diluted with ethyl acetate and washed with water, brine and dried over sodium sulfate. Filtered, concentrated and purified by semi-prep HPLC to provide N-(2-(4-sulfamoylphenylamino) quinazolin-7-yl)acetamide ES/MS m/z 358.0 (MH+).

Example 45

Synthesis 5-bromo-N-(3-chloro-4-morpholinophenyl)-8-(piperidine-4-yloxy) quinazolin-2-amine (Compound 338)

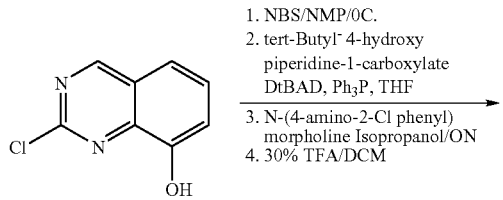

1. NBS/NMP/0C.
2. tert-Butyl 4-hydroxy piperidine-1-carboxylate DtBAD, Ph₃P, THF
3. N-(4-amino-2-Cl phenyl) morpholine Isopropanol/ON
4. 30% TFA/DCM

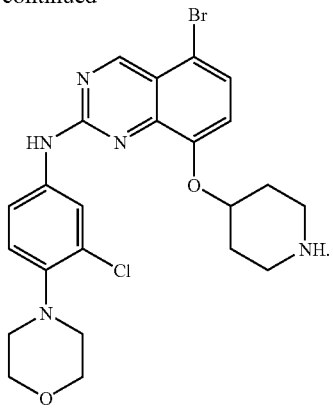

Step 1. Preparation of 5-bromo-2-chloroquinazolin-8-ol

Solid NBS (1 eq) was added to a stirred solution of 2-chloroquinazolin-8-ol (1 eq) (See example 1 for synthesis) in NMP at 0° C. under argon. After stirring at 0° C. for 30 min, LCMS showed that the reaction was complete. The formation of both 5-bromo (Major) and 7-bromo (Minor) isomers along with 5,7 dibromo product was observed. The reaction mixture was diluted with ethyl acetate and washed with satd. sodium bicarbonate, water and brine. Dried, filtered and concentrated. The crude was purified by flash chromatography (3-5% EtOAc/Hexane) to provide 5-bromo-2-chloroquinazolin-8-ol as a white solid in 60% yield. ES/MS m/z 259.2 (MH+).

Step 2. Preparation of tert-butyl 4-(5-bromo-2-chloroquinazolin-8-yloxy)piperidine-1-carboxylate To a solution of triphenylphosphine (2 eq) in THF was added di-terbutylazodicarboxylate (2 eq). The mixture was stirred 15 minutes at ambient temperature under nitrogen atmosphere. To that was added tert.butyl-4-hydroxypiperidine-1-carboxylate (5 eq). The mixture was stirred 15 minutes at ambient temperature followed by addition of 5-bromo-2-chloroquinazolin-8-ol (1 eq). The mixture was stirred overnight at ambient temperature. The reaction mixture was concentrated and the residue was purified by flash column chromatography (25% EtOAc/Hexane) to provide product as a white solid in 90% yield. ES/MS m/z 442.1 (MH+).

Step 3. Preparation of tert-butyl 4-(5-bromo-2-(3-chloro-4-morpholinophenylamino) quinazolin-8-yloxy)piperidine-1-carboxylate A mixture of tert-butyl 4-(5-bromo-2-chloroquinazolin-8-yloxy)piperidine-1-carboxylate (1 eq) and N-(4-amino-2-chlorophenyl) morpholine (1 eq) in isopropanol was heated in a sealed tube at 110° C. for overnight. The reaction mixture was concentrated and proceeds for next step. ES/MS m/z 618.0 (MH+).

Step 4. Preparation of 5-bromo-N-(3-chloro-4-morpholinophenyl)-8-(piperidine-4-yloxy) quinazolin-2-amine A solution of tert-butyl 4-(5-bromo-2-(3-chloro-4-morpholinophenylamino) quinazolin-8-yloxy)piperidine-1-carboxylate in 30% TFA/DCM was stirred at room temperature for 30 min. The solvent was evaporated and crude was purified by semi-prep HPLC to provide 5-bromo-N-(3-chloro-4-morpholinophenyl)-8-(piperidine-4-yloxy) quinazolin-2-amine in 50% yield. ES/MS m/z 518.0 (MH+).

Example 46

Synthesis of N-(3-chloro-4-morpholinophenyl)-5-methyl-8-(piperidine-4-yloxy) quinazolin-2-amine (Compound 602)

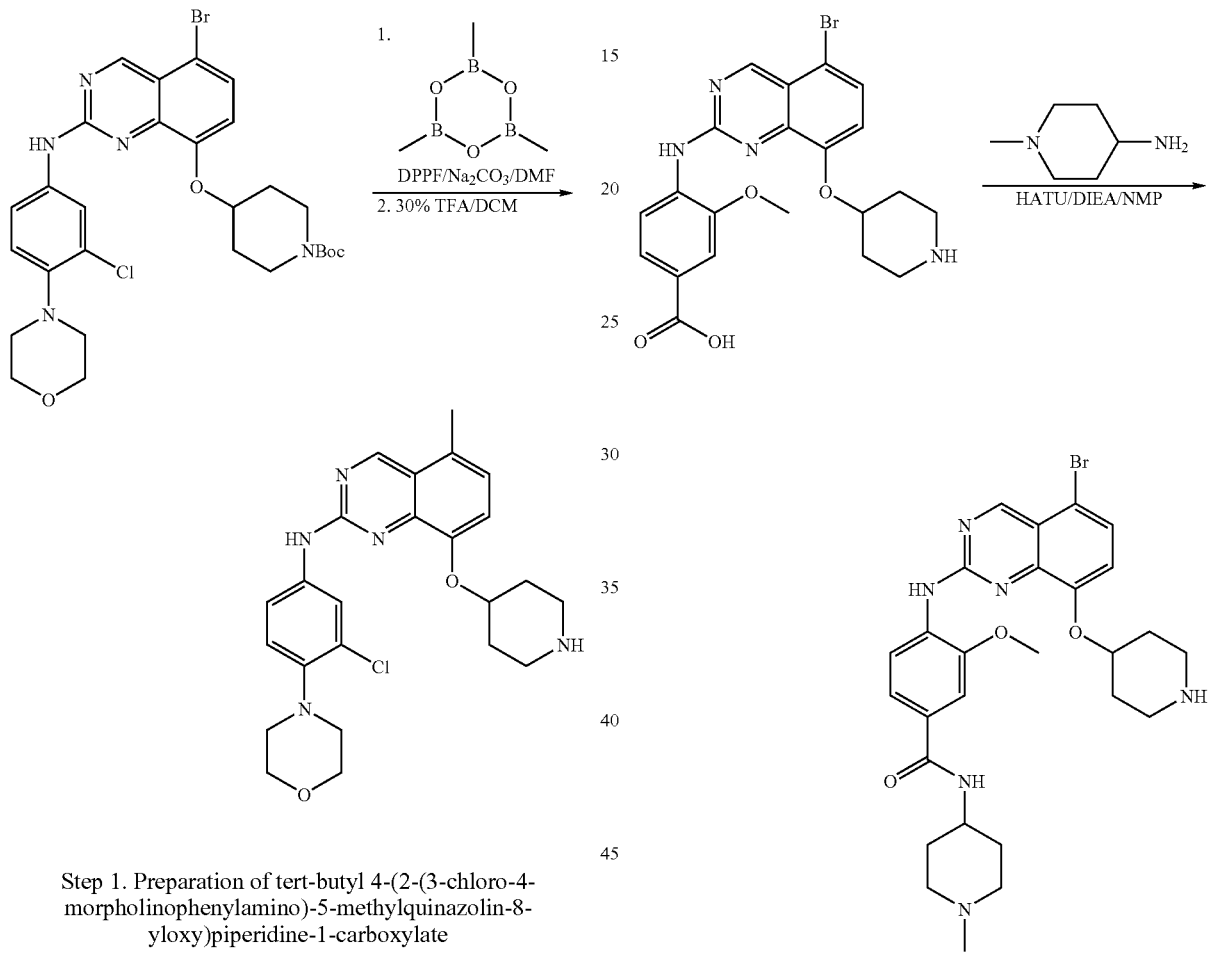

Step 1. Preparation of tert-butyl 4-(2-(3-chloro-4-morpholinophenylamino)-5-methylquinazolin-8-yloxy)piperidine-1-carboxylate To a solution of tert-butyl 4-(5-bromo-2-(3-chloro-4-morpholinophenylamino) quinazolin-8-yloxy)piperidine-1-carboxylate (See example 45 for synthesis) (1 eq) in DMF was added 2M sodium carbonate solution, trimethylboroxine (3 eq) and Pd (dppf)$_2$Cl$_2$·CH$_2$Cl$_2$ (0.05 eq). The reaction mixture was micro waved for 10 min at 120° C. The reaction mixture was then partitioned between ethyl acetate and water. The organic layer was washed with brine, dried, concentrated and purified by semi-preparative HPLC to provide pure product. ES/MS m/z 554.1 (MH+).

Step 2. Preparation of N-(3-chloro-4-morpholinophenyl)-5-methyl-8-(piperidine-4-yloxy) quinazolin-2-amine A solution of tert-butyl 4-(2-(3-chloro-4-morpholinophenylamino)-5-methylquinazolin-8-yloxy) piperidine-1-carboxylate in 30% TFA/DCM was stirred at room temperature for 30 min. The solvent was evaporated and crude was purified by semi-prep HPLC to provide N-(3-chloro-4-morpholinophenyl)-5-methyl-8-(piperidine-4-yloxy) quinazolin-2-amine 50% yield. ES/MS m/z 454.1 (MH+).

Example 47

Synthesis of 4-(5-bromo-8-(piperidin-4-yloxy) quinazolin-2-ylamino)-3-methoxy-N-(1-methylpiperidinyl)benzamide (Compound 371)

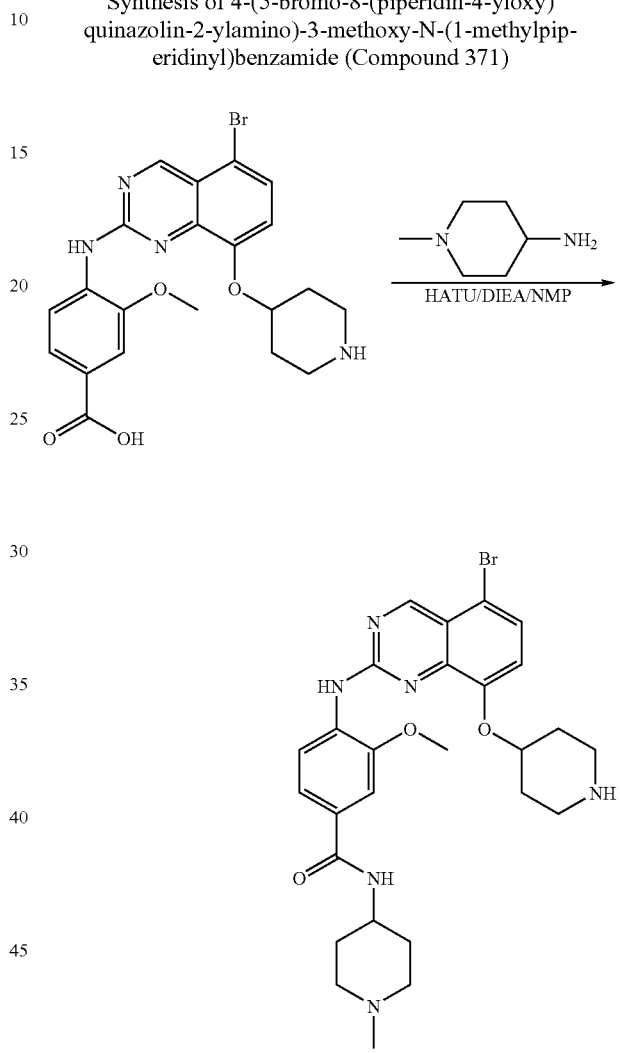

For preparation of the starting material, 4-(5-bromo-8-(piperidine-4-yloxy)quinazolin-2-ylamino)-3-methoxybenzoic acid see example 45. ES/MS m/z 473.0 (MH+).

Preparation of 4-(5-bromo-8-(piperidin-4-yloxy) quinazolin-2-ylamino)-3-methoxy-N-(1-methylpiperidinyl)benzamide A mixture of 4-(5-bromo-8-(piperidine-4-yloxy)quinazolin-2-ylamino)-3-methoxybenzoic acid (1 eq), 4-amino-N-methylpiperidine (2 eq), HATU (1.5 eq) and DIEA (3 eq) in NMP was stirred at room temperature for 4 h. The reaction mixture was concentrated and purified by semi-prep HPLC to provide pure product in 45% yield.

ES/MS m/z 569.1 (MH+).

Example 48

Synthesis (2-chloro-4-(5-chloro-8-(piperidin-4-yloxy) quinazolin-2-ylamino)phenyl) (morpholino) methanone (Compound 692)

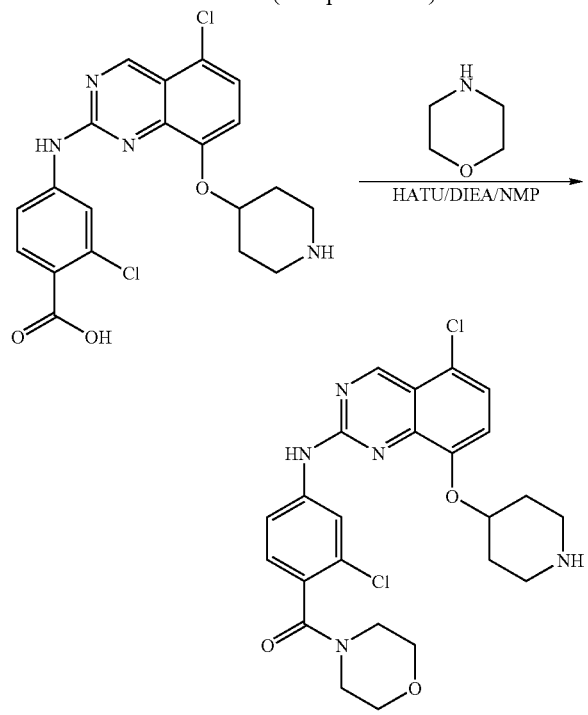

For preparation of the starting material, 2-chloro-4-(5-chloro-8-(piperidin-4-yloxy) quinazolin-2-ylamino) benzoic acid, see example 32 for the synthesis. ES/MS m/z 433.0 (MH$^+$).

Preparation of (2-chloro-4-(5-chloro-8-(piperidin-4-yloxy) quinazolin-2-ylamino)phenyl) (morpholino) methanone A mixture of 2-chloro-4-(5-chloro-8-(piperidin-4-yloxy) quinazolin-2-ylamino) benzoic acid (1 eq), morpholine (3 eq), HATU (1.5 eq) and DIEA (4 eq) in NMP was stirred at room temperature for 4 h. The reaction mixture was concentrated and purified by semi-prep HPLC to provide pure product in 50% yield. ES/MS m/z 502.3 (MH$^+$).

Example 49

Synthesis N-(3-chloro-8-methoxyquinazolin-2-ylamino)-5-((dimethylamino)methyl) phenyl)acetamide (Compound 691)

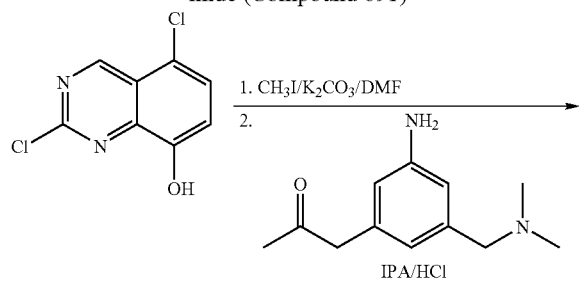

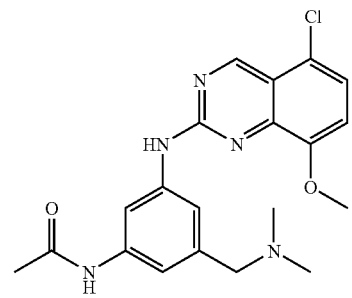

Step 1. Preparation of 2,5-dichloro-8-methoxyquinazoline

To a solution of 2,5-dichloroquinazolin-8-ol (1 eq) (See example 32 for synthesis) in DMF was added iodomethane (3 eq) and potassium carbonate (3 eq). The reaction mixture was stirred at room temperature for overnight. Diluted with ethyl acetate and washed with water and brine and dried over sodium sulfate. Filtered, evaporated and dried to provide product as a yellow solid in quantitative yield. ES/MS m/z 229.0 (MH$^+$). Proceed for next step.

Step 2. Preparation of (3-chloro-8-methoxyquinazolin-2-ylamino)-5-((dimethylamino)methyl) phenyl) acetamide A mixture of 2,5 dichloro-8-methoxyquinazoline (1 eq) and 1-(3-amino-5-((dimethylamino)methyl)phenyl)propan-2-one (1 eq) and 6NHCl (1.1 eq) in isopropanol was heated at 120° C. for overnight. The reaction mixture was concentrated and purified by semi-prep HPLC to provide pure product in 30% yield. ES/MS m/z 400.2 (MH$^+$).

Example 50

Synthesis (4-(5-chloro-8-(1-methylpiperidin-4-ylamino) quinazolin-2-ylamino)phenyl) (morpholino)methanone (Compound 377)

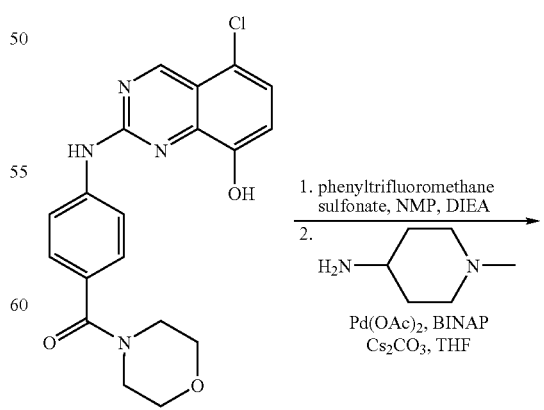

-continued

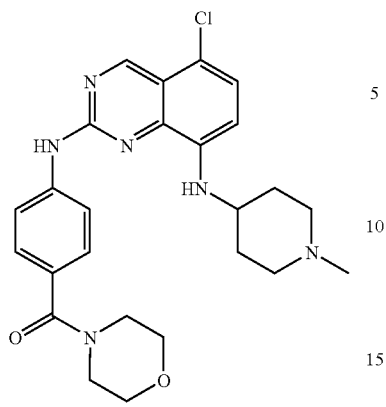

Step 1. Preparation of (4-(5-chloro-8-hydroxyquinazolin-2-ylamino) phenyl) (morpholino)methanone See example 32 for synthesis. ES/MS m/z 385.0 (MH$^+$).

Step 2. Preparation of 5-chloro-2-(4-(morpholino-4-carbonyl)phenylamino) quinazolin-8-yltrifluoromethane sulfonate See example 39, step 1 for synthesis. ES/MS m/z 517.0 (MH$^+$).

Step 3. Preparation of (4-(5-chloro-8-(1-methylpiperidin-4-ylamino) quinazolin-2-ylamino)phenyl) (morpholino)methanone To a mixture of Pd (OAc)$_2$ (0.1 eq), CS$_2$CO$_3$ (1.75 eq) and BINAP (0.2 eq) in THF was purged nitrogen for 10 min. Then added to it were 5-chloro-2-(4-(morpholino-4-carbonyl)phenylamino) quinazolin-8-yltrifluoromethane sulfonate (1 eq) and 4-amino-1-methylpiperidine (2 eq). The reaction mixture was heated in sealed tube in oil bath for 16 h at 110° C. The reaction mixture was concentrated and purified by semi-prep HPLC to provide (4-(5-chloro-8-(1-methylpiperidin-4-ylamino) quinazolin-2-ylamino) phenyl) (morpholino)methanone in 35% yield. ES/MS m/z 481.0 (MH$^+$).

Example 51

Synthesis of 4-(8-methoxy-5-(trifluoromethyl) quinazolin-2-ylamino) phenyl)(morpholino)methanone (Compound 500)

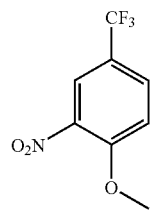

1. Pd/C, H$_2$/Methanol
2. Pivaloyl chlorode TEA/DCM

-continued

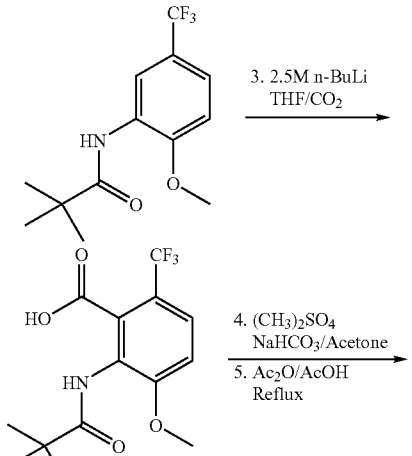

3. 2.5M n-BuLi THF/CO$_2$

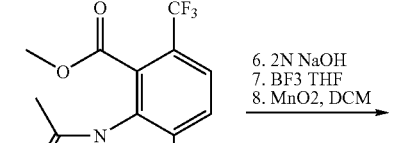

4. (CH$_3$)$_2$SO$_4$ NaHCO$_3$/Acetone
5. Ac$_2$O/AcOH Reflux

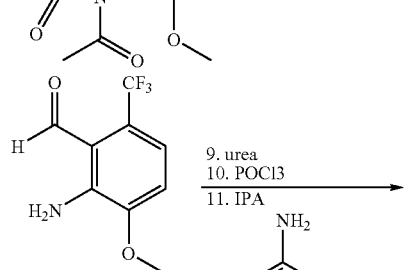

6. 2N NaOH
7. BF3 THF
8. MnO2, DCM

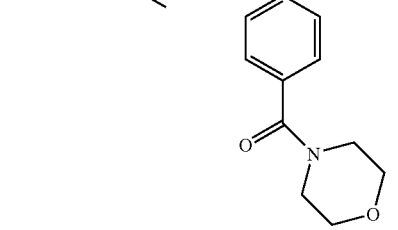

9. urea
10. POCl3
11. IPA

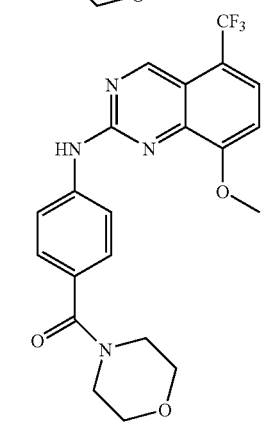

Step 1. Preparation of 2-methoxy-5-(trifluoromethyl) aniline

A mixture of 4-methoxy-3-nitrobenzotrifluoride and 10% of 10% Pd/C in methanol was stirred under H$_2$ atmosphere overnight at room temperature. The reaction mixture was filtered through celite, concentrated and dried under vacuum to provide product as an off white solid in 99% yield. ES/MS m/z 192.1 (MH+).

Step 2. Preparation of N-(2-methoxy-5-(trifluoromethyl)phenyl) pivalamide

To a solution of 2-methoxy-5-(trifluoromethyl) aniline (1 eq) in DCM at 0° C. was added TEA (1 eq) followed by dropwise addition of pivaloyl chloride (1 eq). The reaction mixture was warmed to room temperature and left stirred overnight. Diluted with DCM and washed with satd. sodium bicarbonate, water, brine and dried over sodium sulfate. Filtered, evaporated and dried under vacuum to provide pure product as an off white solid in 95% yield. ES/MS m/z 276.1 (MH+).

Step 3. Preparation of 3-methoxy-2-pivalamido-6-(trifluoromethyl)benzoic acid N-(2-methoxy-5-(trifluoromethyl)phenyl) pivalamide (1 eq) was azeotrope with toluene (x=3). Dissolved in THF, cooled to −50° C. and added n-BuLi (2 eq, 2.5M solution in hexane) dropwise. The reaction mixture was stirred at −50° C. for 1 h then warmed to −10° C. in 30 min. Stirred at this temperature for 30 min then $CO_2$ gas was passed through cylinder into the reaction mixture at −10 to 0° C. for 1 h. The reaction mixture was warmed to room temperature and stirred overnight. The reaction was poured to water and extracted with ethyl acetate. (EtOAc extracts contained starting material). The aq layer pH was adjusted to 1-2 and product was extracted with ethyl acetate (x=3). The ethyl acetate extracts were combined, washed with brine and dried over sodium sulfate.

Filtered, evaporated and dried under vacuum to provide product as yellow solid in 65% yield. ES/MS m/z 320.1 (MH+). Proceeds for next step without any purification.

Step 4. Preparation of methyl-3-methoxy-2-pivalamido-6-(trifluoromethyl)benzoate A mixture of 3-methoxy-2-pivalamido-6-(trifluoromethyl) benzoic acid (1 eq), dimethyl sulfate (1 eq) and sodium bicarbonate (1.3 eq) in acetone was refluxed for 4 h. The reaction mixture was poured to water and extracted with ethyl acetate. The ethyl acetate extracts were combined, washed with brine and dried over sodium sulfate. Filtered, evaporated and dried under vacuum to provide product as yellow solid in 95% yield. ES/MS m/z 334.1 (MH+). Proceeds for next step without any purification.

Step 5. Preparation of methyl-2-(acetylacetamido)-3-methoxy-6-(trifluoromethyl)benzoate A solution of methyl-3-methoxy-2-pivalamido-6-(trifluoromethyl)benzoate in acetic acid and acetic anhydride (1:2) was heated to reflux for 16 h. The reaction mixture was concentrated and residue was partitioned between ether and water. Ether layer was separated and washed with water, satd.sodium bicarbonate and dried over sodium sulfate.

Filtered, evaporated and dried. The residue was triturated with hexane and solid was collected by filtration and dried under vacuum to provide pure product as an off white solid in 60% yield. ES/MS m/z 334.1 (MH+).

Step 6. Preparation of 2-amino-3-methoxy-6-(trifluoromethyl)benzoic acid

A solution of methyl-2-(acetylacetamido)-3-methoxy-6-(trifluoromethyl)benzoate in 2N NaOH was heated to reflux for 4-5 h. The reaction mixture was cooled and pH was adjusted to 2. The product was extracted in ethyl acetate. The ethyl acetate extracts were combined, washed with brine and dried over sodium sulfate. Filtered, evaporated and residue was triturated with hexane. The solid was collected by filtration and dried under vacuum to provide product as light brown solid in 85% yield. ES/MS m/z 236.0 (MH+).

Step 7. Preparation of 2-amino-3-methoxy-6-(trifluoromethyl)phenyl)methanol

To 2-amino-3-methoxy-6-(trifluoromethyl)benzoic acid (1 eq) in THF at 0° C. was added boran tetrahydrofuran complex solution (6 eq, 1 M in THF) at different time interval. The mixture was stirred at room temperature for 48 hrs. The solvent was removed in vacuo and residue was partitioned between water and ethyl acetate. The organic layer was separated, washed with brine, dried with sodium sulfate and concentrated to give product in 85% yield. ES/MS m/z 222.1 (MH+).

Step 8. Preparation of 2-amino-3-methoxy-6-(trifluoromethyl)benzaldehyde

To 2-amino-3-methoxy-6-(trifluoromethyl)phenyl)methanol (1 eq) in dichloromethane was added manganese dioxide (5 eq). The mixture was stirred at room temperature under argon for 48 hrs. The mixture was filtered through celite pad and washed thoroughly with dichloromethane. The filtrated was concentrated in vacuo to give crude product in 90% yield, which was used for the next step without further purification. ES/MS m/z 220.0 (MH+).

Step 9. Preparation of 8-methoxy-5-(trifluoromethyl) quinazolin-2-ol

A mixture of 2-amino-3-methoxy-6-(trifluoromethyl)benzaldehyde (1 eq) (obtained from step 7) and urea (15 equiv.) was heated to 175° C. with vigorous stirring for 2 h. The reaction was cooled to room temperature and water was added. The solid was collected by filtration. Air-dried to give 8-methoxy-5-(trifluoromethyl) quinazolin-2-ol as yellow solid in 70% yield. ES/MS m/z 245.0 (MH+).

Step 10. Preparation of 2-chloro-8-methoxy-5-(trifluoromethyl) quinazoline

The crude 8-methoxy-5-(trifluoromethyl) quinazolin-2-ol was heated in neat phosphooxychloride ($POCl_3$) at 110° C. for 2 h. The resulted mixture was cooled to room temperature and concentrated in vacuo to nearly dryness. Ice water was added and precipitate was filtered, washed and dried to provide 2-chloro-8-methoxy-5-(trifluoromethyl) quinazoline as a light pink solid in 70% yield. ES/MS m/z 263.0 (MH+).

Step 11. Preparation of 4-(8-methoxy-5-(trifluoromethyl) quinazolin-2-ylamino) phenyl)(morpholino) methanone A mixture of 2-chloro-8-methoxy-5-(trifluoromethyl) quinazoline (1 eq) and 4-amino phenyl)(morpholino)methanone (1 eq) in isopropanol was heated in sealed tube at 110°

C. for 16 h. The solvent was evaporated and residue was purified by semi-prep HPLC to provide pure product as yellow solid in 50% yield. ES/MS m/z 433.2 (MH⁺).

Example 52

Synthesis of morpholino(4-(8-piperidin-4-yloxy)-5-(trifluoromethyl) quinazolin-2-ylamino) phenyl) methanone (Compound 383)

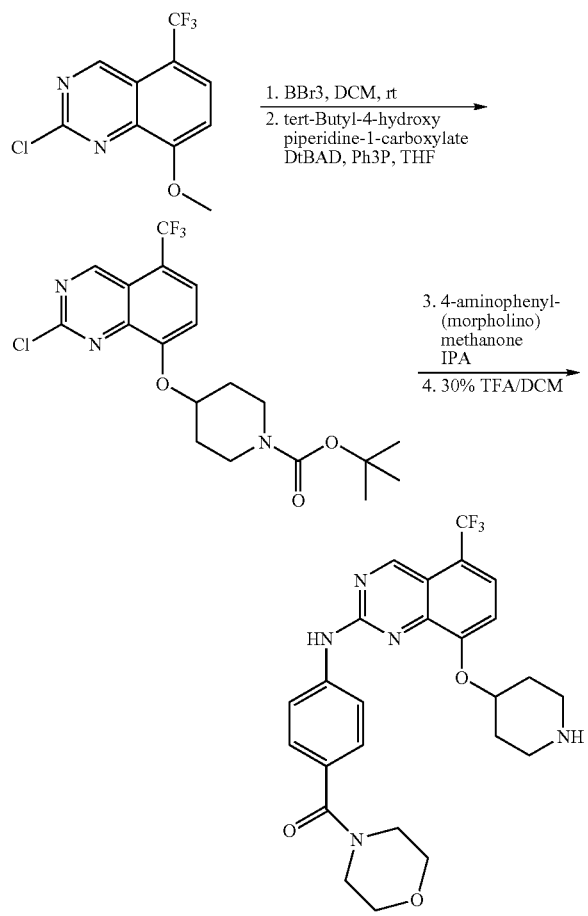

Step 1. Preparation of 2-chloro-5-(trifluoromethyl) quinazolin-8-ol

To a solution of 2-chloro-8-methoxy-5-(trifluoromethyl) quinazoline (1 eq) (See example 51 for synthesis) in DCM was added boron tribromide at 0° C. The reaction mixture was warmed to room temperature and stirred overnight. The reaction mixture was concentrated and residue was treated with ice cold water. Precipitate was filtered, washed and dried in vacuo to provide product as a yellow solid in 78% yield. ES/MS m/z 249.0 (MH⁺).

Step 2. Preparation of tert.butyl-4-(2-chloro-5-(trifluoromethyl) quinazolin-8-yloxy)piperidine-1-carboxylate See example 37, step 2 for the synthesis. ES/MS m/z 431.2 (MH⁺).

Step 3-4. Preparation of morpholino(4-(8-piperidin-4-yloxy)-5-(trifluoromethyl) quinazolin-2-ylamino) phenyl)methanone See example 45, step 3 and 4 for the synthesis. ES/MS m/z 502.2 (MH⁺).

Example 53

Synthesis of N-(3-methoxy-5 (5-methyl-1H-tetrazol-1-yl)phenyl)-7-(piperidin-4-yloxy)-6-(thiazol-2-yl) quinazolin-2-amine (Compound 682)

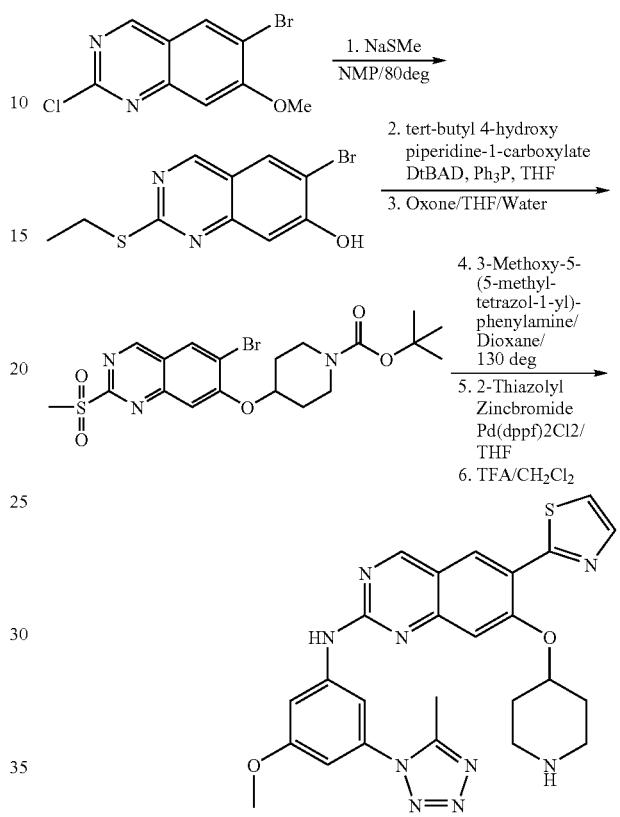

Step 1. Preparation of 6-bromo-2-(ethylthio) quinazolin-7-ol

For preparation, see example 37, step 2. (yield, 60%). ES/MS m/z 270.9 (MH⁺).

Step 2. Preparation of tert-butyl 4-(6-bromo-2-(methylsulfonyl) quinazolin-7-yloxy)piperidine-1-carboxylate Step 2 &3. See example 42, step 2 and 3 for the synthesis. (yield, 70%) ES/MS m/z 454/456

Step 4. Preparation of tert-butyl 4-(6-bromo-2-(3-methoxy-5-(5-methyl-1H-tetrazol-1-yl)phenylamino)) quinazolin-7-yloxy)piperidine-1-carboxylate A mixture of tert-butyl 4-(6-bromo-2-(methylsulfonyl) quinazolin-7-yloxy)piperidine-1-carboxylate (1 eq) and 3-Methoxy-5-(5-methyl-tetrazol-1-yl)-phenylamine (2 eq) in dioxane was heated in sealed tube at 120° C. for 48 h. The product was purified by semi prep HPLC to provide pure product as a brown solid. ES/MS m/z 611.0/613.0 (MH⁺).

Step 5 & 6. Preparation of N-(3-methoxy-5-(5-methyl-1H-tetrazol-1-yl)phenyl)-7-(piperidin-4-yloxy)-6-(thiazol-2-yl) quinazolin-2-amine See example 27 for the synthesis. ES/MS m/z 516.1 (MH⁺).

Example 54

Preparation of 4-(8-(((2-methoxyethyl)(methyl)amino)methyl)quinazolin-2-ylamino)benzenesulfonamide (Compound 392)

The subject compound was prepared according to the general Scheme below:

Step 1

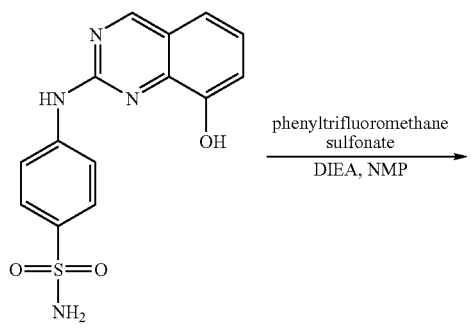

Step 2

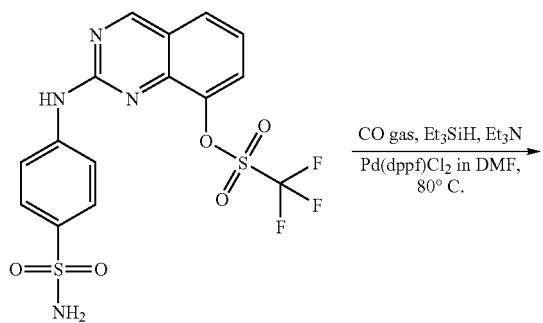

Step 3

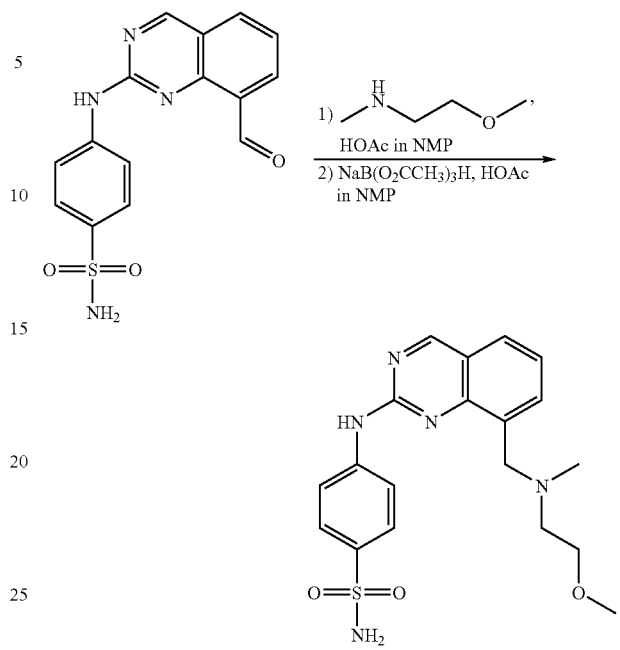

Step 1. Preparation of 2-(4-sulfamoylphenylamino)quinazolin-8-yl-trifluoromethanesulfonate To a solution of 4-(8-hydroxyquinazolin-2-ylamino) benzenesulfonamide in NMP was added phenyltrifluoromethanesulfonate and DIEA and the reaction mixture was stirred over night at ambient temperature. The reaction mixture was then partitioned between ethyl acetate and water. The organic layers were washed with saturated sodium chloride and dried and concentrated. To the crude was added methylene chloride and few drops of methanol. The white solid hence formed was filtered to give 2-(4-sulfamoylphenylamino)quinazolin-8-yltrifluoromethane sulfonate.

Step 2. Preparation of 4-(8-formylquinazolin-2-ylamino)benzenesulfonamide

A mixture of 2-(4-sulfamoylphenylamino)quinazolin-8-yl trifluoromethanesulfonate (900 mg, 2 mmole), Pd(dppf)Cl$_2$ (170 mg, 0.2 mmole), triethylamine (700 ul, 5 mmole) and triethylsilane (960 ul, 6 mmole) in DMF (20 ml) was placed in a stainless steel reactor. CO was bubbled into the mixture in the reactor. The reaction solution was stirred at 85° C. under CO (420 psi) for overnight. The reaction mixture was poured into 80 ml of saturated NaHCO$_3$ and extracted with ethyl acetate (2×250 ml). The combined organic layers were washed with water (2×60 ml) and brine (60 ml), then dried over Na$_2$SO$_4$ and evaporated in vacuo. The residue was purified by flash column chromatography to give 4-(8-formylquinazolin-2-ylamino)benzenesulfonamide (274 mg, 0.83 mmole) as brown solid. ES/MS m/z 328.9 (MH$^+$).

Step 3, Preparation of 4-(8-(((2-methoxyethyl)(methyl)amino)methyl)quinazolin-2-ylamino)benzenesulfonamide To the solution of 4-(8-formylquinazolin-2-ylamino)benzenesulfonamide (11 mg, 30 umole) and 2-methoxy-N-methylethanamine (37 ul, 30 umole) in 500 ul of NMP was added a few drops of acetic acid. The reaction solution was stirred at room temperature for overnight. Sodium triacetoxy borohydride (7 mg, 33 umole) was added. The reaction mixture was stirred for 2 hr at ambient temperature. The reductive amination went to completion to give 4-(8-(((2-methoxyethyl)(methyl)amino)methyl)quinazolin-2-ylamino)benzenesulfonamide that was then purified on prep HPLC to give product as powder. ES/MS m/z 402.2 (MH⁺).

Example 55

Preparation of 4-(8-(6-(2-(pyrrolidin-1-yl)ethylamino)-5-(trifluoromethyl)pyridin-3-yl)quinazolin-2-ylamino)benzenesulfonamide The subject compound was prepared according to the general Scheme below:

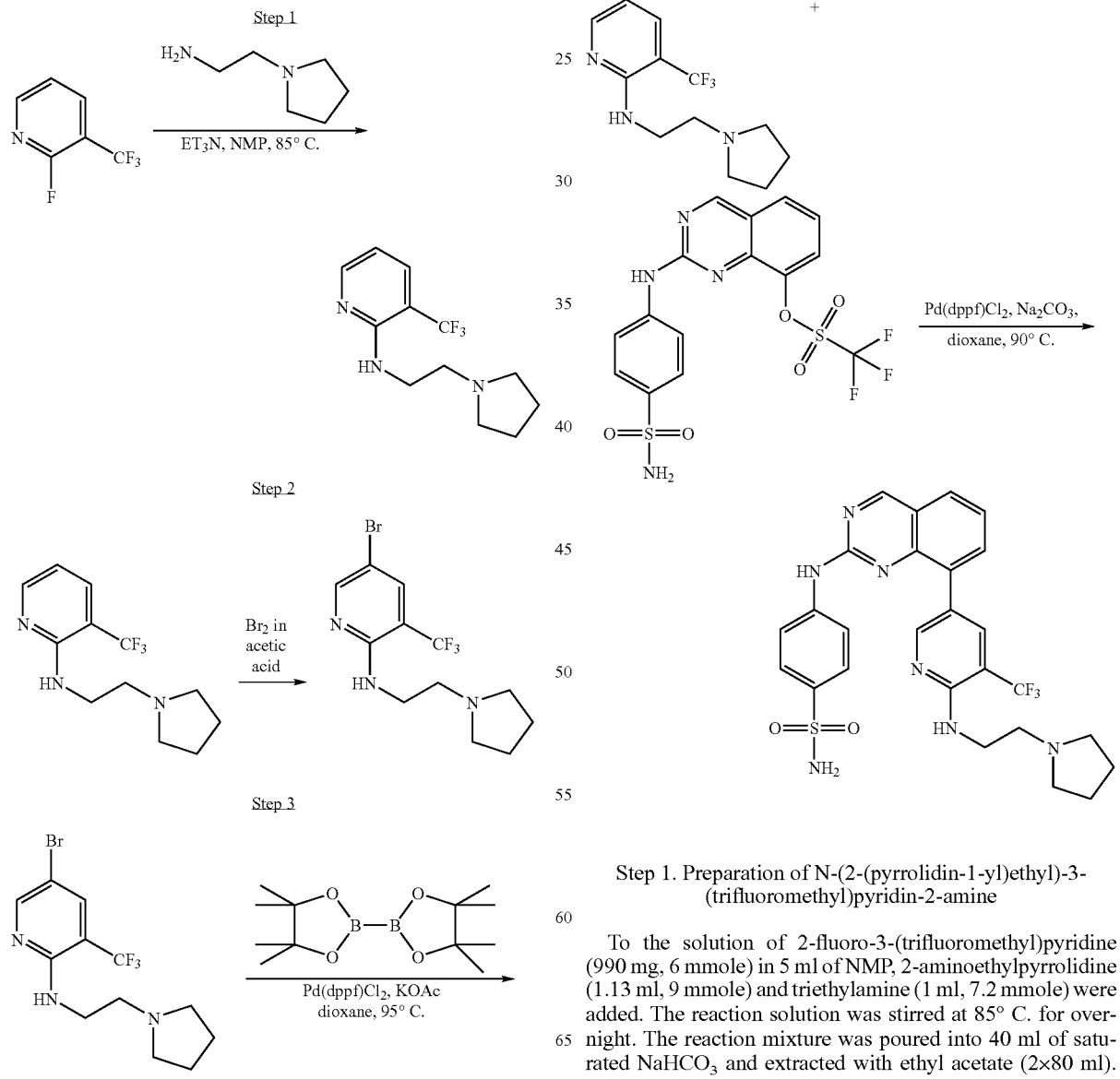

Step 1. Preparation of N-(2-(pyrrolidin-1-yl)ethyl)-3-(trifluoromethyl)pyridin-2-amine To the solution of 2-fluoro-3-(trifluoromethyl)pyridine (990 mg, 6 mmole) in 5 ml of NMP, 2-aminoethylpyrrolidine (1.13 ml, 9 mmole) and triethylamine (1 ml, 7.2 mmole) were added. The reaction solution was stirred at 85° C. for overnight. The reaction mixture was poured into 40 ml of saturated NaHCO₃ and extracted with ethyl acetate (2×80 ml). The combined organic layers were washed with water (2×30 ml) and brine (30 ml), then dried over Na₂SO₄ and evaporated in vacuo to give a brown oily N-(2-(pyrrolidin-1-yl)ethyl)-3-(trifluoromethyl)pyridin-2-amine (1.61 g). ES/MS m/z 260.1 (MH⁺).

Step 2. Preparation of 5-bromo-N-(2-(pyrrolidin-1-yl)ethyl)-3-(trifluoromethyl)pyridin-2-amine To the solution of N-(2-(pyrrolidin-1-yl)ethyl)-3-(trifluoromethyl)pyridin-2-amine (1030 mg, 4 mmole) in 10 ml of acetic acid, bromine (203 ul, 4 mmole) was added. The reaction solution was stirred at room temperature for 1.5 hr and then concentrated under vacuo to give an orange solid. The crude product was dissolved with 40 ml of ethyl acetate to give a yellow milky mixture that was then filtered and washed to give an ivory powder as HBr salt of 5-bromo-N-(2-(pyrrolidin-1-yl)ethyl)-3-(trifluoromethyl)pyridin-2-amine (963 mg). ES/MS m/z 335.9, 337.9 (MH⁺).

Step 3. Preparation of N-(2-(pyrrolidin-1-yl)ethyl)-5-(4,4,5,5-tetramethyl-1,3,2-dioxaborolan-2-yl)-3-(trifluoromethyl)pyridin-2-amine A mixture of 5-bromo-N-(2-(pyrrolidin-1-yl)ethyl)-3-(trifluoromethyl)pyridin-2-amine as TFA salt (356 mg, 789 umole), 4,4,4',4',5,5,5',5'-octamethyl-2,2'-bi(1,3,2-dioxaborolane) (219 mg, 862 umole) and potassium acetate (231 mg, 2.35 mmole) in 4 ml of dioxane, Pd(dppf)Cl₂ (41 mg, 50 umole) was added into the reaction mixture that was stirred at 92° C. for overnight. The reaction mixture was saved for future reaction and analyzed by LCMS to characterize the product as N-(2-(pyrrolidin-1-yl)ethyl)-5-(4,4,5,5-tetramethyl-1,3,2-dioxaborolan-2-yl)-3-(trifluoromethyl)pyridin-2-amine.

Step 4. Preparation of 4-(8-(6-(2-(pyrrolidin-1-yl)ethylamino)-5-(trifluoromethyl)pyridin-3-yl)quinazolin-2-ylamino)benzenesulfonamide To the reaction mixture of N-(2-(pyrrolidin-1-yl)ethyl)-5-(4,4,5,5-tetramethyl-1,3,2-dioxaborolan-2-yl)-3-(trifluoromethyl)pyridin-2-amine (1.2 ml, 235 umole) in dioxane, 2-(4-sulfamoylphenylamino)quinazolin-8-yl trifluoromethanesulfonate (45 mg, 100 umole), Pd(dppf)Cl₂ (9 mg, 11 umole) and 2M Na₂CO₃ (300 ul, 600 umole) were added. The reaction mixture was stirred at 92° C. for 5 hr. The reaction mixture was poured into 30 ml of saturated NaHCO₃ and extracted with ethyl acetate (2×50 ml). The combined organic layers were washed with water (2×20 ml) and brine (30 ml), then dried over Na₂SO₄ and evaporated in vacuo to give a brown solid (150 mg) that then purified on prep HPLC to give 4-(8-(6-(2-(pyrrolidin-1-yl)ethylamino)-5-(trifluoromethyl)pyridin-3-yl)quinazolin-2-ylamino)benzenesulfonamide, as powder (2.7 mg). ES/MS m/z 558 (MH⁺).

Example 56

Preparation of 4-(8-(2-methoxypyridin-4-yl)quinazoline-2-ylamino)benzenesulfonamide (Compound 418)

The subject compound was prepared according to the general Scheme below:

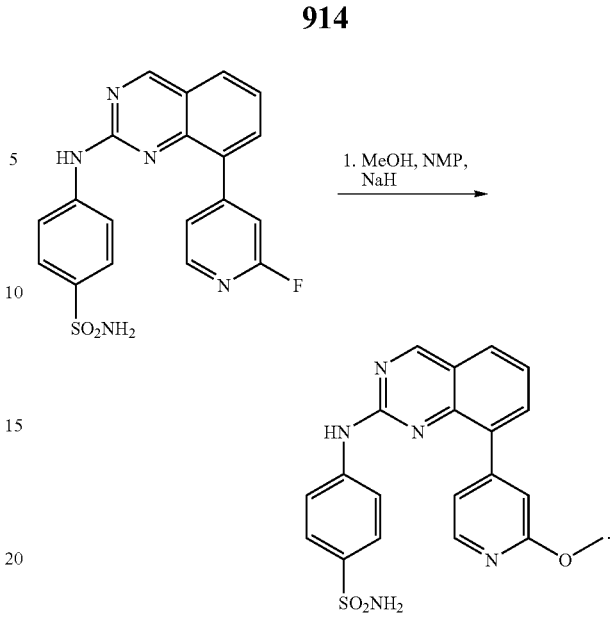

To a solution of 4-(8-(2-fluoropyridin-4-yl)quinazoline-2-ylamino)benzenesulfonamide (9 mg, 0.0227 mMol) in NMP (0.4 ml) and MeOH (0.4 mL) under argon was added (10 eq.) NaH 60% in oil. The reaction was sealed and heated at 65° C. for 5.5 hrs. The crude reaction mixture was concentrated under reduced pressure, purified on prep HPLC and lyophilized to give the desired product (1.2 mg) as TFA salt. ES/MS m/z 408 (MH⁺).

Example 57

Synthesis of 4-(8-(6-fluoropyridin-3-yloxy)quinazolin-2-ylamino)benzenesulfonamide (Compound 413)

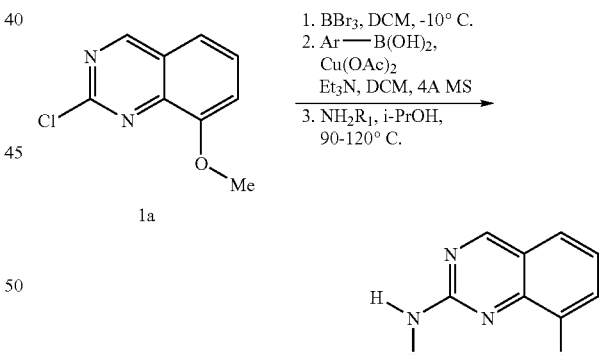

Step 1

To a 0.13 M solution of 1a in DCM was added boron tribromide (2.0 eq. of a 1.0 M solution in DCM) dropwise at −10° C. under a nitrogen atmosphere. The reaction was allowed to warm to room temperature (dark orange color) and stirred for 22 hours. The reaction was then cooled to 0° C. (red solution and precipitate formed) and the precipitate was collected by vacuum filtration and rinsed with cold DCM. The solid was stirred in ice water for one hour then filtered off, washed with water, cold 2-propanol and hexanes. The light tan solid was dried under vacuum to give the desired product in 82% yield as a mixture of the 2-chloro and 2-bromo-quinazolin-8-ol. ES/MS m/z 181.1 and 225.0/227.0 (MH⁺).

Step 2

To a 0.1 M solution of the 2-chloro and 2-bromoquinazolin-8-ol in DCM was added 4 Å MS followed by Cu(OAc)$_2$.H$_2$O (1.0 eq.). The solution was stirred at room temperature for 5 min. (brown color), then 2-fluoropyridine-5-boronic acid was added (2.0 eq.), followed by Et$_3$N (5 eq.). The solution turned dark green and it was allowed to stir for 24 hr. The reaction was then filtered, the filtrate was evaporated and passed through a plug of silica gel eluting with EtOAc. Upon concentration of the fractions, the desired product was obtained in 33% yield. ES/MS m/z 276.0 and 321.9/320.0 (MH⁺).

Step 3

To a 0.13 M solution of the 2-chloro-8-(6-fluoropyridin-3-yloxy)quinazoline and 2-bromo-8-(6-fluoropyridin-3-yloxy)quinazoline mixture in i-PrOH was added sulfanilamide (1.0 eq.) and the solution was heated to refluxed for 12 hr. Cooled to room temperature and the precipitate was filtered off and washed with i-PrOH to give the desired product in 61% yield. The solid was 96% pure by HPLC. ES/MS m/z 412.0 (MH⁺) for 595644-4-(8-(6-fluoropyridin-3-yloxy)quinazolin-2-ylamino)benzenesulfonamide.

Example 58

Synthesis of 4-(7-(2-fluoropyridin-4-yloxy)quinazolin-2-ylamino)benzenesulfonamide (Compound 416)

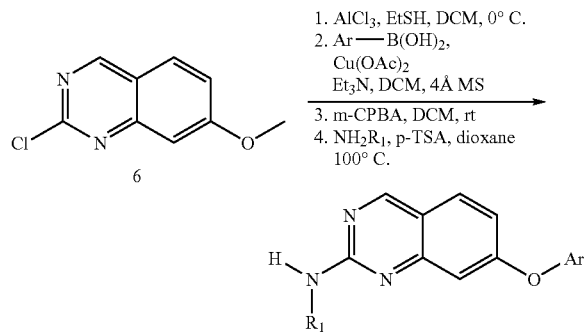

Step 1

To a solution of DCM/ethanethiol (0.3 M, 1:1) was added AlCl$_3$ (6 eq.) and the reaction was cooled to 0° C. under a nitrogen atmosphere. Compound 6 was dissolved in DCM and added dropwise to the above solution dropwise. The reaction was allowed to warm to room temperature and stirred for 36 hr. The solvent was removed under vacuum and the crude was dissolved in EtOAc. Saturated NaHCO$_3$ was added slowly dropwise and the layers were separated. The organic layer was dried with brine and Na$_2$SO$_4$ and concentrated. The crude was triturated in DCM and the precipitate was filtered off to give the desired product as an off-white solid in 83% yield. ES/MS m/z 207.0 (MH⁺).

Step 2

To a 0.1 M solution of the 2-(ethylthio)quinazolin-7-ol in DCM was added 4 Å MS followed by Cu(OAc)$_2$.H$_2$O (1.0 eq.). The solution was stirred at room temperature for 5 min. (brown color), then 2-fluoropyridine-5-boronic acid was added (2.0 eq.), followed by Et$_3$N (5 eq.). The solution turned dark green and it was allowed to stir for 24 hrs. The reaction was then filtered, the filtrate was evaporated and passed through a plug of silica gel eluting with EtOAc. Upon concentration of the fractions, the desired product was obtained in 41% yield. ES/MS m/z 302.0 (MH⁺).

Step 3

To a 0.2 M solution of the 2-(ethylthio)-7-(2-fluoropyridin-4-yloxy)quinazoline in DCM was added m-CPBA (3 eq.) and the solution was stirred for 30 min at room temperature. Quenched the reaction with 1N NaHCO$_3$ and extracted with DCM. The organic layer was dried with Na$_2$SO$_4$ and concentrated. Purification via SiO$_2$ column chromatography eluting with EtOAc and Hexanes (50%) afforded the desired product in 53% yield. ES/MS m/z 334.0 (MH⁺).

Step 4

To a 0.06 M solution of the 2-(ethylsulfonyl)-7-(2-fluoropyridin-4-yloxy)quinazoline in dioxane was added sulfanilamide (2.0 eq.) and p-TSA.H$_2$O (0.8 eq.) and the reaction was heated to 100° C. for 15 hr. The solvent was removed under vacuum and the crude was purified via automated reverse phase HPLC. The pure fractions were lyophilized over 2 days to afford the desired product 4-(7-(2-fluoropyridin-4-yloxy)quinazolin-2-ylamino)benzenesulfonamide in 31% yield as the TFA salt. ES/MS m/z 412.1 (MH⁺).

BIOLOGICAL METHODS

1. PDK1 Kinase Alpha Screen Assay

Reagents/Concentrations: The PDK1-4 peptide substrate, biotin-GGGGRTWTLCG-NH2, was purchased from the Tufts University Core Facility. The final concentration of PDK1-4 peptide substrate was 50 nM The ATP substrate (Adenosine-5'-triphosphate) was purchased from Roche Diagnostics. The final concentration of ATP substrate was 10 uM. Phospho-(Ser/Thr) PKA substrate antibody was purchased from Cell Signaling Technology. The final concentration of antibody was 0.3 mg/ml. The Alpha Screen Protein A detection kit containing donor and acceptor beads was purchased from PerkinElmer Life Sciences. The final concentration of both donor and acceptor beads was 25 µg/ml. Alpha Screen was used for detection. The biotinylated-PDK1-4 peptide was phosphorylated by PDK1 kinase using the ATP substrate. The biotinylated-PDK1-4 peptide substrate was bound to the streptavidin coated donor bead. The antibody was bound to the protein A coated acceptor bead. The antibody bound to the phosphorylated form of the biotinylated PDK-1 peptide substrate, bringing the donor and acceptor beads into close proximity. Laser irradiation of the donor bead at 680 nm generated a flow of short-lived singlet oxygen molecules. When the donor and acceptor beads were in close proximity, the reactive oxygen generated by the irradiation of the donor beads initiated a luminescence/fluorescence cascade in the acceptor beads. This process led to a highly amplified signal with output in the 530-620 nm range. Assays were carried out in 50 mM Tris, pH=7.5, 10 mM MgCl$_2$, 0.1% Bovine Serum Albumin, 0.01% Tween-20, 2 mM Dithiolthreitol, 2.5% Dimethyl Sulfoxide. Reactions were stopped by adding 50 mM Tris, pH=7.5, 90 mM EDTA, 0.1% Bovine Serum Albumin, 0.01% Tween-20.

Procedure: To 10 µl of PDK1-4 peptide, 0.5 µl of test compound in dimethyl sulfoxide is added. PDK1 kinase and ATP are mixed. 10 µl of the PDK1 kinase/ATP mix is added to start the reaction. The reaction is allowed to proceed for 3-18 hours. The reactions are stopped by adding 10 µl of the EDTA-containing stop buffer. Beads are mixed with antibody. 25 µl of the bead/antibody mix is added to the stopped reactions. Plates are incubated at room temperature overnight to allow for detection development before being read. The assay is run is a 384-well format.

Results: Each of the compounds listed in Tables 1-5 was screened according the method above, and exhibited an $IC_{50}$ value of less than or equal to 25 µM, with respect to inhibition of PDK1. Additionally, many of the compounds exhibited an $IC_{50}$ of less than 10 µM, or less than 1 µM, or less than 0.1 µM, or less than 0.01 µM. Accordingly, each of the compounds is preferred individually, and/or as a member of a group that includes the compounds of Formula I, or Formula II or Formula III.

II. CDK1 (CDC2) Kinase Inhibition In Vitro Screen Assay

Reagents/Concentrations: Human full length Cdk1 is purchased from Upstate (#14-450) as a co-purification with Cyclin B. The final enzyme concentration in the assay is 0.8 nM. Histone H1 peptide substrate is purchased from Research Genetics. The peptide, with the sequence lcBiotin-GGCGP-KTPKKAKKL[CONH2], is used in the assay at a final concentration 0.5 µM. The ATP substrate (Adenosine-5'-triphosphate) was purchased from Roche Diagnostics. The final concentration of ATP substrate is 1 µM. $P^{33}$ γ-ATP is purchased from NEN. The biotinylated peptide substrate is phosphorylated by Cdk1/Cyclin B enzyme, in the presence of varying concentrations of compounds, using the ATP substrate. A fraction of ATP in the reaction is radiolabeled to provide a detectable phosphorylation signal. The phosphorylation reaction is stopped with the addition of 25 mM EDTA. The solutions are then transferred to White BioBind Streptavidin Coated Assay plates, purchased from Thermo Electron Corporation. After washing, Microscint 20 scintillation fluid, purchased from Perkin Elmer, is added to each well and counts per minute (cpm) is measured using a Packard TopCount Microscintillation Counter. The highest cpms measured indicates the maximum phosphorylation of the substrate possible under the assay conditions. Reactions run without enzyme present give cpms indicative of complete inhibition of the enzyme. Each concentration of compound produces a measurable percent inhibition from the maximum signal based on these values. Assays were carried out in 50 mM Tris-HCl pH7.5, 10 mM $MgCl_2$, 1 mM DTT, 1 mM EGTA, 25 mM β-glycerol phosphate, 1 mM NaF, 0.01% BSA/PBS, 0.5 uM peptide substrate, and 0.8 mM Cdk1.

Procedure: Distribute 100 uL of Reaction Buffer containing 50 mM Tris-HCl pH7.5, 10 mM $MgCl_2$, 0.01% BSA/PBS, 1.5 mM DTT, 1.5 mM EGTA, 37.5 mM β-glycerol phosphate, 1.5 mM NaF, 0.75 uM peptide substrate, and 1.2 nM Cdk1 to each well. 100% inhibition control wells contain no Cdk1. Add compounds to wells in desired 10× concentrations with 10% DMSO, 50 mM Tris-HCl pH7.5, 10 mM $MgCl_2$, and 0.01% BSA/PBS. Start reactions by adding 15 uL of ATP concentrated at 10 uM, with $P^{33}$ γ-ATP at <10 nM as label. Run reactions for four hours at room temperature with shaking. Streptavidin coated plates are blocked for one hour with 1% BSA in PBS. 100 uL 50 mM EDTA is added to each streptavidin well. 100 uL of each assay solution are transferred to corresponding streptavidin wells containing EDTA. Capture of radiolabeled substrate then takes place by shaking at room temperature for one hour. After binding the wells are washed 4 times with PBS, 200 uL Microscint 20 is added to each well, and cpms are measured. The assay is run in a 96-well format.

Results: Many of the compounds listed in Tables 1-5 were screened according to the method above, and exhibited an $IC_{50}$ value of less than or equal to 25 µm, with respect to inhibition of Cdk1. Additionally, many of the compounds exhibited an $IC_{50}$ of less than 10 µM, or less than 1 µM, or less than 0.1 µM. Accordingly, each of the compounds is preferred individually, and/or as a member of a group that includes the compounds of Formula I, or Formula II or Formula III.

III. CDK2 Kinase Inhibition In Vitro Screen Assay

Reagents/Concentrations: Human full length Cdk2 is purchased from Upstate (#14-407) as a co-purification with Cyclin A. The final enzyme concentration in the assay is 5 nM.

Histone H1 peptide substrate is purchased from Research Genetics. The peptide, with the sequence lcBiotin-GGCGP-KTPKKAKKL[CONH2], is used in the assay at a final concentration 0.5 µM. The ATP substrate (Adenosine-5'-triphosphate) was purchased from Roche Diagnostics. The final concentration of ATP substrate is 1 µM. $P^{33}$ γ-ATP is purchased from NEN. The biotinylated peptide substrate is phosphorylated by Cdk2/Cyclin A enzyme, in the presence of varying concentrations of compounds, using the ATP substrate. A fraction of ATP in the reaction is radiolabeled to provide a detectable phosphorylation signal. The phosphorylation reaction is stopped with the addition of 25 mM EDTA. The solutions are then transferred to White BioBind Streptavidin Coated Assay plates, purchased from Thermo Electron Corporation. After washing, Microscint 20 scintillation fluid, purchased from Perkin Elmer, is added to each well and counts per minute (cpm) is measured using a Packard TopCount Microscintillation Counter. The highest cpms measured indicates the maximum phosphorylation of the substrate possible under the assay conditions. Reactions run without enzyme present give cpms indicative of complete inhibition of the enzyme. Each concentration of compound produces a measurable percent inhibition from the maximum signal based on these values. Assays were carried out in 50 mM Tris-HCl pH7.5, 10 mM $MgCl_2$, 1 mM DTT, 1 mM EGTA, 25 mM β-glycerol phosphate, 1 mM NaF, 0.01% BSA/PBS, 0.5 uM peptide substrate, and 5 mM Cdk1.

Procedure: Distribute 100 uL of Reaction Buffer containing 50 mM Tris-HCl pH7.5, 10 mM $MgCl_2$, 0.01% BSA/PBS, 1.5 mM DTT, 1.5 mM EGTA, 37.5 mM β-glycerol phosphate, 1.5 mM NaF, 0.75 uM peptide substrate, and 7.5 nM Cdk2 to each well. 100% inhibition control wells contain no Cdk2. Add compounds to wells in desired 10× concentrations with 10% DMSO, 50 mM Tris-HCl pH7.5, 10 mM $MgCl_2$, and 0.01% BSA/PBS. Start reactions by adding 15 uL of ATP concentrated at 10 uM, with $P^{33}$ γ-ATP at <10 nM as label. Run reactions for four hours at room temperature with shaking. Streptavidin coated plates are blocked for one hour with 1% BSA in PBS. 100 uL 50 mM EDTA is added to each streptavidin well. 100 uL of each assay solution are transferred to corresponding streptavidin wells containing EDTA. Capture of radiolabeled substrate then takes place by shaking at room temperature for one hour. After binding the wells are washed 4 times with PBS, 200 uL Microscint 20 is added to each well, and cpms are measured. The assay is run in a 96-well format.

Results: Many of the compounds listed in Tables 1-5 were screened according to the method above, and exhibited an $IC_{50}$ value of less than or equal to 25 µM, with respect to inhibition of Cdk2. Additionally, many of the compounds exhibited an $IC_{50}$ of less than 10 μM, or less than 1 μM, or less than 0.1 μM. Accordingly, each of the compounds is preferred individually, and/or as a member of a group that includes the compounds of Formula I, Formula II or Formula III.

IV. Cell Proliferation Assay Protocol:

A2780, PC-3, or PC3MM cells were seeded at 1000 cells/well in 100 μL/well (10.000 cells/mL) growth media in 96-well plates. Cells were allowed to adhere to the bottom of plates for 3-5 hours in a 37° C. 5% $CO_2$ incubator. Compounds were dissolved in DMSO and then transferred to the cell plates. The cells were incubated with the compounds for 3 days in a 37° C. 5% $CO_2$ incubator. The growth medium containing the compounds was then removed from the cells and fresh medium was added, followed by 100 μL of Cell Titer Glo assay reagent (Promega). This mixture was shaken for 1 minute and then incubated without shaking for 10 minutes. Activity determinations for the compounds were made by detection on a Trilux Instrument.

Results: Many of the compounds listed in Tables 1-5 were screened according to the method above, and exhibited an $EC_{50}$ value of less than or equal to 10 μM, with respect to inhibition of cell proliferation. Additionally, many of the compounds exhibited an $IC_{50}$ of less than 5 μM, or less than 1 μM, or less than 0.1 μM.

V. Cell Proliferation Assay Protocol: PC-3 Cell Line

PC-3 cells were seeded at 1000 cells/well in 100 μL/well (10.000 cells/mL) along with growth media into black-walled, clear bottom 96-well plates. The cells were allowed to adhere to the bottom of the plate for 3-5 hours in a 37° C. 5% $CO_2$ incubator.

Test compounds were diluted to 500× in DMSO. The DMSO solutions of six of the compounds were transferred to the cells in the 96 well round bottom plate, column 2, row B-F. A 1:3 serial dilution of each compound was carried out. The serial dilution comprised adding 20 μL of DMSO to the wells containing the compounds and doing a 1:3 dilution across the plate from columns 2-10. Column 11 contained only DMSO. The serial dilution was carried out using a BioMek 2000 protocol "CP Serial Dilution using 250 μL tips" or "Proliferation Compound" (if using 20 μL tips).

To a 96 deep well block, columns 2-11 rows B-F, was transferred 500 μL of growth medium. Using the FX protocol "HH_CellAssay_2 μL to 500 μL", 2 μL of compound from each cell of the compound plate was transferred to the corresponding cell in the 96 deep well block containing 500 μL of growth medium. The instrument was programmed to dilute the compound in growth medium and then transfer 100 μL of that mixture to cell plates containing cells. The cell plates, to which test compounds had been added, were incubated for 3 days at 37° C. Following the incubation, the medium was removed and replaced with fresh medium. Cell Titer Glo (100 μL) was added to each well and the plate was shaken for 1 minute and then incubated without shaking for 10 minutes. The plates were then read using a Trilux instrument.

VI. The pAkt$^{T308}$ ECL Assay Protocol

On Day 1, PC-3 cells were seeded at 15,000 cells/well in 100 μL/well (10.000 cells/mL) growth media into black-walled, clear bottom, poly-L-lysine coated plates. The cells were incubated overnight in a 37° C., 5% $CO_2$ incubator.

On Day 2, a MSD ECL plate was blocked for two hours with 150 μL per well of 3% MSD blocker A.

Test compounds were diluted to 500× in DMSO and then were subjected to further serial dilution using a BioMek 2000 instrument. DMSO diluted compounds were then diluted into growth media and then added to the cell plates.

The cell plates incubated with compounds for six hours in a 37° C., 5% $CO_2$ incubator after which the growth medium was removed and 55 μl of MSD lysis buffer was added to cell plates on ice. The plates were lysed on ice for five minutes followed by 15 minutes of vigorous shaking on a plate shaker at 4° C. The blocked MSD assay plates were washed twice with 1×MSD wash buffer followed by the addition of cell lysate as follows: 30 μl of cell lysate was added to the pAkt308 plates and 13 μl of lysate+12 μl lysis buffer was added to the tAkt plates. The plates were then sealed and shaken at 4° C. overnight.

On Day 3, the MSD plates were washed four times with 1×MSD wash buffer then, 25 μl/well of MSD SULFO-TAG antibodies diluted to 10 nM final concentration in 1% blocker. A buffer was added to the antibody diluent which was added to assay plates. The plates were then sealed and incubated at RT for 1.5 hour. The plates were then washed twice with 1×MSD wash buffer followed by the addition of 150 μl/well of 1.5×MSD read buffer. The plates were read immediately after the addition of read buffer using a Trilux instrument.

Many of tested compounds demonstrated $IC_{50}$ values of less than 5 μM, as shown in Table 1. Some of them even had $IC_{50}$ values as low as less than 5 μM.

The contents of each of the patents, patent applications and journal articles cited above are hereby incorporated by reference herein and for all purposes as if fully set forth in their entireties.

What is claimed is:

1. A compound of Formula I:

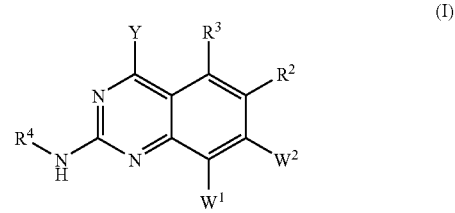

wherein: one of $W^1$ or $W^2$ is $R^1$ and the other is —L—$A^1$;

L is —O—;

$A^1$ is heterocyclyl, or substituted heterocyclyl, wherein said heterocyclyl is piperidinyl;

Y is H, $C_{1-3}$ alkyl, halo, cyano, nitro, or amino;

$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;

$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and $R^4$ is aryl, substituted aryl, heteroaryl, substituted heteroaryl, cycloalkyl, substituted cycloalkyl, heterocyclyl, or substituted heterocyclyl, provided when $R^4$ is heteroaryl or substituted heteroaryl, $W^2$ is not aryl or heteroaryl;

or a stereoisomer, tautomer, or pharmaceutically acceptable salt thereof.

2. The compound of claim 1, a stereoisomer, tautomer, or pharmaceutically acceptable salt thereof, wherein $R^4$ is substituted phenyl.

3. The compound of claim 1, a stereoisomer, tautomer, or pharmaceutically acceptable salt thereof, wherein $R^4$ is phenyl substituted with a group of formula —$X^1N(R_{501})(R_{502})$; wherein $X^1$ is a covalent bond, $SO_2$, or C(=O); and $R_{501}$ and $R_{502}$ are independently selected from H, alkyl, substituted alkyl, alkoxyalkyl, cycloalkyl and heterocyclylalkyl; or $R_{501}$ and $R_{502}$, taken together with the nitrogen atom to which they are attached, form a heterocyclyl group that is optionally substituted with up to three groups independently selected from $C_{1-3}$ alkyl, hydroxyl, halo, alkoxy, amino, and substituted amino.

4. The compound of claim 3, a stereoisomer, tautomer, or pharmaceutically acceptable salt thereof, wherein —$N(R_{501})(R_{502})$ forms —$NH_2$, —NH—CH(CH$_3$)$_2$, —NH—(CH$_2$)$_2$—O—CH$_3$, —NH— cyclopropyl, morpholin-4-yl, 4-methyl-piperizine-1-yl, or —NH—(CH$_2$)$_2$-pyrrolidin-1-yl.

5. The compound of claim 1, a stereoisomer, tautomer, or pharmaceutically acceptable salt thereof, wherein —L—$A^1$ is a heterocyclyloxy group having the structure:

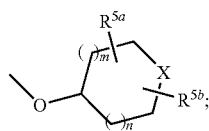

wherein:
X is $NR^6$;
$R^{5a}$ and $R^{5b}$ are each independently H, halo, hydroxy, alkyl, substituted alkyl, alkoxy, substituted alkoxy, amino, or substituted amino;
$R^6$ is H, acyl, substituted carbonyl, sulfonyl, alkyl, or substituted alkyl; and
m and n are each 1.

6. The compound of claim 5, a stereoisomer, tautomer, or pharmaceutically acceptable salt thereof, wherein $W^1$ is $R^1$ and $W^2$ is —L—$A^1$.

7. The compound of claim 6, a stereoisomer, tautomer, or pharmaceutically acceptable salt thereof, wherein $R^4$ is phenyl substituted with a group of formula —$X^1$—$N(R_{501})(R_{502})$; wherein $X^1$ is a covalent bond, $SO_2$, or C(=O); and $R_{501}$ and $R_{502}$ are independently selected from H, alkyl, substituted alkyl, alkoxyalkyl, cycloalkyl and heterocyclylalkyl;

or $R_{501}$ and $R_{502}$, taken together with the nitrogen atom to which they are attached, form a heterocyclyl group that is optionally substituted with up to three groups independently selected from $C_{1-3}$ alkyl, hydroxyl, halo, alkoxy, amino, and substituted amino.

8. The compound of claim 7, a stereoisomer, tautomer, or pharmaceutically acceptable salt thereof, wherein —$N(R_{501})(R_{502})$ forms —$NH_2$, —NH—CH(CH$_3$)$_2$, —NH—(CH$_2$)$_2$—O—CH$_3$, —NH— cyclopropyl, morpholin-4-yl, 4-methyl-piperizine-1-yl, or —NH—(CH$_2$)$_2$-pyrrolidin-1-yl.

9. The compound of claim 8, a stereoisomer, tautomer, or pharmaceutically acceptable salt thereof, wherein $R^2$ is heteroaryl or substituted heteroaryl.

10. The compound of claim 5, a stereoisomer, tautomer, or pharmaceutically acceptable salt thereof, wherein $W^1$ is —L—$A^1$ and $W^2$ is $R^1$.

11. The compound of claim 10, a stereoisomer, tautomer, or pharmaceutically acceptable salt thereof, wherein $R^4$ is phenyl substituted with a group of formula —$X^1$—$N(R_{501})(R_{502})$;

wherein $X^1$ is a covalent bond, $SO_2$, or C(=O); and $R_{501}$ and $R_{502}$ are independently selected from H, alkyl, substituted alkyl, alkoxyalkyl, cycloalkyl and heterocyclylalkyl;

or $R_{501}$ and $R_{502}$, taken together with the nitrogen atom to which they are attached, form a heterocyclyl group that is optionally substituted with up to three groups independently selected from $C_{1-3}$ alkyl, hydroxyl, halo, alkoxy, amino, and substituted amino.

12. The compound of claim 11, a stereoisomer, tautomer, or pharmaceutically acceptable salt thereof, wherein —$N(R_{501})(R_{502})$ forms —$NH_2$, —NH—CH(CH$_3$)$_2$, —NH—(CH$_2$)$_2$—O—CH$_3$, —NH— cyclopropyl, morpholin-4-yl, 4-methyl-piperizine-1-yl, or —NH—(CH$_2$)$_2$-pyrrolidin-1-yl.

13. The compound of claim 12, a stereoisomer, tautomer, or pharmaceutically acceptable salt thereof, wherein $R^2$ is heteroaryl or substituted heteroaryl.

14. The compound of claim 5, a stereoisomer, tautomer, or pharmaceutically acceptable salt thereof, wherein $R^1$ is H, halogen, cyano; or phenyl optionally substituted with —C(=O)—$N(R^{501})(R^{502})$; or a 5- or 6-membered heteroaryl group having 1 or 2 heteroatoms independently selected from O, S and N, that is optionally substituted with up to three substituents selected from alkyl, alkoxy and —$N(R_{501})(R_{502})$;

or a group of formula:

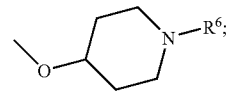

wherein each $R_{501}$ and each $R_{502}$ is independently selected from H, alkyl, alkoxyalkyl, cycloalkyl and heterocyclylalkyl.

15. The compound of claim 1, a stereoisomer, tautomer, or pharmaceutically acceptable salt thereof, wherein $W^1$ is heteroaryl or substituted heteroaryl.

16. The compound of claim 1, a stereoisomer, tautomer, or pharmaceutically acceptable salt thereof, wherein $W^2$ is heteroaryl or substituted heteroaryl.

17. The compound of claim 1, a stereoisomer, tautomer, or pharmaceutically acceptable salt thereof, wherein $R^2$ is heteroaryl or substituted heteroaryl.

18. A compound of Formula I:

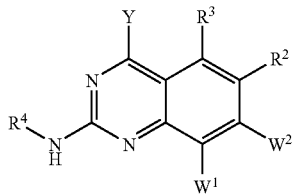

(I)

wherein:
one of $W^1$ or $W^2$ is $R^1$ and the other is —L—$A^1$;
L is —O—;
$A^1$ is heterocyclyl, or substituted heterocyclyl, wherein said heterocyclyl is piperidinyl;
Y is H, $C_{1-3}$ alkyl, halo, cyano, nitro, or amino;
$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;
$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^4$ is aryl, substituted aryl, heteroaryl, or substituted heteroaryl;
or a stereoisomer, tautomer, or pharmaceutically acceptable salt thereof.

19. The compound of claim 18, a stereoisomer, tautomer, or pharmaceutically acceptable salt thereof, wherein $R^4$ is phenyl or substituted phenyl.

20. The compound of claim 19, a stereoisomer, tautomer, or pharmaceutically acceptable salt thereof, wherein $R^4$ is phenyl substituted with a group of formula —$X^1$—$N(R_{501})(R_{502})$;
wherein $X^1$ is a covalent bond, $SO_2$, or C(=O); and $R_{501}$ and $R_{502}$ are independently selected from H, alkyl, substituted alkyl, alkoxyalkyl, cycloalkyl and heterocyclylalkyl;
or $R_{501}$ and $R_{502}$, taken together with the nitrogen atom to which they are attached, form a heterocyclyl group that is optionally substituted with up to three groups independently selected from $C_{1-3}$ alkyl, hydroxyl, halo, alkoxy, amino, and substituted amino.

21. The compound of claim 20, a stereoisomer, tautomer, or pharmaceutically acceptable salt thereof, wherein —$N(R_{501})(R_{502})$ forms —$NH_2$, —NH—CH(CH$_3$)$_2$, —NH—(CH$_2$)$_2$—O—CH$_3$, —NH-cyclopropyl, morpholin-4-yl, 4-methyl-piperizine-1-yl, or —NH—(CH$_2$)$_2$-pyrrolidin-1-yl.

22. The compound of claim 18, a stereoisomer, tautomer, or pharmaceutically acceptable salt thereof, wherein one of $R^2$ and $R^3$ is heteroaryl or substituted heteroaryl.

23. A pharmaceutical composition comprising a compound of Formula I:

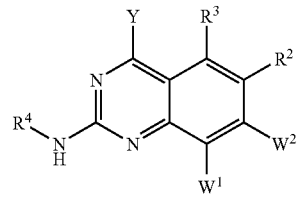

(I)

wherein: one of $W^1$ or $W^2$ is $R^1$ and the other is —L—$A^1$;
L is —O—;
$A^1$ is heterocyclyl, or substituted heterocyclyl, wherein said heterocyclyl is piperidinyl;
Y is H, $C_{1-3}$ alkyl, halo, cyano, nitro, or amino;
$R^1$ is selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, substituted heterocyclyl, aryloxy, substituted aryloxy, heteroaryloxy, substituted heteroaryloxy, cycloalkyloxy, substituted cycloalkyloxy, heterocyclyloxy, and substituted heterocyclyloxy;
$R^2$ and $R^3$ are independently selected from the group consisting of H, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, carboxyl, carboxyl ester, (carboxyl ester)amino, (carboxyl ester)oxy, cyano, halo, hydroxy, nitro, $SO_3H$, sulfonyl, substituted sulfonyl, sulfonyloxy, thioacyl, thiol, alkylthio, substituted alkylthio, aryl, substituted aryl, heteroaryl, substituted heteroaryl, cycloalkyl, substituted cycloalkyl, heterocyclyl, and substituted heterocyclyl; and
$R^4$ is aryl, substituted aryl, heteroaryl, substituted heteroaryl, cycloalkyl, substituted cycloalkyl, heterocyclyl, or substituted heterocyclyl,
provided when $R^4$ is heteroaryl or substituted heteroaryl, $W^2$ is not aryl or heteroaryl;
or a stereoisomer, tautomer, or pharmaceutically acceptable salt thereof;
and a pharmaceutically acceptable carrier.

24. The compound of claim 1, a stereoisomer, tautomer, or pharmaceutically acceptable salt thereof, wherein $A^1$ is optionally substituted by halo, hydroxy, alkyl, substituted alkyl, alkoxy, substituted alkoxy, amino, or substituted amino.

* * * * *